(12) United States Patent
Durrant et al.

(10) Patent No.: US 10,927,168 B2
(45) Date of Patent: Feb. 23, 2021

(54) METHOD OF REDUCING TUMOR RELAPSE RATE IN IMMUNOTHERAPY BY ADMINISTRATION OF LENZILUMAB

(71) Applicant: HUMANIGEN, INC., Burlingame, CA (US)

(72) Inventors: Cameron Durrant, Oxford, FL (US); Dale Chappell, Nidwalden (CH)

(73) Assignee: HUMANICEN, INC., Burlingame, CA (US)

( * ) Notice: Subject to any disclaimer, the term of this patent is extended or adjusted under 35 U.S.C. 154(b) by 0 days.

(21) Appl. No.: 16/248,762

(22) Filed: Jan. 15, 2019

(65) Prior Publication Data
US 2019/0338023 A1 Nov. 7, 2019

Related U.S. Application Data

(63) Continuation-in-part of application No. 16/204,220, filed on Nov. 29, 2018, which is a continuation-in-part of application No. 16/149,346, filed on Oct. 2, 2018.

(60) Provisional application No. 62/567,187, filed on Oct. 2, 2017, provisional application No. 62/729,043, filed on Sep. 10, 2018.

(51) Int. Cl.
*C07K 16/24* (2006.01)
*A61K 35/17* (2015.01)

(52) U.S. Cl.
CPC ............ *C07K 16/243* (2013.01); *A61K 35/17* (2013.01); *C07K 2317/21* (2013.01); *C07K 2317/24* (2013.01); *C07K 2317/34* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | |
|---|---|---|
| 2010/0055116 A1 | 3/2010 | Liou et al. |
| 2013/0156759 A1 | 6/2013 | Bebbington et al. |
| 2014/0127814 A1 | 5/2014 | Chandrasegaran et al. |
| 2014/0234298 A1 | 8/2014 | Steidl |
| 2015/0246121 A1 | 9/2015 | Bebbington et al. |
| 2015/0283178 A1 | 10/2015 | June et al. |
| 2016/0186208 A1 | 6/2016 | Jaenisch et al. |
| 2016/0206656 A1 | 7/2016 | Gilbert |
| 2016/0333089 A1 | 11/2016 | Sass et al. |
| 2018/0252727 A1 | 9/2018 | Garfall et al. |
| 2018/0273932 A1 | 9/2018 | Bothmer et al. |
| 2019/0284271 A1 | 9/2019 | Durrant et al. |

FOREIGN PATENT DOCUMENTS

| | | | |
|---|---|---|---|
| WO | WO03/068920 | 8/2003 | |
| WO | WO2006/055778 | 5/2006 | |
| WO | WO2006/111353 | 10/2006 | |
| WO | WO2006/122797 | 11/2006 | |
| WO | WO2007/092939 | 8/2007 | |
| WO | WO2015/066262 | 5/2015 | |
| WO | WO2016/073381 | 5/2016 | |
| WO | WO2017/011670 | 1/2017 | |
| WO | WO2017040930 | * 3/2017 | ............ G01N 33/50 |
| WO | WO2017/096331 | 5/2017 | |
| WO | WO2017/141243 | 8/2017 | |
| WO | WO2018/093591 | 5/2018 | |
| WO | WO2018/145206 | 8/2018 | |
| WO | WO2019/232370 | 12/2019 | |

OTHER PUBLICATIONS

Lloyd et al., Modelling the human immune response: performance of a 1011 human antibody repertoire against a broad panel of therapeutically relevant antigens. Protein Engineering, Design & Selection vol. 22 No. 3 pp. 159-168, 2009. (Year: 2009).*
Almagro et al., "Humanization of antibodies", Frontiers in Bioscience, US, vol. 13, Jan. 2008, pp. 1619-1633.
Barber et al., "Immunotherapy with Chimeric NKG2D Receptors Leads to Long-Term Tumor-Free Survival and Development of Host Antitumor Immunity in Murine Ovarian Cancer", J Immunol 2008; 180: pp. 72-78.
Hwang et al., "Use of human germline genes in a CDR homology-based approach to antibody humanization", Methods: A Companion to Methods in Enzymology, Academic Press Inc., NY, vol. 36, No. 1, May 2005, pp. 35-42.
Krinner et al., "A human monoclonal IgG1 potently neutralizing the pro-inflammatory cytokine GM-CSF", Molecular Immunology, 44, No. 5 (2007), pp. 916-925.
Lee et al., "Current concepts in the diagnosis and management of cytokine release syndrome", Blood, Jul. 2014; vol. 124, No. 2 pp. 188-195.
Morgan et al., "Case Report of a Serious Adverse Event Following the Administration of T Cells Transduced With a Chimeric Antigen Receptor Recognizing *ERBB2*", Molecular Therapy, 2010, vol. 18, No. 4, pp. 843-851.
Santomasso et al., "Clinical and Biologic Correlates of Neurotoxicity Associated with CART Cell Therapy in Patients with B-cell Acute Lymphoblastic Leukemia (B-ALL)", American Association for Cancer Research 2018, pp. 1-27.

(Continued)

*Primary Examiner* — Elly-Gerald Stoica
(74) *Attorney, Agent, or Firm* — Mark S. Cohen; Pearl Cohen Zedek Latzer Baratz LLP

(57) ABSTRACT

Methods for reducing relapse rate or preventing occurrence of tumor relapse in a subject treated with immunotherapy, in an absence of an incidence of immunotherapy-related toxicity or in a presence of immunotherapy-related toxicity. Methods for reducing a level of a cytokine or chemokine other than GM-CSF in a subject having an incidence of immunotherapy-related toxicity, the methods comprising administering a recombinant GM-CSF antagonist to the subject. Methods for treating or preventing immunotherapy-related toxicity in a subject, the methods comprising administering to the subject chimeric antigen receptor-expressing T-cells (CAR-T cells), the CAR-T cells having a GM-CSF gene knockout (GM-CSF$^{k/o}$ CAR-T cells), and a recombinant hGM-CSF antagonist.

37 Claims, 74 Drawing Sheets
Specification includes a Sequence Listing.

(56) References Cited

OTHER PUBLICATIONS

Schroeder et al., "Preferential utilization of conserved immunoglobulin heavy chain variable gene segments during human fetal life", Proc. Natl. Acad. Sci. USA, Aug. 1990, vol. 87, pp. 6146-6150.
Sentman et al., "Mechanisms of Acute Toxicity in NKG2D Chimeric Antigen Receptor T Cell-Treated Mice", J Immunol, Nov. 2016, pp. 1-13.
Tomlinson et al., "The structural repertoire of the human V domain", The EMBO Journal, 1995, vol. 14, No. 18, pp. 4628-4638.
Teachey et al., "Identification of Predictive Biomarkers for Cytokine Release Syndrome after Chimeric Antigen Receptor T cell Therapy for Acute Lymphoblastic Leukemia", Cancer Discov., 2016, 6(6) pp. 664-679.
Tuaillon et al., "Biased utilization of DHQ52 and JH4 gene segments in a human Ig transgenic minilocus is independent of antigenic selection", J Immunol 1994; 152: pp. 2912-2920.
EP Application No. 18 20 0356 European Search Report dated Nov. 27, 2018.
Cornish et al., "G-CSF and GM-CSF as therapeutic targets in rheumatoid arthritis", Nat. Rev. Rheumatol. (Oct. 2009) vol. 5, 554-559.
Huizinga et al., "Phase 1b randomized, double-blind study of namilumab, an anti-granulocyte macrophage colony-stimulating factor monoclonal antibody, in mild-to-moderate rheumatoid arthritis", Arthritis Research & Therapy (Mar. 2017) vol. 19, No. 53, pp. 1-10.
Li et al., "Human antibodies for immunotherapy development generated via a human B cell hybridoma technology", Proceedings of the National Academy of Sciences of the U.S.A. (Mar. 2006) vol. 103, No. 10, pp. 3557-3562.
McDermott et al., "Role of GM-CSF in the inflammatory cytokine network that regulates neutrophil influx into the colonic mucosa during Clostridium difficile infection in mice", Gut Microbes (Jul. 2014), vol. 5, No. 4, pp. 476-484.
Olsnes et al., "T lymphocyte chemotactic chemokines in acute myelogenous leukemia (AML): local release by native AML blasts and systemic levels of CXCL10 (IP-10), CCL5 (RANTES) and CCL17 (TARC)", Cancer Immunol. Immunother (2006) vol. 55, pp. 830-840.
Shiomi et al., "Pivotal Roles of GM-CSF in Autoimmunity and Inflammation", Mediators of Inflammation (2015), vol. 2015, No. 568543, pp. 1-13.
Sterner et al., "GM-CSF inhibition reduces cytokine release syndrome and neuroinflammation but enhances CAR-T cell function in xenografts", Blood, (Nov. 2018), vol. 2018, entire doc.
International Search Report dated Apr. 15, 2019 in respect of PCT Int'l Application No. PCT/US18/53933.
Constantinescu et al., "Randomized phase 1b trial of MOR103, a human antibody to GM-CSF, in multiple sclerosis"; American Academy of Neurology 2015, Neurology: Neuroimmunology & Neuroinflammation, vol. 1, No. 4, Abstract.
Gauthier et al., "Chimeric antigen-receptor T-cell therapy for hematological malignancies and solid tumors: Clinical data to date, current limitations and perspectives", Curr. Res. In Transl. Med., 2017, vol. 65, pp. 93-102.
Hamilton et al., "Anti-colony-stimulating factor therapies for inflammatory and autoimmune diseases"; Nature Reviews—Drug Discovery 2017, vol. 16, pp. 53-70.
Humanigen, Inc.; "Humanigen Announces Preclinical Findings Presented on Lenzilumab's Potential to Optimize CAR-T Therapy". Press release (online). Globe Newswire, May 2, 2018.
Joung et al., "TALENs: a widely applicable technology for targeted genome editing", Nat Rev Mol Cell Biol. 2012, vol. 14, No. 1, pp. 49-55.
Moyo et al., "Therapy for Chronic Myelomonocytic Leukemia in a New Era", Curr. Hematol. Malig. Rep. 2017, 12:468-477.
Nellan et al., "Paving the road ahead for CD19 CAR T-cell therapy", Curr. Opin. Hematol., 2015, vol. 22, No. 6, pp. 516-520.
Owen et al., "GM-CSF up-regulates the expression of CCL2 by T lymphocytes in mammary tumor-bearing mice", International Journal of Molecular Medicine 2007, 20: pp. 129-136.
Sachdeva et al., "Granulocyte-macrophage colony-stimulating factor inactivation in CAR T-Cells prevents monocyte-dependent release of key cytokine release syndrome mediators", Journal of Biological Chemistry 2019, vol. 294, No. 14, pp. 5430-5437.
Solary et al., "How I treat chronic myelomonocytic leukemia", Blood 2017, vol. 130, No. 2, pp. 126-136.
Taraseviciute et al., "Chimeric Antigen Receptor T Cell-Mediated Neurotoxicity in Nonhuman Primates", Cancer Discov., 2018, vol. 8, No. 6, pp. 750-763.
Wei et al., "Advances of CD19-directed chimeric antigen receptor-modified T cells in refractory/relapsed acute lymphoblastic leukemia", Exp. Hematol. Oncol. 2017, 6:10.
International Search Report dated Feb. 21, 2020 in respect of PCT Int'l Application No. PCT/US19/059275.
International Search Report dated Apr. 14, 2020 in respect of PCT Int'l Application No. PCT/US19/050494.

* cited by examiner

| | |
|---|---|
| VH1 1-02 | QVQLVQSGAEVKKPGASVKVSCKASGYTFTGYYMHWVRQAPGQGLEWMGWINPNSGGTNYAQKFQGRVTMTRDTSISTAYMELSRLRSDDTAVYYCAR |
| VH#1 | QVQLVQSGAEVKKPGASVKVSCKASGYTFTGYYMHWVRQAPGQGLEWMGWINPNSGGTNYAQKFQGRVTMTRDTSISTAYMELSRLRSDDTAVYYCVRRDRFPYYFDYWGQGTLVTVSS |
| | |
| VH1 1-03 | QVQLVQSGAEVKKPGASVKVSCKASGYTFTSYAMHWVRQAPGQRLEWMGWINAGNGNTKYSQKFQGRVTITRDTSASTAYMELSSLRSEDTAVYYCAR |
| VH#2 | QVQLVQSGAEVKKPGASVKVSCKASGYSFTNYYIHWVRQAPGQRLEWMGWINAGNGNTKYSQKFQGRVAITRDTSASTAYMELSSLRSEDTAVYYCARRDRFPYYFDYWGQGTLVTVSS |
| VH#3 | QVQLVQSGAEVKKPGASVKVSCKASGYSFTNYYIHWVRQAPGQRLEWMGWINAGNGNTKYSQKFQGRVAITRDTSASTAYMELSSLRSEDTAVYYCARRDRFPYYFDYWGQGTLVTVSS |
| VH#4 | QVQLVQSGAEVKKPGASVKVSCKASGYSFTNYYIHWVRQAPGQRLEWMGWINAGNGNTKYSQKFQGRVTITRDTSASTAYMELSSLRSEDTAVYYCVRRQRFPYYFDYWGQGTLVTVSS |
| VH#5 | QVQLVQSGAEVKKPGASVKVSCKASGYSFTNYYIHWVRQAPGQRLEWMGWINAGNGNTKYSQKFQGRVTITRDTSASTAYMELSSLRSEDTAVYYCVRRQRFPYYFDYWGQGTLVTVSS |
| | |
| VKIII A27 | EIVLTQSPGTLSLSPGERATLSCRASQSVSSSYLAWYQQKPGQAPRLLIYGASSRATGIPDRFSGSGSGTDFLTISRLEPEDFAVYYCQQYGSSP |
| VK#1 | EIVLTQSPATLSVSPGERATLSCRASQSVGTN-VAWYQQKPGQAPRVLIYSTSSRATGITDRFSGSGSGTDFLTISRLEPEDFAVYYCQQFNRSPLTFGGGTKVEIK |
| VK#2 | EIVLTQSPATLSVSPGERATLSCRASQSVGTN-VAWYQQKPGQAPRVLIYSTSSRATGITDRFSGSGSGTDFLTISRLEPEDFAVYYCQQFNRSPLTFGGGTKVEIK |
| VK#3 | EIVLTQSPATLSVSPGERATLSCRASQSIGSN-LAWYQQKPGQAPRVLIYSTSSRATGITDRFSGSGSGTDFLTISRLEPEDFAVYYCQQFNRSPLTFGGGTKVEIK |
| VK#4 | EIVLTQSPATLSVSPGERATLSCRASQSIGSN—LAWYQQKPGQAPRVLIYSTSSRATGITDRFSGSGSGTDFLTISRLEPEDFAVYYCQQFNKSPLTFGGGTKVEIK |

| Fab | Vh | Vk | Dissociation rate for binding to GM-CSF determined by surface plasmon resonance analysis ($s^{-1}$) |
|---|---|---|---|
| FB42-8 | #2 | #3 | $1.36 \times 10^{-4}$ |
| FB44-5 | #1 | #3 | $8.0 \times 10^{-5}$ |
| FB77-2 | #3 | #1 | $5.57 \times 10^{-5}$ |
| FB92-1 | #4 | #4 | $3.84 \times 10^{-5}$ |
| FB94-1 | #4 | #2 | $3.12 \times 10^{-5}$ |
| FB104-1 | #5 | #1 | $3.57 \times 10^{-5}$ |
| FB106-1 | #5 | #2 | $5.4 \times 10^{-5}$ |

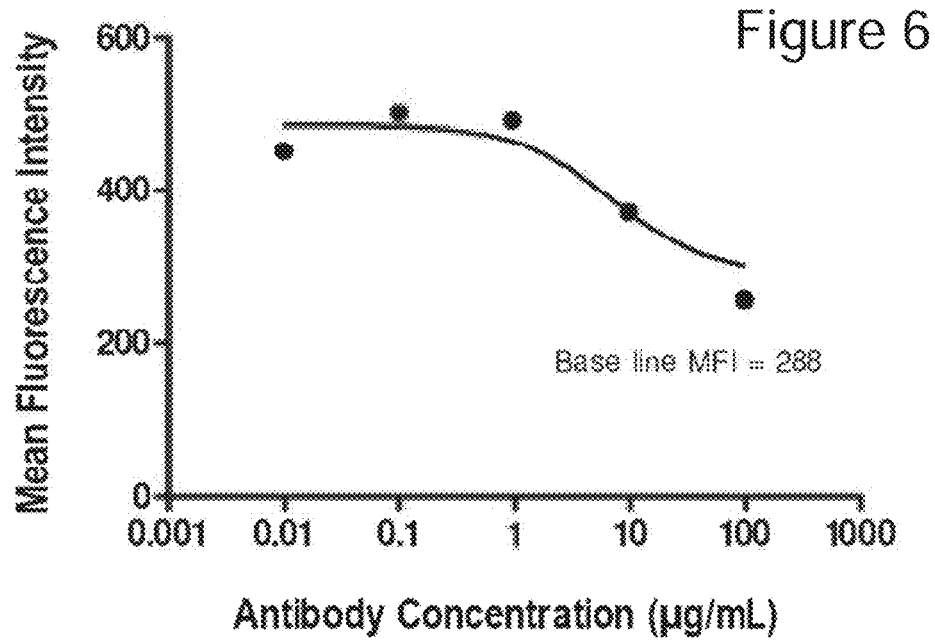

Note: CD11b levels on CD66b-positive granulocytes were determined by flow cytometry. Anti-GM-CSF antibody was added to 10 ng/mL of GM-CSF prior to addition of peripheral blood leukocytes (PBLs). GM-CSF added per assay, 0.5 ng/mL. GM-CSF = granulocyte-macrophage colony-stimulating factor; MFI = mean fluorescence intensity. Source: KaloBios study report 2007-AD-041-R1.

Figure 7

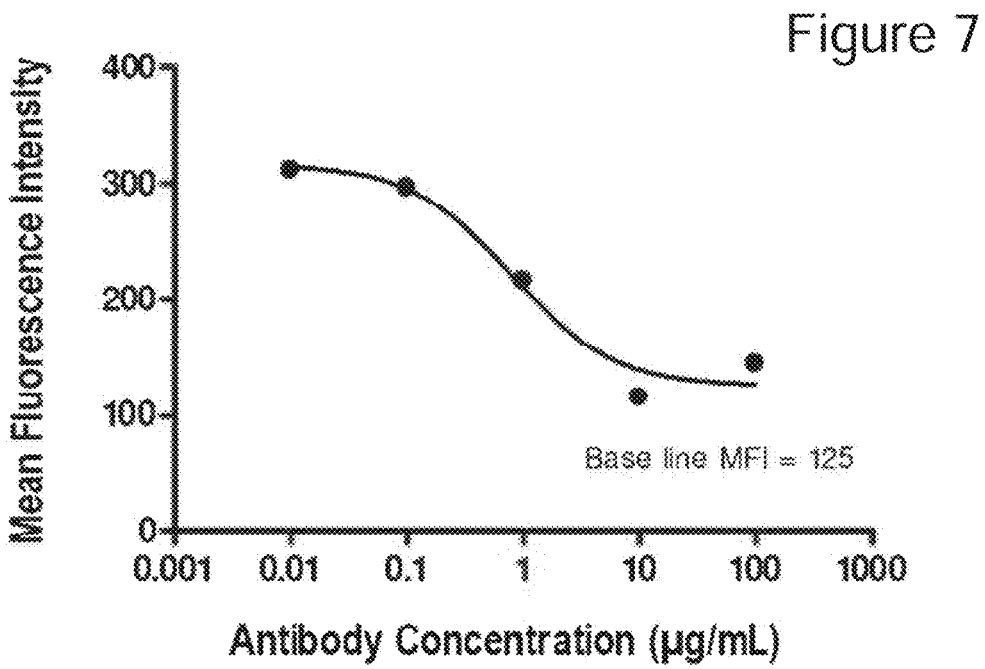

Note: HLA-DR levels on the surface of CD14-positive monocytes/ macrophages were determined by flow cytometry. Anti-GM-CSF antibody was added to 10 ng/mL of GM-CSF prior to addition of peripheral blood mononuclear cells (PBMCs). GM-CSF added per assay, 0.5 ng/mL. GM-CSF = granulocyte-macrophage colony-stimulating factor; HLA-DR = human leukocyte antigen-DR; MFI = mean fluorescence intensity. Source: KaloBios study report 2007-AD-041-R1.

GM-CSF = granulocyte-macrophage colony-stimulating factor;
Source: KaloBios study report 2007-AD-041-R1 (KB003).

GM-CSF CRISPR knockout T cells exhibit reduced expression of GM-CSF but similar levels of other cytokines and degranulation.

GM-CSF CRISPR knockout T cells exhibit reduced expression of GM-CSF but similar levels of other cytokines and degranulation.

GM-CSF neutralizing antibody does not inhibit CART mediated killing, proliferation, or cytokine production but successfully neutralizes GM-CSF.

GM-CSF neutralizing antibody does not inhibit CART mediated killing, proliferation, or cytokine production but successfully neutralizes GM-CSF.

GM-CSF neutralizing antibody does not inhibit
CART mediated killing, proliferation, or cytokine
production but successfully neutralizes GM-CSF.

GM-CSF Neutralizing Ab Safety Profile (>100 Patients*)

| Study* | Population | Objectives | Enrollment/Dose | Safety Results |
|---|---|---|---|---|
| Phase I | | | | |
| Single-dose, dose-escalation | Healthy adult volunteers | • Safety/tolerability<br>• PK<br>• Immunogenicity | (n=12)<br>• 3 / 1 mg/kg<br>• 3 / 3 mg/kg<br>• 3 / 10 mg/kg<br>• 3 / placebo | • <u>Clean safety profile</u><br>• No drug related SAEs<br>• Non-immunogenic |
| Phase II | | | | |
| Dose at weeks 0, 2, 4, 8, 12 | Rheumatoid arthritis | • Efficacy<br>• Safety/tolerability<br>• PK<br>• Immunogenicity | (n=9)<br>• 7 / 600 mg<br>• 2 / placebo | • <u>Clean safety profile</u><br>• No drug related SAEs<br>• Non-immunogenic |
| Dose at weeks 0, 2, 4, 8, 12, 16, 20 | Severe asthma | • Efficacy<br>• Safety/tolerability<br>• PK<br>• Immunogenicity | (n=160)<br>• 78 / 400 mg<br>• 82 placebo | • <u>Clean safety profile</u><br>• No drug related SAEs<br>• Non-immunogenic |

\* 94 patients in studies depicted above, plus 12 patients in ongoing CMML Phase I trial, where drug has been well-tolerated; an additional 76 patients received a chimeric version of a GM—CSF neutralizing Ab (KB002) and showed a similar safety profile
♦ All studies randomized double-blind placebo-controlled, IV administration

Figure 24

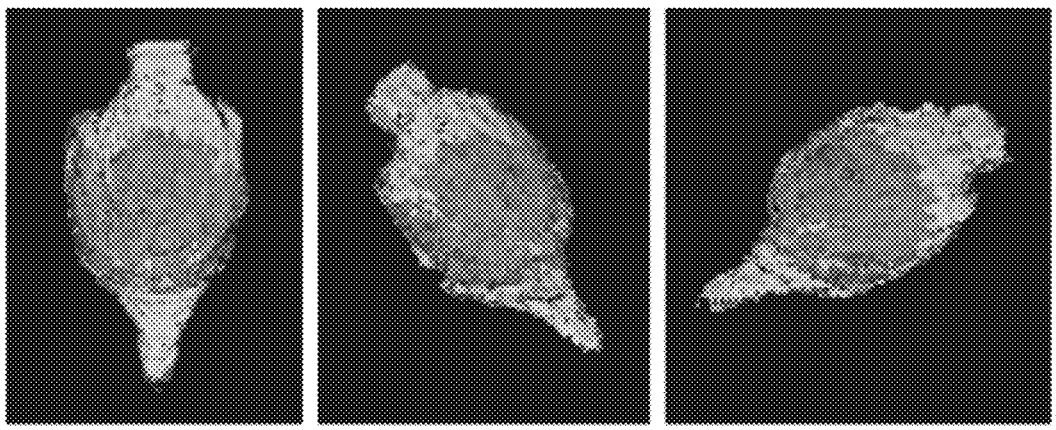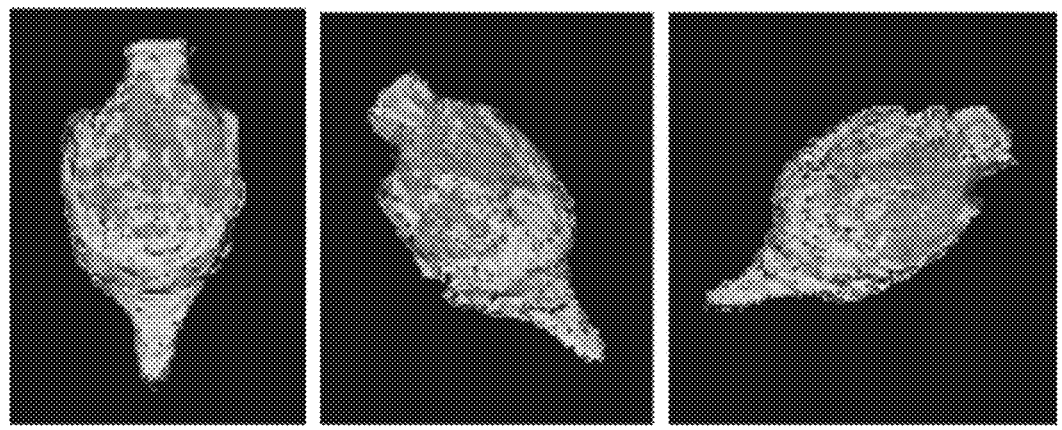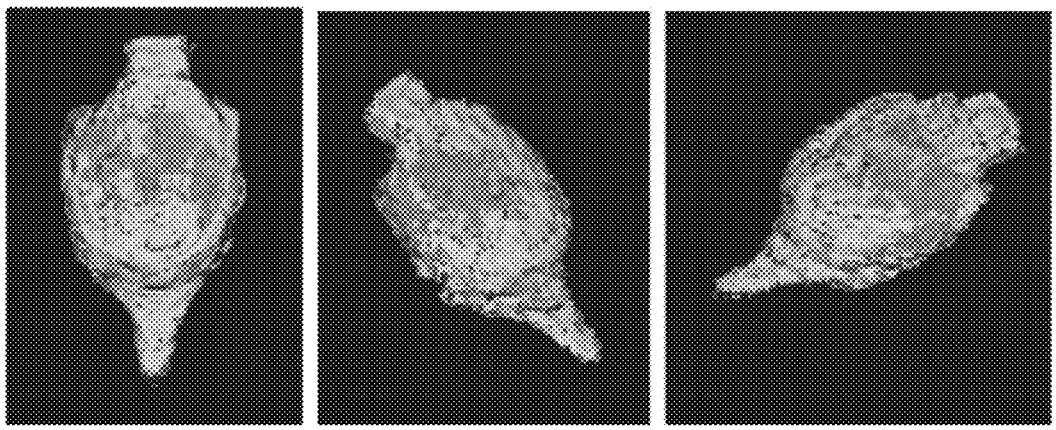
Figure 25A

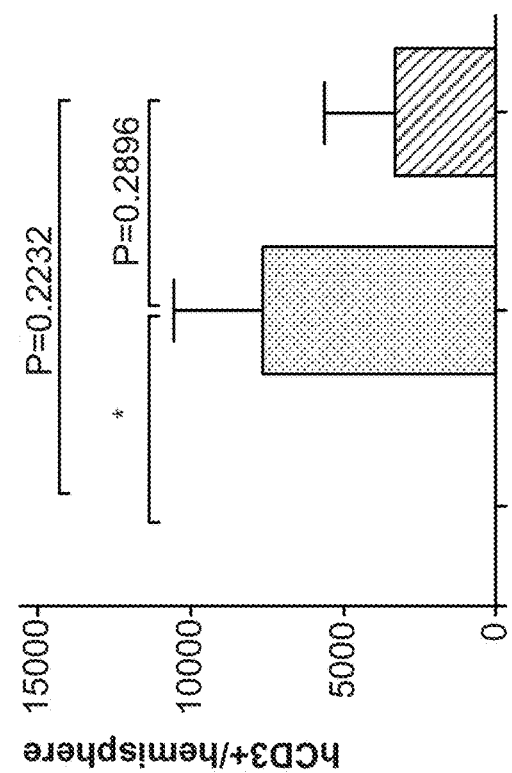
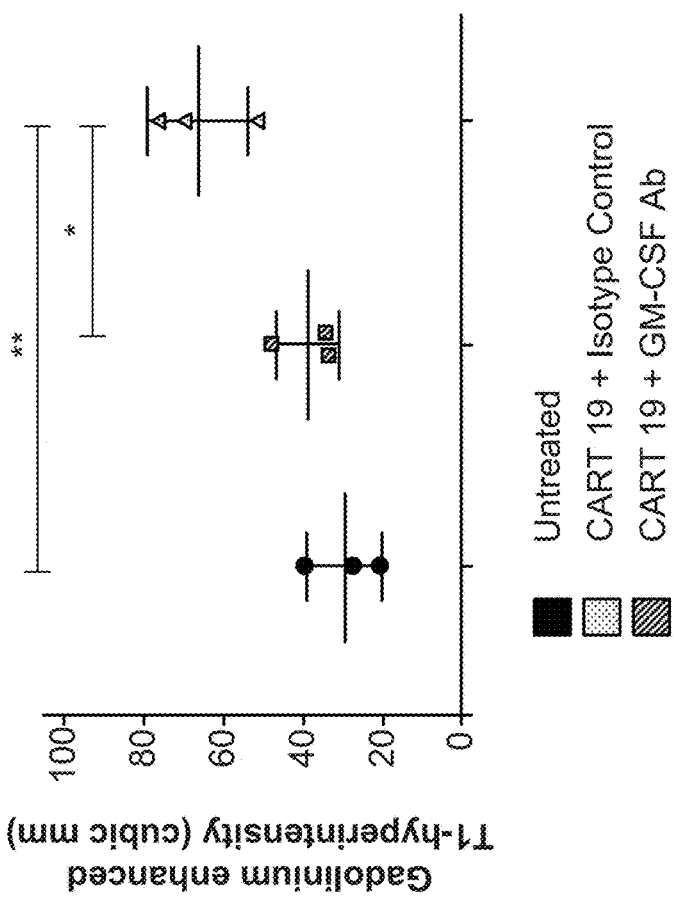
Figure 33C
Figure 33B

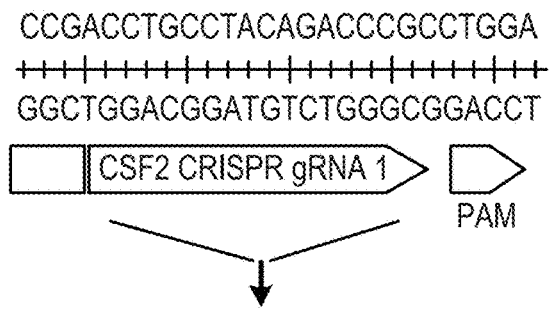
Figure 34A(i)
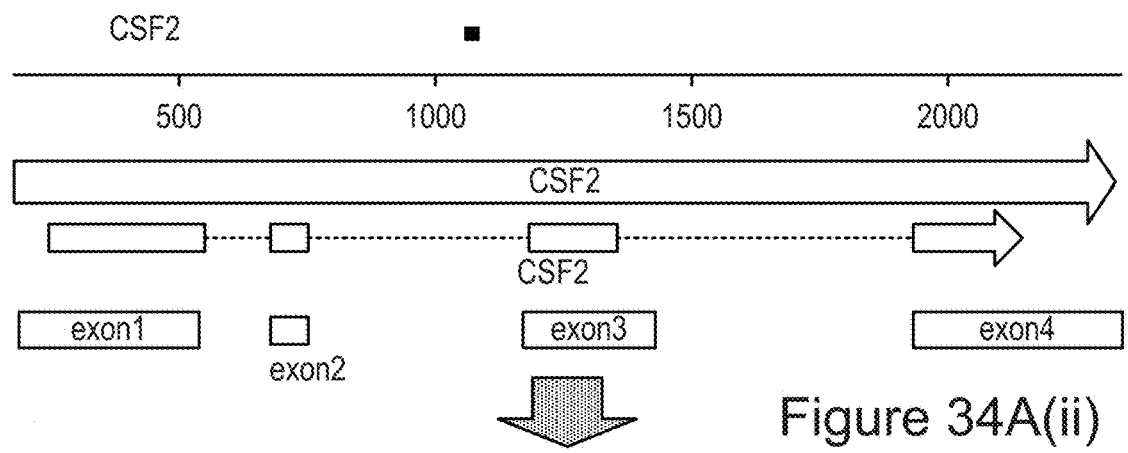
Figure 34A(ii)
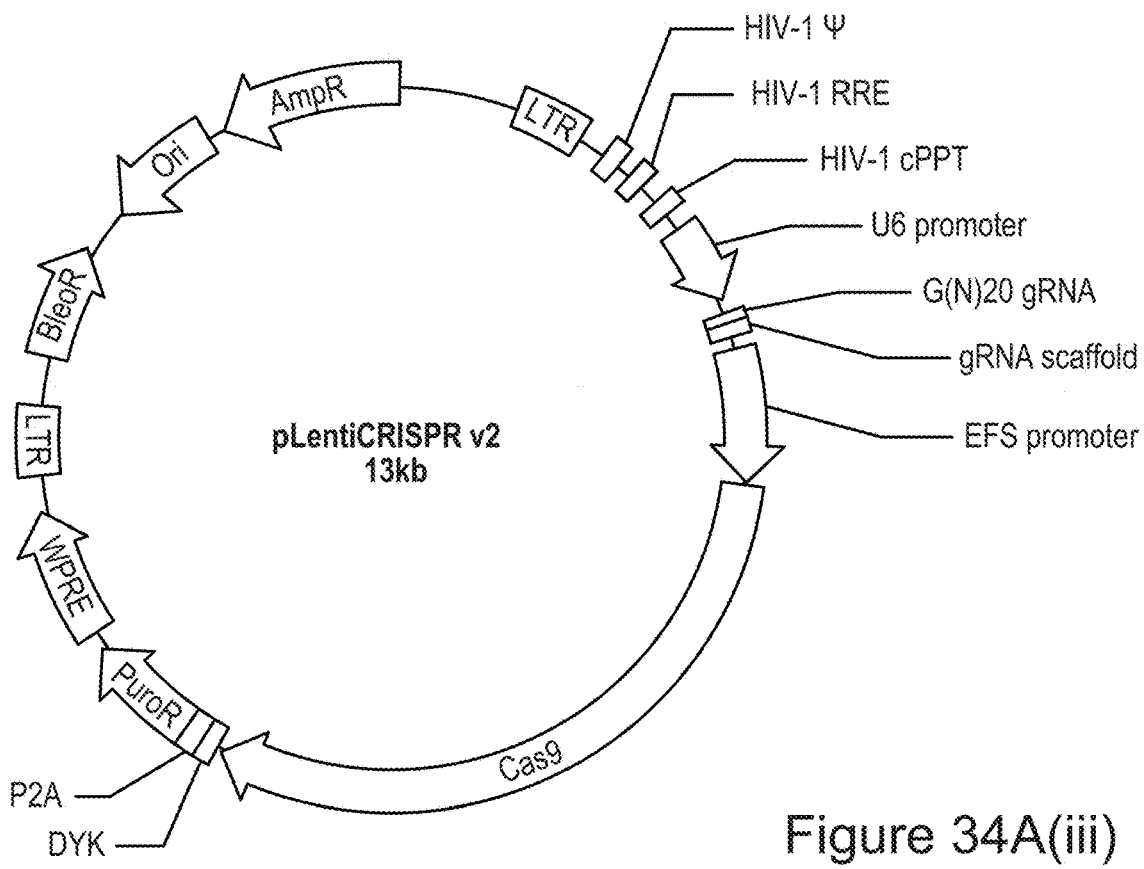
Figure 34A(iii)

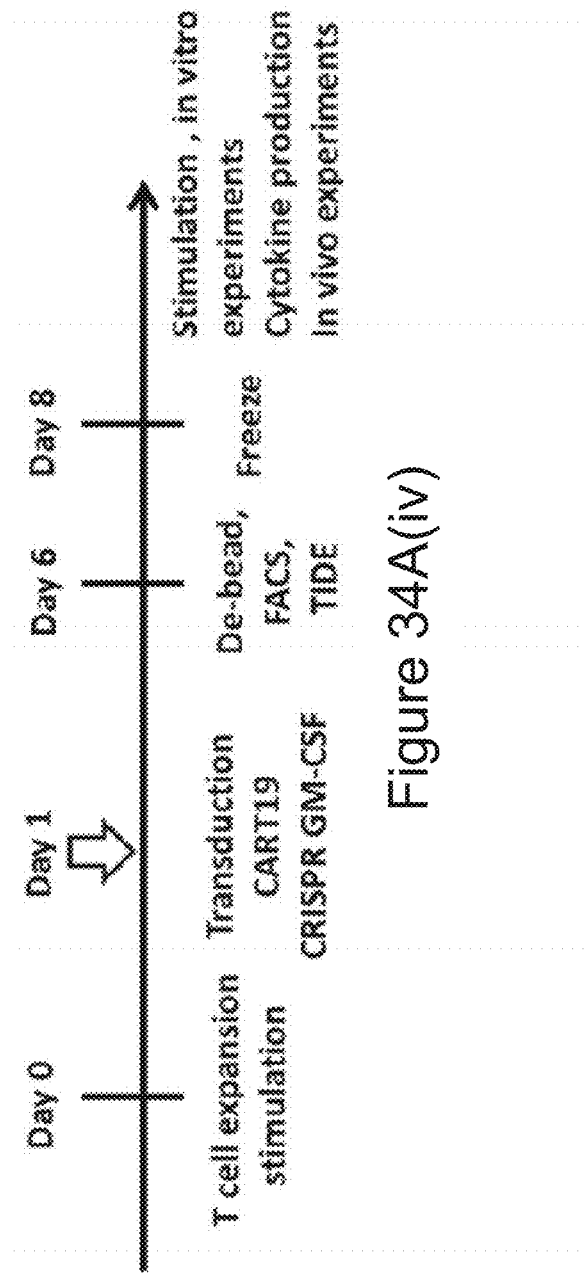

METHOD OF REDUCING TUMOR RELAPSE RATE IN IMMUNOTHERAPY BY ADMINISTRATION OF LENZILUMAB

CROSS-REFERENCE TO RELATED APPLICATIONS

This application is a continuation-in-part application of U.S. application Ser. No. 16/204,220, filed on Nov. 29, 2018, which is a continuation-in-part application of U.S. application Ser. No. 16/149,346, filed on Oct. 2, 2018, which claims priority to U.S. Provisional Application Nos. 62/567,187, filed Oct. 2, 2017, and 62/729,043, filed Sep. 10, 2018, which are hereby incorporated by reference.

FIELD OF THE DISCLOSURE

The invention relates to methods for reducing relapse rate or preventing occurrence of tumor relapse in a subject treated with immunotherapy in an absence of an incidence of immunotherapy-related toxicity. The invention also relates to methods for reducing relapse rate or preventing occurrence of tumor relapse in a subject treated with immunotherapy in a presence of an incidence of immunotherapy-related toxicity. The invention further relates to methods for reducing a level of a cytokine or chemokine other than GM-CSF in a subject having an incidence of immunotherapy-related toxicity, the methods comprising administering a recombinant GM-CSF antagonist to the subject. The invention also relates to methods for treating or preventing immunotherapy-related toxicity in a subject, the method comprising administering to the subject chimeric antigen receptor-expressing T-cells (CAR-T cells), the CAR-T cells having a GM-CSF gene knockout (GM-CSF$^{k/o}$ CAR-T cells), and a recombinant hGM-CSF antagonist. The disclosure herein also provides methods of inhibiting or reducing the incidence and/or the severity of immunotherapy-related toxicity in a subject, the method comprising administering a recombinant GM-CSF antagonist to the subject.

BACKGROUND

Granulocyte-macrophage colony-stimulating factor (GM-CSF) is a cytokine secreted by various cell types including macrophages, T cells, mast cells, natural killer cells, endothelial cells and fibroblasts. GM-CSF stimulates the differentiation of granulocytes and of monocytes. Monocytes, in turn, migrate into tissue and mature into macrophages and dendritic cells. Thus, secretion of GM-CSF leads to a rapid increase in macrophage numbers. GM-CSF is also involved in the inflammatory response in the Central Nervous System (CNS) causing influx of blood-derived monocytes and macrophages, and the activation of astrocytes and microglia. Immuno-related toxicities comprise potentially life-threatening immune responses that occur as a result of the high levels of immune activation occurring from different immunotherapies. Immuno-related toxicity is currently a major complication for the application of immunotherapies in cancer patients. Chimeric antigen receptor T (CAR-T) cell therapy has emerged as a novel and potentially revolutionary therapy to treat cancer. Based on unprecedented responses in B cell malignancies, two CD19 targeted CAR-T (CART19) cell products were approved by the FDA in 2017. However, the wider application of CAR-T cell therapy is limited by the emergence of unique and potentially fatal toxicities. These include the development of cytokine release syndrome (CRS) and neurotoxicity (NT). Up to 50% of patients treated with CART19 cells develop grade 3 or higher CRS or NT and several deaths have been reported. These toxicities are associated with prolonged hospitalization, intensive care unit (ICU) stays, and the long-term effects of NT are unknown. Thus, controlling these CART19 cell related toxicities is imperative to lessen morbidity, mortality, duration of hospitalization, ICU admissions, supportive care required and the significant indirect costs associated with CAR-T cell therapy. It is clear that there remains a critical need for methods of preventing and treating immuno-related toxicity. An ideal method will minimize the risk of these life-threatening complications without affecting the efficacy of the immunotherapy and could potentially even improve the efficacy by allowing, for example, safe increased dosing of immunotherapeutic compounds and/or an expansion of T cells.

BRIEF SUMMARY OF THE INVENTION

In one aspect, this invention provides methods for reducing relapse rate or preventing or delaying occurrence of tumor relapse in a subject treated with immunotherapy in an absence of an incidence of immunotherapy-related toxicity, the method comprising administering to the subject a recombinant hGM-CSF antagonist. In a related aspect, this invention provides methods for reducing relapse rate or preventing occurrence of tumor relapse in a subject treated with immunotherapy in a presence of an incidence of immunotherapy-related toxicity, the method comprising administering to the subject a recombinant hGM-CSF antagonist.

In another aspect, this invention provides a method reducing a level of a cytokine or chemokine other than GM-CSF in a subject having an incidence of immunotherapy-related toxicity, the method comprising administering to the subject a recombinant hGM-CSF antagonist, wherein the level of the cytokine or chemokine is reduced compared to the level thereof in a subject during the incidence of immunotherapy-related toxicity.

In a further aspect, this invention provides a method for treating or preventing immunotherapy-related toxicity in a subject, the method comprising administering to the subject chimeric antigen receptor-expressing T-cells (CAR-T cells), the CAR-T cells having their GM-CSF genes 'knocked-out' (GM-CSF$^{k/o}$ CAR-T cells), and a recombinant hGM-CSF antagonist.

In one aspect, disclosed herein is a method of inhibiting or reducing the incidence or the severity of immunotherapy-related toxicity in a subject, the method comprising a step of administering a recombinant hGM-CSF antagonist to the subject.

In a related aspect, said immunotherapy comprises adoptive cell transfer, administration of monoclonal antibodies, administration of cytokines or chemokines, administration of a cancer vaccine, T cell engaging therapies, or any combination thereof.

In another aspect, adoptive cell transfer comprises administering chimeric antigen receptor-expressing T-cells (CAR T-cells), T-cell receptor (TCR) modified T-cells, tumor-infiltrating lymphocytes (TIL), chimeric antigen receptor (CAR)-modified natural killer cells, or dendritic cells, or any combination thereof. In a related aspect, the monoclonal antibody is selected from a group comprising: anti-CD3, anti-CD52, anti-PD1, anti-PD-L1, anti-CTLA4, anti-CD20, anti-BCMA antibodies, bi-specific antibodies, or bispecific T-cell engager (BiTE) antibodies, or any combination thereof. In a related aspect, the cytokines are selected from a group comprising: IFNα, IFNβ, IFNγ, IFNλ, IL-1, IL-2, IL-6, IL-7, IL-15, IL-21, IL-11, IL-12, IL-18, GM-CSF, TNFα, or any combination thereof.

In another aspect, inhibiting or reducing the incidence or the severity of immunotherapy-related toxicity comprises reducing the concentration of at least one inflammation-associated factor in the serum, tissue fluid, or in the CSF of the subject. In a related aspect, the inflammation-associated factor is selected from a group comprising: C-reactive protein, GM-CSF, IL-1, IL-2, sIL2Rα, IL-5, IL-6, IL-8, IL-10, IP10, IL-15, MCP-1 (AKA CCL2), MIG, MIP1β, IFNγ, CX3CR1, or TNFα, or any combination thereof. In another aspect, the administration of recombinant GM-CSF antagonist does not reduce the efficacy of said immunotherapy. In another aspect, the administration of recombinant GM-CSF antagonist increases the efficacy of said immunotherapy. In another aspect, administration of recombinant GM-CSF antagonist occurs prior to, concurrent with, or following immunotherapy. In a related aspect, the recombinant GM-CSF antagonist is co-administered with corticosteroids, anti-IL-6 antibodies, tocilizumab, anti-IL-1 antibodies, cyclosporine, antiepileptic s, benzodiazepines, acetazolamide, hyperventilation therapy, or hyperosmolar therapy, or any combination thereof.

In another aspect, the immunotherapy-related toxicity comprises a brain disease, damage or malfunction. In a related aspect, the brain disease, damage or malfunction comprises CAR-T cell related NT or CAR-T cell related encephalopathy syndrome (CRES). In a related aspect, inhibiting or reducing incidence of a brain disease, damage or malfunction comprises reducing headaches, delirium, anxiety, tremor, seizure activity, confusion, alterations in wakefulness, hallucinations, dysphasia, ataxia, apraxia, facial nerve palsy, motor weakness, seizures, nonconvulsive EEG seizures, altered levels of consciousness, coma, endothelial activation, vascular leak, intravascular coagulation, or any combination thereof in the subject. In another aspect, the immunotherapy-related toxicity comprises CAR-T induced Cytokine Release Syndrome (CRS). In a related aspect, inhibiting or reducing incidence of CRS comprises reducing or inhibiting, without limitation, high fever, myalgia, nausea, hypotension, hypoxia, or shock, or a combination thereof. In a related aspect, the immunotherapy-related toxicity is life-threatening.

In another aspect, the serum concentration of ANG2 or VWF, or the serum ANG2:ANG1 ratio of the subject is reduced. In a related aspect, the subject has a body temperature above 38° C., an IL-6 serum concentration >16 pg/ml, or an MCP-1 serum concentration above 1,300 pg/ml during the first 36 hours after infusion of said CAR-T cells. In a related aspect, the subject is predisposed to have said brain disease, damage or malfunction. In a related aspect, the subject has an ANG2:ANG1 ratio in serum above 1 prior to the infusion of said CAR-T cells.

In another aspect, the immunotherapy-related toxicity comprises hemophagocytic lymphohistiocytosis (HLH) or macrophage-activation syndrome (MAS). In a related aspect, inhibiting or reducing incidence of HLH or MAS comprises increasing survival time and/or time to relapse, reducing macrophage activation, reducing T cell activation, reducing the concentration of IFNγ in the peripheral circulation, or reducing the concentration of GM-CSF in the peripheral circulation, or any combination thereof.

In another aspect, the subject presents with fever, splenomegaly, cytopenias involving two or more lines, hypertriglyceridemia, hypofibrinogenemia, hemophagocytosis, low or absent NK-cell activity, ferritin serum concentration above 500 U/ml, or soluble CD25 serum concentration above 2400 U/ml, or any combination thereof. In a related aspect, the subject is predisposed to acquiring HLH or MAS. In a related aspect, the subject carries a mutation in a gene selected from: PRF1, UNC13D, STX11, STXBP2, or RAB27A, or has reduced expression of perforin, or any combination thereof.

In one embodiment, the GM-CSF antagonist is an anti-hGM-CSF antibody. In another embodiment, the anti-hGM-CSF antibody blocks binding of hGM-CSF to the alpha subunit of the hGM-CSF receptor. In another embodiment, the anti-hGM-CSF antibody is a polyclonal antibody. In another embodiment, the anti-hGM-CSF antibody is a monoclonal antibody. In another embodiment, the anti-hGM-CSF antibody is an antibody fragment that is a Fab, a Fab', a F(ab')2, a scFv, or a dAB. In some embodiments, the monoclonal anti-hGM-CSF antibody, the single-chain Fv, and the Fab may be generated in the chicken; chicken IgY are avian equivalents of mammalian IgG antibodies. (Park et al., Biotechnology Letters (2005) 27:289-295; Finley et al., Appl. Environ. Microbiol., May 2006, p. 3343-3349). Chicken IgY antibodies have the following advantages: higher avidity, i.e., overall strength of binding between an antibody and an antigen, higher specificity (less cross reactivity with mammalian proteins other than the immunogen); high yield in the egg yolk, and lower background (the structural difference in the Fc region of IgY and IgG results in less false positive staining). In another embodiment, the anti-hGM-CSF antibody may be a camelid, e.g., a llama-derived single variable domain on a heavy chain antibodies lacking light chains (also called sdAbs, VHHs and Nanobodies®); the VHH domain (about 15 kDa) is the smallest known antigen recognition site that occurs in mammals having full binding capacity and affinities (equivalent to conventional antibodies). (Garaicoechea et al. (2015) PLoS ONE 10(8): e0133665; Arbabi-Ghahroudi M (2017) Front. Immunol. 8:1589; Wu et al., Translational Oncology (2018) 11, 366-373). In another embodiment, the antibody fragment is conjugated to polyethylene glycol. In another embodiment, the anti-hGM-CSF antibody has an affinity ranging from about 5 pM to about 50 pM. In another embodiment, anti-hGM-CSF antibody is a neutralizing antibody. In another embodiment, the anti-hGM-CSF antibody is a recombinant or chimeric antibody. In another embodiment, the anti-hGM-CSF antibody is a human antibody. In another embodiment, the anti-hGM-CSF antibody comprises a human variable region. In another embodiment, the anti-hGM-CSF antibody comprises an engineered human variable region. In another embodiment the anti-hGM-CSF antibody comprises a humanized variable region. In another embodiment, the anti-hGM-CSF antibody comprises an engineered human variable region. In another embodiment the anti-hGM-CSF antibody comprises a humanized variable region.

In one embodiment, the anti-hGM-CSF antibody comprises a human light chain constant region. In another embodiment, the anti-hGM-CSF antibody comprises a human heavy chain constant region. In another embodiment, the human heavy chain constant region is a gamma chain. In another embodiment, the anti-hGM-CSF antibody binds to the same epitope as chimeric 19/2. In another embodiment, the anti-hGM-CSF antibody comprises the VH region CDR3 and VL region CDR3 of chimeric 19/2. In another embodiment, the anti-GM-CSF antibody comprises the VH region and VL region CDR1, CDR2, and CDR3 of chimeric 19/2.

In one embodiment, the anti-hGM-CSF antibody comprises a heavy chain variable region that comprises a CDR3 binding specificity determinant RQRFPY (SEQ ID NO: 12)

or RDRFPY (SEQ ID NO: 13), a J segment, and a V-segment, wherein the J-segment comprises at least 95% identity to human JH4 (YFDYWGQGTLVTVSS (SEQ ID NO: 14)) and the V-segment comprises at least 90% identity to a human germ line VH1 1-02 (SEQ ID NO: 19) or VH1 1-03 (SEQ ID NO:20) sequence; or a heavy chain variable region that comprises a CDR3 binding specificity determinant comprising RQRFPY (SEQ ID NO: 12). In another embodiment, the J segment comprises YFDYWGQGTLVTVSS (SEQ ID NO: 14). In another embodiment, the CDR3 comprises RQRFPYYFDY (SEQ ID NO: 15) or RDRFPYYFDY (SEQ ID NO: 16). In another embodiment, the heavy chain variable region CDR1 or CDR2 can be a human germline VH1 sequence; or both the CDR1 and CDR2 can be human germline VH1. In another embodiment, the antibody comprises a heavy chain variable region CDR1 or CDR2, or both CDR1 and CDR2, as shown in a $V_H$ region set forth in FIG. 1. In another embodiment, the anti-hGM-CSF antibody has a V-segment that has a $V_H$ V-segment sequence shown in FIG. 1. In another embodiment, the $V_H$ that has the sequence of VH #1 (SEQ ID NO:1), VH #2 (SEQ ID NO:2), VH #3 (SEQ ID NO:3), VH #4 (SEQ ID NO:4), or VH #5 (SEQ ID NO:5) set forth in FIG. 1.

In another embodiment, the anti-hGM-CSF antibody, e.g., that has a heavy chain variable region as described in the paragraph above, comprises a light chain variable region that comprises a CDR3 binding specificity determinant comprising the amino acid sequence FNK or FNR.

In another embodiment, the anti-hGM-CSF antibody comprises a VL region that comprises a CDR3 comprising the amino acid sequence FNK or FNR. In one embodiment, the anti-GM-CSF antibody comprises a human germline JK4 region. In another embodiment, the antibody $V_L$ region CDR3 comprises QQFN(K/R)SPLT (SEQ ID NO: 17). In another embodiment, the anti-GM-CSF antibody comprises a VL region that comprises a CDR3 comprising QQFNKSPLT (SEQ ID NO: 18). In another embodiment, the VL region comprises a CDR1, or a CDR2, or both a CDR1 and CDR2, of a $V_L$ region shown in FIG. 1. In another embodiment, the VL region comprises a V segment that has at least 95% identity to the VKIIIA27 (SEQ ID NO: 21) V-segment sequence as shown in FIG. 1. In another embodiment, the $V_L$ region has the sequence of VK #1 (SEQ ID NO: 6), VK #2 (SEQ ID NO: 7), VK #3 (SEQ ID NO: 8), or VK #4 (SEQ ID NO: 9) set forth in FIG. 1.

In one embodiment, the anti-hGM-CSF antibody has a VH region CDR3 binding specificity determinant RQRFPY (SEQ ID NO: 12) or RDRFPY (SEQ ID NO: 13) and a VL region that has a CDR3 comprising QQFNKSPLT (SEQ ID NO: 18). In another embodiment, the anti-hGM-CSF antibody has a VH region sequence set forth in FIG. 1 and a VL region sequence set forth in FIG. 1. In another embodiment, the VH region or the VL region, or both the VH and VL region amino acid sequences comprise a methionine at the N-terminus. In another embodiment, the GM-CSF antagonist is selected from the group comprising of an anti-hGM-CSF receptor antibody or a soluble GM-CSF receptor, a cytochrome b562 antibody mimetic, a hGM-CSF peptide analog, an adnectin, a lipocalin scaffold antibody mimetic, a calixarene antibody mimetic, and an antibody like binding peptidomimetic.

In one embodiment, disclosed herein is a method of increasing the efficacy of CAR-T immunotherapy in a subject, the method comprising a step of administering a recombinant hGM-CSF antagonist to the subject, wherein said administering increases the efficacy of CAR-T immunotherapy in said subject. In another embodiment, said administering a recombinant hGM-CSF antagonist occurs prior to, concurrent with, or following said CAR-T immunotherapy. In another embodiment, said increased efficacy comprises increased CAR-T cell expansion, reduced myeloid-derived suppressor cell (MDSC) number that inhibit T-cell function, synergy with a checkpoint inhibitor, or any combination thereof. In another embodiment, said increased CAR-T cell expansion comprises at least a 50% increase compared to a control. In another embodiment, said increased CAR-T cell expansion comprises at least a one quarter log expansion compared to a control. In another embodiment, said increased cell expansion comprises at least a one-half log expansion compared to a control. In another embodiment, said increased cell expansion comprises at least a one log expansion compared to a control. In another embodiment, said increased cell expansion comprises a greater than one log expansion compared to a control.

In an embodiment, the hGM-CSF antagonist comprises a neutralizing antibody. In another embodiment, the neutralizing antibody is a monoclonal antibody.

In an embodiment, disclosed herein is a method of inhibiting or reducing the incidence or the severity of CAR-T related toxicity in a subject, the method comprising a step of administering a recombinant hGM-CSF antagonist to the subject, wherein said administering inhibits or reduces the incidence or the severity of CAR-T related toxicity in said subject. In an embodiment, said CAR-T related toxicity comprises NT, CRS, or a combination thereof. In some embodiments, the CAR-T cell related NT is reduced by about 50% compared to a reduction in NT in a subject treated with CAR-T cells and a control antibody. In various embodiments, the recombinant hGM-CSF antagonist is a hGM-CSF neutralizing antibody in accordance with embodiments described herein.

In another embodiment, said inhibiting or reducing incidence of CRS comprises increasing survival time and/or time to relapse, reducing macrophage activation, reducing T cell activation, or reducing the concentration of circulating hGM-CSF, or any combination thereof. In another embodiment, said subject presents with fever (with or without rigors, malaise, fatigue, anorexia, myalgia, arthralgia, nausea, vomiting, headache, skin rash, diarrhea, tachypnea, hypoxemia, hypoxia, shock, cardiovascular tachycardia, widened pulse pressure, hypotension, capillary leak, increased early cardiac output, diminished late cardiac output, elevated D-dimer, hypofibrinogenemia with or without bleeding, azotemia, transaminitis, hyperbilirubinemia, mental status changes, confusion, delirium, frank aphasia, hallucinations, tremor, dysmetria, altered gait, seizures, organ failure, or any combination thereof.

In another embodiment, the inhibiting or reducing the incidence or the severity of CAR-T related toxicity comprises preventing the onset of CAR-T related toxicity.

In another embodiment, disclosed herein is a method of blocking or reducing GM-CSF expression in a cell, comprising knocking out or silencing GM-CSF gene expression in a cell. In an embodiment, the blocking or reducing of GM-CSF expression comprises short interfering RNS (siRNA), CRISPR, RNAi, DNA-directed RNA interference (ddRNAi), which is a gene-silencing technique that uses DNA constructs to activate an animal cell's endogenous RNA interference (RNAi) pathways, or targeted genome editing with engineered transcription activator-like effector nucleases (TALENs), i.e., artificial proteins composed of a customizable sequence-specific DNA-binding domain fused to a nuclease that cleaves DNA in a nonsequence-specific manner. (Joung and Sander, Nat Rev Mol Cell Biol. 2013 January; 14(1): 49-55), which is incorporated herein in its entirety by reference. In an embodiment, the cell is a CAR-T cell.

In one embodiment, the subject is a human.

In one embodiment, disclosed herein is a hGM-CSF antagonist for use in a method of inhibiting or reducing the incidence or severity of immunotherapy-related toxicity in a subject, the method comprising a step of administering a recombinant hGM-CSF antagonist to the subject. In one embodiment, disclosed herein is a pharmaceutical composition comprising an anti-hGM-CSF antagonist.

BRIEF DESCRIPTION OF THE DRAWINGS

FIG. 1 provides exemplary $V_H$ and $V_L$ sequences of anti-GM-CSF antibodies.

FIG. 6 illustrates dose-dependent inhibition of GM-CSF-stimulated CD11b on human granulocytes by anti-GM-CSF antibody.

FIG. 7 illustrates dose-dependent inhibition of GM-CSF-induced HLA-DR on CD14+ human, primary monocytes/macrophages by anti-GM-CSF antibody.

FIG. 23A illustrates an increased ex-vivo expansion of GM-CSF$^{k/o}$ CAR-T cells compared to control CAR-T cells. FIG. 23B illustrates a more robust CAR-T cell proliferation after treatment with a GM-CSF neutralizing antibody in accordance with embodiments described herein. (See Example 13).

FIG. 24 illustrates a safety profile of GM-CSF neutralizing antibody in accordance with embodiments described herein. (See Example 14).

FIGS. 25A-25D illustrate that GM-CSF neutralizing antibody when added to CAR-T cell therapy demonstrates a 90% reduction in neuroinflammation in mouse preclinical model. FIG. 25A illustrates MRI data (T1 hyperintensity indicative of BBB disruption and neuroinflammation) in which mice brains are protected from neuroinflammation after administration of CAR-T cells and GM-CSF neutralizing antibody in accordance with embodiments described herein compared to mice brains showing signs of neurotoxicity after administration of CAR-T cells and a control antibody (top row) and compared to untreated (baseline) mice brains (bottom row). FIG. 25B quantitatively illustrates the percent increase of T1 hyperintensity from baseline: there was an approximately 10% percent increase in brain T1 hyperintensity from baseline in mice administered CAR-T and GM-CSF neutralizing antibody in accordance with embodiments described herein compared to the slightly over 100% increase in mice that had been administered CAR-T cells and control antibody. As shown in the comparative graph, the ~10% increase in brain T1 hyperintensity from baseline in mice administered the CAR-T and GM-CSF neutralizing antibody is a 90% reduction in neuroinflammation, as measured by brain T1 hyperintensity from baseline, compared to the quantity of neuroinflammation present in mice that received CAR-T cells and control antibody. FIGS. 25C-25D show that compared to untreated mice (which had 500,000 to 1.5M leukemic cells) and CAR-T plus control antibody (which had between 15,000 and 100,000 leukemic cells), treatment with CAR-T plus GM-CSF neutralizing antibody in accordance with embodiments described herein led to a significant reduction in the number of leukemic cells (decreased to between 500 and 5,000 cells) with improved overall disease control (See Example 15).

FIG. 26A shows CART19 and lenzilumab treated CART19 are equally effective in survival outcomes in a high tumor burden NALM6 relapse model compared to UTD (untransduced T cells) (7-8 mice per group, n=2). FIGS. 26B-26D show Lenzilumab & anti-mouse GM-CSF antibody-controlled CRS induced weight loss, neutralized serum human GM-CSF, and reduced expression of serum mouse MCP-1 (monocyte chemoattractant protein-1) in a primary ALL xenograft CART19 CRS/NT model (3 mice per group, * p<0.05). FIG. 26E shows Lenzilumab & anti-mouse GM-CSF antibody reduced brain inflammation as shown by MRI in a primary ALL xenograft CART19 CRS/NT model (3 mice per group, * p<0.05, ** p<0.01). FIGS. 26F-26G show an improved efficacy of CART19+Lenzilumab treated mice compared to anti-mouse GM-CSF antibody treated mice, i.e., CART19+anti-hGM-CSF antibody, showed reduced CD19+ brain leukemic burden and reduced percentage of brain macrophages in a primary ALL xenograft CART19 CRS/NT model (3 mice per group). FIG. 26H shows CRISPR Cas9 K/O of GM-CSF reduces its expression via intracellular staining in CART19 and UTD with NALM6 stimulation. (Representative experiment, n=2) FIG. 26I shows CART19 and GM-CSF K/O CART19 control tumor burden better than UTD, and an improved efficacy of GM/CSF K/O CART19 cells controlling tumor burden slightly better than CART19 in a high tumor burden NALM6 relapse model (6 mice per group, * p<0.05, **** p<0.0001). Error bars SEM.

FIG. 27A graphically depicts Lenzilumab (a hGM-CSF neutralizing antibody) neutralization of CAR-T cell produced hGM-CSF in vitro compared to isotype control treatment as assayed by multiplex after 3 days of culture with CART19 in media alone or CART19 co-cultured with NALM6, n=2 experiments, 2 replicates per experiment, representative experiment depicted, * p<0.001 between lenzilumab and isotype control treatment, t test, mean+SEM. FIG. 27B graphically shows that hGM-CSF neutralizing antibody treatment did not inhibit the ability of CAR-T cells to proliferate as assayed by CSFE flow cytometry proliferation assay of live CD3 cells, n=3 donors, 2 replicates per donor, representative experiment at 3-day time point depicted, ns p>0.05 between lenzilumab and isotype control treatment, t test, mean+SEM. Alone: CART19 in media alone, MOLM13: CART19+MOLM13, PMA/ION: CART19 plus 5 ng/mL PMA and 0.1 ug/mL ION, NALM6: CART19+ NALM6. FIG. 27C graphically depicts Lenzilumab enhancing the proliferation of CART19 by neutralization of hGM- CSF compared to isotype control treated with CART19 when co-cultured with human monocytes, n=3 donors at 3-day time point, 2 replicates per donor, ** p<0.0001, mean+SEM. FIG. 27D graphically shows that Lenzilumab treatment did not inhibit cytotoxicity of CART19 or untransduced T cells (UTD) when cultured with NALM6, n=3 donors, 2 replicates per donor, representative experiment at 48 hr time point depicted, ns p>0.05 between lenzilumab and isotype control treatment, t test, mean+SEM.

FIG. 28 A illustrates the experimental schema: NSG mice were injected with the CD19+ luciferase+ cell line NALM6 (1×106 cells per mouse I.V). 4-6 days later, mice were imaged, randomized, and received 1-1.5×106CAR-T19 or equivalent number of total cells of control UTD cells the following day with either lenzilumab or control IgG (10 mg/Kg, given IP daily for 10 days, starting on the day of CAR-T injection). Mice were followed with serial bioluminescence imaging to assess disease burden beginning day 7 post CAR-T cell injection and were followed for overall survival. Tail vein bleeding was performed 7-8 days after CAR-T cell injection. FIG. 28B depicts Lenzilumab neutralization of CAR-T produced serum hGMCSF in vivo compared to isotype control treatment as assayed by hGM-CSF singleplex, n=2 experiments, 7-8 mice per group, representative experiment, serum from day 8 post CAR-T cell/UTD injection, * p<0.001 between lenzilumab and isotype control treatment, t test, mean+SEM. FIG. 28C graphically depicts Lenzilumab treated CAR-T in vivo are equally effective at controlling tumor burden compared to isotype control treated CAR-T in a high tumor burden relapse xenograft model of ALL, day 7 post CAR-T injection, n=2 experiments, 7-8 mice per group, representative experiment depicted, * p<0.001, * p<0.05, ns p>0.05, t test, mean+SEM. FIG. 28 D depicts mouse images from FIG. 28C. FIG. 28E illustrates the experimental schema: NSG mice were injected with the blasts derived from patients with ALL (1×106 cells per mouse I.V). Mice were bled serially and when the CD19+ cells >1/uL, mice were randomized to receive 2.5×106 CART19 with either lenzilumab or control IgG (10 mg/Kg, given IP daily for 10 days, starting on the day of CAR-T injection). Mice were followed with serial tail vein bleeding to assess disease burden beginning day 14 post CAR-T cell injection and were followed for overall survival. FIG. 28F graphically depicts that Lenzilumab treatment with CAR-T therapy results in more sustained control of tumor burden over time in a primary acute lymphoblastic leukemia (ALL) xenograft model compared to isotype control treatment with CAR-T therapy, 6 mice per group, ** p<0.01, * p<0.05, ns p>0.05, t test, mean+SEM.

FIG. 29A illustrates that the CRISPR Cas9 GM-CSF$^{k/o}$ CART19 exhibit reduced GM-CSF production compared to wild type CART19, but other cytokine production and degranulation are not inhibited by the GM-CSF gene disruption, CART19 and GM-CSF$^{k/o}$ CART19 stimulated with NALM6, n=3 experiments, 2 replicates per experiment, *** p<0.001, * p<0.05, ns p>0.05 comparing GM-CSF$^{k/o}$ CART19 and CAR19, t test, mean+SEM. FIG. 29B illustrates that GM-CSF$^{k/o}$ CAR-T have reduced serum human GM-CSF in vivo compared to CAR-T treatment as assayed by multiplex, 5-6 mice per group (4-6 at time of bleed, 8 days post CAR-T cell injection), ** p<0.0001, * p<0.001 between GM-CSF$^{k/o}$ CART19 and wild type CART19, t test, mean+SEM. FIG. 29C illustrates that GM-CSF$^{k/o}$ CART19 in vivo enhances overall survival compared to wild type CART19 in a high tumor burden relapse xenograft model of ALL utilizing a NALM6 cell line, 5-6 mice per group,  p<0.01, log-rank. FIGS. 29D-29E show human (FIG. 29D) and mouse (FIG. 29E) cytokines and chemokines from multiplex of serum, other than hGM-CSF, show no statistical differences between the GM-CSF$^{k/o}$ CART19 and wild type CART19, further implicating critical T-cell cytokines and chemokines are not adversely depleted by reducing GM-CSF expression, 5-6 mice per group (4-6 at time of bleed), ** p<0.0001, t test.

FIG. 30A shows the experimental schema: Mice received 1-3×106 primary blasts derived from the peripheral blood of patients with primary ALL. Mice were monitored for engraftment for ≥10-13 weeks via tail vein bleeding. When serum CD19+ cells were >10 cells/uL, the mice received CART19 (2-5×106 cells) and commenced antibody therapy for a total of 10 days, as indicated. Mice were weighed on a daily basis as a measure of their wellbeing. Mouse brain MRIs were performed 5-6 days post CART19 injection and tail vein bleeding for cytokine/chemokine and T cell analysis was performed 4-11 days post CART19 injection, 2 independent experiments. FIG. 30B illustrates that a combination of GM-CSF neutralization with CART19 is equally effective as isotype control antibodies combined with CART19 in controlling CD19+ burden of ALL cells, representative experiment, 3 mice per group, 11 days post CART19 injection, * p<0.05 between GM-CSF neutralization+CART19 and isotype control+CART19, t test, mean+SEM. FIG. 30C illustrates brain MRI data showing CART19 therapy exhibits T1 enhancement, suggestive of brain blood-brain barrier disruption and possible edema. 3 mice per group, 5-6 days post CART19 injection, representative image. FIG. 30D illustrates high tumor burden primary ALL xenografts treated with CART19 show human CD3 cell infiltration of the brain compared to untreated PDX controls. 3 mice per group, representative image.

FIG. 32A shows Lenzilumab and anti-mouse GM-CSF antibody prevent CRS induced weight loss compared to mice treated with CART19 and isotype control antibodies, 3 mice per group, 2-way anova, mean+SEM. FIG. 32B shows human GM-CSF was neutralized in patient derived xenografts treated with lenzilumab and mouse GM-CSF neutralizing antibody, 3 mice per group, *** p<0.001, * p<0.05, t test, mean+SEM. FIG. 32C shows human cytokine/chemokine heat map (serum collected 11 days after CART19 injection) exhibits increases in cytokines and chemokines typical of CRS after CART19 treatment. GMCSF neutralization results in a significant decrease in several cytokines and chemokines compared to mice treated with CART19 and isotype control antibodies, including several myeloid associated cytokines and chemokines, as indicated in the panel, 3 mice per group, serum from day 11 post CART19 injection, * p<0.001,  p<0.01, * p<0.05, comparing GM-CSF neutralizing antibody treated and isotype control treated mice that received CAR-T cell therapy, t test. FIG.

32D shows mouse cytokine/chemokine heat map (serum collected 11 days after CART19 injection) exhibit increase in mouse cytokines and chemokines typical of CRS after CART19 treatment. GM-CSF neutralization results in a significant decrease in several cytokines and chemokines compared to treatment with CART19 with control antibodies, including several myeloid differentiating cytokines and chemokines, as indicated in the panel, 3 mice per group, serum from day 11 post CART19 injection, * p<0.05, comparing GM-CSF neutralizing antibody treated and isotype control treated mice that received CAR-T cell therapy, t test.

Figure 33A:
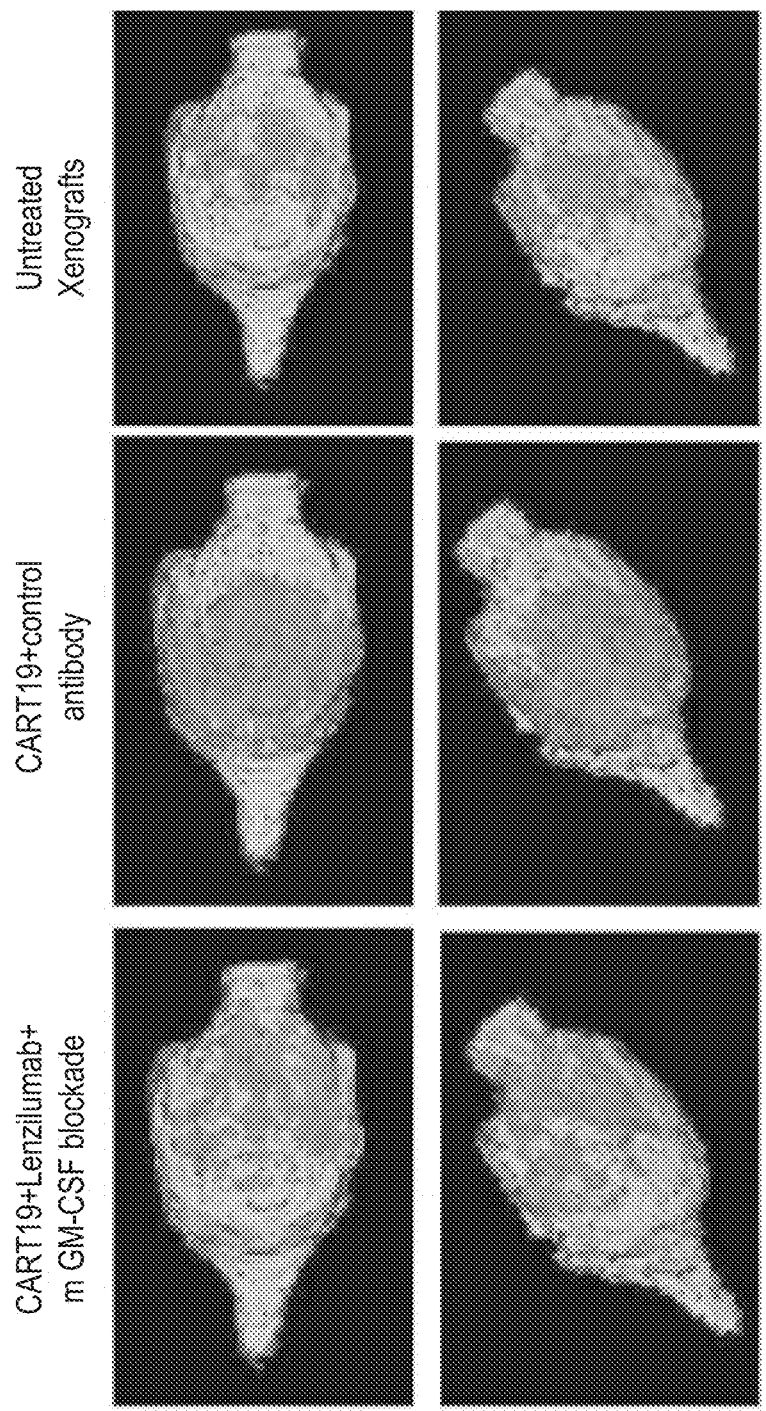
Figure 33D:
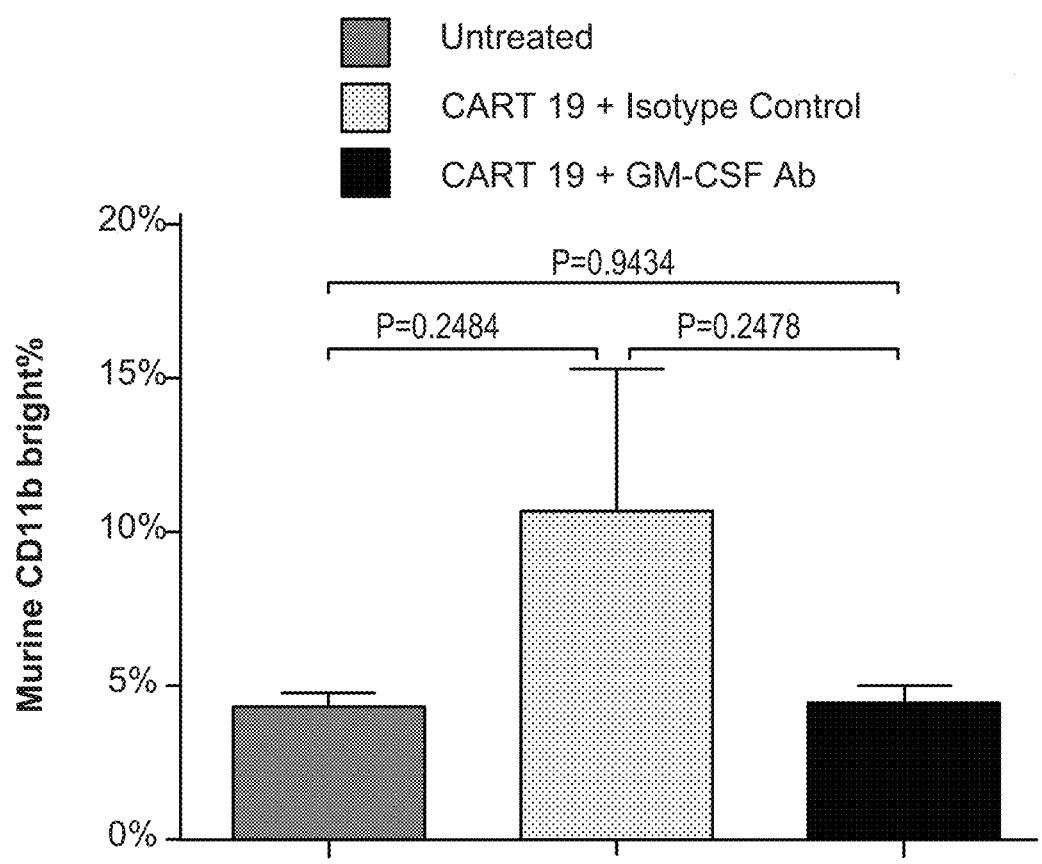

FIGS. 33A-33D demonstrate GM-CSF neutralization in vivo ameliorates neuro-inflammation after CART19 therapy in a xenograft model. FIGS. 33A-33B depict gadolinium enhanced T1-hyperintensity (cubic mm) MRI showed that GM-CSF neutralization helped reduced brain inflammation, blood-brain barrier disruption, and possible edema compared to isotype control (A) representative images, (33B) 3 mice per group, ** p<0.01, * p<0.05, 1-way ANOVA, mean+SD. FIG. 33C shows human CD3 T cells were present in the brain after treatment with CART19 therapy. GM-CSF neutralization resulted in a trend toward decreased CD3 infiltration in the brain as assayed by flow cytometry in brain hemispheres, 3 mice per group, mean+SEM. FIG. 33D depicts CD11b+ bright macrophages were decreased in the brains of mice receiving GM-CSF neutralization during CAR-T therapy compared to isotype control during CAR-T therapy as assayed by flow cytometry in brain hemispheres, 3 mice per group, mean+SEM.

FIGS. 34A(i)-34B illustrate the generation of GM-CSF$^{k/o}$ CART19 cells. FIGS. 34A(i)-34A(iv) show the experimental schema; FIG. 34B shows the gRNA sequence and primer sequences for generation of GM-CSF$^{k/o}$ CART19. To generate GM-CSF$^{k/o}$ CART19 cells, gRNA was cloned into a Cas9 lentivirus vector under the control of a U6 promotor and used for lentivirus production. T cells derived from normal donors were stimulated with CD3/CD28 beads and dual transduced with CAR19 virus and CRISPR/Cas9 virus 24 hours later. CD3/CD28 magnetic bead removal was performed on Day +6, and GM-CSF$^{k/o}$ CART19 cells or control CART19 cells were cryopreserved on Day 8.

Figure 35:
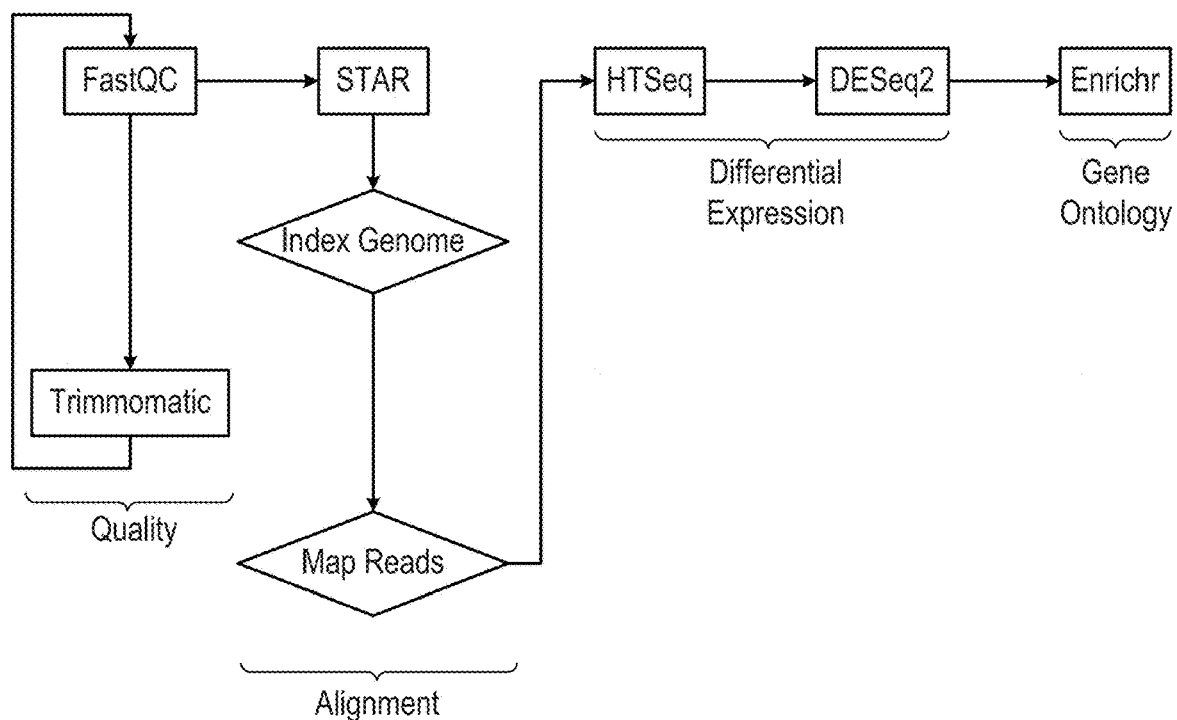

FIG. 35 shows a flow chart for procedures used in RNA sequencing. The binary base call data was converted to fastq using Illumina bcl2fastq software. The adapter sequences were removed using Trimmomatic, and FastQC was used to check for quality. The latest human (GRCh38) and mouse (GRCm38) reference genomes were downloaded from NCBI. Genome index files were generated using STAR, and the paired end reads were mapped to the genome for each condition. HTSeq was used to generate expression counts for each gene, and DeSeq2 was used to calculate differential expression. Gene ontology was assessed using Enrichr.

Figure 36:
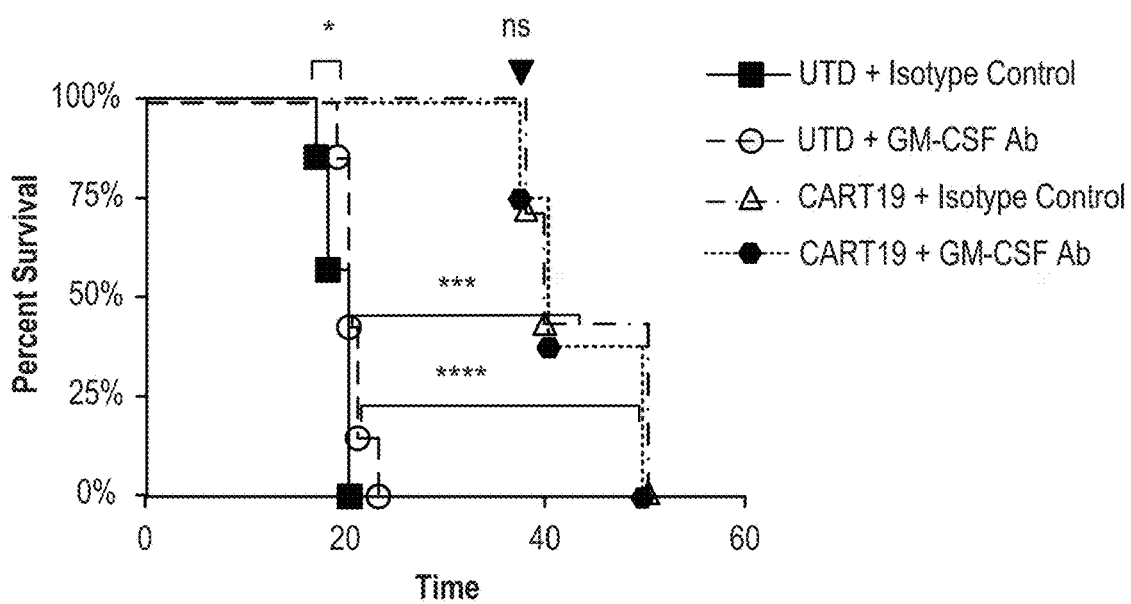

FIG. 36 shows that Lenzilumab plus CAR-T cell treated mice have comparable survival compared to isotype control antibody plus CAR-T cell treated mice in a high tumor burden relapse xenograft model of ALL. n=2 experiments, 7-8 mice per group, representative experiment depicted, ** p<0.0001, * p<0.001, * p<0.05, log-rank.

Figure 37:
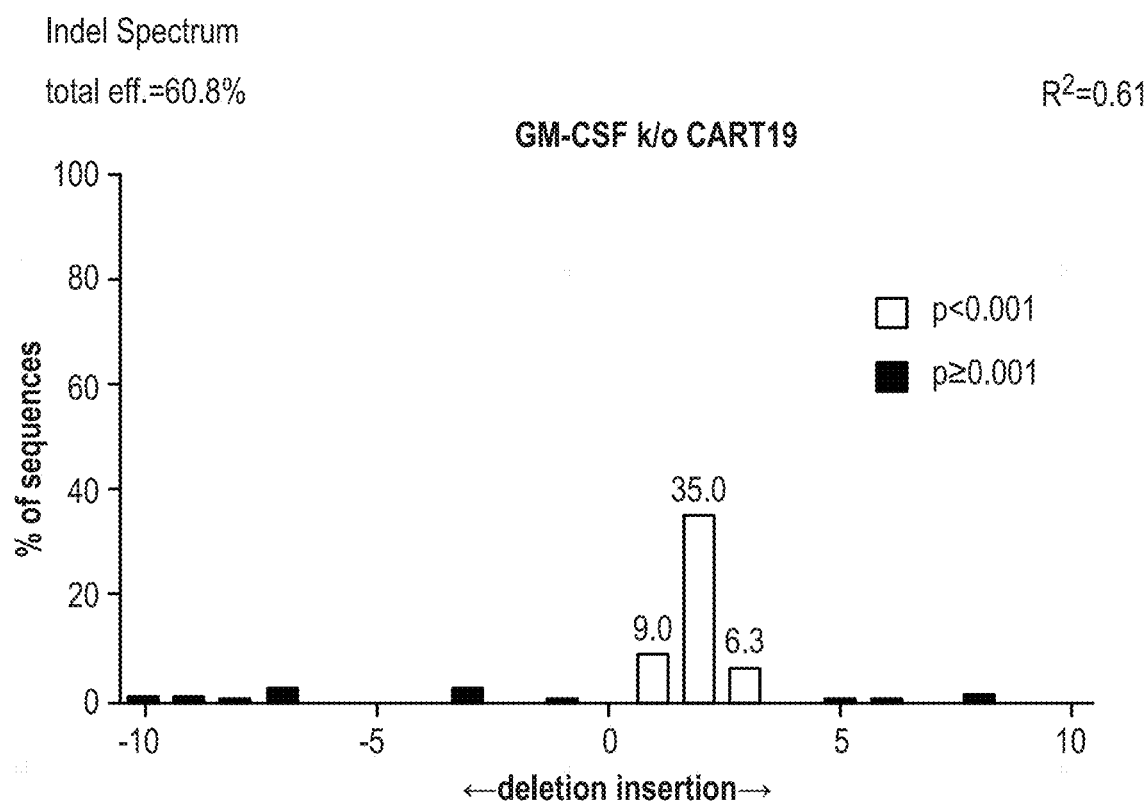

FIG. 37 shows a representative TIDE sequence to verify genome alteration in the GM-CSF CRISPR Cas9 knockout CAR-T cells. n=2 experiments, representative experiment depicted.

Figure 38:
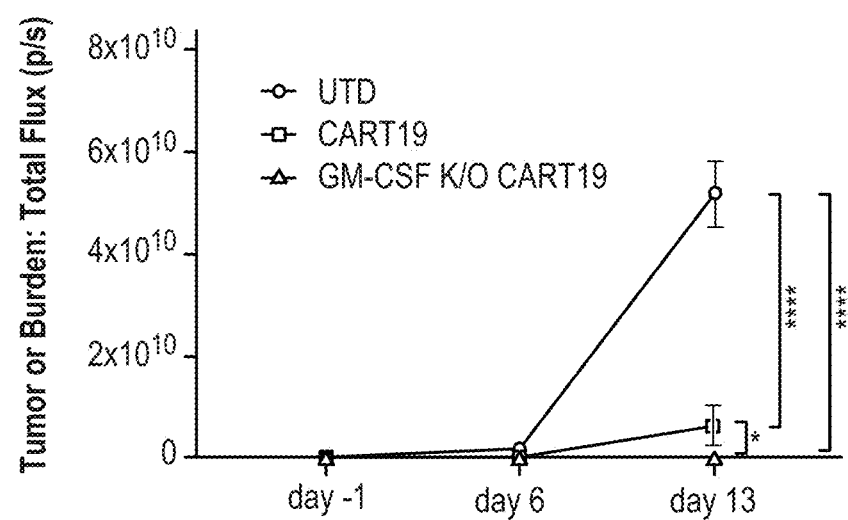

FIG. 38 shows GM-CSF knockout CAR-T cells in vivo show slightly enhanced control of tumor burden compared to wild type CAR-T cells in a high tumor burden relapse xenograft model of ALL. Days post CAR-T cell injection listed on x-axis, 5-6 mice per group (2 remained in UTD group at day 13), representative experiment depicted, **** p<0.0001, * p<0.05, 2-way ANOVA, mean+SEM.

Figure 39:
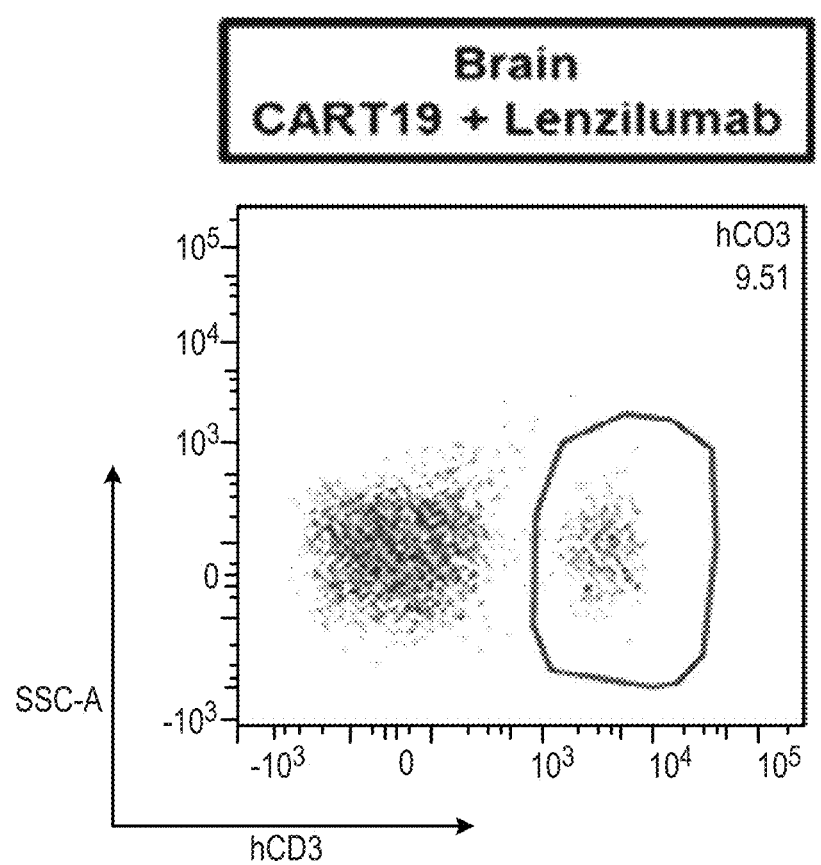

FIG. 39 demonstrates a patient derived xenograft model for neuro-inflammation and CRS with CART19+ anti-hGM-CSF antibody treatment. High tumor burden primary ALL xenografts treated CART19+anti-hGM-CSF antibody treatment show human CD3 cell infiltration of the brain (FIG. 39) compared to untreated PDX controls (FIG. 30D). 3 mice per group, representative image.

DETAILED DESCRIPTION OF THE INVENTION

The present subject matter may be understood more readily by reference to the following detailed description which forms a part of this disclosure. It is to be understood that this disclosure is not limited to the specific products, methods, conditions or parameters described and/or shown herein, and that the terminology used herein is for the purpose of describing particular embodiments by way of example only and is not intended to be limiting of the claimed disclosure.

Immunotherapy-Related Toxicity

A skilled artisan would appreciate that the term "immunotherapy-related toxicity" refers to a spectrum of inflammatory symptoms resulting from high levels of immune activation. Different types of toxicity are associated with different immunotherapy approaches. In some embodiments, immunotherapy-related toxicity comprises capillary leak syndrome, cardiac disease, respiratory disease, CAR-T-cell-related encephalopathy syndrome (CRES), neurotoxicity, colitis, convulsions, cytokine release syndrome (CRS), cytokine storm, decreased left ventricular ejection fraction, diarrhea, disseminated intravascular coagulation, edema, encephalopathy, exanthema, gastrointestinal bleeding, gastrointestinal perforation, hemophagocytic lymphohistiocytosis (HLH), hepatosis, hypertension, hypophysitis, immune related adverse events, immunohepatitis, immunodeficiencies, ischemia, liver toxicity, macrophage-activation syndrome (MAS), pleural effusions, pericardial effusions, pneumonitis, polyarthritis, posterior reversible encephalopathy syndrome (PRES), pulmonary hypertension, thromboembolism, and transaminitis.

While different types of toxicities differ in their pathophysiology and clinical manifestations, they are usually associated with an increase in inflammation-associated factors, such as C-reactive protein, GM-CSF, IL-1, IL-2, sIL-2Rα, IL-5, IL-6, IL-8, IL-10, IP10, IL-15, MCP-1 (AKA CCL2), MIG, MIP-1β, IFNγ, CX3CR1, or TNFα. A skilled artisan would appreciate that, in some embodiments, the term "inflammation-associated factor" comprises molecules, small molecules, peptides, gene transcripts, oligonucleotides, proteins, hormones, and biomarkers that are affected during inflammation. A skilled artisan would appreciate that systems affected during inflammation comprises upregulation, downregulation, activation, de-activation, or any kind of molecular modification. The serum concentration of inflammation-associated factors, such as cytokines, can be used as an indicator of immunotherapy-related toxicities, and may be expressed as—fold increase, percent (%) increase, net increase or rate of change in cytokine levels or concentration. The concentration of inflammation-associated factors in body fluids other than serum can also be used as indicators of immunotherapy-related toxicities. In some embodiments, absolute cytokine levels or concentrations above a certain level or concentration may be an indication of a subject undergoing or about to experience an immunotherapy-related toxicity. In another embodiment, absolute (Lee, et al., Blood 2014; 124:188-195, which is incorporated in its entirety herein by reference.).

TABLE 1A

Method for Grading Neurotoxicity - Criteria for Adverse Events (CTCAE)

| Symptom or sign | Grade 1 | Grade 2 | Grade 3 | Grade 4 |
|---|---|---|---|---|
| Level of consciousness | Mild drowsiness/ sleepiness | Moderate somnolence, limiting instrumental ADL | Obtundation or stupor | Life-threatening needing urgent intervention or mechanical ventilation |
| Orientation/ Confusion | Mild disorientation/ confusion | Moderate disorientation, limiting instrumental ADL | Severe disorientation, limiting self-care ADL | Life-threatening needing urgent intervention or mechanical ventilation |
| ADL/ Encephalopathy | Mild limiting of ADL | Limiting instrumental ADL | Limiting self-care ADL | Life-threatening needing urgent intervention or mechanical ventilation |
| Speech | Dysphasia not impairing ability to communicate | Dysphasia with moderate impairment in ability to communicate spontaneously | Severe receptive or expressive dysphasia, impairing ability to read, write or communicate intelligibly | — |
| Seizure | Brief partial seizure; no loss of consciousness | Brief generalized seizure | Multiple seizures despite medical intervention | Life-threatening; prolonged repetitive seizures |
| Incontinent or motor weakness | | | Bowel/bladder incontinence; Weakness limiting selfcare ADL, disabling | |
| MD Anderson Cancer Center (MDACC) 10-point Neurotoxicity grade | Mild (7-9) | Moderate (3-6) | Severe (1-2), grade 1 and 2 papilledema with CSF opening pressure (op) <20 mmHg | Critical (Obtunded; convulsive status epilepticus; motor weakness, grade 3, 4 & 5 papilledema, CSF op ≥20 mmHg, cerebral edema) | cytokine levels or concentration at a certain level, for example a level or concentration normally found in a control subject, may be an indication of a method for inhibiting or reducing the incidence of an immunotherapy-related toxicity in a subject. A skilled artisan would appreciate that the term "cytokine level" may encompass a measure of concentration, a measure of fold change, a measure of percent (%) change, or a measure of rate change. Further, the methods for measuring cytokines in blood, cerebrospinal fluid (CSF), saliva, serum, urine, and plasma are well known in the art.

A number of approaches have been elaborated to classify the type of neurotoxicity and manage it accordingly. These classifications are based on clinical and biological symptoms, as fever, hypotension, hypoxia, organ toxicity, cardiac dysfunction, respiratory dysfunction, gastrointestinal dysfunction, hepatic dysfunction, renal dysfunction, coagulopathy, seizure presence, intracranial pressure, muscle tone, motor performance, ferritin levels, and haemagophagocytosis. Similarly, each type of neurotoxicity can be graded according to its severity. Table 1A (taken from Cellular Therapy Implementation: the MDACC Approach, P. Kebriaei, Feb. 24, 2017) discloses a method for grading neurotoxicity according to its severity into Grade 1, Grade 2, Grade 3, and Grade 4. However, some of the foregoing symptoms are not typically associated with neurotoxicity.

Patients with body temperature above 38.9° C., IL-6 serum concentration above 16 pg/ml, or MCP-1 (AKA CCL2) serum concentration above 1,343.5 pg/ml in the first 36 hours after immunotherapy infusion had higher probabilities of developing severe neurotoxicity (Gust, et al. *Cancer Discov.* 2017 Oct. 12).

CRS is a serious condition and life-threatening adverse effect because of abnormal cytokine regulation and thus, severe inflammation. Symptoms can include, without limitation, fever, disordered heartbeat and breathing, nausea, vomiting, and seizures. CRS can be graded by assessing symptoms and their severities, such as, for example: Grade 1 CRS: Fever, constitutional symptoms; Grade 2 CRS: Hypotension—responds to fluids or one low dose pressor, Hypoxia—responds to <40% $O_2$, Organ toxicity; grade 2; Grade 3 CRS: Hypotension—requires multiple pressors or high dose pressors, Hypoxia—requires ≥40% $O_2$, Organ toxicity—grade 3, grade 4 transaminitis; Grade 4 CRS: Mechanical ventilation, Organ toxicity—grade 4, excluding transaminitis. (Lee, et al., Blood 2014; 124:188-195, which is incorporated in its entirety herein by reference.).

CRES can be graded, for example, by combining neurological assessment with other parameters as papilloedema, CSF opening pressure, imaging assessment, and the presence of seizures and motor weakness. A method for grading CRES is described in Neelapu et al., *Nat Rev Clin Oncol.* 15(1):47-62 (2018) (Epub 2017 Sep. 19), which is incorporated in its entirety herein by reference. Table 1B (taken from Neelapu et al., *Nat Rev Clin Oncol.* 15(1):47-62 (2018)) discloses a method for grading CRES according to its severity into Grade 1, Grade 2, Grade 3, and Grade 4.

TABLE 1B

Method for grading CRES. In CARTOX-10, a point is assigned for each of the following tasks performed correctly: orientation to year, month, city, hospital, and President/Prime Minister of country of residence (1 point for each); naming three objects (1 point for each); writing a standard sentence; counting backwards from 100 in tens.

| Symptom or sign | Grade 1 | Grade 2 | Grade 3 | Grade 4 |
|---|---|---|---|---|
| Neurological assessment score (by CARTOX-10) | 7-9 (mild impairment) | 3-6 (moderate impairment) | 0-2 (severe impairment) | Patient in critical condition, and/or obtunded and cannot perform assessment of tasks |
| Raised intracranial pressure | NA | NA | Stage 1-2 papilloedema, or CSF opening pressure <20 mmHg | Stage 3-5 papilloedema, or CSF opening pressure ≥20 mmHg, or cerebral oedema |
| Seizures or motor weakness | NA | NA | Partial seizure, or non-convulsive seizures on EEG with response to benzodiazepine | Generalized seizures, or convulsive or non-convulsive status epilepticus, or new motor weakness |

NT, CRS, and CRES manifestations can include encephalopathy, headaches, delirium, anxiety, tremor, seizure activity, confusion, alterations in wakefulness, decreased level of consciousness, hallucinations, dysphasia, aphasia, ataxia, apraxia, facial nerve palsy, motor weakness, seizures, non-convulsive EEG seizures, cerebral edema, and coma. CRES is associated with elevated concentrations of circulating cytokines, as C-reactive protein, GM-CSF, IL-1, IL-2, sIL2Rα, IL-5, IL-6, IL-8, IL-10, IP10, IL-15, MCP-1, MIG, MIP1β, IFNγ, CX3CR1, and TNFα.

The cytokine concentration gradient between serum and CSF observed in normal conditions is reduced or lost during CRES. Additionally, CAR T-cells and high protein concentrations are observed in the CSF of patients and is correlated with the severity of the condition. All this indicates a blood-brain barrier dysfunction following immunotherapy. Increased vascular permeability can be partially explained by increased concentrations of ANG2 and increased ANG2:ANG1 ratio in patients with neurotoxicity. While ANG1 induces endothelial cell quiescence, ANG2 causes endothelial cell activation and microvascular permeability. Patients with increased endothelial activation before immunotherapy were reported to have higher probability of suffering neurotoxicity (Gust, et al. *Cancer Discov.* 2017 Oct. 12).

Hemophagocytic lymphohistiocytosis (HLH) comprises severe hyperinflammation caused by uncontrolled proliferation of benign lymphocytes and macrophages that secrete high amounts of inflammatory cytokines. In some embodiments, HLH can be classified as one of the cytokine storm syndromes. In some embodiments, HLH occurs after strong immunologic activation, such as systemic infections, immunodeficiency, malignancies. or immunotherapy. In some embodiments, the term "HLH" may be used interchangeably with the terms "hemophagocytic lymphohistiocytosis", "hemophagocytic syndrome", or "hemophagocytic syndrome" having all the same qualities and meanings.

Primary HLH comprises a heterogeneous autosomal recessive disorder. Patients with homozygous mutations in one of several genes, exhibit loss of function of proteins involved in cytolytic granule exocytosis. In some embodiments, HLH can present in infancy with minimal or no trigger. Secondary HLH, or acquired HLH, occurs after strong immunologic activation, such as that which occurs with systemic infection, immunodeficiency, an underlying malignancy, or immunotherapies. Both forms of HLH are characterized by an overwhelming activation of normal T lymphocytes and macrophages, invariably leading to clinical and haematologic alterations and death in the absence of treatment.

In some embodiments, HLH can be initiated by viral infections, EBV, CMV, parvovirus, HSV, VZV, HHV8, HIV, influenza, hepatitis A, hepatitis B, hepatitis C, bacterial infections, gram-negative rods, *Mycoplasma* species and *Mycobacterium tuberculosis*, parasitic infections, *Plasmodium* species, *Leishmania* species, *Toxoplasma* species, fungal infections, *Cryptococcal* species, *Candidal* species and *Pneumocystis* species, among others.

Macrophage-activation syndrome (MAS) comprises a condition comprising uncontrolled activation and proliferation of macrophages, and T lymphocytes, with a marked increase in circulating cytokine levels, such as IFNγ, and GM-CSF. MAS is closely related to secondary HLH. MAS manifestations include high fever, hepatosplenomegaly, lymphadenopathy, pancytopenia, liver dysfunction, disseminated intravascular coagulation, hemophagocytosis, hypofibrinogenemia, hyperferritinemia, and hypertriglyceridemia.

CRS comprises a non-antigen-specific immune response similar to that found in severe infection. CRS is characterized by any or all of the following symptoms: fever with or without rigors, malaise, fatigue, anorexia, myalgias, arthalgias, nausea, vomiting, headache, skin rash, diarrhea, tachypnea, hypoxemia, hypoxia, shock, cardiovascular tachycardia, widened pulse pressure, hypotension, capillary leak, increased cardiac output (early), potentially diminished cardiac output (late), elevated D-dimer, hypofibrinogenemia with or without bleeding, azotemia, transaminitis, hyperbilirubinemia, headache, mental status changes, confusion, delirium, word finding difficulty or frank aphasia, hallucinations, tremor, dysmetria, altered gait, seizures, organ failure, multi-organ failure. Deaths have also been reported. Severe CRS has been reported to occur in up to 60% of patients receiving CAR-T19.

Cytokine storm comprises an immune reaction consisting of a positive feedback loop between cytokines and white blood cells, with highly elevated levels of various cytokines. The term "cytokine storm" may be used interchangeably with the terms "cytokine cascade" and "hypercytokinemia" having all the same qualities and meanings. In some embodiments, a cytokine storm is characterized by IL-2 release and lymphoproliferation. Cytokine storm leads to potentially life-threatening complications including cardiac dysfunction, adult respiratory distress syndrome, neurologic toxicity, renal and/or hepatic failure, and disseminated intravascular coagulation.

As noted, CAR-T cell therapy is currently limited by the risk of life-threatening neurotoxicity and CRS. Despite active management, all CAR-T responders experience some degree of CRS. Up to 50% of patients treated with CD19 CAR-T have at least Grade 3 CRS or neurotoxicity. GM-CSF levels and T-cell expansion are the factors most associated with grade 3 or higher CRS and neurotoxicity.

Reducing or eliminating CRS and neurotoxicity in immunotherapies such as CAR-T cell therapy is of great value and it is crucial to determine what is driving or exacerbating the signature CAR-T inflammatory response. Although many cytokines, signaling molecules, and cell types are involved in this pathway, GM-CSF is the one cytokine that appears to be at the center of the pathway. Normally undetectable in human serum, it is central to the cyclical positive feedback loop that drives inflammation to the extremes of cytokine storms and endothelial cell activation. Neurotoxicity and cytokine storms are not the result of a simultaneous release of cytokines, but rather a cascade of inflammation initiated by GM-CSF resulting in the trafficking and recruitment of myeloid cells to the tumor site. These myeloid cells produce the cytokines observed in CRS and neurotoxicity, perpetuating the inflammatory cascade.

Granulocyte Macrophage-Colony Stimulating Factor (GM-CSF)

As used herein, "Granulocyte Macrophage-Colony Stimulating Factor" (GM-CSF) refers to a small, naturally occurring glycoprotein with internal disulfide bonds having a molecular weight of approximately 23 kDa. In some embodiments, GM-CSF refers to human GM-CSF. In some embodiments, GM-CSF refers to non-human GM-CSF. In humans, it is encoded by a gene located within the cytokine cluster on human chromosome 5. The sequence of the human gene and protein are known. The protein has an N-terminal signal sequence, and a C-terminal receptor binding domain (Rasko and Gough In: The Cytokine Handbook, A. Thomson, et al, Academic Press, New York (1994) pages 349-369). Its three-dimensional structure is similar to that of the interleukins, although the amino acid sequences are not similar GM-CSF is produced in response to a number of inflammatory mediators by mesenchymal cells present in the hemopoietic environment and at peripheral sites of inflammation. GM-CSF is able to stimulate the production of neutrophilic granulocytes, macrophages, and mixed granulocyte-macrophage colonies from bone marrow cells and can stimulate the formation of eosinophil colonies from fetal liver progenitor cells. GM-CSF can also stimulate some functional activities in mature granulocytes and macrophages. GM-CSF, a cytokine present in the bone marrow microenvironment, recruits inflammatory monocyte-derived dendritic cells, stimulates the secretion of high levels of IL-6 and CCL2/MCP-1, and leads to a feedback loop, recruiting more monocytes, inflammatory dendritic cells to inflammatory sites.

As noted, CRS involves the increase of several cytokines and chemokines, including IFN-γ, IL-6, IL-8, CCL2 (MCP-1), CCL3 (MIP1a), and GM-CSF. (Teachey, D. et al. (June 2016), *Cancer Discovery*, CD-16-0040; Morgan R., et al., (April 2010), *Molecular Therapy*.). IL-6, one of the key inflammatory cytokines, is not produced by CAR-T cells. (Barrett, D. et al. (2016), *Blood*). Instead, it is produced by myeloid cells, which are recruited to the tumor site. GM-CSF mediates this recruitment, which induces chemokine production that activates myeloid cells and causes them to traffic to the tumor site. Elevated GM-CSF levels serve as both a predictive biomarker for CRS and an indicator of its severity. More than a critical component of the inflammation cascade, GM-CSF is the key initiator, responsible for both CRS and NT. As described herein, in vivo studies using murine models indicate that genetic silencing of GM-CSF prevents cytokine storm—while still maintaining CAR-T efficacy. GM-CSF knockout mice have normal levels of INF-γ, IL-6, IL-10, CCL2 (MCP1), CCL3/4 (MIG-1) in vivo and do not develop CRS. (Sentman, M.-L., et al (2016), *The Journal of Immunology*, 197(12), 4674-4685.). GM-CSF knockout CAR-T models recruit fewer NK cells, CD8 cells, myeloid cells, and neutrophils to the tumor site in comparison to GM-CSF+ CAR-T.

The term "soluble granulocyte macrophage-colony stimulating factor receptor" (sGM-CSFR) refers to a non-membrane bound receptor that binds GM-CSF, but does not transduce a signal when bound to the ligand.

As used herein, a "peptide GM-CSF antagonist" refers to a peptide that interacts with GM-CSF, or its receptor, to reduce or block (either partially or completely) signal transduction that would otherwise result from the binding of GM-CSF to its cognate receptor expressed on cells. GM-CSF antagonists may act by reducing the amount of GM-CSF ligand available to bind the receptor (e.g., antibodies that once bound to GM-CSF increase the clearance rate of GM-CSF) or prevent the ligand from binding to its receptor either by binding to GM-CSF or the receptor (e.g., neutralizing antibodies). GM-CSF antagonists may also include other peptide inhibitors, which may include polypeptides that bind GM-CSF or its receptor to partially or completely inhibit signaling. A peptide GM-CSF antagonist can be, e.g., an antibody; a natural or synthetic GM-CSF receptor ligand that antagonizes GM-CSF, or other polypeptides. An exemplary assay to detect GM-CSF antagonist activity is provided in Example 1. Typically, a peptide GM-CSF antagonist, such as a neutralizing antibody, has an EC50 of 10 nM or less.

A "purified" GM-CSF antagonist as used herein refers to a GM-CSF antagonist that is substantially or essentially free from components that normally accompany it as found in its native state. For example, a GM-CSF antagonist such as an anti-GM-CSF antibody that is purified from blood or plasma is substantially free of other blood or plasma components such as other immunoglobulin molecules. Purity and homogeneity are typically determined using analytical chemistry techniques such as polyacrylamide gel electrophoresis or high-performance liquid chromatography. A protein that is the predominant species present in a preparation is substantially purified. Typically, "purified" means that the protein is at least 85% pure, more preferably at least 95% pure, and most preferably at least 99% pure relative to the components with which the protein naturally occurs.

Antibodies

As used herein, an "antibody" refers to a protein functionally defined as a binding protein and structurally defined as comprising an amino acid sequence that is recognized by one of skill as being derived from the framework region of an immunoglobulin-encoding gene of an animal that produces antibodies. An antibody can consist of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain ($V_H$) refer to these light and heavy chains, respectively.

The term "antibody" includes antibody fragments that retain binding specificity. For example, there are a number of well characterized antibody fragments. Thus, for example, pepsin digests an antibody C-terminal to the disulfide linkages in the hinge region to produce F(ab')2, a dimer of Fab which itself is a light chain joined to VH-CH1 by a disulfide bond. The F(ab')2 may be reduced under mild conditions to break the disulfide linkage in the hinge region thereby converting the (Fab')2 dimer into a Fab' monomer. The Fab' monomer is essentially a Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that fragments can be synthesized de novo either chemically or by utilizing recombinant DNA methodology. Thus, the term antibody, as used herein also includes antibody fragments either produced by the modification of whole antibodies or synthesized using recombinant DNA methodologies.

Antibodies include dimers such as $V_H$-$V_L$ dimers, $V_H$ dimers, or $V_L$ dimers, including single chain antibodies (antibodies that exist as a single polypeptide chain), such as single chain Fv antibodies (sFv or scFv), in which a variable heavy and a variable light region are joined together (directly or through a peptide linker) to form a continuous polypeptide. The single chain Fv antibody is a covalently linked $V_H$-$V_L$ heterodimer which may be expressed from a nucleic acid including $V_H$- and $V_L$-encoding sequences either joined directly or joined by a peptide-encoding linker (e.g., Huston, et al. Proc. Nat. Acad. Sci. USA, 85:5879-5883, 1988). While the $V_H$ and $V_L$ are connected to each as a single polypeptide chain, the $V_H$ and $V_L$ domains associate non-covalently. Alternatively, the antibody can be another fragment, such as a disulfide-stabilized Fv (dsFv). Other fragments can also be generated, including using recombinant techniques. The scFv antibodies and a number of other structures converting the naturally aggregated, but chemically separated light and heavy polypeptide chains from an antibody V region into a molecule that folds into a three-dimensional structure substantially similar to the structure of an antigen-binding site and are known to those of skill in the art (see e.g., U.S. Pat. Nos. 5,091,513, 5,132,405, and 4,956,778). In some embodiments, antibodies include those that have been displayed on phage or generated by recombinant technology using vectors where the chains are secreted as soluble proteins, e.g., scFv, Fv, Fab, (Fab')2 or generated by recombinant technology using vectors where the chains are secreted as soluble proteins. Antibodies for use in the invention can also include diantibodies and miniantibodies.

Antibodies of the invention also include heavy chain dimers, such as antibodies from camelids. Since the $V_H$ region of a heavy chain dimer IgG in a camelid does not have to make hydrophobic interactions with a light chain, the region in the heavy chain that normally contacts a light chain is changed to hydrophilic amino acid residues in a camelid. $V_H$ domains of heavy-chain dimer IgGs are called VHH domains. Antibodies for use in the current invention include single domain antibodies (dAbs) and nanobodies (see, e.g., Cortez-Retamozo, et al., Cancer Res. 64:2853-2857, 2004).

As used herein, "V-region" refers to an antibody variable region domain comprising the segments of Framework 1, CDR1, Framework 2, CDR2, and Framework 3, including CDR3 and Framework 4, which segments are added to the V-segment as a consequence of rearrangement of the heavy chain and light chain V-region genes during B-cell differentiation. A "V-segment" as used herein refers to the region of the V-region (heavy or light chain) that is encoded by a V gene. The V-segment of the heavy chain variable region encodes FR1-CDR1-FR2-CDR2 and FR3. For the purposes of this invention, the V-segment of the light chain variable region is defined as extending though FR3 up to CDR3.

As used herein, the term "J-segment" refers to a subsequence of the variable region encoded comprising a C-terminal portion of a CDR3 and the FR4. An endogenous J-segment is encoded by an immunoglobulin J-gene.

As used herein, "complementarity-determining region (CDR)" refers to the three hypervariable regions in each chain that interrupt the four "framework" regions established by the light and heavy chain variable regions. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, for example, a $V_H$ CDR3 is located in the variable domain of the heavy chain of the antibody in which it is found, whereas a $V_L$ CDR1 is the CDR1 from the variable domain of the light chain of the antibody in which it is found.

The sequences of the framework regions of different light or heavy chains are relatively conserved within a species. The framework region of an antibody, that is the combined framework regions of the constituent light and heavy chains, serves to position and align the CDRs in three-dimensional space.

The amino acid sequences of the CDRs and framework regions can be determined using various well-known definitions in the art, e.g., Kabat, Chothia, international ImMunoGeneTics database (IMGT), and AbM (see, e.g., Johnson et al., supra; Chothia & Lesk, 1987, Canonical structures for the hypervariable regions of immunoglobulins. J. Mol. Biol. 196, 901-917; Chothia C. et al., 1989, Conformations of immunoglobulin hypervariable regions. Nature 342, 877-883; Chothia C. et al., 1992, structural repertoire of the human VH segments J. Mol. Biol. 227, 799-817; Al-Lazikani et al., J. Mol. Biol 1997, 273(4)). Definitions of antigen combining sites are also described in the following: Ruiz et al., IMGT, the international ImMunoGeneTics database. Nucleic Acids Res., 28, 219-221 (2000); and Lefranc, M.-P. IMGT, the international ImMunoGeneTics database. Nucleic Acids Res. January 1; 29(1):207-9 (2001); MacCallum et al, Antibody-antigen interactions: Contact analysis and binding site topography, *J. Mol. Biol.*, 262 (5), 732-745 (1996); and Martin et al, *Proc. Natl Acad. Sci. USA,* 86, 9268-9272 (1989); Martin, et al, *Methods Enzymol.,* 203, 121-153, (1991); Pedersen et al, *Immunomethods,* 1, 126, (1992); and Rees et al, In Sternberg M. J. E. (ed.), Protein Structure Prediction. Oxford University Press, Oxford, 141-172 1996).

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

The term "binding specificity determinant" or "BSD" as used in the context of the current invention refers to the minimum contiguous or non-contiguous amino acid sequence within a CDR region necessary for determining the binding specificity of an antibody. In the current invention, the minimum binding specificity determinants reside within a portion or the full-length of the CDR3 sequences of the heavy and light chains of the antibody.

As used herein, "anti-GM-CSF antibody" or "GM-CSF antibody" are used interchangeably to refer to an antibody that binds to GM-CSF and inhibits GM-CSF receptor binding and activation. Such antibodies may be identified using any number of art-recognized assays that assess GM-CSF binding and/or function. For example, binding assays such as ELISA assays that measure the inhibition of GM-CSF binding to the alpha receptor subunit may be used. Cell-based assays for GM-CSF receptor signaling, such as assays which determine the rate of proliferation of a GM-CSF-dependent cell line in response to a limiting amount of GM-CSF, are also conveniently employed, as are assays that measure amounts of cytokine production, e.g., IL-8 production, in response to GM-CSF exposure.

As used herein, "neutralizing antibody" refers to an antibody that binds to GM-CSF and inhibits signaling by the GM-CSF receptor, or prevents binding of GM-CSF to its receptor.

As used herein, "human Granulocyte Macrophage-Colony Stimulating Factor" (hGM-CSF) refers to a small naturally occurring glycoprotein with internal disulfide bonds having a molecular weight of approximately 23 kDa; the source and the target of the GM-CSF are human; as such, anti-hGM-CSF antibody, as described in embodiments herein, binds only human and primate GM-CSF, but not mouse, rat, and other mammalian GM-CSF. The hGM-CSF antibodies, as described in embodiments herein, neutralize human GM-CSF. In some embodiments, the hGM-CSF in humans is encoded by a gene located within the cytokine cluster on human chromosome 5. The sequences of the human gene and protein are known. The protein has an N-terminal signal sequence, and a C-terminal receptor binding domain (Rasko and Gough In: The Cytokine Handbook, A. Thomson, et al., Academic Press, New York (1994) pages 349-369). Its three-dimensional structure is similar to that of the interleukins, although the amino acid sequences are not similar. GM-CSF is produced in response to a number of inflammatory mediators present in the hemopoietic environment and at peripheral sites of inflammation. GM-CSF is able to stimulate the production of neutrophilic granulocytes, macrophages, and mixed granulocyte-macrophage colonies from bone marrow cells and can stimulate the formation of eosinophil colonies from fetal liver progenitor cells. GM-CSF can also stimulate some functional activities in mature granulocytes and macrophages and inhibits apoptosis of granulocytes and macrophages.

The term "equilibrium dissociation constant" or "affinity" abbreviated ($K_D$), refers to the dissociation rate constant ($k_d$, time$^{-1}$) divided by the association rate constant ($k_a$, time$^{-1}$ M$^{-1}$). Equilibrium dissociation constants can be measured using any known method in the art. The antibodies of the present invention are high affinity antibodies. Such antibodies have a monovalent affinity better (less) than about 10 nM, and often better than about 500 pM or better than about 50 pM as determined by surface plasmon resonance analysis performed at 37° C. Thus, in some embodiments, the antibodies of the invention have an affinity (as measured using surface plasmon resonance), of less than 50 pM, typically less than about 25 pM, or even less than 10 pM.

In some embodiments, an anti-GM-CSF antibody of the invention has a slow dissociation rate with a dissociation rate constant (kd) determined by surface plasmon resonance analysis at 37° C. for the monovalent interaction with GM-CSF less than approximately 10$^{-4}$ s$^{-1}$, preferably less than 5×10$^{-5}$ s$^{-1}$ and most preferably less than 10$^{-5}$ s$^{-1}$.

As used herein, "chimeric antibody" refers to an immunoglobulin molecule in which (a) the constant region, or a portion thereof, is altered, replaced or exchanged so that the antigen binding site (variable region) is linked to a constant region of a different or altered class, effector function and/or species, or an entirely different molecule that confers new properties to the chimeric antibody, e.g., an enzyme, toxin, hormone, growth factor, drug, etc.; or (b) the variable region, or a portion thereof, is altered, replaced or exchanged with a variable region, or portion thereof, having a different or altered antigen specificity; or with corresponding sequences from another species or from another antibody class or subclass.

As used herein, "humanized antibody" refers to an immunoglobulin molecule in CDRs from a donor antibody are grafted onto human framework sequences. Humanized antibodies may also comprise residues of donor origin in the framework sequences. The humanized antibody can also comprise at least a portion of a human immunoglobulin constant region. Humanized antibodies may also comprise residues which are found neither in the recipient antibody nor in the imported CDR or framework sequences. Humanization can be performed using methods known in the art (e.g., Jones et al., *Nature* 321:522-525; 1986; Riechmann et al., *Nature* 332:323-327, 1988; Verhoeyen et al., *Science* 239:1534-1536, 1988); Presta, *Curr. Op. Struct. Biol.* 2:593-596, 1992; U.S. Pat. No. 4,816,567), including techniques such as "superhumanizing" antibodies (Tan et al., *J. Immunol.* 169: 1119, 2002) and "resurfacing" (e.g., Staelens et al., *Mol. Immunol.* 43: 1243, 2006; and Roguska et al., *Proc. Natl. Acad. Sci USA* 91: 969, 1994).

A "HUMANEERED®" antibody in the context of this invention refers to an engineered human antibody having a binding specificity of a reference antibody. An engineered human antibody for use in this invention has an immunoglobulin molecule that contains minimal sequence derived from a donor immunoglobulin. In some embodiments, the engineered human antibody may retain only the minimal essential binding specificity determinant from the CDR3 regions of a reference antibody. Typically, an engineered human antibody is engineered by joining a DNA sequence encoding a binding specificity determinant (BSD) from the CDR3 region of the heavy chain of the reference antibody to human $V_H$ segment sequence and a light chain CDR3 BSD from the reference antibody to a human $V_L$ segment sequence. A "BSD" refers to a CDR3-FR4 region, or a portion of this region that mediates binding specificity. A binding specificity determinant therefore can be a CDR3-FR4, a CDR3, a minimal essential binding specificity determinant of a CDR3 (which refers to any region smaller than the CDR3 that confers binding specificity when present in the V region of an antibody), the D segment (with regard to a heavy chain region), or other regions of CDR3-FR4 that confer the binding specificity of a reference antibody. Methods for engineering human antibodies are provided in US patent application publication no. 20050255552 and US patent application publication no. 20060134098.

The term "human antibody" as used herein refers to an antibody that is substantially human, i.e., has FR regions, and often CDR regions, from a human immune system. Accordingly, the term includes humanized and humaneered antibodies as well as antibodies isolated from mice reconstituted with a human immune system and antibodies isolated from display libraries.

The term "heterologous" when used with reference to portions of a nucleic acid indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid. Similarly, a heterologous protein will often refer to two or more subsequences that are not found in the same relationship to each other in nature.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under-expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operable linkage of different sequences is achieved. Thus, an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid.

The phrase "specifically (or selectively) binds" to an antibody or is "specifically (or selectively) immunoreactive with", refers to a binding reaction where the antibody binds to the antigen of interest. In the context of this invention, the antibody typically binds to the antigen, e.g., GM-CSF, with an affinity of 500 nM or less, and has an affinity of 5000 nM or greater, for other antigens.

The terms "identical" or percent "identity," in the context of two or more polypeptide (or nucleic acid) sequences, refer to two or more sequences or subsequences that are the same or have a specified percentage of amino acid residues (or nucleotides) that are the same (i.e., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site). Such sequences are then said to be "substantially identical." "Substantially identical" sequences also includes sequences that have deletions and/or additions, as well as those that have substitutions, as well as naturally occurring, e.g., polymorphic or allelic variants, and man-made variants. As described below, the preferred algorithms can account for gaps and the like. Preferably, protein sequence identity exists over a region that is at least about 25 amino acids in length, or more preferably over a region that is 50-100 amino acids=in length, or over the length of a protein.

A "comparison window", as used herein, includes reference to a segment of one of the number of contiguous positions selected from the group consisting typically of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

An indication that two polypeptides are substantially identical is that the first polypeptide is immunologically cross reactive with the antibodies raised against the second polypeptide. Thus, a polypeptide is typically substantially identical to a second polypeptide, e.g., where the two peptides differ only by conservative substitutions.

Preferred examples of algorithms that are suitable for determining percent sequence identity and sequence similarity include the BLAST and BLAST 2.0 algorithms, which are described in Altschul et al., *Nuc. Acids Res.* 25:3389-3402 (1977) and Altschul et al., *J. Mol. Biol.* 215:403-410 (1990). BLAST and BLAST 2.0 are used, with the parameters described herein, to determine percent sequence identity for the nucleic acids and proteins of the invention. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc.*

*Natl. Acad. Sci. USA* 89:10915 (1989)) alignments (B) of 50, expectation (E) of 10, M=5, N=−4, and a comparison of both strands.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high-performance liquid chromatography. A protein that is the predominant species present in a preparation is substantially purified. The term "purified" in some embodiments denotes that a protein gives rise to essentially one band in an electrophoretic gel. Preferably, it means that the protein is at least 85% pure, more preferably at least 95% pure, and most preferably at least 99% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an a carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refer to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables and substitution matrices such as BLOSUM providing functionally similar amino acids are well known in the art. Such conservatively modified variants are in addition to and do not exclude polymorphic variants, interspecies homologs, and alleles of the invention. Typical conservative substitutions for one another include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Methods for Preventing or Treating an Immunotherapy-Related Toxicity

In some embodiments, disclosed herein are methods of inhibiting immunotherapy-related toxicity in a subject. In some embodiments, herein are methods of reducing the incidence of immunotherapy-related toxicity in a subject. In some embodiments, disclosed herein are methods of neutralizing hGM-CSF. In some embodiment, the methods comprise a step of administering a recombinant hGM-CSF antagonist to the subject. In some embodiments, the method comprises hGM-CSF gene silencing. In some embodiments, the method comprises hGM-CSF gene knockout. Methods of gene silencing and gene knockout are well known to those of ordinary skill in the art, and may include, without limitation, RNA interference (RNAi), CRISPR, short interfering RNS (siRNA), DNA-directed RNA interference (ddRNAi), targeted genome editing with engineered transcription activator-like effector nucleases (TALENs) or other suitable techniques.

In some embodiments, inhibiting or reducing the incidence or the severity of immunotherapy-related toxicity comprises reducing immune activation. In some embodiments, inhibiting or reducing the incidence or the severity of immunotherapy-related toxicity comprises ameliorating capillary leak syndrome. In some embodiments, inhibiting or reducing the incidence or the severity of immunotherapy-related toxicity comprises ameliorating a cardiac dysfunction. In some embodiments, inhibiting or reducing the incidence or the severity of immunotherapy-related toxicity comprises ameliorating encephalopathy. In some embodiments, inhibiting or reducing the incidence or the severity of immunotherapy-related toxicity comprises alleviating colitis. In some embodiments, inhibiting or reducing the incidence or the severity of immunotherapy-related toxicity comprises inhibiting convulsions. In some embodiments, inhibiting or reducing the incidence or the severity of immunotherapy-related toxicity comprises ameliorating CRS. In some embodiments, inhibiting or reducing the incidence or the severity of immunotherapy-related toxicity comprises ameliorating neurotoxicity. In various embodiments, the CAR-T cell related neurotoxicity in a subject is reduced by about 90% compared to a reduction in neurotoxicity in a subject treated with CAR-T cells and a control antibody. In certain embodiments, the recombinant GM-CSF antagonist is an antibody, in particular, a GM-CSF neutralizing antibody in accordance with embodiments described herein, including Example 15.

In some embodiments, inhibiting or reducing the incidence or the severity of immunotherapy-related toxicity comprises reducing cytokine storm symptoms. In some embodiments, inhibiting or reducing the incidence or the severity of immunotherapy-related toxicity comprises increasing impaired left ventricular ejection fraction. In some embodiments, inhibiting or reducing the incidence or the severity of immunotherapy-related toxicity comprises ameliorating diarrhea. In some embodiments, inhibiting or reducing the incidence or the severity of immunotherapy-related toxicity comprises ameliorating disseminated intravascular coagulation.

In some embodiments, inhibiting or reducing the incidence or the severity of immunotherapy-related toxicity comprises reducing edema. In some embodiments, inhibiting or reducing the incidence or the severity of immunotherapy-related toxicity comprises alleviating exanthema. In some embodiments, inhibiting or reducing the incidence or the severity of immunotherapy-related toxicity comprises reducing gastrointestinal bleeding. In some embodiments, inhibiting or reducing the incidence or the severity of immunotherapy-related toxicity comprises treating a gastrointestinal perforation. In some embodiments, inhibiting or reducing the incidence or the severity of immunotherapy-related toxicity comprises treating hemophagocytic lymphohistiocytosis (HLH). In some embodiments, inhibiting or reducing the incidence or the severity of immunotherapy-related toxicity comprises treating hepatosis. In some embodiments, inhibiting or reducing the incidence or the severity of immunotherapy-related toxicity comprises reducing hypotension. In some embodiments, inhibiting or reducing the incidence or the severity of immunotherapy-related toxicity comprises reducing hypophysitis.

In some embodiments, inhibiting or reducing the incidence or the severity of immunotherapy-related toxicity comprises inhibiting immune related adverse events. In some embodiments, inhibiting or reducing the incidence or the severity of immunotherapy-related toxicity comprises reducing immunohepatitis. In some embodiments, inhibiting or reducing the incidence or the severity of immunotherapy-related toxicity comprises reducing immunodeficiencies. In some embodiments, inhibiting or reducing the incidence or the severity of immunotherapy-related toxicity comprises treating ischemia. In some embodiments, inhibiting or reducing the incidence or the severity of immunotherapy-related toxicity comprises reducing liver toxicity. In some embodiments, inhibiting or reducing the incidence or the severity of immunotherapy-related toxicity comprises treating macrophage-activation syndrome (MAS). In some embodiments, inhibiting or reducing the incidence or the severity of immunotherapy-related toxicity comprises reducing neurotoxicity symptoms.

In some embodiments, inhibiting or reducing the incidence or the severity of immunotherapy-related toxicity comprises reducing pleural effusions. In some embodiments, inhibiting or reducing the incidence or the severity of immunotherapy-related toxicity comprises reducing pericardial effusions. In some embodiments, inhibiting or reducing the incidence or the severity of immunotherapy-related toxicity comprises reducing pneumonitis.

In some embodiments, inhibiting or reducing the incidence or the severity of immunotherapy-related toxicity comprises reducing polyarthritis. In some embodiments, inhibiting or reducing the incidence or the severity of immunotherapy-related toxicity comprises treating posterior reversible encephalopathy syndrome (PRES). In some embodiments, inhibiting or reducing the incidence or the severity of immunotherapy-related toxicity comprises reducing pulmonary hypertension. In some embodiments, inhibiting or reducing the incidence or the severity of immunotherapy-related toxicity comprises treating thromboembolism. In some embodiments, inhibiting or reducing the incidence or the severity of immunotherapy-related toxicity comprises reducing transaminitis. In some embodiments, inhibiting or reducing the incidence or the severity of immunotherapy-related toxicity comprises reducing a patient's CRES, neurotoxicity (NT), and/or cytokine release syndrome (CRS) grade. In some embodiments, inhibiting or reducing the incidence or the severity of immunotherapy-related toxicity comprises improving a patient's CARTOX-10 score.

In one aspect, this invention further provides a method for treating or preventing immunotherapy-related toxicity in a subject, the method comprising administering to the subject chimeric antigen receptor-expressing T-cells (CAR-T cells), the CAR-T cells having a GM-CSF gene knockout (GM-CSF$^{k/o}$ CAR-T cells), and a recombinant hGM-CSF antagonist, as demonstrated in Examples 6 and 20-21. In some embodiments, the GM-CSF$^{k/o}$ CAR-T cells express a reduced level of GM-CSF compared to a level of GM-CSF expression by wild-type CAR-T cells. In certain embodiments, the GM-CSF$^{k/o}$ CAR-T cells express a level of one or more cytokine and/or chemokine that is lower than or equivalent to a level of the one or more cytokine and/or chemokine expressed by wild-type CAR-T cells. In particular embodiments, the one or more cytokine is a human cytokine selected from the group consisting of IFN-γ, GRO, MDC, IL-2, IL-3, IL-5, IL-7, IP-10, CD107a, TNF-α and VEGF. In some embodiments the one or more cytokine is selected from the group consisting of IFN-γ, IL-1a, IL-1b, IL-2, IL-4, IL-5, IL-6, IL7, IL-9, IL-10, IL-12p40, IL-12p70, ILF, IL-13, LIX, IL-15, IP-10, KC, MCP-1, MIP-1a, MIP-1b, M-CSF MIP-2, MIG, RANTES, and TNF-a, eotaxin, G-CSF and a combination thereof. In various embodiments, the recombinant GM-CSF antagonist is an hGM-CSF antagonist. In some embodiments, the recombinant GM-CSF antagonist is an anti-GM-CSF antibody. In particular embodiments, the anti-GM-CSF antibody binds a human GM-CSF. In other embodiments, the anti-GM-CSF antibody binds a primate GM-CSF. In various embodiments, the anti-GM-CSF antibody binds a mammalian GM-CSF. In some embodiments, the anti-GM-CSF antibody is an anti-hGM-CSF antibody. In certain embodiments, the anti-hGM-CSF antibody is a monoclonal antibody. In various embodiments, the anti-hGM-CSF antibody is an antibody fragment that is a Fab, a Fab', a F(ab')2, a scFv, or a dAB. In some embodiments, the anti-hGM-CSF antibody is a human GM-CSF neutralizing antibody. In certain embodiments, the anti-hGM-CSF antibody is a recombinant or chimeric antibody. In various embodiments, the anti-hGM-CSF antibody is a human antibody. In some embodiments, the CAR-T cells are CD19 CAR-T cells. In particular embodiments, the GM-CSF$^{k/o}$ CAR-T cells enhance anti-tumor activity of the recombinant hGM-CSF antagonist. In specific embodiments, the GM-CSF$^{k/o}$ CAR-T cells improve overall survival of the subject compared to survival in a subject treated by administration of wild-type CAR-T cells. In particular embodiments, administering to the subject the CAR-T cells having a GM-CSF gene knockout (GM-CSF$^{k/o}$ CAR-T cells) and a recombinant hGM-CSF antagonist is a durable treatment for preventing or treating an immunotherapy-related toxicity, such as CRS, neurotoxicity and neuroinflammation. In some embodiments, the subject has cancer. In various embodiments, the cancer is acute lymphoblastic leukemia.

Methods for Reducing Relapse Rate or Preventing Occurrence

In one aspect, this invention provides a method for reducing relapse rate or preventing occurrence of tumor relapse in a subject treated with immunotherapy, the method comprising administering to the subject a recombinant GM-CSF antagonist. In some embodiments, the reducing relapse rate or preventing occurrence of tumor relapse in the subject occurs in an absence of an incidence of immunotherapy-related toxicity. In certain embodiments, the reducing relapse rate or preventing occurrence of tumor relapse in the subject occurs in a presence of an incidence of immunotherapy-related toxicity. In some embodiments, the recombinant GM-CSF antagonist is an hGM-CSF antagonist. In various embodiments, the recombinant GM-CSF antagonist is an anti-GM-CSF antibody. In some embodiments, the anti-GM-CSF antibody binds a human GM-CSF. In certain embodiments, the anti-GM-CSF antibody binds a primate GM-CSF. In various embodiments, the primate is selected from a monkey, a baboon, a macaque, a chimpanzee, a gorilla, a lemur, a lorise, a tarsier, a galago, a potto, a sifaka, an indri, an aye-ayes or an ape. In some embodiments, the anti-GM-CSF antibody binds a mammalian GM-CSF.

In particular embodiments, the anti-GM-CSF antibody is an anti-hGM-CSF antibody. As described above, the anti-GM-CSF antibody is a monoclonal antibody. In another embodiment, the anti-hGM-CSF antibody is an antibody fragment that is a Fab, a Fab', a F(ab')2, a scFv, or a dAB. In some embodiments, the anti-hGM-CSF antibody is a human GM-CSF neutralizing antibody. In certain embodiments, the anti-hGM-CSF antibody is a recombinant or chimeric antibody. In various embodiments, the anti-hGM-CSF antibody is a human antibody. In some embodiments, the anti-hGM-CSF antibody binds to the same epitope as chimeric 19/2 antibody. In certain embodiments, the anti-hGM-CSF antibody comprises the VH region CDR3 and VL region CDR3 of chimeric 19/2 antibody. In various embodiments, the anti-hGM-CSF antibody comprises the VH region and VL region CDR1, CDR2, and CDR3 of chimeric 19/2. In some embodiments, the anti-hGM-CSF antibody comprises a VH region that comprises a CDR3 binding specificity determinant RQRFPY (SEQ ID NO: 12) or RDRFPY (SEQ ID NO: 13), a J segment, and a V-segment, wherein the J-segment comprises at least 95% identity to human JH4 (YFD YWGQGTL VTVSS (SEQ ID NO: 14)) and the V-segment comprises at least 90% identity to a human germ line VHl 1-02 or VHl 1-03 sequence; or a VH region that comprises a CDR3 binding specificity determinant RQRFPY(SEQ ID NO: 12). In particular embodiments, the J segment comprises YFDYWGQGTLVTVSS (SEQ ID NO: 14). In additional embodiments, the CDR3 comprises RQRFPYYFDY (SEQ ID NO: 15) or RDRFPYYFDY (SEQ ID NO: 16). In some embodiments, the VH region CDR1 is a human germline VHl CDR1; the VH region CDR2 is a human germline VHl CDR2; or both the CDR1 and CDR2 are from a human germline VHl sequence.

In certain embodiments, the anti-hGM-CSF antibody comprises a VH CDR1, or a VH CDR2, or both a VH CDR1 and a VH CDR2 as shown in a VH region set forth in FIG. 1. In various embodiments, the V-segment sequence has a VH V segment sequence shown in FIG. 1. In certain embodiments, the VH has the sequence of VH #1 (SEQ ID NO:1), VH #2 (SEQ ID NO:2), VH #3 (SEQ ID NO:3), VH #4 (SEQ ID NO:4), or VH #5 (SEQ ID NO:5) set forth in FIG. 1. In some embodiments, the anti-hGM-CSF antibody comprises a VL-region that comprises a CDR3 comprising the amino acid sequence FNK or FNR. In some embodiments, the anti-hGM-CSF antibody comprises a human germline JK4 region. In certain embodiments, the VL region CDR3 comprises QQFN(K/R)SPLT (SEQ ID NO: 17). In various embodiments, the anti-hGM-CSF antibody comprises a VL region that comprises a CDR3 comprising QQFNKSPLT (SEQ ID NO: 18). In some embodiments, the VL region comprises a CDR1, or a CDR2, or both a CDR1 and CDR2 of a VL region shown in FIG. 1. In particular embodiments, the VL region comprises a V segment that has at least 95% identity to the VKIII A27 (SEQ ID NO: 21) V-segment sequence as shown in FIG. 1. In some embodiments, the VL region has the sequence of VK #1 (SEQ ID NO: 6), VK #2 (SEQ ID NO: 7), VK #3 (SEQ ID NO: 8), or VK #4 (SEQ ID NO: 9) set forth in FIG. 1. In certain embodiments, the anti-hGM-CSF antibody has a VH region CDR3 binding specificity determinant RQRFPY (SEQ ID NO: 12) or RDRFPY (SEQ ID NO: 13) and a VL region that has a CDR3 comprising QQFNKSPLT (SEQ ID NO: 18). In some embodiments, the anti-hGM-CSF antibody has a VH region sequence set forth in FIG. 1 and a VL region sequence set forth in FIG. 1. In other embodiments, the VH region or the VL region, or both the VH and VL region amino acid sequences comprise a methionine at the N-terminus.

In some embodiments, the hGM-CSF antagonist is selected from the group comprising of an anti-hGM-CSF receptor antibody or a soluble hGM-CSF receptor, a cytochrome b562 antibody mimetic, a hGM-CSF peptide analog, an adnectin, a lipocalin scaffold antibody mimetic, a calixarene antibody mimetic, and an antibody like binding peptidomimetic. In certain embodiments, the CAR-T cells are CD19 CAR-T cells. In particular embodiments, the immunotherapy-related toxicity is CAR-T related toxicity. In some embodiments, the CAR-T related toxicity is CRS, NT or neuro-inflammation.

In particular embodiments, the tumor relapse occurrence is reduced by from 50% to 100% in the first one-quarter of a year after administering the recombinant GM-CSF antagonist compared to tumor relapse occurrence in a subject treated with immunotherapy and not administered a recombinant GM-CSF antagonist. In certain embodiments, the tumor relapse occurrence is reduced by from 50% to 95% in the first half-year after administering the recombinant GM-CSF antagonist. In various embodiments, the tumor relapse occurrence is reduced by from 50% to 90% in the first year after administering the recombinant GM-CSF antagonist. In some embodiments, the tumor relapse occurrence is prevented long-term. As used herein the term "long-term" means during an extended period of time of at least a year, i.e. 12 months, from the last date of treatment with a recombinant hGM-CSF antagonist. In some embodiments, the recombinant hGM-CSF antagonist is a hGM-CSF neutralizing antibody. In various embodiments, the recombinant hGM-CSF antagonist is an anti-hGM-CSF antibody, e.g., Lenzilumab. In certain embodiments, the tumor relapse occurrence is prevented by 12-36 months. In some embodiments, the tumor relapse occurrence is prevented "completely" (100%), which as used herein means that there is no recurrence of the tumor for at least 12 months, from the last date of treatment with a recombinant hGM-CSF antagonist. In certain embodiments, the subject has acute lymphoblastic leukemia.

In various embodiments of the herein provided methods for reducing relapse rate or preventing occurrence of tumor relapse in a subject treated with immunotherapy, the subject has a "refractory cancer", which as used herein is (a) a malignancy (also called "cancer" or a "tumor" herein) for which surgery is ineffective and is (b) either initially unresponsive or resistant to treatment, wherein the treatment is chemotherapy, radiation or a combination thereof, or is (b) a malignancy which becomes or has become unresponsive to the aforementioned treatment(s). In some embodiments, the subject has a "relapsed" cancer, which as used herein is a cancer that responded but to treatment, but has returned. In particular embodiments, the refractory cancer or the relapsed cancer is non-Hodgkin lymphoma (NHL). In various embodiments, the refractory cancer or the relapsed cancer is non-Hodgkin lymphoma (NHL). In certain embodiments, the refractory cancer is refractory aggressive B cell non-Hodgkin lymphoma. In some embodiments, the refractory cancer or the relapsed cancer is chemo-refractory B cell lymphoma. In various embodiments, the refractory cancer or the relapsed cancer is hormone-refractory prostate cancer. In certain embodiments, the refractory cancer or the relapsed cancer is a pediatric cancer. In some embodiments, the refractory pediatric cancer or the relapsed pediatric cancer is neuroblastoma. In particular embodiments, the refractory pediatric cancer or the relapsed pediatric cancer is a pediatric leukemia selected from the group consisting of acute lymphoblastic leukemia (ALL), acute myelogenous leukemia (AML) or an uncommon pediatric leukemia which is juvenile myelomonocytic leukemia or chronic myeloid leukemia. In certain embodiments, the refractory cancer or the relapsed cancer is a pediatric bone cancer. In some embodiments, the refractory cancer or the relapsed cancer is an adrenal cancer. In various embodiments, the refractory cancer or the relapsed cancer is a breast cancer. In certain embodiments, the refractory cancer or the relapsed cancer is a colon cancer, rectal cancer or colorectal cancer. In particular embodiments, the refractory cancer or the relapsed cancer is a T-cell lymphoma. In some embodiments, the refractory cancer or the relapsed cancer is a head and neck cancer. In some embodiments, the refractory cancer or the relapsed cancer is a brain and/or spinal cord cancer, including but not limited to glioma an glioblastoma. In additional embodiments, the refractory cancer or the relapsed cancer is a tumor of bone or soft tissue, including but not limited to a chondrosarcoma. In various embodiments, the refractory cancer or the relapsed cancer is a bone cancer. In some embodiments, the refractory cancer or the relapsed cancer is esophageal cancer. In certain embodiments, the refractory cancer or the relapsed cancer is a gall bladder cancer. In some embodiments, the refractory cancer or the relapsed cancer is a kidney cancer. In various embodiments, the refractory cancer or the relapsed cancer is melanoma. In some embodiments, the refractory cancer or the relapsed cancer is an ovary cancer. In certain embodiments, the refractory cancer or the relapsed cancer is a pancreatic cancer. In some embodiments, the refractory cancer or the relapsed cancer is a skin cancer selected from a basal cell carcinoma, a squamous cell carcinoma or a melanoma. In various embodiments, the refractory cancer or the relapsed cancer is a lung cancer. In some embodiments, the refractory cancer or the relapsed cancer is a salivary gland cancer. In additional embodiments, the refractory cancer or the relapsed cancer is a uterine smooth muscle cancer. In some embodiments, the refractory cancer or the relapsed cancer is a testicular cancer. In various embodiments, the refractory cancer or the relapsed cancer is a stomach cancer or a gastrointestinal cancer. In certain embodiments, the refractory cancer or the relapsed cancer is a bladder cancer. In additional embodiments, the refractory cancer or the relapsed cancer is an adipose tissue neoplasm. In some embodiments, the refractory pediatric cancer or the relapsed pediatric cancer is an adenocarcinoma. In certain embodiments, the refractory cancer or the relapsed cancer is a thymoma. In various embodiments, the refractory cancer or the relapsed cancer is an angiosarcoma, i.e., a cancer of the lining of blood vessels, which can occur in any part of the body, including but not limited to skin, breast, liver, spleen and deep tissue, i.e., deep-seated tumors. In some embodiments, the refractory cancer or the relapsed cancer is a metastasis of any one of the aforementioned refractory cancer or the relapsed cancer.

In some embodiments, the immunotherapy is an activation immunotherapy. In some embodiments, immunotherapy is provided as a cancer treatment. In some embodiments, immunotherapy comprises adoptive cell transfer.

In some embodiments, adoptive cell transfer comprises administration of a chimeric antigen receptor-expressing T-cell (CAR T-cell). A skilled artisan would appreciate that CARs are a type of antigen-targeted receptor composed of intracellular T-cell signaling domains fused to extracellular tumor-binding moieties, most commonly single-chain variable fragments (scFvs) from monoclonal antibodies. CARs directly recognize cell surface antigens, independent of MHC-mediated presentation, permitting the use of a single receptor construct specific for any given antigen in all patients. Initial CARs fused antigen-recognition domains to the CD3ζ activation chain of the T-cell receptor (TCR) complex. While these first-generation CARs induced T-cell effector function in vitro, they were largely limited by poor antitumor efficacy in vivo. Subsequent CAR iterations have included secondary costimulatory signals in tandem with CD3, including intracellular domains from CD28 or a variety of TNF receptor family molecules such as 4-1BB (CD137) and OX40 (CD134). Further, third generation receptors include two costimulatory signals in addition to CD3ζ, most commonly from CD28 and 4-1BB. Second and third generation CARs dramatically improve antitumor efficacy, in some cases inducing complete remissions in patients with advanced cancer. In one embodiment, a CAR T-cell is an immunoresponsive cell modified to express CARs, which is activated when CARs bind to its antigen.

In one embodiment, a CAR T-cell is an immunoresponsive cell comprising an antigen receptor, which is activated when its receptor binds to its antigen. In one embodiment, the CAR T-cells used in the compositions and methods as disclosed herein are first generation CAR T-cells. In another embodiment, the CAR T-cells used in the compositions and methods as disclosed herein are second generation CAR T-cells. In another embodiment, the CAR T-cells used in the compositions and methods as disclosed herein are third generation CAR T-cells. In another embodiment, the CAR T-cells used in the compositions and methods as disclosed herein are fourth generation CAR T-cells.

In some embodiments, adoptive cell transfer comprises administering T-cell receptor (TCR) modified T-cells. A skilled artisan would appreciate that TCR modified T-cells are manufactured by isolating T-cells from tumor tissue and isolating their TCRα and TCRβ chains. These TCRα and TCRβ are later cloned and transfected into T cells isolated from peripheral blood, which then express TCRα and TCRβ from T-cells recognizing the tumor.

In some embodiments, adoptive cell transfer comprises administering tumor infiltrating lymphocytes (TIL). In some embodiments, adoptive cell transfer comprises administering chimeric antigen receptor (CAR)-modified NK cells. A skilled artisan would appreciate that CAR-modified NK cells comprise NK cells isolated from the patient or commercially available NK engineered to express a CAR that recognizes a tumor-specific protein.

In some embodiments, adoptive cell transfer comprises administering dendritic cells.

In some embodiments, immunotherapy comprises administering monoclonal antibodies. In some embodiments, monoclonal antibodies attach to specific proteins on cancer cells, thus flagging the cells for the immune system finding and destroying them. In some embodiments, monoclonal antibodies work by inhibiting immune checkpoints, thus hindering the inhibition of the immune system by cancer cells. In some embodiments, monoclonal antibodies improve utility of CAR-T to synergize with checkpoint inhibitors.

In some embodiments, the antibody targets a protein selected from the group comprising: 5AC, 5T4, activin receptor-like kinase 1, AGS-22M6, alpha-fetoprotein, angiopoietin 2, angiopoietin 3, B7-H3, BAFF, BCMA, C242 antigen, CA-125, carbonic anhydrase 9, CCR4, CD125, CD152, CD184, CD19, CD2, CD20, CD200, CD22, CD221, CD23, CD25, CD27, CD274, CD276, CD28, CD3, CD30, CD33, CD37, CD38, CD4, CD40, CD41, CD44 v6, CD49b, CD5, CD51, CD52, CD54, CD56, CD6, CD70, CD74, CD79B, CD80, CEA, CFD, CGRP, ch4D5, CLDN18.2, clumping factor A, CSF1R, CSF2, CTGF, CTLA-4, DLL3, DLL4, DPP4, DR5, EGFL7, EGFR, endoglin, EpCAM, ephrin receptor A3, episialin, ERBB3 (HER3), FAP, FGF 23, fibrin II, beta chain, fibronectin extra domain-B, folate hydrolase, folate receptor, Frizzled receptor, GCGR, GD2 ganglioside, GD3 ganglioside, GDF-8, glypican 3, GM-CSF, GM-CSF receptor α-chain, GPNMB, GUCY2C, HER1, HER2/neu, HGF, HHGFR, histone complex, human scatter factor receptor kinase, human TNF, ICOSL, IFN-α, IGF1, IGF2, IGHE, IL-17A, IL-13, IL1A, IL-2, IL-6, IL-6 receptor, IL-8, IL-9, ILGF2, integrin α4, integrin α5β1, integrin α7 β7, integrin αvβ3, IP10, KIR2D, KLRC1, Lewis-Y antigen, MAGE-A, MCP-1, mesothelin, MIF, MIG, MIP1β, MS4A1, MSLN, MUC1, mucin CanAg, N-glycolylneuraminic acid, NOGO-A, Notch 1, Notch receptor, NRP1, OX-40, PD-1, PDCD1, PDGF-R α, phosphate-sodium co-transporter, phosphatidylserine, platelet-derived growth factor receptor beta, prostatic carcinoma cells, RHD, RON, RTN4, SDC1, sIL2Rα, SLAMF7, SOST, sphingosine-1-phosphate, *Staphylococcus aureus*, STEAP1, TAG-72, T-cell receptor, TEM1, tenascin C, TFPI, TGF beta 1, TGF beta 2, TGF-β, TNFR superfamily member 4, TNF-α, TRAIL-R1, TRAIL-R2, TRP-1, TRP-2, TSLP, tumor antigen CTAA16.88, tumor specific glycosylation of MUC1, tumor-associated calcium signal transducer 2, TWEAK receptor, TYRP1 (glycoprotein 75), VEGFA, VEGFR-1, VEGFR2, vimentin, and VWF.

In some embodiments, the antibody is a bi-specific antibody. In some embodiments, the antibody is a bispecific T-cell engager (BiTE) antibody. In some embodiments, the antibody is selected from a group comprising: ipilimumab, nivolumab, pembrolizumab, atezolizumab, avelumab, durvalumab, rituximab, TGN1412, alemtuzumab, OKT3 or any combination thereof.

In some embodiments, immunotherapy comprises administering cytokines. A skilled artisan would appreciate that cytokines can be administered in order to enhance the immune system to attack the tumor by increasing its recognition and killing by immune cytotoxic cells. In some embodiments, the cytokine is selected from a group comprising: IFNα, IFNβ, IFNγ, IFNλ, IL-1, IL-2, IL-6, IL-7, IL-15, IL-21, IL-11, IL-12, IL-18, GM-CSF, TNFα, or any combination thereof.

In some embodiments, immunotherapy comprises administering immune checkpoint inhibitors. A skilled artisan would appreciate that immune checkpoints are membranal proteins that keep T cells from attacking the cells that express it. Immune checkpoints are often expressed by cancer cells, thus preventing T cells from attacking them. In some embodiments, checkpoint proteins comprise PD-1/PD-L1 and CTLA-4/B7-1/B7-2. Blocking checkpoint proteins was shown to disengage the inhibition of T cells to attack and kill cancer cells. In some embodiments, checkpoint inhibitors are selected from a group comprising molecules blocking CTLA-4, PD-1, or PD-L1. In some embodiments, the checkpoint inhibitors are antibodies or parts thereof.

In some embodiments, immunotherapy comprises administering polysaccharides. A skilled artisan would appreciate that certain polysaccharides found in mushroom enhance the immune system and its anti-cancer properties. In some embodiments, polysaccharides are beta-glucans or lentinan.

In some embodiments, immunotherapy comprises administering or a cancer vaccine. A skilled artisan would appreciate that a cancer vaccine exposes the immune system to a cancer-specific antigen and an adjuvant. In some embodiments, the cancer vaccine is selected from a group comprising: sipuleucel-T, GVAX, ADXS11-001, ADXS31-001, ADXS31-164, ALVAC-CEA vaccine, AC Vaccine, talimogene laherparepvec, BiovaxID, Prostvac, CDX110, CDX1307, CDX1401, CimaVax-EGF, CV9104, DNDN, NeuVax, Ae-37, GRNVAC, tarmogens, GI-4000, GI-6207, GI-6301, ImPACT Therapy, IMA901, hepcortespenlisimut-L, Stimuvax, DCVax-L, DCVax-Direct, DCVax Prostate, CBLI, Cvac, RGSH4K, SCIB1, NCT01758328, and PVX-410.

Methods for Reducing a Level of a Cytokine or Chemokine Other than GM-CSF

In some embodiments, inhibiting or reducing the incidence or the severity of immunotherapy-related toxicity comprises decreasing the concentration of at least one inflammation-associated factor in a body fluid. In some embodiments, inhibiting or reducing the incidence or the severity of immunotherapy-related toxicity comprises decreasing the concentration of at least one inflammation-associated factor in the serum. In some embodiments, inhibiting or reducing the incidence or the severity of immunotherapy-related toxicity comprises decreasing the concentration of at least one inflammation-associated factor in the cerebrospinal fluid (CSF). In some embodiments, disclosed herein are methods for decreasing the concentration of at least one inflammation-associated factor in serum. In some embodiments, disclosed herein are methods for decreasing the concentration of at least one inflammation-associated factor in a tissue fluid. In some embodiments, disclosed herein are methods for decreasing the concentration of at least one inflammation-associated factor in CSF. In some embodiments, the concentration of at least one inflammation-associated factor in serum is decreased. In some embodiments, the concentration of at least one inflammation-associated factor in a tissue fluid is decreased. In some embodiments, the concentration of at least one inflammation-associated factor in CSF is decreased. A skilled artisan would appreciate that decreasing the concentration of an inflammation-associated factor comprises decreasing or inhibiting the production of said inflammation-associated factor in a subject, or inhibiting or reducing the incidence or the severity of immunotherapy-related toxicity in a subject. In another embodiment, decreasing or inhibiting the production of an inflammation-associated factor comprises treating immunotherapy-related toxicity. In another embodiment, decreasing or inhibiting the production of an inflammation-associated factor comprises preventing immunotherapy-related toxicity. In another embodiment, decreasing or inhibiting the production of an inflammation-associated factor levels comprises alleviating immunotherapy-related toxicity. In another embodiment, decreasing or inhibiting the production of an inflammation-associated factor comprises ameliorating immunotherapy-related toxicity.

In some embodiments, the inflammation-associated factor is a cytokine. In some embodiments, inhibiting or reducing the incidence or the severity of immunotherapy-related toxicity comprises decreasing the concentration of at least one cytokine in the serum. In some embodiments, inhibiting or reducing the incidence or the severity of immunotherapy-related toxicity comprises decreasing the concentration of at least one cytokine in the CSF.

In some embodiments, the cytokine is hGM-CSF. In some embodiments, the cytokine is interleukin (IL)-1β. In some embodiments, the cytokine is IL-2. In some embodiments, the cytokine is sIL2Rα. In some embodiments, the cytokine is IL-5. In some embodiments, the cytokine is IL-6. In some embodiments, the cytokine is IL-8. In some embodiments, the cytokine is IL-10. In some embodiments, the cytokine is IP10. In some embodiments, the cytokine is IL-13. In some embodiments, the cytokine is IL-15. In some embodiments, the cytokine is tumor necrosis factor α (TNFα). In some embodiments, the cytokine is interferon γ (IFNγ). In some embodiments, the cytokine is monokine induced by gamma interferon (MIG). In some embodiments, the cytokine is macrophage inflammatory protein (MIP) 1β. In some embodiments, the cytokine is C-reactive protein. In some embodiments, decreasing or inhibiting the production of cytokine levels comprises decreasing or inhibiting the production of one cytokine. In some embodiments, decreasing or inhibiting the production of cytokine levels comprises decreasing or inhibiting the production of at least one cytokine. In some embodiments, decreasing or inhibiting the production of cytokine levels comprises decreasing or inhibiting the production of a number of cytokines.

In one aspect, this invention provides a method reducing a level of a cytokine or chemokine other than GM-CSF in a subject having an incidence of immunotherapy-related toxicity, the method comprising administering to the subject a recombinant hGM-CSF antagonist, wherein the level of the cytokine or chemokine is reduced compared the level thereof in a subject administered an isotype control antibody during the incidence of immunotherapy-related toxicity. In some embodiments, the immunotherapy comprises adoptive cell transfer, administration of monoclonal antibodies, administration of a cancer vaccine, T cell engaging therapies, or any combination thereof. In certain embodiments, the adoptive cell transfer comprises administering chimeric antigen receptor-expressing T-cells (CAR T-cells), T-cell receptor (TCR) modified T-cells, tumor-infiltrating lymphocytes (TIL), chimeric antigen receptor (CAR)-modified natural killer cells, or dendritic cells, or any combination thereof. In some embodiments, the CAR-T cells are CD19 CAR-T cells. In certain embodiments, the recombinant GM-CSF antagonist is an hGM-CSF antagonist. In various embodiments, the recombinant GM-CSF antagonist is an anti-GM-CSF antibody. In particular embodiments, the anti-GM-CSF antibody binds a human GM-CSF. In other embodiments, the anti-GM-CSF antibody binds a primate GM-CSF, as described above. In some embodiments, the anti-GM-CSF antibody binds a mammalian GM-CSF. In certain embodiments, the anti-GM-CSF antibody is an anti-hGM-CSF antibody. In some embodiments, the anti-hGM-CSF antibody is a monoclonal antibody. In various embodiments, the anti-hGM-CSF antibody is an antibody fragment that is a Fab, a Fab', a F(ab')2, a scFv, or a dAB. In some embodiments, the anti-hGM-CSF antibody is a human GM-CSF neutralizing antibody. In certain embodiments, the anti-hGM-CSF antibody is a recombinant or chimeric antibody. In some embodiments, the anti-hGM-CSF antibody is a human antibody. In particular embodiments, the cytokine or chemokine is a human cytokine or chemokine selected from the group consisting of IP-10, IL-2, IL-3, IL-5, IL-1Ra, VEGF, TNF-a, FGF-2, IFN-γ, IL-12p40, IL-12p70, sCD40L, MDC, MCP-1, MIP-1a, MIP-1b or a combination thereof, as demonstrated in Example 22. In some embodiments, the cytokine or chemokine is selected from the group consisting of IL-1a, IL-1b, IL-2, IL-4, IL-6, IL-9, IL-10, IP-10, KC, MCP-1, MIP or a combination thereof (see Example 22). In certain embodiments, the subject has acute lymphoblastic leukemia.

In one embodiment, the methods disclosed herein do not affect the efficacy of the immunotherapy. In another embodiment, the methods disclosed herein reduce the efficacy of the immunotherapy by less than about 5%. In another embodiment, the methods disclosed herein reduce the efficacy of the immunotherapy by less than about 10%. In another embodiment, the methods disclosed herein reduce the efficacy of the immunotherapy by less than about 15%. In another embodiment, the methods disclosed herein reduce the efficacy of the immunotherapy by less than about 20%. In another embodiment, the methods disclosed herein reduce the efficacy of the immunotherapy by less than about 50%.

In one embodiment, the methods described herein increase the efficacy of the immunotherapy. In one embodiment, increasing the efficacy allows for improvement of the clinical management, patient outcomes, and therapeutic index of the immunotherapy. In another embodiment, the increased efficacy enables administration of higher immunotherapy doses. In another embodiment, the increased efficacy reduces hospitalization stay and additional treatments and monitoring. In an embodiment, the immunotherapy comprises CAR-T.

Any appropriate method of quantifying cytotoxicity can be used to determine whether the immunotherapy efficacy remains substantially unchanged. For example, cytotoxicity can be quantified using a cell culture-based assay such as the cytotoxic assays described in the Examples. Cytotoxicity assays can employ dyes that preferentially stain the DNA of dead cells. In other cases, fluorescent and luminescent assays that measure the relative number of live and dead cells in a cell population can be used. For such assays, protease activities serve as markers for cell viability and cell toxicity, and a labeled cell permeable peptide generates fluorescent signals that are proportional to the number of viable cells in the sample. In another embodiment, a measure of cytotoxicity may be qualitative. In another embodiment, a measure of cytotoxicity may be quantitative.

In an embodiment, said increased efficacy comprises increased CAR-T cell expansion, reduced number and/or activity of myeloid-derived suppressor cells (MDSC) that inhibit T-cell function, synergy with a checkpoint inhibitor, or any combination thereof. In another embodiment, said increased CAR-T cell expansion comprises at least a 50% increase compared to a control. In another embodiment, said increased CAR-T cell expansion comprises at least a one quarter log expansion compared to a control. In another embodiment, said increased cell expansion comprises at least a one-half log expansion compared to a control. In another embodiment, said increased cell expansion comprises at least a one log expansion compared to a control. In another embodiment, said increased cell expansion comprises a greater than one log expansion compared to a control.

In one embodiment, immunotherapy-related toxicity appears between 2 days to 4 weeks after administration of immunotherapy. In one embodiment, immunotherapy-related toxicity appears between 0 to 2 days after administration of immunotherapy. In some embodiments, the hGM-CSF antagonist is administered to subjects at the same time as immunotherapy as prophylaxis. In another embodiment, the hGM-CSF antagonist is administered to subjects 0-2 days after administration of immunotherapy. In another embodiment, the hGM-CSF antagonist is administered to subjects 2-3 days after administration of immunotherapy. In another embodiment, the hGM-CSF antagonist is administered to subjects 7 days after administration of immunotherapy. In another embodiment, the hGM-CSF antagonist is administered to subjects 10 days after administration of immunotherapy. In another embodiment, the hGM-CSF antagonist is administered to subjects 14 days after administration of immunotherapy. In another embodiment, the hGM-CSF antagonist is administered to subjects 2-14 days after administration of immunotherapy.

In another embodiment, the hGM-CSF antagonist is administered to subjects 2-3 hours after administration of immunotherapy. In another embodiment, the hGM-CSF antagonist is administered to subjects 7 hours after administration of immunotherapy. In another embodiment, the hGM-CSF antagonist is administered to subjects 10 hours after administration of immunotherapy. In another embodiment, the GM-CSF antagonist is administered to subjects 14 hours after administration of immunotherapy. In another embodiment, the hGM-CSF antagonist is administered to subjects 2-14 hours after administration of immunotherapy.

In an alternative embodiment, the hGM-CSF antagonist is administered to subjects prior to immunotherapy as prophylaxis. In another embodiment, the hGM-CSF antagonist is administered to subjects 1 day before administration of immunotherapy. In another embodiment, the hGM-CSF antagonist is administered to subjects 2-3 days before administration of immunotherapy. In another embodiment, the hGM-CSF antagonist is administered to subjects 7 days before administration of immunotherapy. In another embodiment, the hGM-CSF antagonist is administered to subjects 10 days before administration of immunotherapy. In another embodiment, the hGM-CSF antagonist is administered to subjects 14 days before administration of immunotherapy. In another embodiment, the hGM-CSF antagonist is administered to subjects 2-14 days before administration of immunotherapy.

In another embodiment, the hGM-CSF antagonist is administered to subjects 2-3 hours before administration of immunotherapy. In another embodiment, the hGM-CSF antagonist is administered to subjects 7 hours before administration of immunotherapy. In another embodiment, the hGM-CSF antagonist is administered to subjects 10 hours before administration of immunotherapy. In another embodiment, the hGM-CSF antagonist is administered to subjects 14 hours before administration of immunotherapy. In another embodiment, the hGM-CSF antagonist is administered to subjects 2-14 hours before administration of immunotherapy.

In another embodiment, the hGM-CSF antagonist may be administered therapeutically, once immunotherapy-related toxicity has occurred. In one embodiment, the hGM-CSF antagonist may be administered once pathophysiological processes leading up to or attesting to the beginning of immunotherapy-related toxicity are detected. In one embodiment, the hGM-CSF antagonist can terminate the pathophysiological processes and avoid its sequelae. In some embodiments, the pathophysiological processes comprise at least one of the following: increased cytokine concentrations in serum, increased cytokine concentrations in CSF, increased C-reactive protein (CRP) in serum, increased ferritin in the serum, increased IL-6 in serum, endothelial activation, disseminated intravascular coagulation (DIC), increased ANG2 serum concentration, increased ANG2:ANG1 ratio in serum, CAR T-cell presence in CSF, increased Von Willebrand factor (VWF) serum concentration, blood-brain-barrier (BBB) leakage, or any combination thereof.

In another embodiment, the hGM-CSF antagonist may be administered therapeutically, at multiple time points. In another embodiment, administration of the hGM-CSF antagonist is at least at two time points. In another embodiment, administration of the hGM-CSF antagonist is at least at three time points.

In one embodiment, the hGM-CSF antagonist is administered once. In another embodiment, the hGM-CSF antagonist is administered twice. In another embodiment, the hGM-CSF antagonist is administered three times. In another embodiment, the hGM-CSF antagonist is administered four times. In another embodiment, the hGM-CSF antagonist is administered at least four times. In another embodiment, the hGM-CSF antagonist is administered more than four times.

A skilled artisan would appreciate that immunotherapy-related toxicity is managed by different treatments. In some embodiments, the hGM-CSF antagonist is co-administered with other treatments. In some embodiments, other treatments are selected from a group comprising: cytokine-directed therapy, anti-IL-6 therapy, corticosteroids, tocilizumab, siltuximab, low-dose vasopressors, inotropic agents, supplemental oxygen, diuresis, thoracentesis, antiepileptics, benzodiazepines, levetiracetam, phenobarbital, hyperventilation, hyperosmolar therapy, and standard therapies for specific organ toxicities.

In some embodiments, immunotherapy-related toxicity comprises a brain disease, damage or malfunction. In some embodiments, immunotherapy-related toxicity comprises CAR T-cell related NT. In some embodiments, immunotherapy-related toxicity comprises CAR T-cell-related encephalopathy syndrome (CRES). In some embodiments, provided herein methods for inhibiting or reducing the incidence of a brain disease, damage or malfunction.

In some embodiments, inhibiting or reducing the incidence of CRES comprises ameliorating headaches. In some embodiments, inhibiting or reducing the incidence of CRES comprises alleviating delirium. In some embodiments, inhibiting or reducing the incidence of CRES comprises reducing anxiety. In some embodiments, inhibiting or reducing the incidence of CRES comprises reducing tremors. In some embodiments, inhibiting or reducing the incidence of CRES comprises decreasing seizure activity. In some embodiments, inhibiting or reducing the incidence of CRES comprises decreasing confusion. In some embodiments, inhibiting or reducing the incidence of CRES comprises reducing alterations in wakefulness.

In some embodiments, inhibiting or reducing the incidence of CRES comprises reducing hallucinations. In some embodiments, inhibiting or reducing the incidence of CRES comprises reducing dysphasia. In some embodiments, inhibiting or reducing the incidence of CRES comprises reducing ataxia. In some embodiments, inhibiting or reducing the incidence of CRES comprises reducing apraxia. In some embodiments, inhibiting or reducing the incidence of CRES comprises ameliorating facial nerve palsy. In some embodiments, inhibiting or reducing the incidence of CRES comprises reducing motor weakness. In some embodiments, inhibiting or reducing the incidence of CRES comprises reducing seizures. In some embodiments, inhibiting or reducing the incidence of CRES comprises reducing non-convulsive EEG seizures. In some embodiments, inhibiting or reducing the incidence or severity of CRES comprises improving coma recovery.

In some embodiments, inhibiting or reducing the incidence or severity of CRES comprises reducing endothelial activation. A skilled artisan would appreciate that endothelial activation is an inflammatory and procoagulant state of endothelial cells characterized by increased interactions with leukocytes.

In some embodiments, inhibiting or reducing the incidence of CRES comprises reducing vascular leak. The term "vascular leak" may be used interchangeably with the terms "vascular leak syndrome" and "capillary leak syndrome" having all the same qualities and meanings. A skilled artisan would appreciate that vascular leak is associated with endothelial cells are separated allowing a leakage of plasma and transendothelial migration of inflammatory cells into body tissues, resulting in tissue and organ damage. In addition, neutrophils can cause microcirculatory occlusion, leading to decreased tissue perfusion. In some embodiments reducing the incidence of CRES comprises reducing intravascular coagulation.

In some embodiments, inhibiting or reducing the incidence of CRES comprises reducing the concentration of at least one circulating cytokine. In some embodiments, the cytokine is selected from a group comprising: hGM-CSF, IFNγ, IL-1, IL-15, IL-6, IL-8, IL-10, and IL-2. In some embodiments, inhibiting or reducing the incidence of CRES comprises reducing serum concentration of ANG2. In some embodiments, inhibiting or reducing the incidence of CRES comprises reducing ANG2:ANG1 ratio in serum.

In some embodiments, inhibiting or reducing the incidence of CRES comprises reducing the CRES grade. In some embodiments, inhibiting or reducing the incidence of CRES comprises improving CARTOX-10 score. In some embodiments, inhibiting or reducing the incidence of CRES comprises reducing a raise in intracranial pressure. In some embodiments, inhibiting or reducing the incidence of CRES comprises reducing seizures. In some embodiments, inhibiting or reducing the incidence of CRES comprises reducing motor weakness.

In some embodiments, immunotherapy-related toxicity comprises CAR T-cell related CRS. In some embodiments, provided herein are methods for inhibiting or reducing the incidence or severity of CRS and/or NT.

In some embodiments, inhibiting or reducing the incidence of CRS or NT comprises, without limitation, ameliorating fever (with or without rigors, malaise, fatigue, anorexia, myalgia, arthralgia, nausea, vomiting, headache, skin rash, diarrhea, tachypnea, hypoxemia, hypoxia, shock, cardiovascular tachycardia, widened pulse pressure, hypotension, capillary leak, increased early cardiac output, diminished late cardiac output, elevated D-dimer, hypofibrinogenemia with or without bleeding, azotemia, transaminitis, hyperbilirubinemia, mental status changes, confusion, delirium, frank aphasia, hallucinations, tremor, dysmetria, altered gait, seizures, organ failure, or any combination thereof, or any other symptom or characteristic known in the art to be associated with CRS.

In some embodiments, inhibiting or reducing the incidence of CRS comprises reducing the concentration of at least one circulating cytokine. In some embodiments, the cytokine is selected from a group comprising: GM-CSF, IFNγ, IL-1, IL-15, IL-6, IL-8, IL-10, and IL-2.

In some embodiments, inhibiting or reducing the incidence of CRS comprises reducing the CRS grade. In some embodiments, inhibiting or reducing the incidence of NT comprises reducing the NT grade. In some embodiments, inhibiting or reducing the incidence of CRS comprises improving CARTOX-10 score. In some embodiments, inhibiting or reducing the incidence of NT comprises improving CARTOX-10 score. In some embodiments, inhibiting or reducing the incidence of CRS comprises reducing raised intracranial pressure. In some embodiments, inhibiting or reducing the incidence of CRS comprises reducing seizures. In some embodiments, inhibiting or reducing the incidence of CRS comprises reducing motor weakness. In some embodiments, inhibiting or reducing the incidence of NT or CRS comprises inhibiting or reducing the incidence to less than 60%. In some embodiments, inhibiting or reducing the incidence of NT or CRS comprises inhibiting or reducing the incidence to less than 50%. In some embodiments, inhibiting or reducing the incidence of NT or CRS comprises inhibiting or reducing the incidence to less than 40%. In some embodiments, inhibiting or reducing the incidence of NT or CRS comprises inhibiting or reducing the incidence to less than 30%. In some embodiments, inhibiting or reducing the incidence of NT or CRS comprises inhibiting or reducing the incidence to less than 20% of patients. In some embodiments, inhibiting or reducing the incidence of NT or CRS comprises eliminating NT or CRS.

In some embodiments, the subject has Grade 1 CRS and/or NT. In some embodiments, the subject has Grade 2 CRS and or NT. In some embodiments, the subject has Grade 3 CRS and/or NT. In some embodiments, the subject has Grade 4 CRS and/or NT. In some embodiments, the subject has any combination of the above.

In some embodiments, inhibiting or reducing the incidence of NT or CRS comprises reducing the CRS grade, the NT grade, or both. In some embodiments, the grade is reduced to ≤3 NT and/or CRS in 95% of patients.

In some embodiments, the subject has a body temperature above 37° C. following immunotherapy administration. In some embodiments, the subject has a body temperature above 38° C. following immunotherapy administration. In some embodiments, the subject has a body temperature above 39° C. following immunotherapy administration. In some embodiments, the subject has a body temperature above 40° C. following immunotherapy administration. In some embodiments, the subject has a body temperature above 41° C. following immunotherapy administration. In some embodiments, the subject has a body temperature above 42° C. following immunotherapy administration.

In some embodiments, the subject has IL-6 serum concentration above 10 pg/mL following immunotherapy administration. In some embodiments, the subject has IL-6 serum concentration above 12 pg/mL following immunotherapy administration. In some embodiments, the subject has IL-6 serum concentration above 14 pg/mL following immunotherapy administration. In some embodiments, the subject has IL-6 serum concentration above 16 pg/mL following immunotherapy administration. In some embodiments, the subject has IL-6 serum concentration above 18 pg/mL following immunotherapy administration. In some embodiments, the subject has IL-6 serum concentration above 20 pg/mL following immunotherapy administration. In some embodiments, the subject has IL-6 serum concentration above 22 pg/mL following immunotherapy administration.

In some embodiments, the subject has an MCP-1 serum concentration above 200 pg/ml following immunotherapy administration. In some embodiments, the subject has an MCP-1 serum concentration above 400 pg/ml following immunotherapy administration. In some embodiments, the subject has an MCP-1 serum concentration above 600 pg/ml following immunotherapy administration. In some embodiments, the subject has an MCP-1 serum concentration above 800 pg/ml following immunotherapy administration. In some embodiments, the subject has an MCP-1 serum concentration above 1000 pg/ml following immunotherapy administration. In some embodiments, the subject has an MCP-1 serum concentration above 1200 pg/ml following immunotherapy administration. In some embodiments, the subject has an MCP-1 serum concentration above 1400 pg/ml following immunotherapy administration. In some embodiments, the subject has an MCP-1 serum concentration above 1600 pg/ml following immunotherapy administration. In some embodiments, the subject has an MCP-1 serum concentration above 1800 pg/ml following immunotherapy administration. In some embodiments, the subject has an MCP-1 serum concentration above 2000 pg/ml following immunotherapy administration.

In some embodiments, the subject has Grade 1 CRES. In some embodiments, the subject has Grade 2 CRES. In some embodiments, the subject has Grade 3 CRES. In some embodiments, the subject has Grade 4 CRES.

In some embodiments, the subject is predisposed to have a brain disease, damage or malfunction prior to immunotherapy. In some embodiments, the predisposition is genetic. In some embodiments, the predisposition is acquired. In some embodiments, the predisposition regards an existing medical condition. In some embodiments, the predisposition is diagnosed prior to immunotherapy. In some embodiments, the predisposition is not diagnosed. In some embodiments, the subject goes through medical evaluations in order to determine predisposition to acquire an immunotherapy-related brain disease, damage or malfunction prior to immunotherapy.

In some embodiments, medical evaluations comprise determining ANG1 concentration in a body fluid. In some embodiments, medical evaluations comprise determining ANG1 concentration in serum. In some embodiments, medical evaluations comprise determining ANG2 concentration in a body fluid. In some embodiments, medical evaluations comprise determining ANG2 concentration in serum. In some embodiments, medical evaluations comprise calculating the ANG2:ANG1 ratio in serum. In some embodiments, subjects with serum ANG2:ANG1 ratio above 0.5 prior to immunotherapy are predisposed to CRES. In some embodiments, subjects with serum ANG2:ANG1 ratio above 0.7 prior to immunotherapy are predisposed to CRES. In some embodiments, subjects with serum ANG2:ANG1 ratio above 0.9 prior to immunotherapy are predisposed to CRES.

In some embodiments, subjects with serum ANG2:ANG1 ratio above 1 prior to immunotherapy are predisposed to CRES. In some embodiments, subjects with serum ANG2:ANG1 ratio above 1.1 prior to immunotherapy are predisposed to CRES. In some embodiments, subjects with serum ANG2:ANG1 ratio above 1.3 prior to immunotherapy are predisposed to CRES. In some embodiments, subjects with serum ANG2:ANG1 ratio above 1.5 prior to immunotherapy are predisposed to CRES.

In some embodiments, immunotherapy-related toxicity comprises hemophagocytic lymphohistiocytosis (HLH). In some embodiments, immunotherapy-related toxicity comprises macrophage-activation syndrome (MAS). In some embodiments, provided herein methods for inhibiting or reducing the incidence of HLH. In some embodiments, provided herein methods for inhibiting or reducing the incidence of MAS.

In some embodiments, inhibiting or reducing the incidence of HLH comprises increasing survival of the subject. In some embodiments, inhibiting reducing the incidence of HLH comprises increasing time to relapse. In some embodiments, inhibiting or reducing the incidence of MAS comprises increasing survival of the subject. In some embodiments, inhibiting reducing the incidence of MAS comprises increasing time to relapse.

In some embodiments, inhibiting or reducing the incidence of HLH or MAS comprises inhibiting macrophage activation and/or proliferation. In some embodiments, inhibiting or reducing the incidence of HLH or MAS comprises inhibiting T lymphocytes activation and/or proliferation. In some embodiments, inhibiting or reducing the incidence of HLH or MAS comprises reducing the concentration of circulating IFNγ. In some embodiments, inhibiting or reducing the incidence of HLH or MAS comprises reducing the concentration of circulating of GM-CSF.

In some embodiments the subject presents with fever following immunotherapy. In some embodiments the subject presents with splenomegaly following immunotherapy. In some embodiments the subject presents with cytopenia following immunotherapy. In some embodiments the subject presents with cytopenia in two or more cell lines following immunotherapy. In some embodiments the subject presents with hypertriglyceridemia following immunotherapy. In some embodiments the subject presents with hypofibrinogenemia following immunotherapy. In some embodiments the subject presents with hemophagocytosis following immunotherapy. In some embodiments hemophagocytosis is observed in bone marrow. In some embodiments the subject presents with low NK-cell activity following immunotherapy. In some embodiments the subject presents with absent NK activity following immunotherapy.

In some embodiments the subject presents with ferritin serum concentrations above 100 U/ml following immunotherapy. In some embodiments the subject presents with ferritin serum concentrations above 300 U/ml following immunotherapy. In some embodiments the subject presents with ferritin serum concentrations above 500 U/ml following immunotherapy. In some embodiments the subject presents with ferritin serum concentrations above 700 U/ml following immunotherapy. In some embodiments the subject presents with ferritin serum concentrations above 900 U/ml following immunotherapy.

In some embodiments the subject presents with soluble CD25 serum concentration above 1200 U/ml following immunotherapy. In some embodiments the subject presents with soluble CD25 serum concentration above 1500 U/ml following immunotherapy. In some embodiments the subject presents with soluble CD25 serum concentration above 1800 U/ml following immunotherapy. In some embodiments the subject presents with soluble CD25 serum concentration above 2000 U/ml following immunotherapy. In some embodiments the subject presents with soluble CD25 serum concentration above 2200 U/ml following immunotherapy. In some embodiments the subject presents with soluble CD25 serum concentration above 2400 U/ml following immunotherapy. In some embodiments the subject presents with soluble CD25 serum concentration above 2700 U/ml following immunotherapy. In some embodiments the subject presents with soluble CD25 serum concentration above 3000 U/ml following immunotherapy.

In some embodiments, the subject is predisposed to have HLH. In some embodiments, the predisposition is genetic. In some embodiments, the predisposition regards an existing medical condition. A skilled artisan would appreciate that sporadic HLH has been associated with a number of genetic mutations. In some embodiments, the subject carries a mutation in a gene selected from PRF1, UNC13D, STX11, STXBP2, or RAB27A, or any combination thereof. In some embodiments, the subject has reduced or absent expression of perforin.

hGM-CSF Antagonists hGM-CSF antagonists suitable for use selectively interfere with the induction of signaling by the hGM-CSF receptor by causing a reduction in the binding of hGM-CSF to the receptor. Such antagonists may include antibodies that bind the hGM-CSF receptor, antibodies that bind to hGM-CSF, GM-CSF analogs such as E21R, and other proteins or small molecules that compete for binding of hGM-CSF to its receptor or inhibit signaling that normally results from the binding of the ligand to the receptor.

In many embodiments, the hGM-CSF antagonist used in the invention is a polypeptide e.g., an anti-hGM-CSF antibody, an anti-hGM-CSF receptor antibody, a soluble hGM-CSF receptor, or a modified GM-CSF polypeptide that competes for binding with hGM-CSF to a receptor, but is inactive. Such proteins are often produced using recombinant expression technology. Such methods are widely known in the art. General molecular biology methods, including expression methods, can be found, e.g., in instruction manuals, such as, Sambrook and Russell (2001) Molecular Cloning: A laboratory manual 3rd ed. Cold Spring Harbor Laboratory Press; Current Protocols in Molecular Biology (2006) John Wiley and Sons ISBN: 0-471-50338-X.

A variety of prokaryotic and/or eukaryotic based protein expression systems may be employed to produce a hGM-CSF antagonist protein. Many such systems are widely available from commercial suppliers.

hGM-CSF Antibodies

The hGM-CSF antibodies of the present invention are antibodies that bind with high affinity to hGM-CSF and are antagonists of hGM-CSF. The antibodies comprise variable regions with a high degree of identity to human germ-line $V_H$ and $V_L$ sequences. In preferred embodiments, the BSD sequence in CDRH3 of an antibody of the invention comprises the amino acid sequence RQRFPY (SEQ ID NO: 12) or RDRFPY(SEQ ID NO: 13). The BSD in CDRL3 comprises FNK or FNR.

Complete V-regions are generated in which the BSD forms part of the CDR3 and additional sequences are used to complete the CDR3 and add a FR4 sequence. Typically, the portion of the CDR3 excluding the BSD and the complete FR4 are comprised of human germ-line sequences. In some embodiments, the CDR3-FR4 sequence excluding the BSD differs from human germ-line sequences by not more than 2 amino acids on each chain. In some embodiments, the J-segment comprises a human germline J-segment. Human germline sequences can be determined, for example, through the publicly available international ImMunoGeneTics database (IMGT) and V-base (on the worldwide web at vbase.mrc-cpe.cam.ac.uk).

The human germline V-segment repertoire consists of 51 heavy chain V-regions, 40 K light chain V-segments, and 31λ light chain V-segments, making a total of 3,621 germline V-region pairs, in addition, there are stable allelic variants for most of these V-segments, but the contribution of these variants to the structural diversity of the germline repertoire is limited. The sequences of all human germ-line V-segment genes are known and can be accessed in the V-base database, provided by the MRC Centre for Protein Engineering, Cambridge, United Kingdom (see, also Chothia et al., 1992, *J Mol Biol* 227:776-798; Tomlinson et al., 1995, *EMBO J* 14:4628-4638; and Williams et al., 1996, *J Mol Biol* 264:220-232).

Antibodies or antibodies fragments as described herein can be expressed in prokaryotic or eukaryotic microbial systems or in the cells of higher eukaryotes such as mammalian cells.

An antibody that is employed in the invention can be in any format. For example, in some embodiments, the antibody can be a complete antibody including a constant region, e.g., a human constant region, or can be a fragment or derivative of a complete antibody, e.g., an Fd, a Fab, Fab', F(ab')$_2$, scFv, Fv, an Fv fragment, or a single domain antibody, such as a nanobody or a camelid antibody. Such antibodies may additionally be recombinantly engineered by methods well known to persons of skill in the art. As noted above, such antibodies can be produced using known techniques.

In some embodiments, the hGM-CSF antagonist is an antibody that binds to hGM-CSF or an antibody that binds to the hGM-CSF receptor α or β subunit. The antibodies can be raised against hGM-CSF (or hGM-CSF receptor) proteins, or fragments, or produced recombinantly. Antibodies to GM-CSF for use in the invention can be neutralizing or can be non-neutralizing antibodies that bind GM-CSF and increase the rate of in vivo clearance of hGM-CSF such that the hGM-CSF level in the circulation is reduced. Often, the hGM-CSF antibody is a neutralizing antibody.

Methods of preparing polyclonal antibodies are known to the skilled artisan (e.g., Harlow & Lane, Antibodies, A Laboratory Manual (1988); Methods in Immunology). Polyclonal antibodies can be raised in a mammal by one or more injections of an immunizing agent and, if desired, an adjuvant. The immunizing agent includes a GM-CSF or GM-CSF receptor protein, e.g., a human GM-CSF or GM-CSF receptor protein, or fragment thereof.

In some embodiment, a GM-CSF antibody for use in the invention is purified from human plasma. In such embodiments, the GM-CSF antibody is typically a polyclonal antibody that is isolated from other antibodies present in human plasma. Such an isolation procedure can be performed, e.g., using known techniques, such as affinity chromatography.

In some embodiments, the GM-CSF antagonist is a monoclonal antibody.

Monoclonal antibodies may be prepared using hybridoma methods, such as those described by Kohler & Milstein, Nature 256:495 (1975). In a hybridoma method, a mouse, hamster, or other appropriate host animal, is typically immunized with an immunizing agent, such as human GM-CSF, to elicit lymphocytes that produce or are capable of producing antibodies that will specifically bind to the immunizing agent. Alternatively, the lymphocytes may be immunized in vitro. The immunizing agent preferably includes human GM-CSF protein, fragments thereof, or fusion protein thereof.

Human monoclonal antibodies can be produced using various techniques known in the art, including phage display libraries (Hoogenboom & Winter, J. Mol. Biol. 227:381 (1991); Marks et al, J. Mol. Biol. 222:581 (1991)). The techniques of Cole et al. and Boerner et al. are also available for the preparation of human monoclonal antibodies (Cole et al., Monoclonal Antibodies and Cancer Therapy, p. 77 (1985) and Boerner et al., J. Immunol. 147(1):86-95 (1991)). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, e.g., in U.S. Pat. Nos. 5,545,807; 5,545,806; 5,569,825; 5,625,126; 5,633,425; 5,661,016, and in the following scientific publications: Marks et al., Bio/Technology 10:779-783 (1992); Lonberg et al, Nature 368: 856-859 (1994); Morrison, Nature 368:812-13 (1994); Fishwild et al, Nature Biotechnology 14:845-51 (1996); Neuberger, Nature Biotechnology 14:826 (1996); Lonberg & Huszar, Intern. Rev. Immunol. 13:65-93 (1995).

In some embodiments the anti-GM-CSF antibodies are chimeric or humanized monoclonal antibodies. As noted supra, humanized forms of antibodies are chimeric immunoglobulins in which residues from a complementary determining region (CDR) of human antibody are replaced by residues from a CDR of a non-human species such as mouse, rat or rabbit having the desired specificity, affinity and capacity.

In some embodiments of the invention, the antibody is additionally engineered to reduced immunogenicity, e.g., so that the antibody is suitable for repeat administration. Methods for generating antibodies with reduced immunogenicity include humanization/humaneering procedures and modification techniques such as de-immunization, in which an antibody is further engineered, e.g., in one or more framework regions, to remove T cell epitopes.

In some embodiments, the antibody is a humaneered antibody. A humaneered antibody is an engineered human antibody having a binding specificity of a reference antibody, obtained by joining a DNA sequence encoding a binding specificity determinant (BSD) from the CDR3 region of the heavy chain of the reference antibody to human VH segment sequence and a light chain CDR3 BSD from the reference antibody to a human VL segment sequence. Methods for Humaneering are provided in US patent application publication no. 20050255552 and US patent application publication no. 20060134098. Methods for signal-less secretion of antibody fragments from E. coli are described in US patent application 20070020685.

An antibody can further be de-immunized to remove one or more predicted T-cell epitopes from the V-region of an antibody. Such procedures are described, for example, in WO 00/34317.

The heavy chain constant region is often a gamma chain constant region, for example, a gamma-1, gamma-2, gamma-3, or gamma-4 constant region. In some embodiments, e.g., where the antibody is a fragment, the antibody can be conjugated to another molecule, e.g., to provide an extended half-life in vivo such as a polyethylene glycol (pegylation) or serum albumin. Examples of PEGylation of antibody fragments are provided in Knight et al (2004) Platelets 15: 409 (for abciximab); Pedley et al (1994) Br. J. Cancer 70: 1126 (for an anti-CEA antibody) Chapman et al (1999) Nature Biotech. 17: 780.

An antibody for use in the invention binds to hGM-CSF or hGM-CSF receptor. Any number of techniques can be used to determine antibody binding specificity. See, e.g., Harlow & Lane, Antibodies, A Laboratory Manual (1988) for a description of immunoassay formats and conditions that can be used to determine specific immunoreactivity of an antibody.

An exemplary antibody suitable for use with the present invention is cl9/2 (a mouse/69 human chimeric anti-hGM-CSF antibody). In some embodiments, a monoclonal antibody that competes for binding to the same epitope as cl9/2, or that binds the same epitope as cl9/2, is used. The ability of a particular antibody to recognize the same epitope as another antibody is typically determined by the ability of the first antibody to competitively inhibit binding of the second antibody to the antigen. Any of a number of competitive binding assays can be used to measure competition between two antibodies to the same antigen. For example, a sandwich ELISA assay can be used for this purpose. This is carried out by using a capture antibody to coat the surface of a well. A subsaturating concentration of tagged-antigen is then added to the capture surface. This protein will be bound to the antibody through a specific antibody-epitope interaction. After washing a second antibody, which has been covalently linked to a detectable moiety (e.g., HRP, with the labeled antibody being defined as the detection antibody) is added to the ELISA. If this antibody recognizes the same epitope as the capture antibody it will be unable to bind to the target protein as that particular epitope will no longer be available for binding. If, however this second antibody recognizes a different epitope on the target protein it will be able to bind and this binding can be detected by quantifying the level of activity (and hence antibody bound) using a relevant substrate. The background is defined by using a single antibody as both capture and detection antibody, whereas the maximal signal can be established by capturing with an antigen specific antibody and detecting with an antibody to the tag on the antigen. By using the background and maximal signals as references, antibodies can be assessed in a pairwise manner to determine epitope specificity.

A first antibody is considered to competitively inhibit binding of a second antibody, if binding of the second antibody to the antigen is reduced by at least 30%, usually at least about 40%, 50%, 60% or 75%, and often by at least about 90%, in the presence of the first antibody using any of the assays described above.

In some embodiments of the invention, an antibody is employed that competes with binding, or bind, to the same epitope as a known antibody, e.g., cl9/2. Method of mapping epitopes are well known in the art. For example, one approach to the localization of functionally active regions of human granulocyte-macrophage colony-stimulating factor (hGM-CSF) is to map the epitopes recognized by neutralizing anti-hGM-CSF monoclonal antibodies. For example, the epitope to which cl9/2 (which has the same variable regions as the neutralizing antibody LMM 102) binds has been defined using proteolytic fragments obtained by enzymic digestion of bacterially synthesized hGM-CSF (Dempsey, et al, Hybridoma 9:545-558, 1990). RP-HPLC fractionation of a tryptic digest resulted in the identification of an immunoreactive "tryptic core" peptide containing 66 amino acids (52% of the protein). Further digestion of this "tryptic core" with *S. aureus* V8 protease produced a unique immunoreactive hGM-CSF product comprising two peptides, residues 86-93 and 112-127, linked by a disulfide bond between residues 88 and 121. The individual peptides were not recognized by the antibody.

In some embodiments, the antibodies suitable for use with the present invention have a high affinity binding for human GM-CSF or hGM-CSF receptor. High affinity binding between an antibody and an antigen exists if the dissociation constant (KD) of the antibody is <about 10 nM, typically <1 nM, and preferably <100 pM. In some embodiments, the antibody has a dissociation rate of about $10^{-4}$ per second or better.

A variety of methods can be used to determine the binding affinity of an antibody for its target antigen such as surface plasmon resonance assays, saturation assays, or immunoassays such as ELISA or RIA, as are well known to persons of skill in the art. An exemplary method for determining binding affinity is by surface plasmon resonance analysis on a BIAcore™ 2000 instrument (Biacore AB, Freiburg, Germany) using CM5 sensor chips, as described by Krinner et al, (2007) Mol. Immunol. February; 44(5):916-25. (Epub 2006 May H)).

In some embodiments, the hGM-CSF antagonists are neutralizing antibodies to hGM-CSF, its receptor or its receptor subunit, which bind in a manner that interferes with the binding of hGM-CSF to its receptor or receptor subunit. In some embodiments, an anti-hGM-CSF antibody for use in the invention inhibits binding to the alpha subunit of the hGM-CSF receptor. Such an antibody can, for example, bind to hGM-CSF at the region where hGM-CSF binds to the receptor and thereby inhibit binding. In another embodiments, the anti-hGM-CSF antibody inhibits hGM-CSF functioning without blocking its binding to the alpha subunit of the hGM-CSF receptor.

II. Heavy Chains

A heavy chain of an anti-hGM-CSF antibody of the invention comprises a heavy-chain V-region that comprises the following elements:

1) human heavy-chain V-segment sequences comprising FR1-CDR1-FR2-CDR2-FR3

2) a CDRH3 region comprising the amino acid sequence R(Q/D)RFPY (SEQ ID NO: 22)

3) a FR4 contributed by a human germ-line J-gene segment.

Examples of V-segment sequences that support binding to hGM-CSF in combination with a CDR3-FR4 segment described above together with a complementary VL region are shown in FIG. 1. The V-segments can be, e.g., from the human VH1 subclass. In some embodiments, the V-segment is a human $V_H1$ sub-class segment that has a high degree of amino-acid sequence identity, e.g., at least 80%, 85%, or 90% or greater identity, to the germ-line segment VH1 1-02 (SEQ ID NO: 19) or VH1 1-03 (SEQ ID NO: 20). In some embodiments, the V-segment differs by not more than 15 residues from VH1 1-02 (SEQ ID NO: 19) or VH1 1-03 (SEQ ID NO: 20) and preferably not more than 7 residues.

The FR4 sequence of the antibodies of the invention is provided by a human JH1, JH3, JH4, JH5 or JH6 gene germline segment, or a sequence that has a high degree of amino-acid sequence identity to a human germline JH segment. In some embodiments, the J segment is a human germline JH4 sequence.

The CDRH3 also comprises sequences that are derived from a human J-segment. Typically, the CDRH3-FR4 sequence excluding the BSD differs by not more than 2 amino acids from a human germ-line J-segment. In typical embodiments, the J-segment sequences in CDRH3 are from the same J-segment used for the FR4 sequences. Thus, in some embodiments, the CDRH3-FR4 region comprises the BSD and a complete human JH4 germ-line gene segment. An exemplary combination of CDRH3 and FR4 sequences is shown below, in which the BSD is in bold and human germ-line J-segment JH4 residues are underlined:

CDR3
(SEQ ID NO: 23)
R(Q/D)RFPYYFDYWGQGTLVTVSS

In some embodiments, an antibody of the invention comprises a V-segment that has at least 90% identity, or at least 91%, 92% 93%, 94%, 95%, 96%, 97%, 98%, 99%, or 100% identity to the germ-line segment VH 1-02 or VH1-03; or to one of the V-segments of the $V_H$ regions shown in FIG. 1, such as a V-segment portion of VH #1 (SEQ ID NO: 1), VH #2 (SEQ ID NO:2), VH #3 (SEQ ID NO:3), VH #4 (SEQ ID NO:4), or VH #5 (SEQ ID NO: 5).

In some embodiments, the V-segment of the $V_H$ region has a CDR1 and/or CDR2 as shown in FIG. 1. For example, an antibody of the invention may have a CDR1 that has the sequence GYYMH (SEQ ID NO: 24) or NYYIH (SEQ ID NO: 25); or a CDR2 that has the sequence WINPNSGGTNYAQKFQG (SEQ ID NO: 26) or WINAGNGNTKYSQKFQG (SEQ ID NO: 27).

In particular embodiments, an antibody has both a CDR1 and a CDR2 from one of the $V_H$ region V-segments shown in FIG. 1 and a CDR3 that comprises R(Q/D)RFPY (SEQ ID NO: 22), e.g., RDRFPYYFDY (SEQ ID NO: 16) or RQRFPYYFDY (SEQ ID NO: 15). Thus, in some embodiments, an anti-GM-CSF antibody of the invention, may for example, have a CDR3-FR4 that has the sequence R(Q/D)RFPYYFDYWGQGTLVTVSS (SEQ ID NO: 23) and a CDR1 and/or CDR2 as shown in FIG. 1.

In some embodiments, a $V_H$ region of an antibody of the invention has a CDR3 that has a binding specificity determinant R(Q/D)RFPY (SEQ ID NO: 22), a CDR2 from a human germline VH1 segment or a CDR1 from a human germline VH1. In some embodiments, both the CDR1 and CDR2 are from human germline VH1 segments.

III. Light Chains

A light chain of an anti-hGM-CSF antibody of the invention comprises at light-chain V-region that comprises the following elements:

1) human light-chain V-segment sequences comprising FR1-CDR1-FR2-CDR2-FR3

2) a CDRL3 region comprising the sequence FNK or FNR, e.g., QQFNRSPLT (SEQ ID NO: 28) or QQFNKSPLT (SEQ ID NO: 18).

3) a FR4 contributed by a human germ-line J-gene segment.

The $V_L$ region comprises either a Vlambda or a Vkappa V-segment. An example of a Vkappa sequence that supports binding in combination with a complementary $V_H$-region is provided in FIG. 1.

The $V_L$ region CDR3 sequence comprises a J-segment derived sequence. In typical embodiments, the J-segment sequences in CDRL3 are from the same J-segment used for FR4. Thus, the sequence in some embodiments may differ by not more than 2 amino acids from human kappa germ-line V-segment and J-segment sequences. In some embodiments, the CDRL3-FR4 region comprises the BSD and the complete human JK4 germline gene segment. Exemplary CDRL3-FR4 combinations for kappa chains are shown below in which the minimal essential binding specificity determinant is shown in bold and JK4 sequences are underlined:

```
CDR3
                                          (SEQ ID NO: 29)
QQFNRSPLTFGGGTKVEIK (SEQ ID NO: 30)
QQFNKSPLTFGGGTKVEIK
```

The Vkappa segments are typically of the V KIII subclass. In some embodiments, the segments have at least 80% sequence identity to a human germline VKIII subclass, e.g., at least 80% identity to the human germ-line VKIIIA27 (SEQ ID NO: 21) sequence. In some embodiments, the Vkappa segment may differ by not more than 18 residues from VKIIIA27 (SEQ ID NO: 21). In other embodiments, the VL region V-segment of an antibody of the invention has at least 85% identity, or at least 90%, 91%, 92%, 93%, 94%, 95%, 96%, 97%, 98%, 99%, or 100% identity to the human kappa V-segment sequence of a $V_L$ region shown in FIG. 1, for example, the V-segment sequence of VK #1 (SEQ ID NO: 6), VK #2 (SEQ ID NO: 7), VK #3 (SEQ ID NO: 8), or VK #4 (SEQ ID NO: 9).

In some embodiments, the variable region is comprised of human V-gene sequences. For example, a variable region sequence can have at least 80% identity, or at least 85% identity, at least 90% identity, at least 95% identity, at least 96% identity, at least 97% identity, at least 98% identity, or at least 99% identity, or greater, with a human germ-line V-gene sequence.

In some embodiments, the V-segment of the VL region has a CDR1 and/or CDR2 as shown in FIG. 1. For example, an antibody of the invention may have a CDR1 sequence of RASQSVGTNVA (SEQ ID NO: 31) or RASQSIGSNLA (SEQ ID NO: 32) RASQS(V/I)G(T/S)N(V/L)A (SEQ ID NO: 39); or a CDR2 sequence STSSRAT (SEQ ID NO: 33).

In particular embodiments, an anti-GM-CSF antibody of the invention may have a CDR1 and a CDR2 in a combination as shown in one of the V-segments of the VL regions set forth in FIG. 1 and a CDR3 sequence that comprises FNK or FNR, e.g., the CDR3 may be QQFNKSPLT (SEQ ID NO: 18) or QQFNRSPLT (SEQ ID NO: 28). In some embodiments, such a GM-CSF antibody may comprise an FR4 region that is FGGGTKVEIK (SEQ ID NO: 34). Thus, an anti-GM-CSF antibody of the invention, can comprise, e.g., both the CDR1 and CDR2 from one of the VL regions shown in FIG. 1 and a CDR3-FR4 region that is FGGGTKVEIK (SEQ ID NO: 34).

IV. Preparation of hGM-CSF Antibodies

An antibody of the invention may comprise any of the $V_H$ regions VH #1 (SEQ ID NO: 1), VH #2 (SEQ ID NO: 2), VH #3 (SEQ ID NO: 3), VH #4 (SEQ ID NO: 4), or VH #5 (SEQ ID NO: 5) as shown in FIG. 1. In some embodiment, an antibody of the invention may comprise any of the $V_L$ regions VK #1 (SEQ ID NO: 6), VK #2 (SEQ ID NO: 7), VK #3 (SEQ ID NO: 8), or VK #4 (SEQ ID NO: 9) as shown in FIG. 1. In some embodiments, the antibody has a $V_H$ region VH #1 (SEQ ID NO: 1), VH #2 (SEQ ID NO: 2), VH #3 (SEQ ID NO: 3), VH #4 (SEQ ID NO: 4), or VH #5 (SEQ ID NO: 5) as shown in FIG. 1; and a VL region VK #1 (SEQ ID NO: 6), VK #2 (SEQ ID NO: 7), VK #3 (SEQ ID NO: 8), or VK #4 (SEQ ID NO: 9) as shown in FIG. 1, as described, e.g., in U.S. Pat. Nos. 8,168,183 and 9,017,674, each of which is incorporated herein by reference in its entirety.

An antibody may be tested to confirm that the antibody retains the activity of antagonizing hGM-CSF activity. The antagonist activity can be determined using any number of endpoints, including proliferation assays. Neutralizing antibodies and other hGM-CSF antagonists may be identified or evaluated using any number of assays that assess hGM-CSF function. For example, cell-based assays for hGM-CSF receptor signaling, such as assays which determine the rate of proliferation of a hGM-CSF-dependent cell line in response to a limiting amount of hGM-CSF, are conveniently used. The human TF-1 cell line is suitable for use in such an assay. See, Krinner et al., (2007) *Mol. Immunol.* In some embodiments, the neutralizing antibodies of the invention inhibit hGM-CSF stimulated TF-I cell proliferation by at least 50%, when a hGM-CSF concentration is used which stimulates 90% maximal TF-I cell proliferation. Thus, typically, a neutralizing antibody, or other hGM-CSF antagonist for use in the invention, has an EC50 of less than 10 nM (e.g., Table 2). Additional assays suitable for use in identifying neutralizing antibodies suitable for use with the present invention will be well known to persons of skill in the art. In other embodiments, the neutralizing antibodies inhibit hGM-CSF stimulated proliferation by at least about 75%, 80%, 90%, 95%, or 100%, of the antagonist activity of the antibody chimeric cl9/2, e.g., WO03/068920, which has the variable regions of the mouse monoclonal antibody LMM102 and the CDRs.

An exemplary chimeric antibody suitable for use as a hGM-CSF antagonist is cl9/2. The c 19/2 antibody binds hGM-CSF with a monovalent binding affinity of about 10 pM as determined by surface plasmon resonance analysis. The heavy and light chain variable region sequences of cl9/2 are known (e.g., WO03/068920). The CDRs, as defined according to Kabat, are:

```
CDRH1
                                          (SEQ ID NO: 35)
DYNIH

CDRH2
                                          (SEQ ID NO: 36)
YIAPYSGGTGYNQEFKN

CDRH3
                                          (SEQ ID NO: 16)
RDRFPYYFDY

CDRL1
                                          (SEQ ID NO: 37)
KASQNVGSNVA

CDRL2
                                          (SEQ ID NO: 38)
SASYRSG

CDRL3
                                          (SEQ ID NO: 28)
QQFNRSPLT.
```

The CDRs can also be determined using other well-known definitions in the art, e.g., Chothia, international ImMunoGeneTics database (IMGT), and AbM.

In some embodiments, an antibody used in the invention competes for binding to, or binds to, the same epitope as cl9/2. The GM-CSF epitope recognized by cl9/2 has been identified as a product that has two peptides, residues 86-93 and residues 112-127, linked by a disulfide bond between residues 88 and 121. The cl9/2 antibody inhibits the GM-CSF-dependent proliferation of a human TF-I leukemia cell line with an EC50 of 30 pM when the cells are stimulated with 0.5 ng/ml GM-CSF. In some embodiments, the antibody used in the invention binds to the same epitope as cl9/2.

An antibody for administration, such as cl9/2, can be additionally Humaneered. For example, the cl9/2 antibody can be further engineered to contain human V gene segments.

A high-affinity antibody may be identified using well known assays to determine binding activity and affinity. Such techniques include ELISA assays as well as binding determinations that employ surface plasmon resonance or interferometry. For example, affinities can be determined by biolayer interferometry using a ForteBio (Mountain View, Calif.) Octet biosensor. An antibody of the invention typically binds with similar affinity to both glycosylated and non-glycosylated form of hGM-CSF.

Antibodies of the invention compete with cl9/2 for binding to hGM-CSF. The ability of an antibody described herein to block or compete with cl9/2 for binding to hGM-CSF indicates that the antibody binds to the same epitope cl9/2 or to an epitope that is close to, e.g., overlapping, with the epitope that is bound by cl9/2. In other embodiments an antibody described herein, e.g., an antibody comprising a $V_H$ and $V_L$ region combination as shown in the table provided in FIG. 1, can be used as a reference antibody for assessing whether another antibody competes for binding to hGM-CSF. A test antibody is considered to competitively inhibit binding of a reference antibody, if binding of the reference antibody to the antigen is reduced by at least 30%, usually at least about 40%, 50%, 60% or 75%, and often by at least about 90%, in the presence of the test antibody. Many assays can be employed to assess binding, including ELISA, as well as other assays, such as immunoblots. In some embodiments, an antibody of the invention has a dissociation rate that is at least 2 to 3-fold slower than a reference chimeric cl9/2 monoclonal antibody assayed under the same conditions, but has a potency that is at least 6-10 times greater than that of the reference antibody in neutralizing hGM-CSF activity in a cell-based assay that measures hGM-CSF activity.

Methods for the isolation of antibodies with V-region sequences close to human germ-line sequences have previously been described (US patent application publication nos. 20050255552 and 20060134098). Antibody libraries may be expressed in a suitable host cell including mammalian cells, yeast cells or prokaryotic cells. For expression in some cell systems, a signal peptide can be introduced at the N-terminus to direct secretion to the extracellular medium. Antibodies may be secreted from bacterial cells such as *E. coli* with or without a signal peptide. Methods for signal-less secretion of antibody fragments from *E. coli* are described in US patent application 20070020685.

In some embodiments, an hGM-CSF-binding antibody of the invention is generated where, an antibody that has a CDR from one of the VH-regions of the invention shown in FIG. 1, is combined with an antibody having a CDR of one of the $V_L$-regions shown in FIG. 1, and expressed in any of a number of formats in a suitable expression system. Thus, the antibody may be expressed as a scFv, Fab, Fab' (containing an immunoglobulin hinge sequence), F(ab')$_2$, (formed by di-sulfide bond formation between the hinge sequences of two Fab' molecules), whole immunoglobulin or truncated immunoglobulin or as a fusion protein in a prokaryotic or eukaryotic host cell, either inside the host cell or by secretion. A methionine residue may optionally be present at the N-terminus, for example, in polypeptides produced in signal-less expression systems. Each of the $V_H$-regions described herein may be paired with each of the VL regions to generate an anti-hGM-CSF antibody. In an embodiment, a fusion protein comprises an anti-hGM-CSF-binding antibody of the invention or a fragment thereof (in non-limiting examples, an anti-hGM-CSF antibody fragment is a Fab, a Fab', a F(ab')2, a scFv, or a dAB), and human transferrin, wherein the human transferrin is fused to the antibody at the end of the heavy chain constant region 1 ($C_H$1), after the hinge, or after $C_H$3, as described in Shin, S-U., et al. Proc. Natl. Acad. Sci. USA, Vol. 92, pp. 2820-2824, 1995, which is incorporated herein by reference in its entirety.

Exemplary combinations of heavy and light chains are shown in the table provided in FIG. 1. In some embodiment, the antibody VL region, e.g., VK #1 (SEQ ID NO: 6), VK #2 (SEQ ID NO: 7), VK #3 (SEQ ID NO: 8), or VK #4 (SEQ ID NO: 9) of FIG. 1, is combined with a human kappa constant region to form the complete light-chain. Further, in some embodiments, the VH region is combined a human gamma-1 constant regions. Any suitable gamma-1 allotype can be chose, such as the f-allotype. Thus, in some embodiments, the antibody is an IgG, e.g., having an f-allotype, that has a VH selected from VH #1 (SEQ ID NO:1), VH #2 (SEQ ID NO:2), VH #3 (SEQ ID NO:3), VH #4 (SEQ ID NO:4), or VH #5 (SEQ ID NO:5) (FIG. 1), and a VL selected from VK #1 (SEQ ID NO: 6), VK #2 (SEQ ID NO: 7), VK #3 (SEQ ID NO: 8), or VK #4 (SEQ ID NO: 9) (FIG. 1).

The antibodies of the invention inhibit hGM-CSF receptor activation, e.g., by inhibiting hGM-CSF binding to the receptor, and exhibit high affinity binding to hGM-CSF, e.g., 500 pM. In some embodiments, the antibody has a dissociation constant of about $10^{-4}$ per sec or less. Not to be bound by theory, an antibody with a slower dissociation constant provides improved therapeutic benefit. For example, an antibody of the invention that has a three-fold slower off-rate than cl9/2, produced a 10-fold more potent hGM-CSF neutralizing activity, e.g., in a cell-based assay such as IL-8 production (see, e.g., Example 2).

Antibodies may be produced using any number of expression systems, including both prokaryotic and eukaryotic expression systems. In some embodiments, the expression system is a mammalian cell expression, such as a CHO cell expression system. Many such systems are widely available from commercial suppliers. In embodiments in which an antibody comprises both a $V_H$ and $V_L$ region, the $V_H$ and $V_L$ regions may be expressed using a single vector, e.g., in a dicistronic expression unit, or under the control of different promoters. In other embodiments, the $V_H$ and $V_L$ region may be expressed using separate vectors. A $V_H$ or $V_L$ region as described herein may optionally comprise a methionine at the N-terminus.

An antibody of the invention may be produced in any number of formats, including as a Fab, a Fab', a F(ab')$_2$, a scFv, or a dAB. An antibody of the invention can also include a human constant region. The constant region of the light chain may be a human kappa or lambda constant region. The heavy chain constant region is often a gamma chain constant region, for example, a gamma-1, gamma-2, gamma-3, or gamma-4 constant region. In other embodiments, the antibody may be an IgA.

In some embodiments of the invention, the antibody $V_L$ region, e.g., VK #1 (SEQ ID NO: 6), VK #2 (SEQ ID NO: 7), VK #3 (SEQ ID NO: 8), or VK #4 (SEQ ID NO: 9) of FIG. 1, is combined with a human kappa constant region (e.g., SEQ ID NO:10) to form the complete light-chain.

In some embodiments of the invention, the $V_H$ region is combined a human gamma-1 constant region. Any suitable gamma-1 f allotype can be chosen, such as the f-allotype. Thus, in some embodiments, the antibody is an IgG having an f-allotype constant region, e.g., SEQ ID NO:11, that has a $V_H$ selected from VH #1 (SEQ ID NO:1), VH #2 (SEQ ID NO:2), VH #3 (SEQ ID NO:3), VH #4 (SEQ ID NO:4), or VH #5 (SEQ ID NO:5) (FIG. 1). In some embodiments, the antibody has a $V_L$ selected from VK #1 (SEQ ID NO: 6), VK #2 (SEQ ID NO: 7), VK #3 (SEQ ID NO: 8), or VK #4 (SEQ ID NO: 9) (FIG. 1.) In particular embodiments, the antibody has a kappa constant region as set forth in SEQ ID NO:10, and a heavy chain constant region as set forth in SEQ ID NO:11, where the heavy and light chain variable regions comprise one of the following combinations from the sequences set forth in FIG. 1: a) VH #2 (SEQ ID NO:2), VK #3 (SEQ ID NO:8); b) VH #1 (SEQ ID NO:1), VK #3 (SEQ ID NO:8); c) VH #3 (SEQ ID NO:3), VK #1 (SEQ ID NO:6); d) VH #3 (SEQ ID NO:3), VK #3 (SEQ ID NO:8); e) VH #4 (SEQ ID NO:4), VK #4 (SEQ ID NO:9); f) VH #4 (SEQ ID NO:4), VK #2 (SEQ ID NO:7); g) VH #5 (SEQ ID NO:5), VK #1 (SEQ ID NO:6); h) VH #5 (SEQ ID NO:5), VK #2 (SEQ ID NO:7); i) VH #3 (SEQ ID NO:3), VK #4 (SEQ ID NO:9); or j) VH #3 (SEQ ID NO:3), VK #3 (SEQ ID NO:8).

In some embodiments, e.g., where the antibody is a fragment, the antibody can be conjugated to another molecule, e.g., polyethylene glycol (PEGylation) or serum albumin, to provide an extended half-life in vivo. Examples of PEGylation of antibody fragments are provided in Knight et al. *Platelets* 15:409, 2004 (for abciximab); Pedley et al., *Br. J. Cancer* 70:1126, 1994 (for an anti-CEA antibody); Chapman et al., *Nature Biotech.* 17:780, 1999; and Humphreys, et al., *Protein Eng. Des.* 20: 227, 2007).

In some embodiments, the antibodies of the invention are in the form of a Fab' fragment. A full-length light chain is generated by fusion of a $V_L$-region to human kappa or lambda constant region. Either constant region may be used for any light chain; however, in typical embodiments, a kappa constant region is used in combination with a Vkappa variable region and a lambda constant region is used with a Vlambda variable region.

The heavy chain of the Fab' is a Fd' fragment generated by fusion of a $V_H$-region of the invention to human heavy chain constant region sequences, the first constant (CH1) domain and hinge region. The heavy chain constant region sequences can be from any of the immunoglobulin classes, but is often from an IgG, and may be from an IgG1, IgG2, IgG3 or IgG4. The Fab' antibodies of the invention may also be hybrid sequences, e.g., a hinge sequence may be from one immunoglobulin sub-class and the CH1 domain may be from a different sub-class.

V. Administration of Anti-hGM-CSF Antibodies for the Treatment of Diseases in which GM-CSF is a Target.

The invention also provides methods of treating a patient that has a disease involving hGM-CSF in which it is desirable to inhibit hGM-CSF activity, i.e., in which hGM-CSF is a therapeutic target. In some embodiments, such a patient has a chronic inflammatory disease, e.g., arthritis, e.g., rheumatoid arthritis, psoriatic arthritis, ankylosing spondylitis, juvenile idiopathic arthritis, systemic-onset Still's disease and other inflammatory diseases of the joints; inflammatory bowel diseases, e.g., ulcerative colitis, Crohn's disease, Barrett's syndrome, ileitis, enteritis, eosinophilic esophagitis and gluten-sensitive enteropathy; inflammatory disorders of the respiratory system, such as asthma, eosinophilic asthma, adult respiratory distress syndrome, allergic rhinitis, silicosis, chronic obstructive pulmonary disease, hypersensitivity lung diseases, interstitial lung disease, diffuse parenchymal lung disease, bronchiectasis; inflammatory diseases of the skin, including psoriasis, scleroderma, and inflammatory dermatoses such as eczema, atopic dermatitis, urticaria, and pruritis; disorders involving inflammation of the central and peripheral nervous system, including multiple sclerosis, idiopathic demyelinating polyneuropathy, Guillain-Barre syndrome, chronic inflammatory demyelinating polyneuropathy, neurofibromatosis and neurodegenerative diseases such as Alzheimer's disease. Various other inflammatory diseases can be treated using the methods of the invention. These include systemic lupus erythematosis, immune-mediated renal disease, e.g., glomerulonephritis, and spondyloarthropathies; and diseases with an undesirable chronic inflammatory component such as systemic sclerosis, idiopathic inflammatory myopathies, Sjogren's syndrome, vasculitis, sarcoidosis, thyroiditis, gout, otitis, conjunctivitis, sinusitis, sarcoidosis, Behcet's syndrome, autoimmune lymphoproliferative syndrome (or ALPS, also known as Canale-Smith syndrome), Ras-associated autoimmune leukoproliferative disorder (or RALD), Noonan syndrome, hepatobiliary diseases such as hepatitis, primary biliary cirrhosis, granulomatous hepatitis, and sclerosing cholangitis. In some embodiments, the patient has inflammation following injury to the cardiovascular system. Various other inflammatory diseases include Kawasaki's disease, Multicentric Castleman's Disease, tuberculosis and chronic cholecystitis. Additional chronic inflammatory diseases are described, e.g., in Harrison's Principles of Internal Medicine, 12th Edition, Wilson, et al., eds., McGraw-Hill, Inc.). In some embodiments, a patient treated with an antibody has a cancer in which GM-CSF contributes to tumor or cancer cell growth, including but not limited to, e.g., acute myeloid leukemia, plexiform neurofibromatosis, autoimmune lymphoproliferative syndrome (or ALPS, also known as Canale-Smith syndrome), Ras-associated autoimmune leukoproliferative disorder (or RALD), Noonan syndrome, chronic myelomonocytic leukemia, juvenile myelomonocytic leukemia, and acute myeloid leukemia. In some embodiments, a patient treated with an antibody of the invention has, or is at risk of heart failure, e.g., due to ischemic injury to the cardiovascular system such as ischemic heart disease, stroke, and atherosclerosis. In some embodiments, a patient treated with an antibody of the invention has asthma. In some embodiments, a patient treated with an antibody of the invention has Alzheimer's disease. In some embodiments, a patient treated with an antibody of the invention has osteopenia, e.g., osteoporosis. In some embodiments, a patient treated with an antibody of the invention has thrombocytopenia purpura. In some embodiments, the patient has Type I or Type II diabetes. In some embodiments, a patient may have more than one disease in which GM-CSF is a therapeutic target, e.g., a patient may have rheumatoid arthritis and heart failure, or osteoporosis and rheumatoid arthritis, etc.

Two other examples of neutralizing anti-GM-CSF antibody are the human E10 antibody and human G9 antibody described in Li et al, (2006) PNAS 103(10):3557-3562. E1O and G9 are IgG class antibodies. E1O has an 870 pM binding affinity for GM-CSF and G9 has a 14 pM affinity for GM-CSF. Both antibodies are specific for binding to human GM-CSF and show strong neutralizing activity as assessed with a TF1 cell proliferation assay.

An additional exemplary neutralizing anti-GM-CSF antibody is the MT203 antibody described by Krinner et al, (Mol Immunol. 44:916-25, 2007; Epub 2006 May 112006). MT203 is an IgG1 class antibody that binds GM-CSF with picomolar affinity. The antibody shows potent inhibitory activity as assessed by TF-I cell proliferation assay and its ability to block IL-8 production in U937 cells.

Additional antibodies suitable for use with the present invention will be known to persons of skill in the art.

hGM-CSF antagonists that are anti-hGM-CSF receptor antibodies can also be employed with the methods of the present disclosure. Such hGM-CSF antagonists include antibodies to the hGM-CSF receptor alpha chain or beta chain. An anti-hGM-CSF receptor antibody employed in the invention can be in any antibody format as explained above, e.g., intact, chimeric, monoclonal, polyclonal, antibody fragment, humanized, Humaneered, and the like. Examples of anti-hGM-CSF receptor antibodies, e.g., neutralizing, high-affinity antibodies, suitable for use in the invention are known (see, e.g., U.S. Pat. No. 5,747,032 and Nicola et al., Blood 82: 1724, 1993).

Non-Antibody GM-CSF Antagonists

Other proteins that may interfere with the productive interaction of hGM-CSF with its receptor include mutant hGM-CSF proteins and secreted proteins comprising at least part of the extracellular portion of one or both of the hGM-CSF receptor chains that bind to hGM-CSF and compete with binding to cell-surface receptor. For example, a soluble hGM-CSF receptor antagonist can be prepared by fusing the coding region of the sGM-CSFR alpha with the CH2-CH3 regions of murine IgG2a. An exemplary soluble hGM-CSF receptor is described by Raines et al. (1991) Proc. Natl. Acad. Sci USA 88: 8203. An example of a GM-CSFR alpha-Fc fusion protein is provided, e.g., in Brown et al (1995) Blood 85: 1488. In some embodiments, the Fc component of such a fusion can be engineered to modulate binding, e.g., to increase binding, to the Fc receptor.

Other hGM-CSF antagonists include hGM-CSF mutants. For example, hGM-CSF having a mutation of amino acid residue 21 of hGM-CSF to Arginine or Lysine (E21R or E21K) described by Hercus et al. Proc. Natl. Acad. Sci USA 91:5838, 1994 has been shown to have in vivo activity in preventing dissemination of hGM-CSF-dependent leukemia cells in mouse xenograft models (Iversen et al. Blood 90:4910, 1997). As appreciated by one of skill in the art, such antagonists can include conservatively modified variants of hGM-CSF that have substitutions, such as the substitution noted at amino acid residue 21, or hGM-CSF variants that have, e.g., amino acid analogs to prolong half-life.

In some embodiments, the hGM-CSF antagonist may be a peptide. For example, an hGM-CSF peptide antagonist may be a peptide designed to structurally mimic the positions of specific residues on the B and C helices of human GM-CSF that are implicated in receptor binding and bioactivity (e.g., Monfardini et al, J. Biol. Chem 271:2966-2971, 1996).

In other embodiments, the hGM-CSF antagonist is an "antibody mimetic" that targets and binds to the antigen in a manner similar to antibodies. Certain of these "antibody mimics" use non-immunoglobulin protein scaffolds as alternative protein frameworks for the variable regions of antibodies. For example, Ku et al. (Proc. Natl. Acad. Sci. U.S.A. 92(14):6552-6556 (1995)) discloses an alternative to antibodies based on cytochrome b562 in which two of the loops of cytochrome b562 were randomized and selected for binding against bovine serum albumin. The individual mutants were found to bind selectively with BSA similarly with anti-BSA antibodies. U.S. Pat. Nos. 6,818,418 and 7,115,396 disclose an antibody mimic featuring a fibronectin or fibronectin-like protein scaffold and at least one variable loop. Known as Adnectins, these fibronectin-based antibody mimics exhibit many of the same characteristics of natural or engineered antibodies, including high affinity and specificity for any targeted ligand. The structure of these fibronectin-based antibody mimics is similar to the structure of the variable region of the IgG heavy chain. Therefore, these mimics display antigen binding properties similar in nature and affinity to those of native antibodies. Further, these fibronectin-based antibody mimics exhibit certain benefits over antibodies and antibody fragments. For example, these antibody mimics do not rely on disulfide bonds for native fold stability, and are, therefore, stable under conditions which would normally break down antibodies. In addition, since the structure of these fibronectin-based antibody mimics is similar to that of the IgG heavy chain, the process for loop randomization and shuffling may be employed in vitro that is similar to the process of affinity maturation of antibodies in vivo.

Beste et al. (Proc. Natl. Acad. Sci. U.S.A. 96(5):1898-1903 (1999)) disclose an antibody mimic based on a lipocalin scaffold (Anticalin®). Lipocalins are composed of a β-barrel with four hypervariable loops at the terminus of the protein. The loops were subjected to random mutagenesis and selected for binding with, for example, fluorescein. Three variants exhibited specific binding with fluorescein, with one variant showing binding similar to that of an anti-fluorescein antibody. Further analysis revealed that all of the randomized positions are variable, indicating that Anticalin would be suitable to be used as an alternative to antibodies. Thus, Anticalins are small, single chain peptides, typically between 160 and 180 residues, which provides several advantages over antibodies, including decreased cost of production, increased stability in storage and decreased immunological reaction.

U.S. Pat. No. 5,770,380 discloses a synthetic antibody mimetic using the rigid, non-peptide organic scaffold of calixarene, attached with multiple variable peptide loops used as binding sites. The peptide loops all project from the same side geometrically from the calixarene, with respect to each other. Because of this geometric confirmation, all of the loops are available for binding, increasing the binding affinity to a ligand. However, in comparison to other antibody mimics, the calixarene-based antibody mimic does not consist exclusively of a peptide, and therefore it is less vulnerable to attack by protease enzymes. Neither does the scaffold consist purely of a peptide, DNA or RNA, meaning this antibody mimic is relatively stable in extreme environmental conditions and has a long life-span. Further, since the calixarene-based antibody mimic is relatively small, it is less likely to produce an immunogenic response.

Murali et al. (Cell Mol Biol 49(2):209-216 (2003)) describe a methodology for reducing antibodies into smaller peptidomimetics, they term "antibody-like binding peptidomimetics" (ABiP) which may also be useful as an alternative to antibodies.

In addition to non-immunoglobulin protein frameworks, antibody properties have also been mimicked in compounds comprising RNA molecules and unnatural oligomers (e.g., protease inhibitors, benzodiazepines, purine derivatives and beta-turn mimics). Accordingly, non-antibody GM-CSF antagonists can also include such compounds.

Therapeutic Administration

In some embodiments, the methods of the present disclosure comprise administering a hGM-CSF antagonist, (e.g., an anti-hGM-CSF antibody) as a pharmaceutical composition to a subject having a CRS or a cytokine storm. In some embodiments, the hGM-CSF antagonist is administered in a therapeutically effective amount using a dosing regimen suitable for treatment of the disease.

In some embodiments, a therapeutically effective amount is an amount that at least partially arrests the condition or its symptoms. For example, a therapeutically effective amount may arrest immune activation, may decrease the levels of circulating cytokines, may decrease T-cell activation, or may ameliorate fever, malaise, fatigue, anorexia, myalgias, arthalgias, nausea, vomiting, headache, skin rash, nausea, vomiting, diarrhea, tachypnea, hypoxemia, cardiovascular tachycardia, widened pulse pressure, hypotension, increased cardiac output (early), potentially diminished cardiac output (late), elevated D-dimer, hypofibrinogenemia with or without bleeding, azotemia, transaminitis, hyperbilirubinemia, headache, mental status changes, confusion, delirium, word finding difficulty or frank aphasia, hallucinations, tremor, dysmetria, altered gait, or seizures.

The methods of the invention comprise administering an anti-hGM-CSF antibody as a pharmaceutical composition to a patient in a therapeutically effective amount using a dosing regimen suitable for treatment of the disease. The composition can be formulated for use in a variety of drug delivery systems. One or more physiologically acceptable excipients or carriers can also be included in the compositions for proper formulation. Suitable formulations for use in the present invention are found in *Remington: The Science and Practice of Pharmacy,* 21st Edition, Philadelphia, Pa. Lippincott Williams & Wilkins, 2005. For a brief review of methods for drug delivery, see, Langer, Science 249: 1527-1533 (1990).

The anti-hGM-CSF antibody for use in the methods of the invention is provided in a solution suitable for injection into the patient such as a sterile isotonic aqueous solution for injection. The antibody is dissolved or suspended at a suitable concentration in an acceptable carrier. In some embodiments the carrier is aqueous, e.g., water, saline, phosphate buffered saline, and the like. The compositions may contain auxiliary pharmaceutical substances as required to approximate physiological conditions, such as pH adjusting and buffering agents, tonicity adjusting agents, and the like.

The pharmaceutical compositions of the invention are administered to a patient, e.g., a patient that has osteopenia, rheumatoid arthritis, juvenile idiopathic arthritis, systemic-onset Still's disease, asthma, eosinophilic asthma, eosinophilic esophagitis, multiple sclerosis, psoriasis, atopic dermatitis, plexiform neurofibromatosis, autoimmune lymphoproliferative syndrome (or ALPS, also known as Canale-Smith syndrome), Ras-associated autoimmune leukoproliferative disorder (or RALD), Noonan syndrome, chronic myelomonocytic leukemia, juvenile myelomonocytic leukemia, acute myeloid leukemia, Multicentric Castleman's Disease, chronic obstructive pulmonary disease, interstitial lung disease, diffuse parenchymal lung disease, idiopathic thrombocytopenia purpura, Alzheimer's disease, heart failure, Kawasaki's Disease, cardiac damage due to an ischemic event, or diabetes, in an amount sufficient to cure or at least partially arrest the disease or symptoms of the disease and its complications. An amount adequate to accomplish this is defined as a "therapeutically effective dose." A therapeutically effective dose is determined by monitoring a patient's response to therapy. Typical benchmarks indicative of a therapeutically effective dose includes amelioration of symptoms of the disease in the patient. Amounts effective for this use will depend upon the severity of the disease and the general state of the patient's health, including other factors such as age, weight, gender, administration route, etc. Single or multiple administrations of the antibody may be administered depending on the dosage and frequency as required and tolerated by the patient. In any event, the methods provide a sufficient quantity of anti-hGM-CSF antibody to effectively treat the patient.

The antibody may be administered alone, or in combination with other therapies to treat the disease of interest.

The antibody can be administered by injection or infusion through any suitable route including but not limited to intravenous, sub-cutaneous, intramuscular or intraperitoneal routes. In some embodiments, the antibody may be administered by insufflation. In an exemplary embodiment, the antibody may be stored at 10 mg/ml in sterile isotonic aqueous saline solution for injection at 4° C. and is diluted in either 100 ml or 200 ml 0.9% sodium chloride for injection prior to administration to the patient. The antibody is administered by intravenous infusion over the course of 1 hour at a dose of between 0.2 and 10 mg/kg. In other embodiments, the antibody is administered, for example, by intravenous infusion over a period of between 15 minutes and 2 hours. In still other embodiments, the administration procedure is via sub-cutaneous or intramuscular injection.

In some embodiments, the hGM-CSF antagonist, e.g., an anti-hGM-CSF antibody, is administered by a perispinal route. Perispinal administration involves anatomically localized delivery performed so as to place the therapeutic molecule directly in the vicinity of the spine at the time of initial administration. Perispinal administration is described, e.g., in U.S. Pat. No. 7,214,658 and in Tobinick & Gross, J. Neuroinflammation 5:2, 2008.

The dose of hGM-CSF antagonist is chosen in order to provide effective therapy for a subject that has been diagnosed with CRS or cytokine storm. The dose is typically in the range of about 0.1 mg/kg body weight to about 50 mg/kg body weight or in the range of about 1 mg to about 2 g per patient. The dose is often in the range of about 1 to about 20 mg/kg or approximately about 50 mg to about 2000 mg/patient. The dose may be repeated at an appropriate frequency which may be in the range once per day to once every three months, depending on the pharmacokinetics of the antagonist (e.g. half-life of the antibody in the circulation) and the pharmacodynamic response (e.g. the duration of the therapeutic effect of the antibody). In some embodiments where the antagonist is an antibody or modified antibody fragment, the in vivo half-life of between about 7 and about 25 days and antibody dosing is repeated between once per week and once every 3 months. In other embodiments, the antibody is administered approximately once per month.

A $V_H$ region and/or $V_L$ region of the invention may also be used for diagnostic purposes. For example, the $V_H$ and/or $V_L$ region may be used for clinical analysis, such as detection of GM-CSF levels in a patient. A $V_H$ or $V_L$ region of the invention may also be used, e.g., to produce anti-Id antibodies.

Unless otherwise defined herein, scientific and technical terms used in connection with the present application shall have the meanings that are commonly understood by those of skill in the art. Further, unless otherwise required by context, singular terms shall include pluralities and plural terms shall include the singular.

In one embodiment, "treating" comprises therapeutic treatment and "preventing" comprises prophylactic or preventative measures, wherein the object is to prevent or lessen the targeted pathologic condition or disorder as described hereinabove. Thus, in one embodiment, treating may include directly affecting or curing, suppressing, inhibiting, preventing, reducing the severity of, delaying the onset of, reducing symptoms associated with the disease, disorder or condition, or a combination thereof. Thus, in one embodiment, "treating," "ameliorating," and "alleviating" refer inter alia to delaying progression, expediting remission, inducing remission, augmenting remission, speeding recovery, increasing efficacy of or decreasing resistance to alternative therapeutics, or a combination thereof. In one embodiment, "preventing" refers, inter alia, to delaying the onset of symptoms, preventing relapse to a disease, decreasing the number or frequency of relapse episodes, increasing latency between symptomatic episodes, or a combination thereof. In one embodiment, "suppressing" or "inhibiting", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

In the present disclosure the singular forms "a," "an," and "the" include the plural reference, and reference to a particular numerical value includes at least that particular value, unless the context clearly indicates otherwise. The term "plurality", as used herein, means more than one. When a range of values is expressed, another embodiment includes from the one particular and/or to the other particular value.

Similarly, when values are expressed as approximations, by use of the antecedent "about," it is understood that the particular value forms another embodiment. All ranges are inclusive and combinable. In some embodiments, the term "about", refers to a deviance of between 0.0001-5% from the indicated number or range of numbers. In some embodiments, the term "about", refers to a deviance of between 1-10% from the indicated number or range of numbers. In some embodiments, the term "about", refers to a deviance of up to 25% from the indicated number or range of numbers. The term "comprises" means encompasses all the elements listed, but may also include additional, unnamed elements, and it may be used interchangeably with the terms "encompasses", "includes", or "contains" having all the same qualities and meanings. The term "consisting of" means being composed of the recited elements or steps, and it may be used interchangeably with the terms "composed of" having all the same qualities and meanings.

EXAMPLES

Example 1—Exemplary Humaneered Antibodies to GM-CSF

A panel of engineered Fab' molecules with the specificity of cl9/2 were generated from epitope-focused human V-segment libraries as described in US patent application publication nos. 20060134098 and 20050255552. Epitope-focused libraries were constructed from human V-segment library sequences linked to a CDR3-FR4 region containing BSD sequences in CDRH3 and CDRL3 together with human germ-line J-segment sequences. For the heavy chain, human germ-line JH4 sequence was used and for the light chain, human germ-line JK4 sequence was used.

Full-length Humaneered V-regions from a Vh1-restricted library were selected that supported binding to recombinant human GM-CSF. The "full-length" V-kappa library was used as a base for construction of "cassette" libraries as described in US patent application publication no. 20060134098, in which only part of the murine cl9/2 V-segment was initially replaced by a library of human sequences. Two types of cassettes were constructed. Cassettes for the V-kappa chains were made by bridge PCR with overlapping common sequences within the framework 2 region. In this way "front-end" and "middle" human cassette libraries were constructed for the human V-kappa III isotype. Human V-kappa III cassettes which supported binding to GM-CSF were identified by colony-lift binding assay and ranked according to affinity in ELISA. The V-kappa human "front-end" and "middle" cassettes were fused together by bridge PCR to reconstruct a fully human V-kappa region that supported GM-CSF binding activity. The Humaneered Fibs thus consist of Humaneered V-heavy and V-kappa regions that support binding to human GM-CSF.

Binding activity was determined by surface plasmon resonance (spr) analysis. Biotinylated GM-CSF was captured on a streptavidin-coated CM5 biosensor chip. Humaneered Fab fragments expressed from $E.\ coli$ were diluted to a starting concentration of 30 nM in 10 mM HEPES, 150 mM NaCl, 0.1 mg/ml BSA and 0.005% P20 at pH 7.4. Each Fab was diluted 4 times using a 3-fold dilution series and each concentration was tested twice at 37 degrees C. to determine the binding kinetics with the different density antigen surfaces. The data from all three surfaces were fit globally to extract the dissociation constants.

Binding kinetics were analyzed by Biacore 3000 surface plasmon resonance (SPR). Recombinant human GM-CSF antigen was biotinylated and immobilized on a streptavidin CM5 sensor chip. Fab samples were diluted to a starting concentration of 3 nM and run in a 3-fold dilution series. Assays were run in 10 mM HEPES, 150 mM NaCl, 0.1 mg/mL BSA and 0.005% p20 at pH 7.4 and 37° C. Each concentration was tested twice. Fab' binding assays were run on two antigen density surfaces providing duplicate data sets. The mean affinity (KD) for each of 6 various humaneered anti-GM-CSF Fab clones, calculated using a 1: 1 Langmuir binding model, is shown in Table 2.

Fabs were tested for GM-CSF neutralization using a TF-I cell proliferation assay. GM-CSF-dependent proliferation of human TF-I cells was measured after incubation for 4 days with 0.5 ng/ml GM-CSF using a MTS assay (Cell titer 96, Promega) to determine viable cells. All Fabs inhibited cell proliferation in this assay indicating that these are neutralizing antibodies. There is a good correlation between relative affinities of the anti-GM-CSF Fabs and EC50 in the cell-based assay. Anti-GM-CSF antibodies with monovalent affinities in the range 18 pM-104 pM demonstrate effective neutralization of GM-CSF in the cell-based assay.

Exemplary engineered anti-GM-CSF V region sequences are shown in FIG. 1.

TABLE 2

Affinity of anti-GM-CSF Fabs determined by surface plasmon resonance analysis in comparison with activity (EC50) in a GM-CSF dependent TF-I cell proliferation assay

| Fab | Monovalent binding affinity determined by SPR (pM) | $EC_{50}$ (pM) in TF-1 cell proliferation assay |
| --- | --- | --- |
| 94 | 18 | 165 |
| 104 | 19 | 239 |
| 77 | 29 | 404 |
| 92 | 58 | 539 |
| 42 | 104 | 3200 |
| 44 | 81 | 7000 |

Example 2—Evaluation of a Humaneered GM-CSF Antibody

This example evaluates the binding activity and biological potency of a humaneered anti-GM-CSF antibody in a cell-based assay in comparison to a chimeric IgG1k antibody (Ab2) having variable regions from the mouse antibody LMM102 (Nice et al., *Growth Factors* 3:159, 1990). Ab1 is a humaneered IgG1k antibody against GM-CSF having identical constant regions to Ab2.

Surface Plasmon Resonance Analysis of Binding of Human GM-CSF to Ab1 and Ab2

Surface Plasmon resonance analysis was used to compare binding kinetics and monovalent affinities for the interaction of Ab1 and Ab2 with glycosylated human GM-CSF using a Biacore 3000 instrument. Ab1 or Ab2 was captured onto the Biacore chip surface using polyclonal anti-human F(ab')2. Glycosylated recombinant human GM-CSF expressed from human 293 cells was used as the analyte. Kinetic constants were determined in 2 independent experiments (see FIGS. 2A-2B and Table 3). The results show that GM-CSF bound to Ab2 and Ab1 with comparable monovalent affinity in this experiment. However, Ab1 had a two-fold slower "on-rate" than Ab2, but an "off-rate" that was approximately three-fold slower.

TABLE 3

Figure 2A:
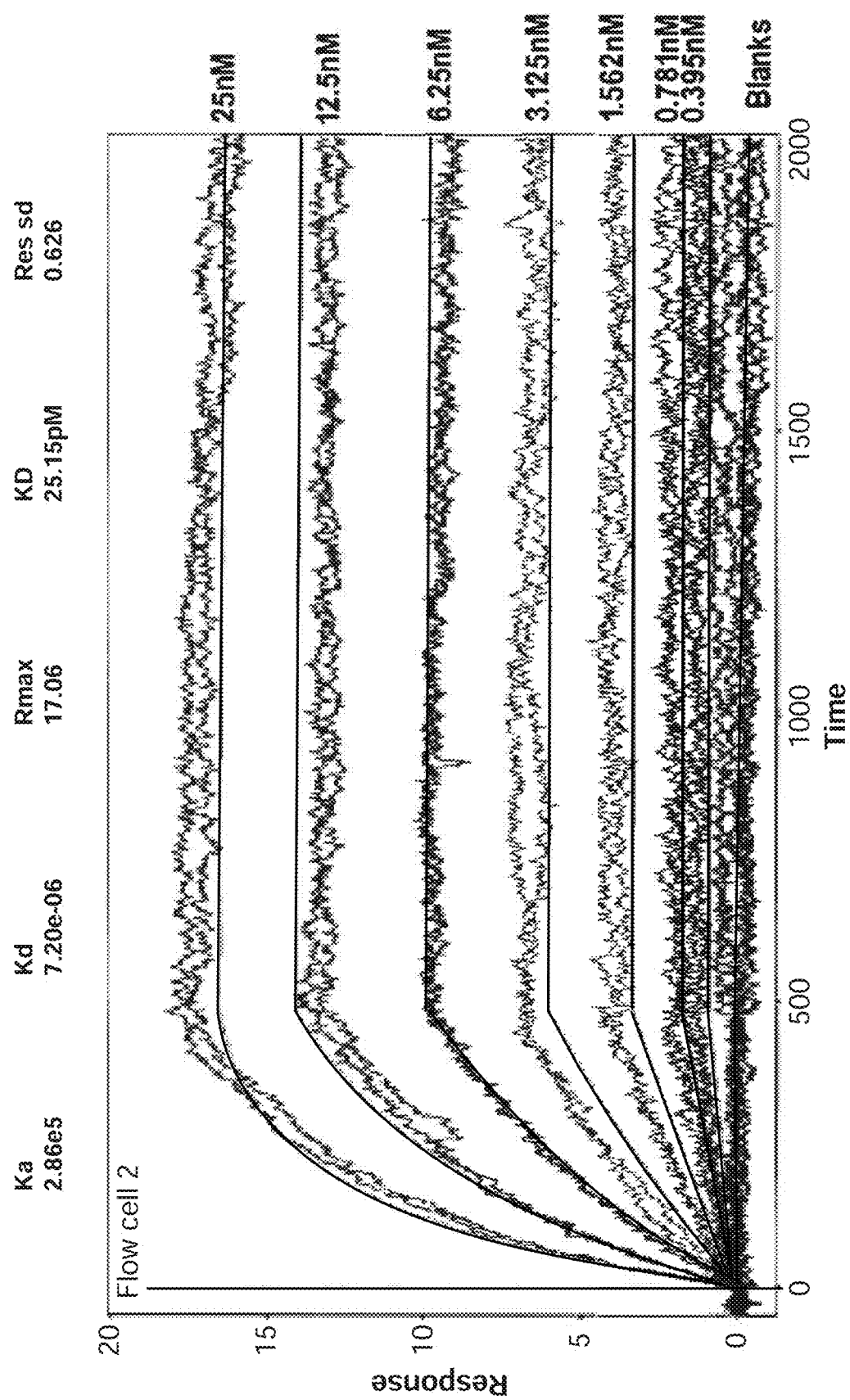
FIGS. 2A-2B illustrates binding of GM-CSF to Ab1 (FIG. 2A) or Ab2 (FIG. 2B) determined by surface plasmon resonance analysis at 37° C. (Biacore 3000). Ab1 and Ab2 were captured on anti Fab polyclonal antibodies immobilized on the Biacore chip. Different concentrations of GM-CSF were injected over the surface as indicated. Global fit analysis was carried out assuming a 1:1 interaction using Scrubber2 software.
Figure 2B:
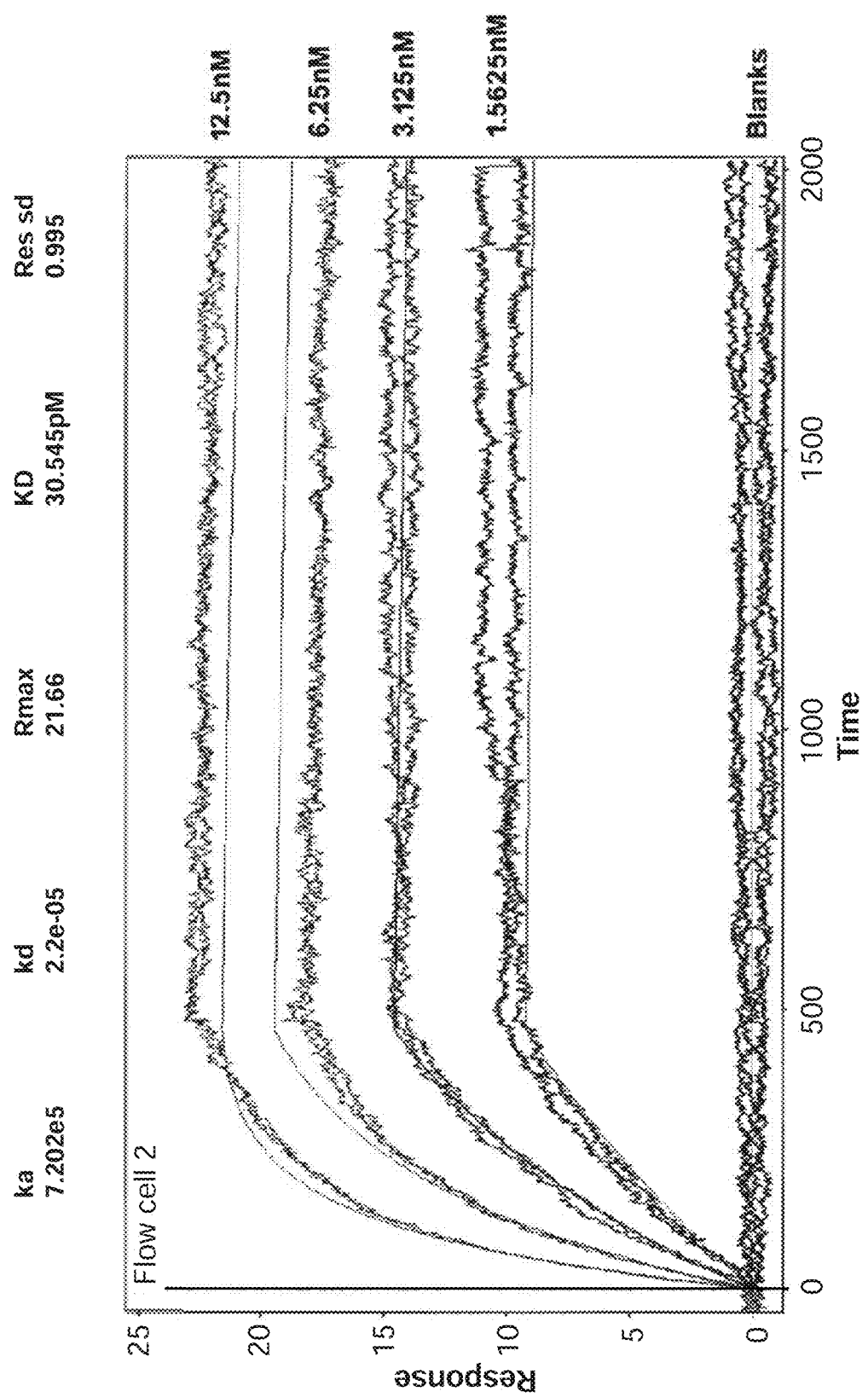

Kinetic constants at 37° C. determined from the surface plasmon resonance analysis in FIGS. 2A-2B; association constant ($k_a$), dissociation constant ($k_d$) and calculated affinity (KD) are shown.

|  | $k_a$ (M$^{-1}$s$^{-1}$) | $k_d$ (s$^{-1}$) | KD (pM) |
|---|---|---|---|
| Ab2 | 7.20 × 10$^5$ | 2.2 × 10$^{-5}$ | 30.5 |
| Ab1 | 2.86 × 10$^5$ | 7.20 × 10$^{-6}$ | 25.1 |

GM-CSF is naturally glycosylated at both N-linked and O-linked glycosylation sites although glycosylation is not required for biological activity. In order to determine whether GM-CSF glycosylation affects the binding of Ab1 or Ab2, the antibodies were compared in an ELISA using recombinant GM-CSF from two different sources; GM-CSF expressed in *E. coli* (non-glycosylated) and GM-CSF expressed from human 293 cells (glycosylated). The results in FIGS. 3A-3B and Table 4 showed that both antibodies bound glycosylated and non-glycosylated GM-CSF with equivalent activities. The two antibodies also demonstrated comparable $EC_{50}$ values in this assay.

TABLE 4

Figure 3A:
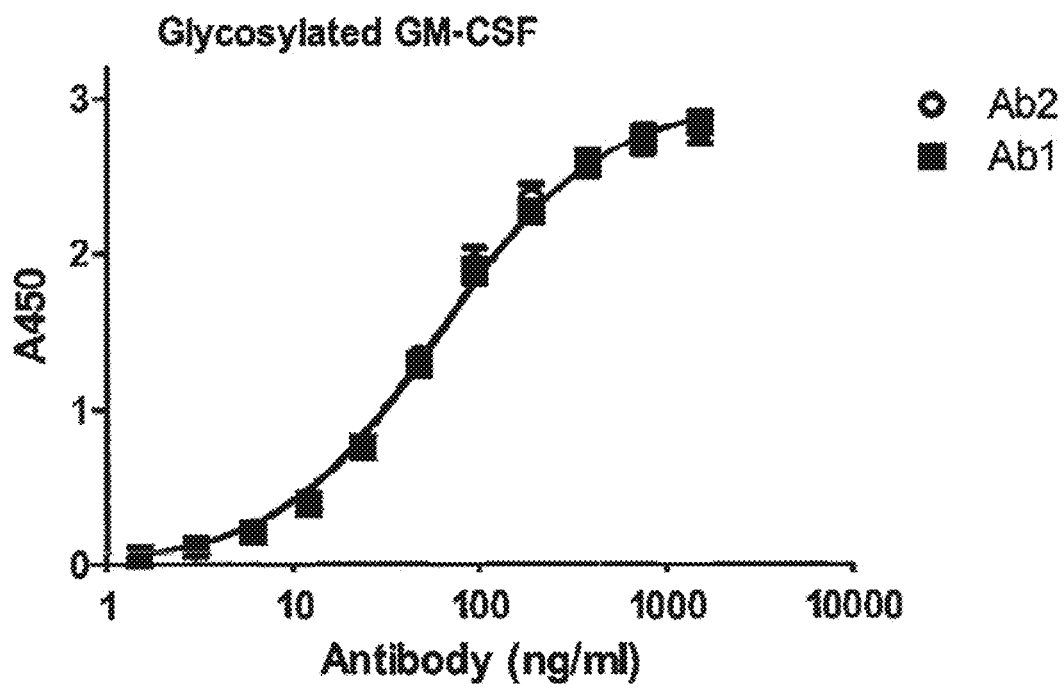
FIGS. 3A-3B illustrates binding of Ab1 and Ab2 to glycosylated (FIG. 3A) and non-glycosylated GM-CSF (FIG. 3B). Binding to glycosylated GM-CSF expressed from human 293 cells or non-glycosylated GM-CSF expressed in *E. coli* was determined by ELISA. Representative results from a single experiment are shown (exp 1). Two-fold dilutions of Ab1 and Ab2 starting from 1500 ng/ml were applied to GM-CSF coated wells. Each point represents mean±standard error for triplicate determinations. Sigmoidal curve fit was performed using Prism 5.0 Software (Graphpad).
Figure 3B:
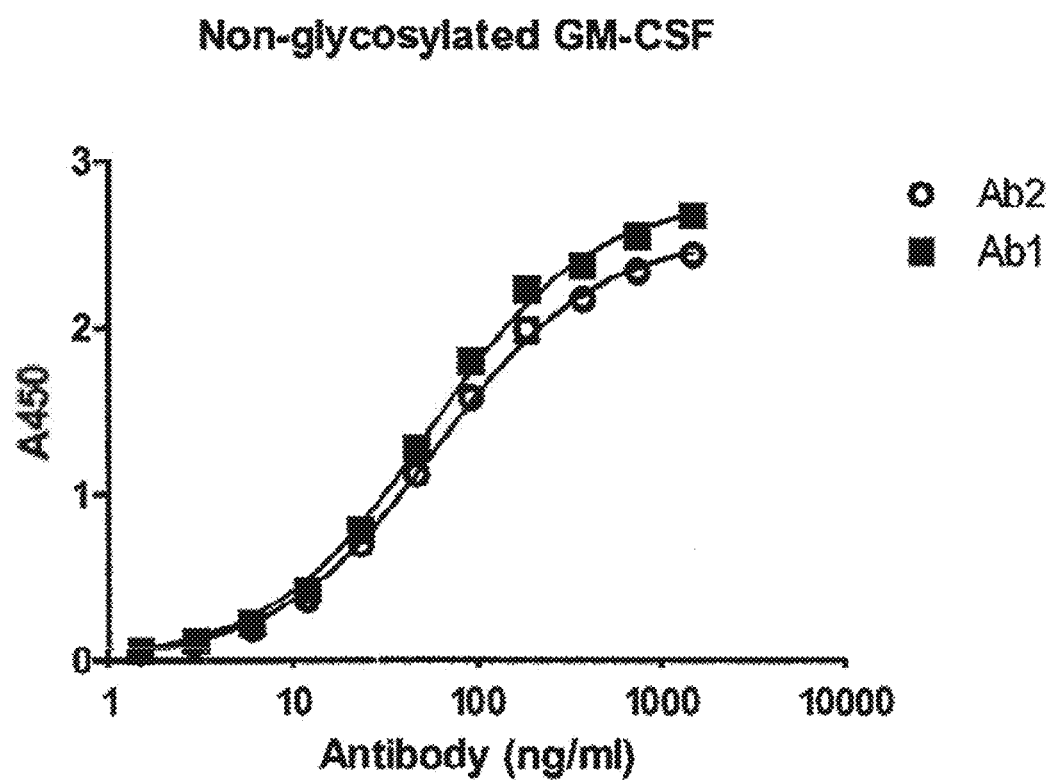

Summary of $EC_{50}$ for binding of Ab2 and Ab1 to human GM-CSF from two different sources determined by ELISA. Binding to recombinant GM-CSF from human 293 cells (glycosylated) or from *E. coli* (non-glycosylated) was determined from two independent experiments. Experiment 1 is shown in FIGS. 3A-3B.

|  | Non-glycosylated (exp 1) | Non-glycosylated (exp 2) | Glycosylated (exp 1) |
|---|---|---|---|
| Ab2 | 400 pM | 433 pM | 387 pM |
| Ab1 | 373 pM | 440 pM | 413 pM |

Ab1 is a Humaneered antibody that was derived from the mouse variable regions present in Ab2. Ab1 was tested for overlapping epitope specificity (Ab2) by competition ELISA.

Figure 4A:
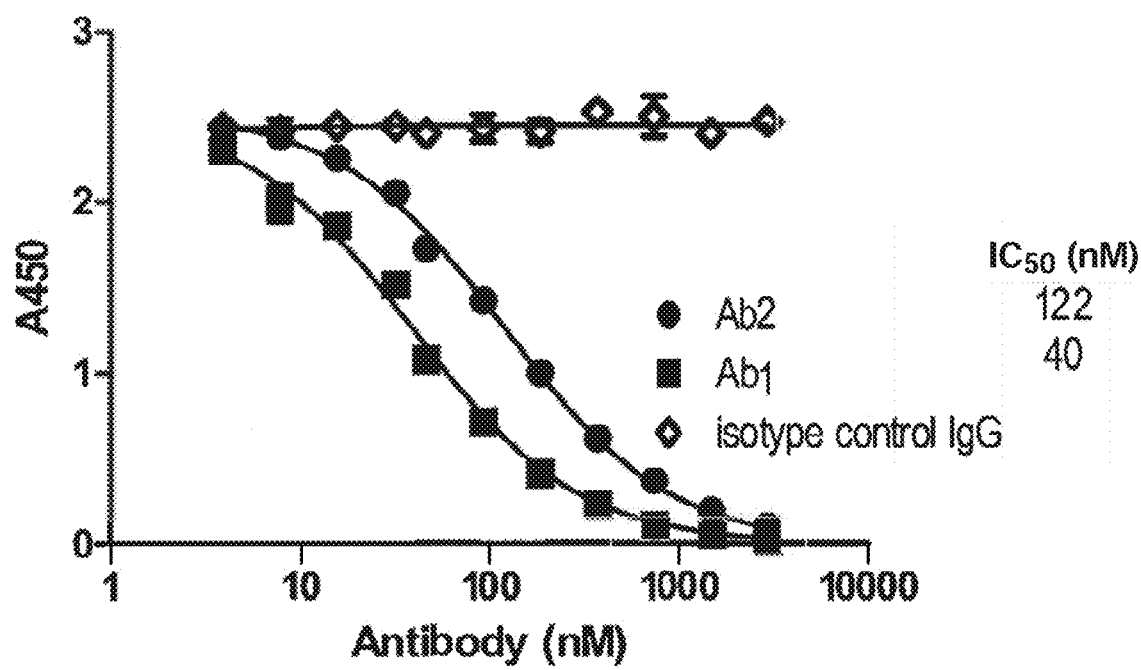
FIGS. 4A-4B illustrates competition ELISA demonstrating binding of Ab1 and Ab2 to a shared epitope. ELISA plates coated with 50 ng/well of recombinant GM-CSF were incubated with various concentrations of antibody (Ab2, Ab1 or isotype control antibody) together with 50 nM biotinylated Ab2. Biotinylated antibody binding was assayed using neutravidin-HRP conjugate. Competition for binding to GM-CSF was for 1 hr (FIG. 4A) or for 18 hrs (FIG. 4B). Each point represents mean±standard error for triplicate determinations. Sigmoidal curve fit was performed using Prism 5.0 Software (Graphpad).
Figure 4B:
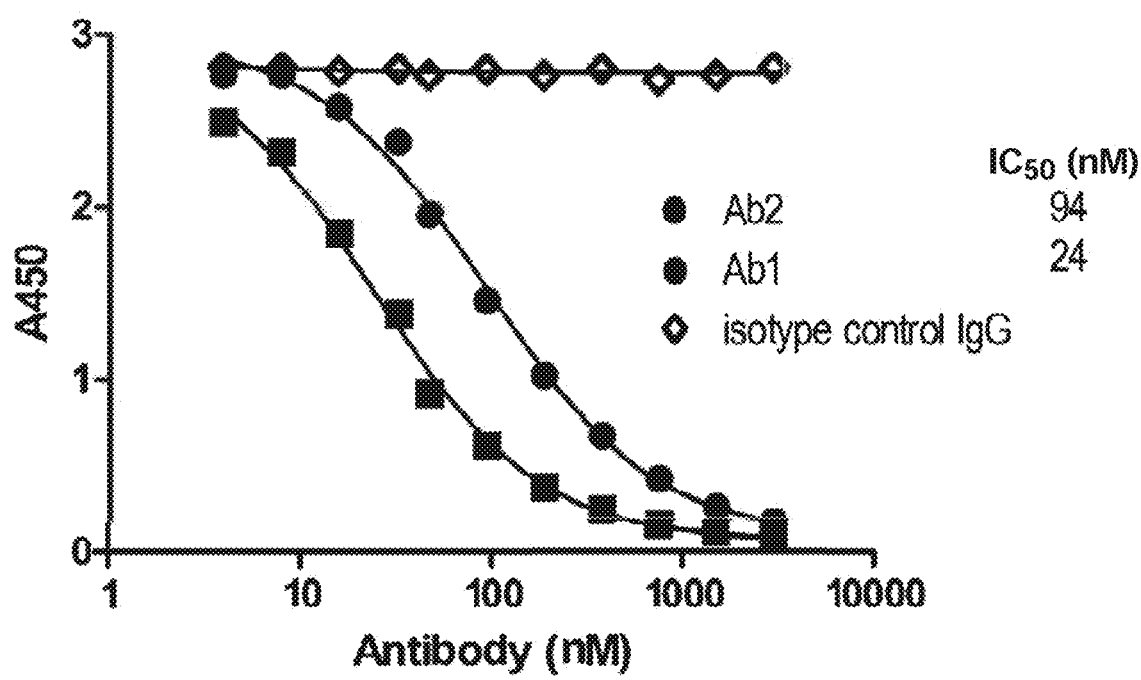

Biotinylated Ab2 was prepared using known techniques. Biotinylation did not affect binding of Ab2 to GM-CSF as determined by ELISA. In the assay, Ab2 or Ab1 was added in varying concentrations with a fixed amount of biotinylated Ab2. Detection of biotinylated Ab2 was assayed in the presence of unlabeled Ab or Ab1 competitor (FIGS. 4A-4B). Both Ab1 and Ab2 competed with biotinylated Ab2 for binding to GM-CSF, thus indicating binding to the same epitope. Ab1 competed more effectively for binding to GM-CSF than Ab2, consistent with the slower dissociation kinetics for Ab1 when compared with Ab2 by surface plasmon resonance analysis.

Neutralization of GM-CSF Activity by Ab1 and Ab2

A cell-based assay for neutralization of GM-CSF activity was employed to evaluate biological potency. The assay measures IL-8 secretion from U937 cells induced with GM-CSF. IL-8 secreted into the culture supernatant is determined by ELISA after 16 hours induction with 0.5 ng/ml *E. coli*-derived GM-CSF.

Figure 5:
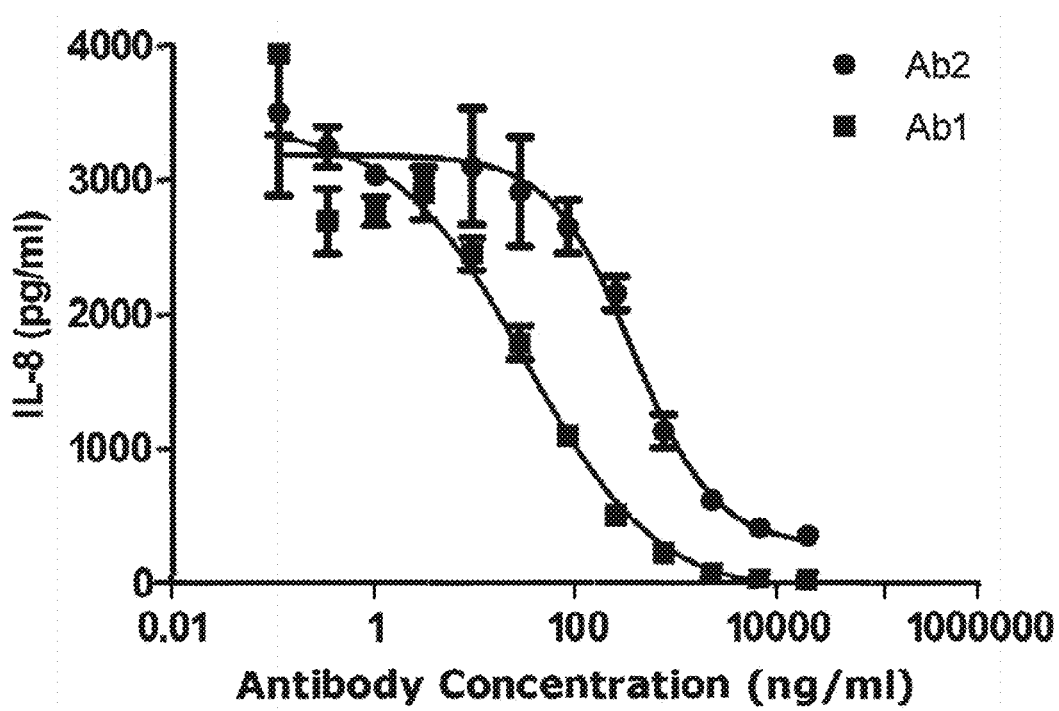
FIG. 5 illustrates inhibition of GM-CSF-induced IL-8 expression. Various amounts of each antibody were incubated with 0.5 ng/ml GM-CSF and incubated with U937 cells for 16 hrs. IL-8 secreted into the culture supernatant was determined by ELISA.
Figure 8:
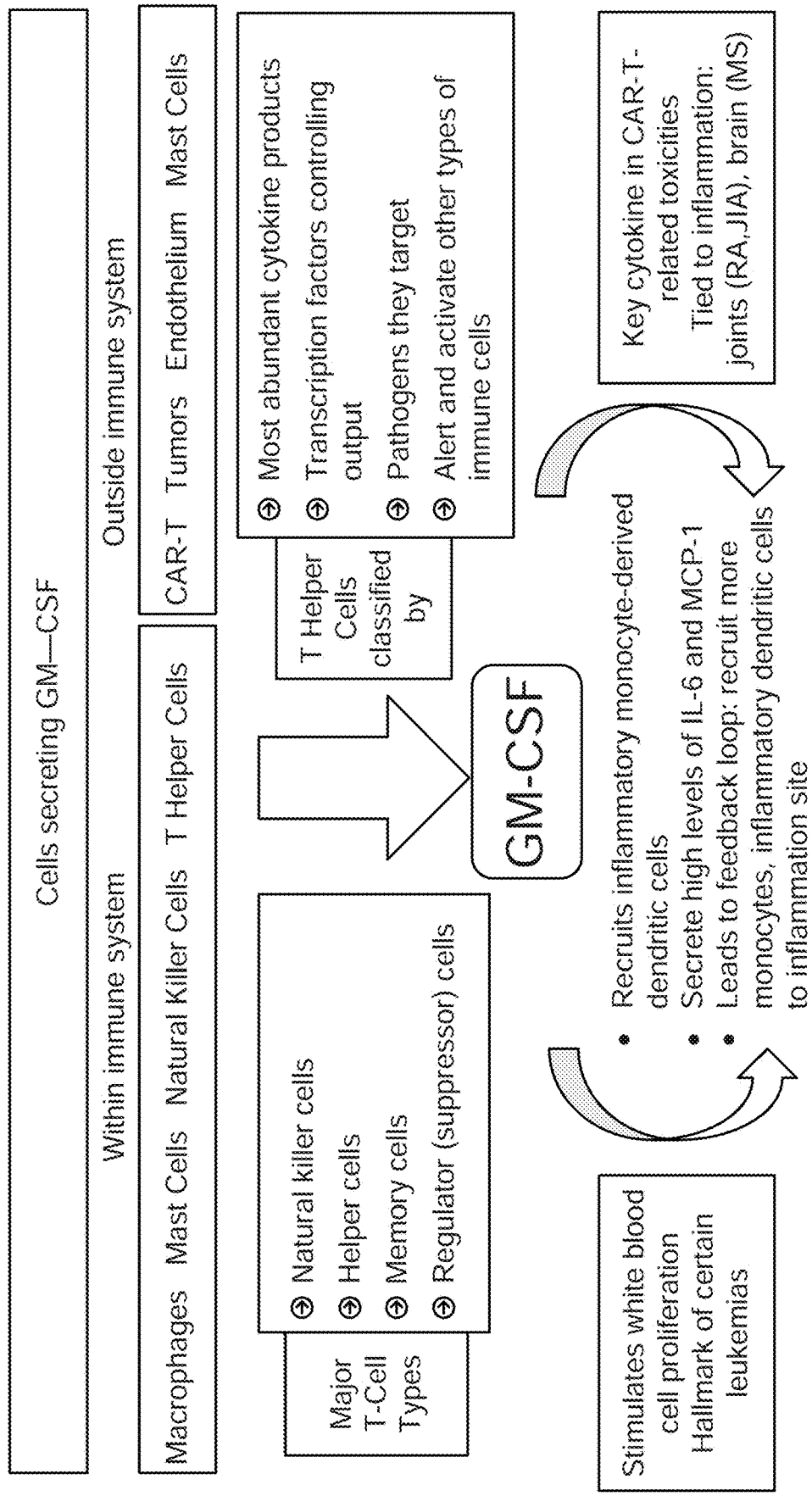
FIG. 8 illustrates the role of GM-CSF (Myeloid Inflammatory Factor) as a key cytokine in CAR-T-related activity and in stimulation of white blood cell proliferation, which is a characteristic feature in certain leukemias, e.g., acute myeloid leukemia (AML).
Figure 9:
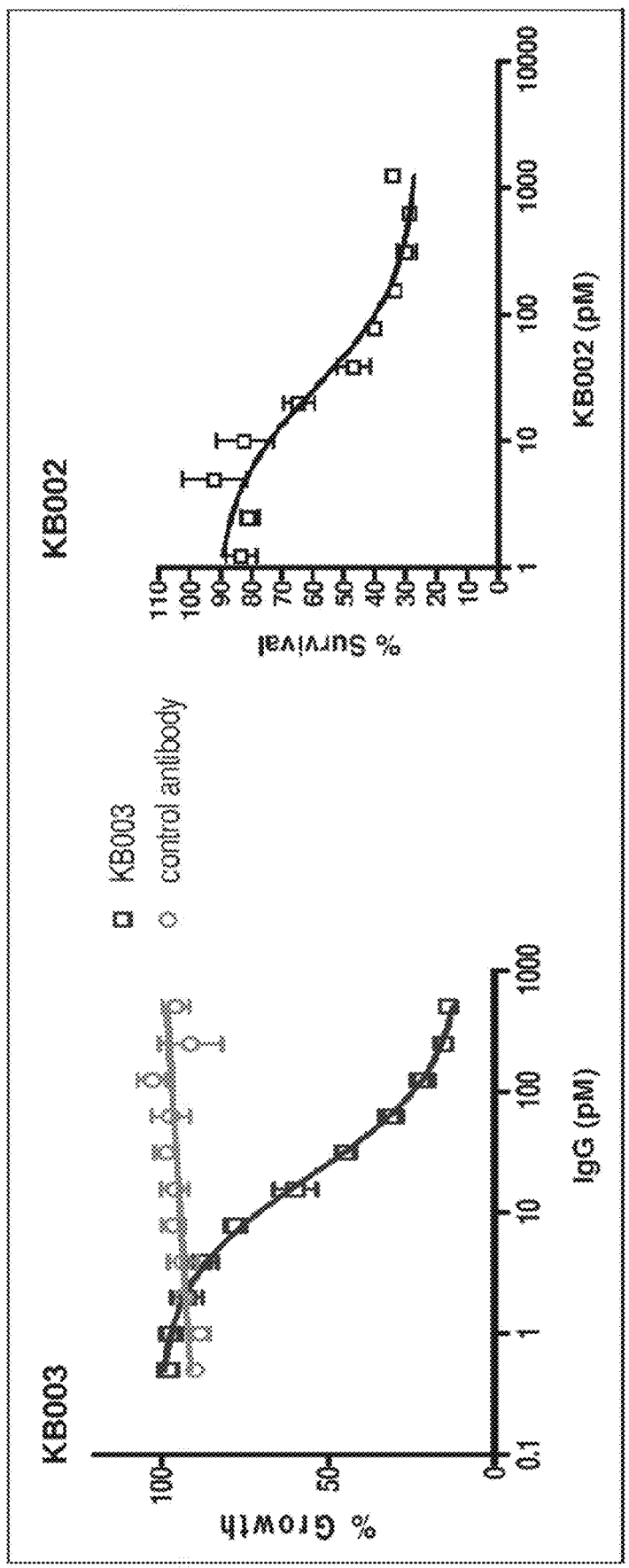
FIG. 9 illustrates inhibition of GM-CSF-dependent human TF-1 cell proliferation (human erythroleukemia) by neutralization of human GM-CSF with anti-GM-CSF antibody. KB003 is a recombinant monoclonal antibody designed to target and neutralize human GM-CSF. KB002 is a mouse/human chimeric monoclonal antibody, that targets and neutralizes hGM-CSF.
Figure 10:
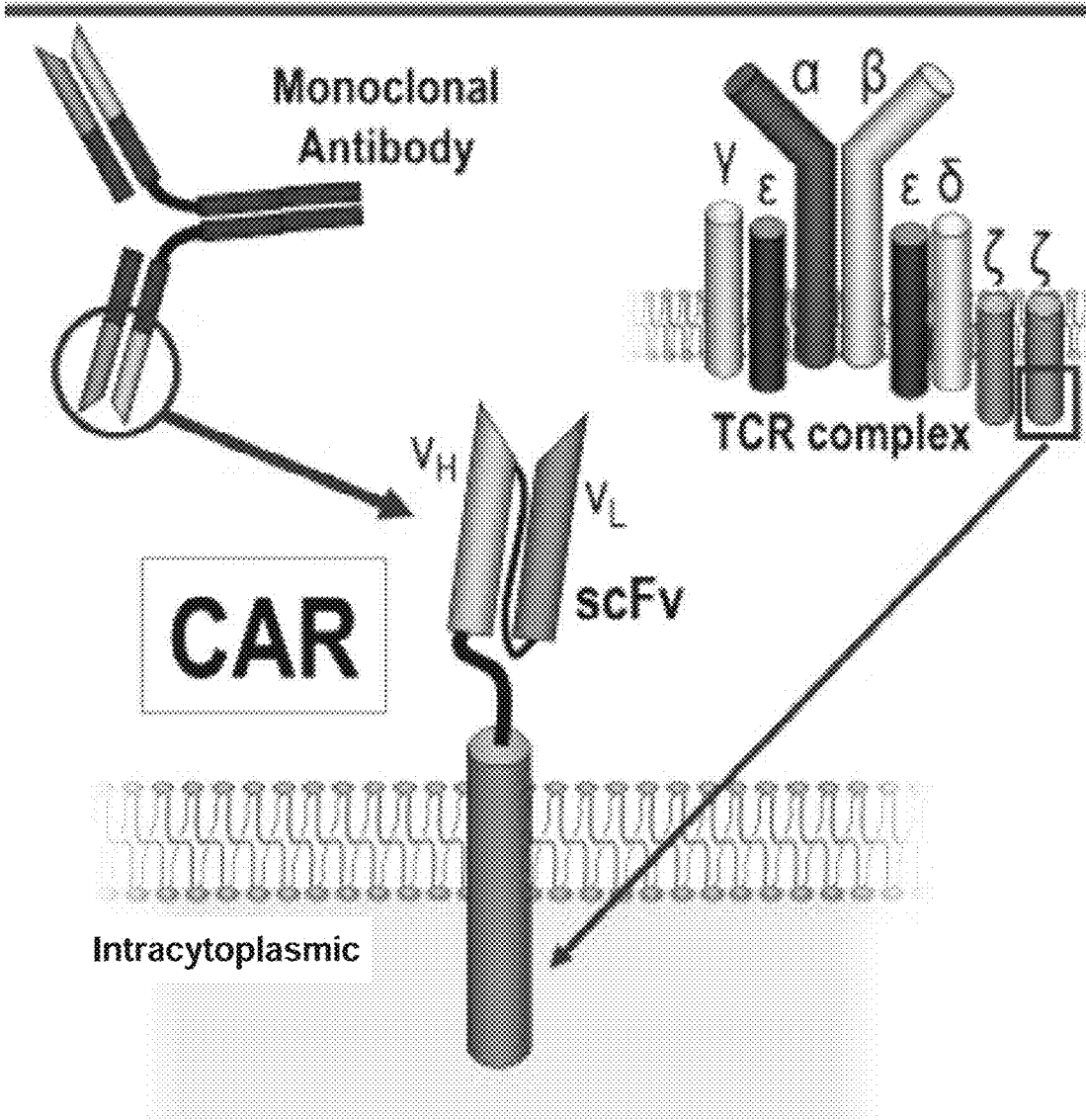
FIG. 10 is a depiction of a chimeric antigen receptor.
Figure 11:
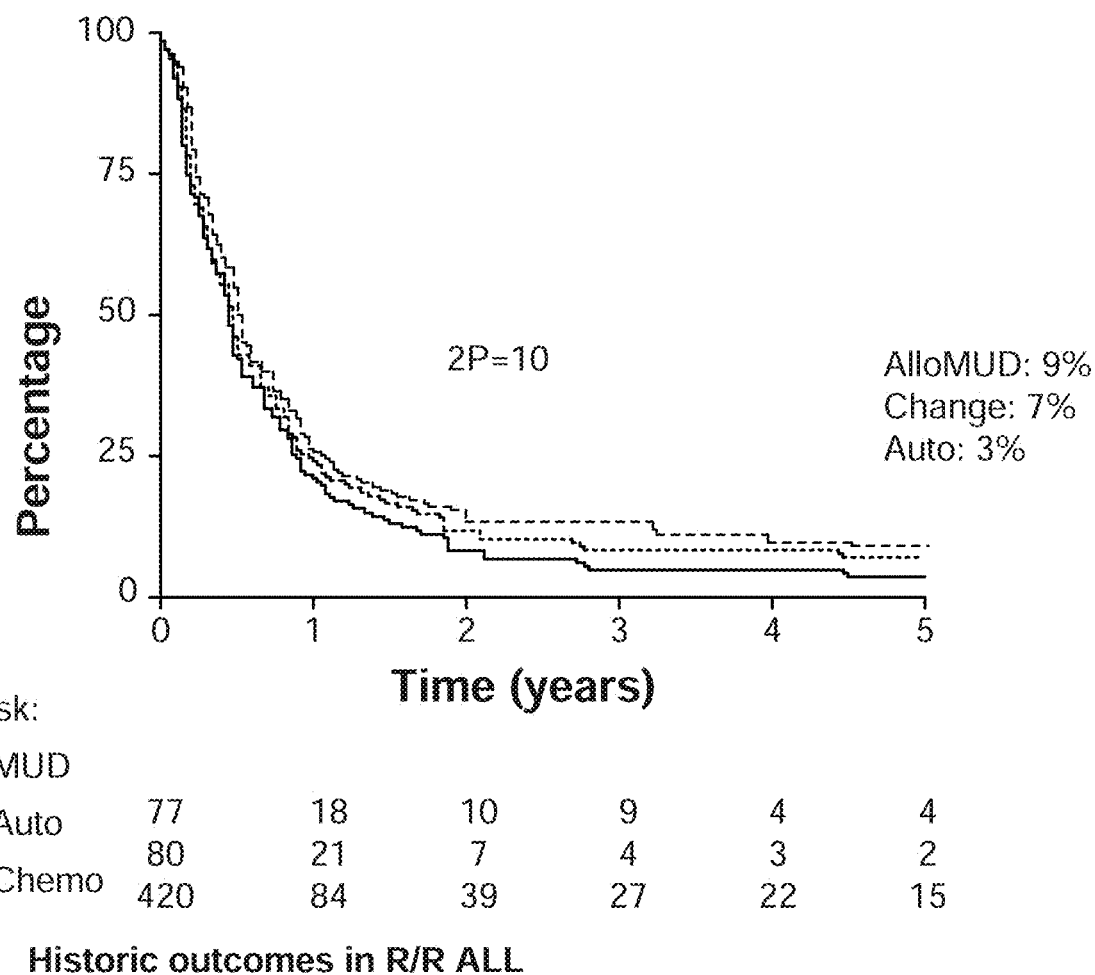
FIG. 11 illustrates CAR-T19 therapy results in high response rates in relapsed refractory ALL. Data show historic outcomes in R/R ALL and outcomes in R/R ALL after CAR-T19 therapy. (Maude, et al NEJM 2014).
Figure 11:
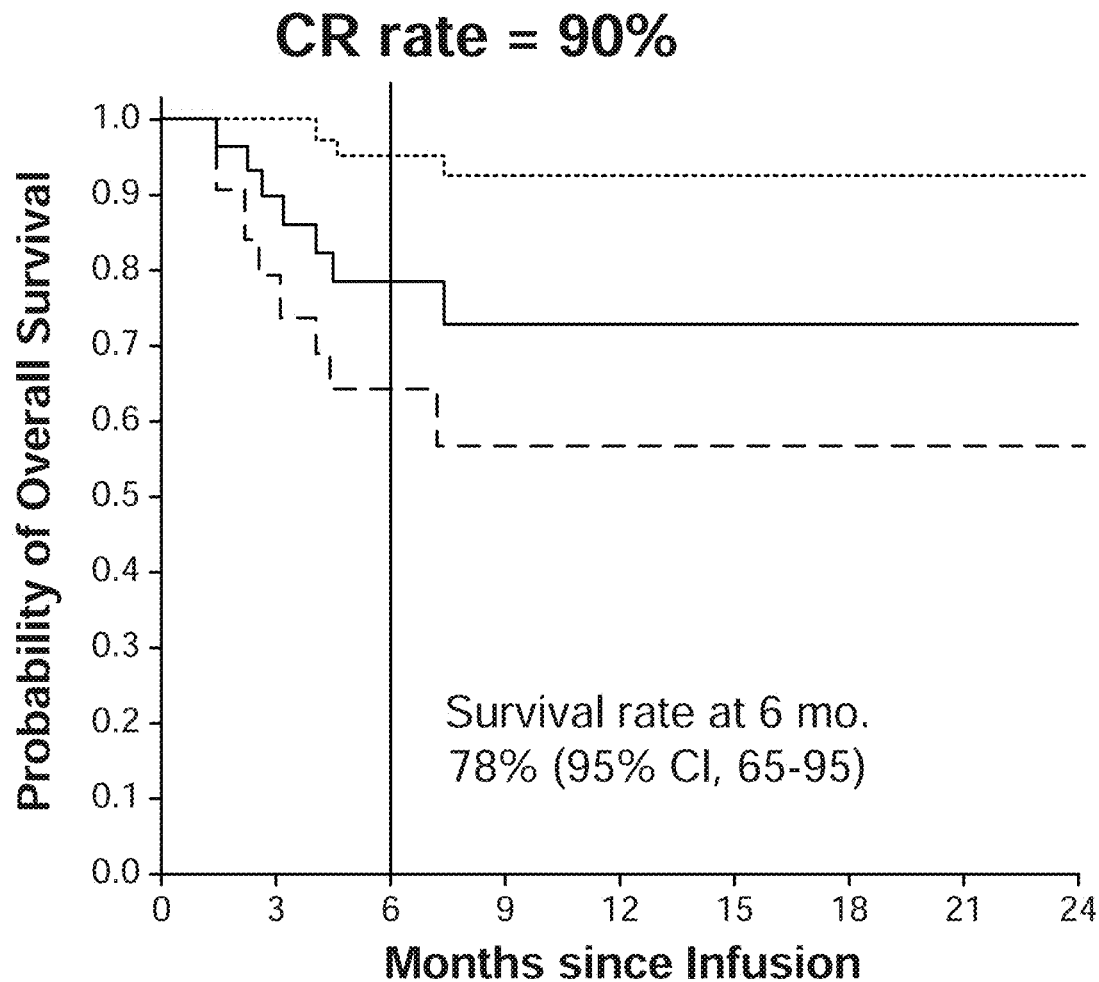
Figure 12:
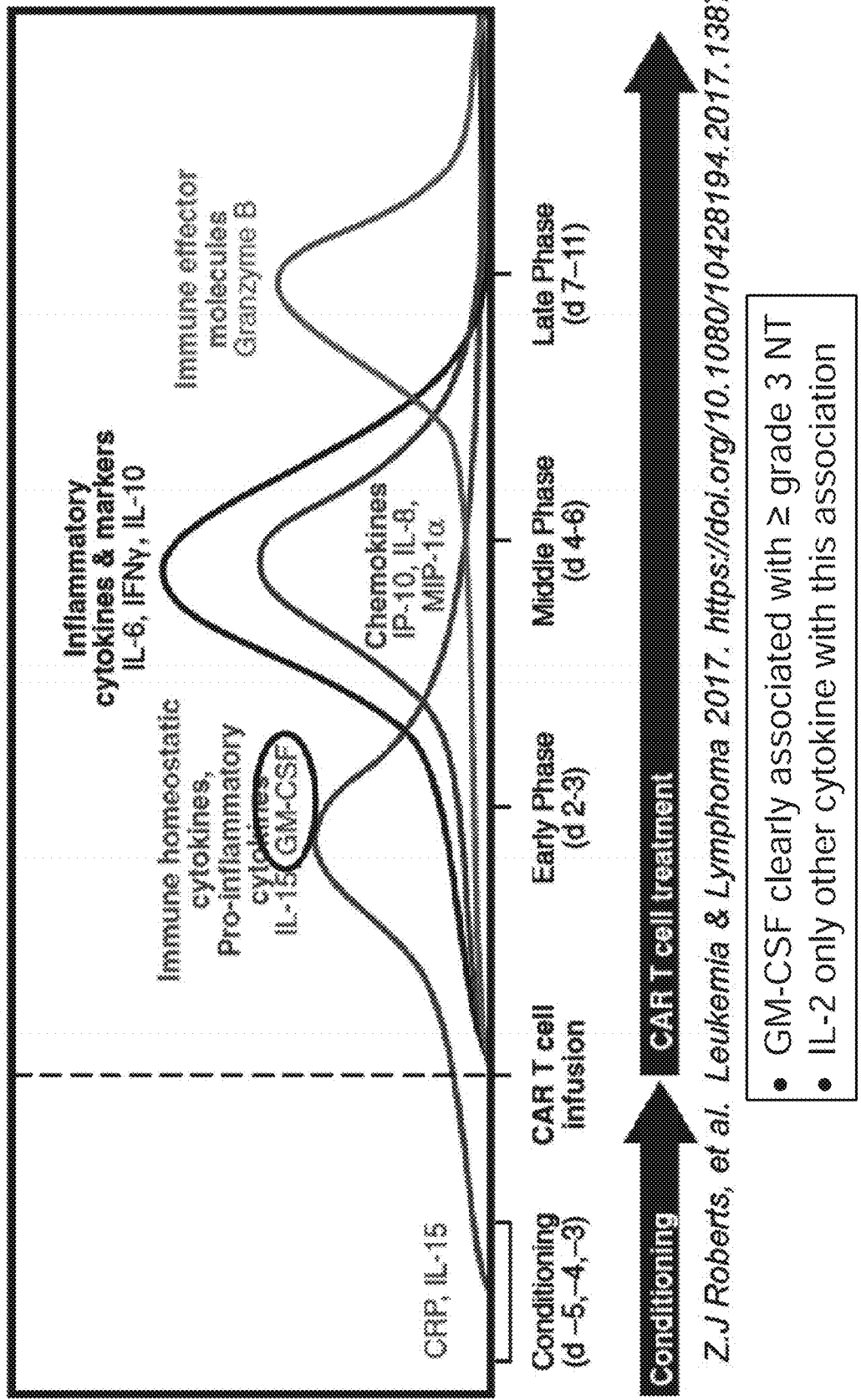
FIG. 12 illustrates evidence showing a significant GM-CSF link to NT. GM-CSF levels correlate with serious adverse effects after CAR-T cell therapy. GM-CSF levels precede and modulate other cytokines other than IL-15. Elevated GM-CSF is clearly associated with ≥grade 3 NT. IL-2 is only other cytokine with this association.
Figure 12:
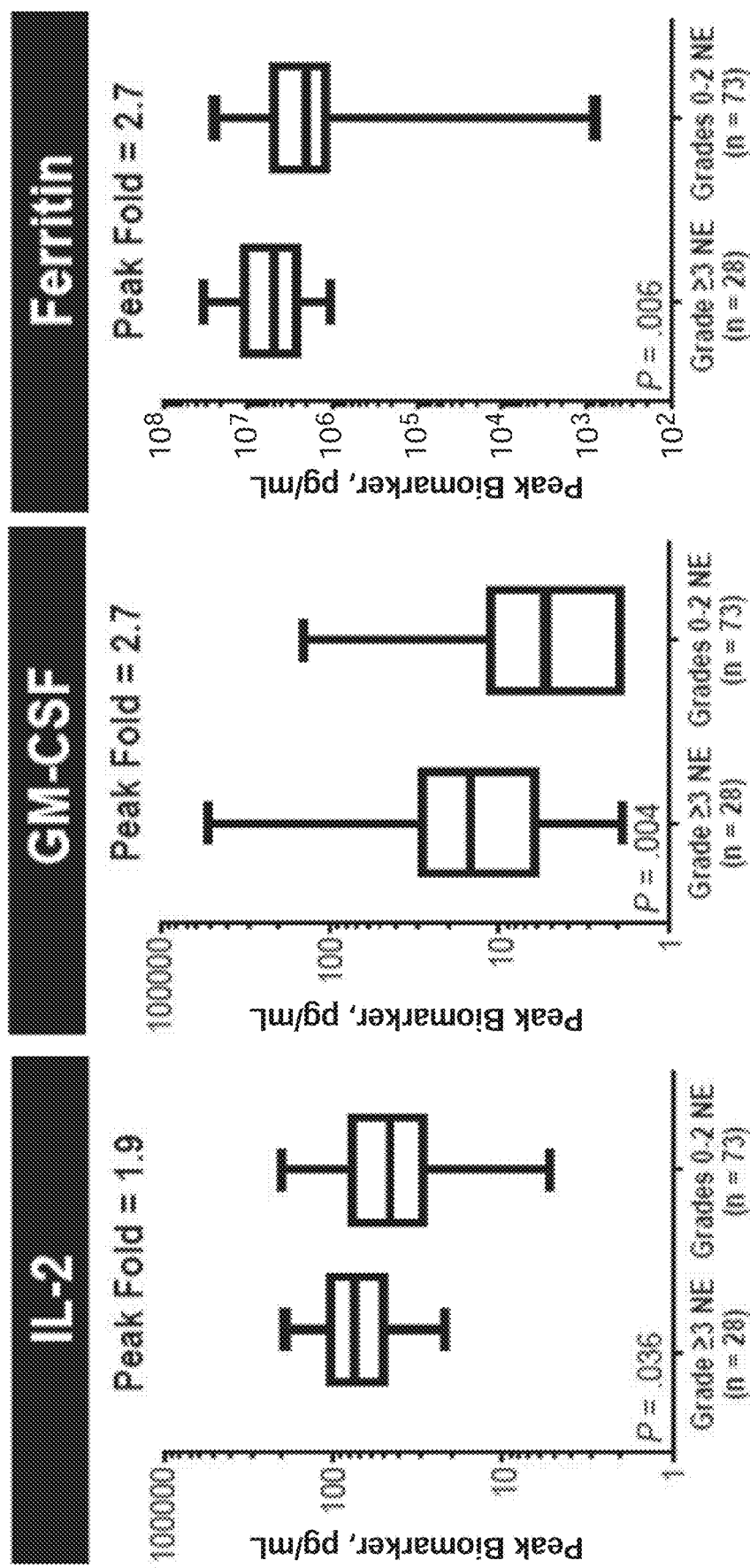
Figure 13:
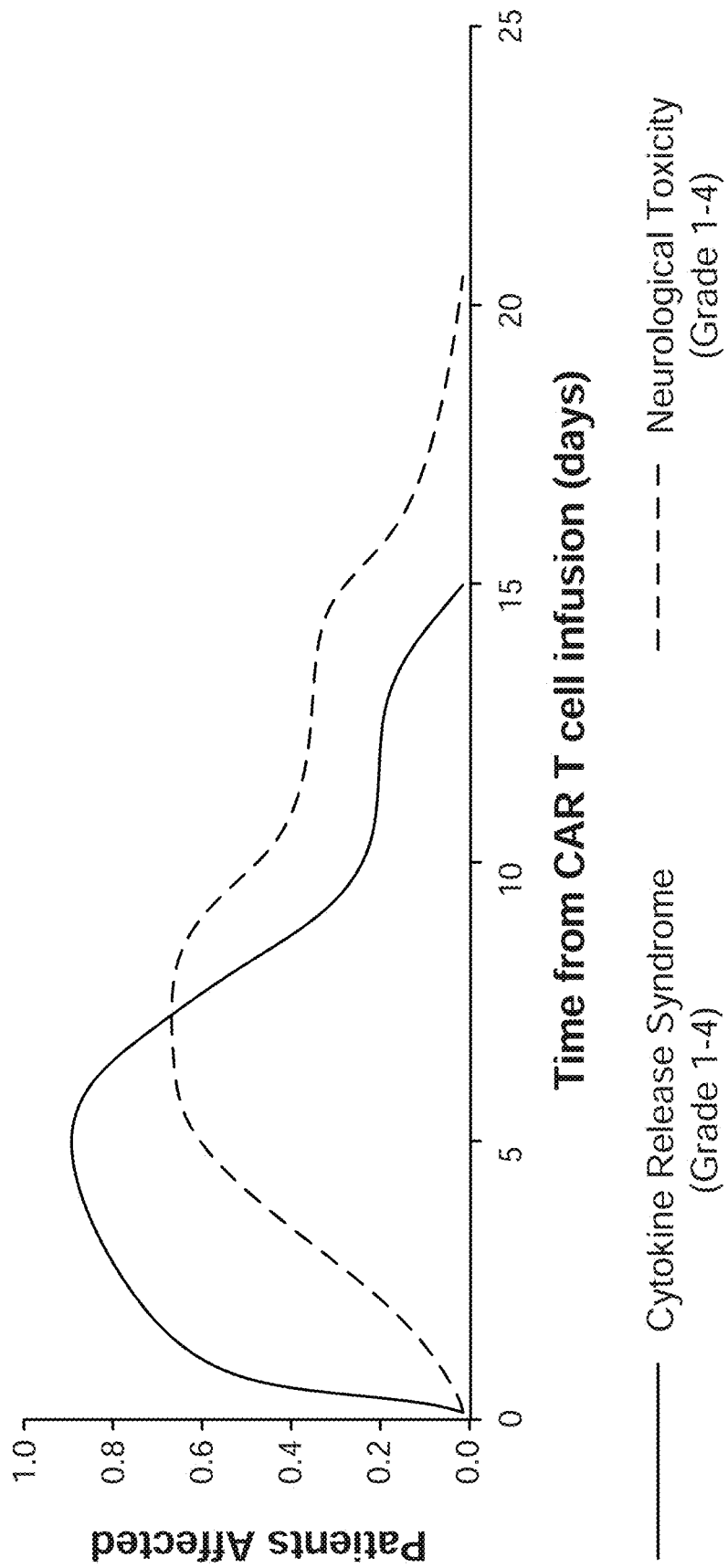
FIG. 13 illustrates an estimated time course of CRS and NT following CD19 CAR-T cell therapy. Timing of symptom onset and CRS severity depends on the inducing agent, type of cancer, age of patient, and the magnitude of immune cell activation. CAR-T related CRS symptom onset typically occurs days to occasionally weeks after the T-cell infusion, coinciding with maximal T-cell expansion. Similar to CRS associated with mAb therapy, CRS associated with adoptive T-cell therapies has been consistently associated with elevated IFNγ, IL-6, TNFα, IL-1, IL-2, IL-6, GM-CSF, IL-10, IL-8, and IL-5. No clear CAR-T cell dose-response relationship for CRS exists, but very high doses of T cells may result in earlier onset of symptoms.
Figure 14:
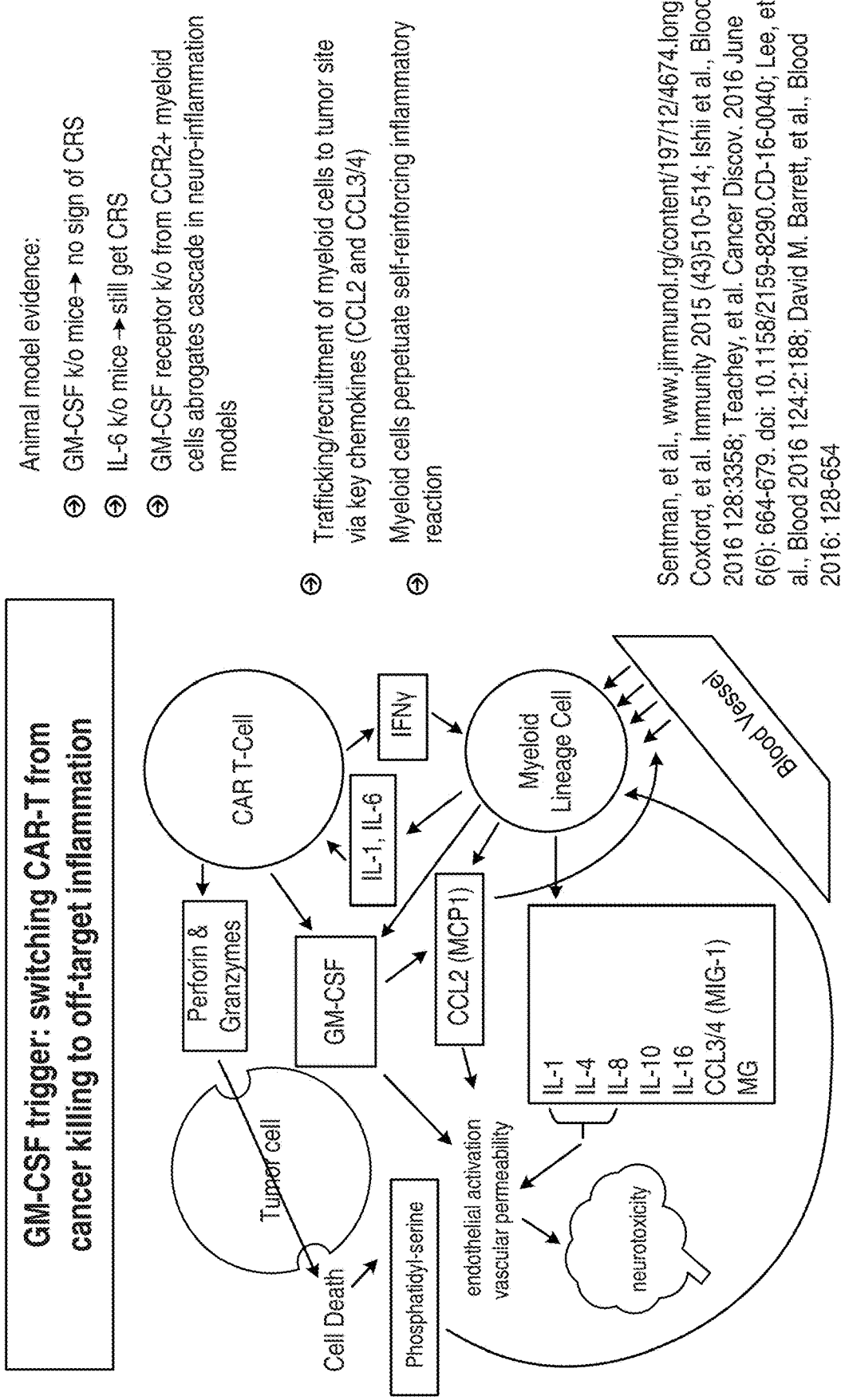
FIG. 14 illustrates that GM-CSF is a key initiator of CAR-T adverse effects. The figure depicts the central role of GM-CSF in CRS and NT. Perforin allows granzymes to penetrate the tumor cell membrane. CAR-T produced GM-CSF recruits CCR2+ myeloid cells to the tumor site, which produce CCL2 (MCP1). CCL2 positively reinforces its own production by CCR2+ myeloid cell recruitment. IL-1 and IL-6 from myeloid cells form another positive feedback loop with CAR-T by inducing production of GM-CSF. Phosphatidyl serine is exposed as a result of perforin and granzyme cell membrane destruction. Phosphatidyl-serine stimulates myeloid cell production of CCL2, IL-1, IL-6, and other inflammatory effectors. The final outcome of this self-reinforcing feedback loop results in endothelial activation, vascular permeability, and ultimately, CRS and NT. Moreover, animal model evidence shows GM-CSF knockout mice show no sign of CRS, but IL-6 knockout mice can still develop CRS. GM-CSF receptor k/o from CCR2+ myeloid cells abrogates cascade in neuro-inflammation models. (Sentman, et al., *J. Immunol.*; Coxford, et al. *Immunity* 2015 (43)510-514; Ishii et al., *Blood* 2016 128:3358; Teachey, et al. *Cancer Discov.* 2016 Jun. 6(6): 664-679; Lee, et al., *Blood* 2016 124:2:188; Barrett, et al., *Blood* 2016: 128-654, each of which is incorporated in its entirety herein by reference.).
Figure 15A:
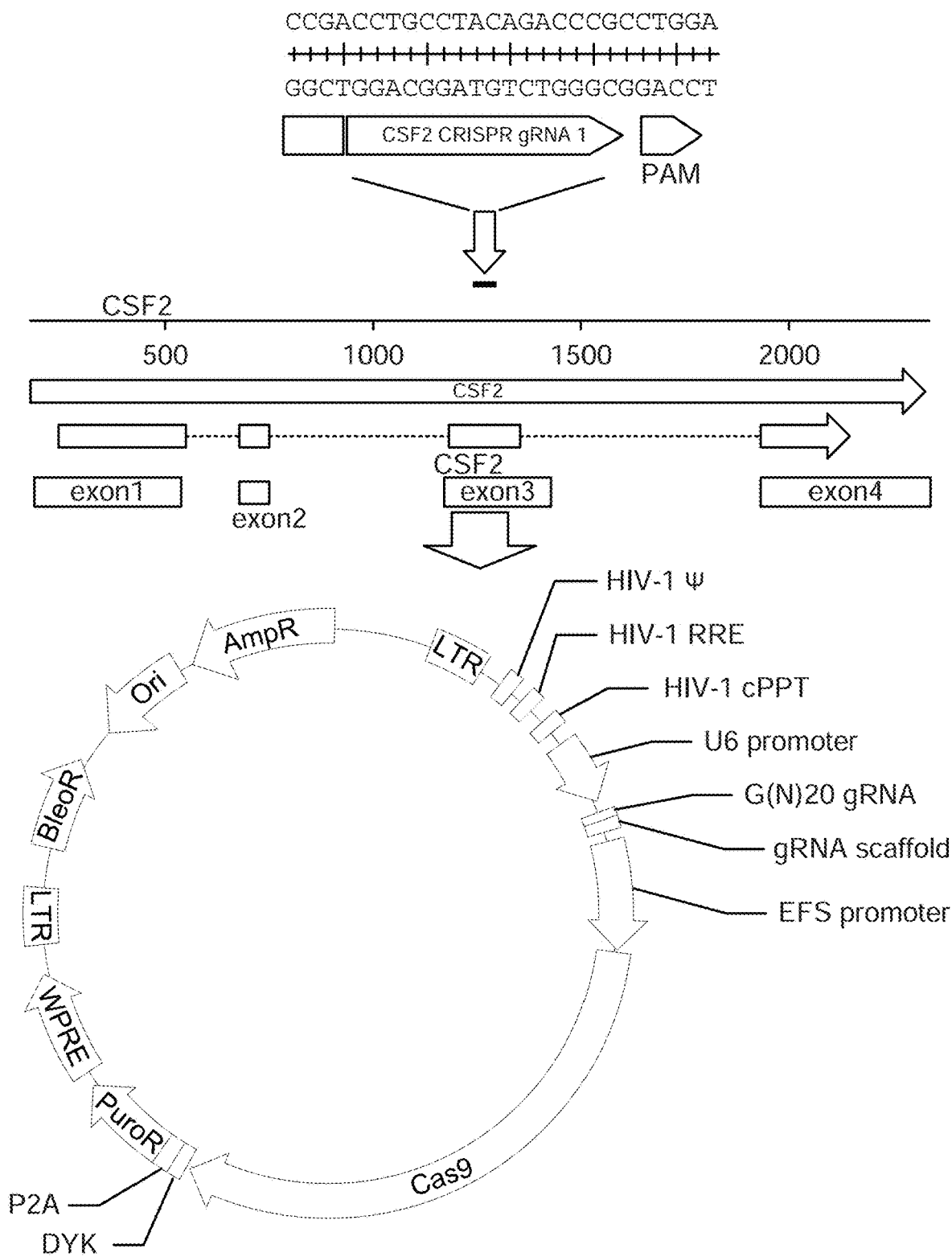
FIGS. 15A-15G illustrate that GM-CSF CRISPR knockout T-cells exhibit reduced expression of GM-CSF but similar levels of other cytokines and degranulation. a. Generation of GM-CSF knockout CAR-Ts. (See Example 6).
Figure 15A:
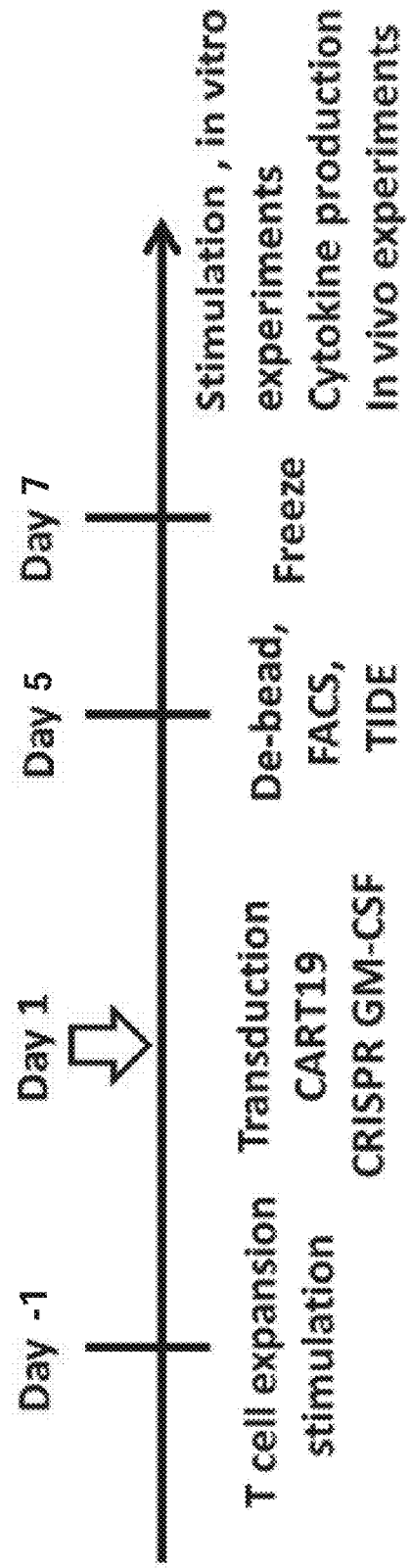
Figure 15B:
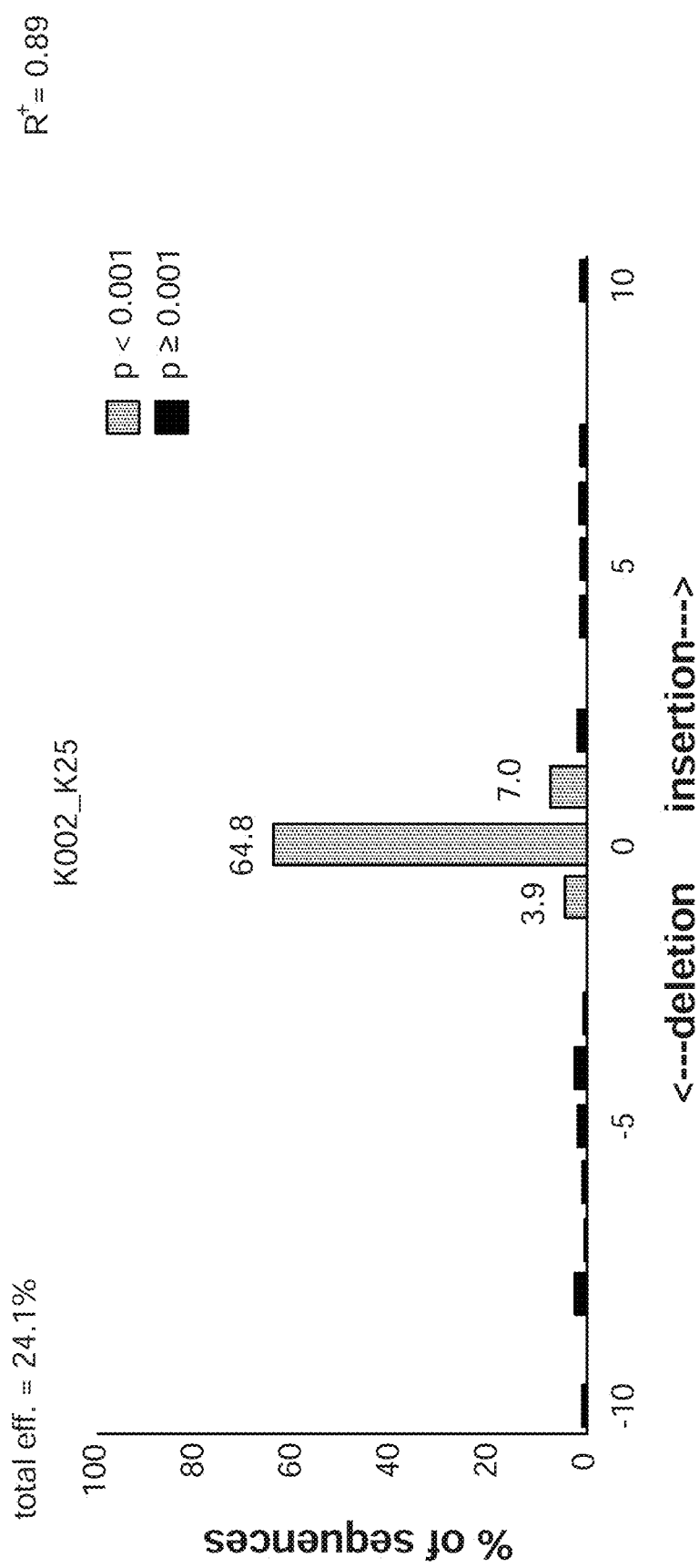
Figure 15C:
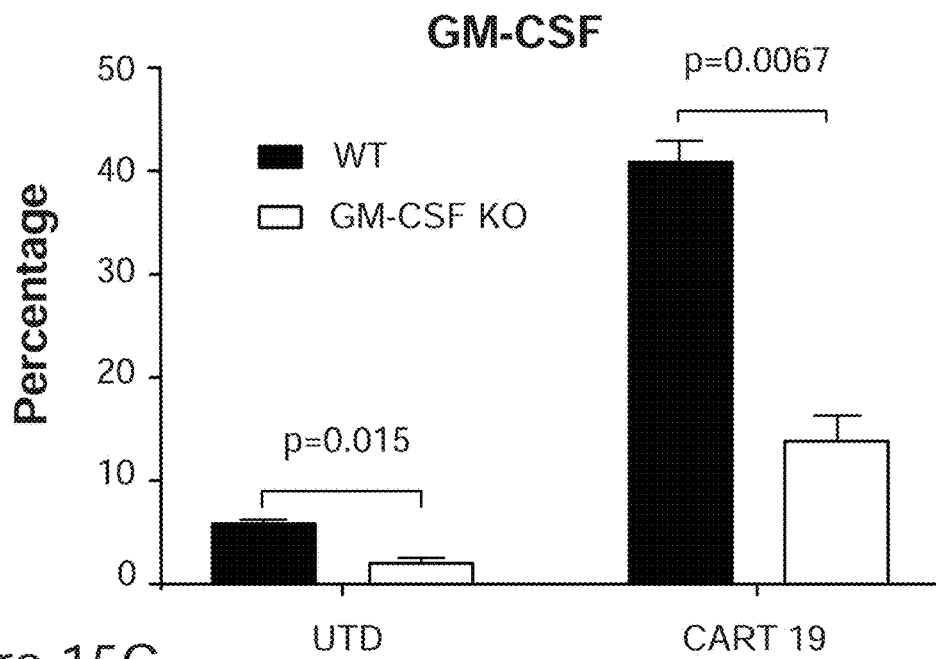
Figure 15D:
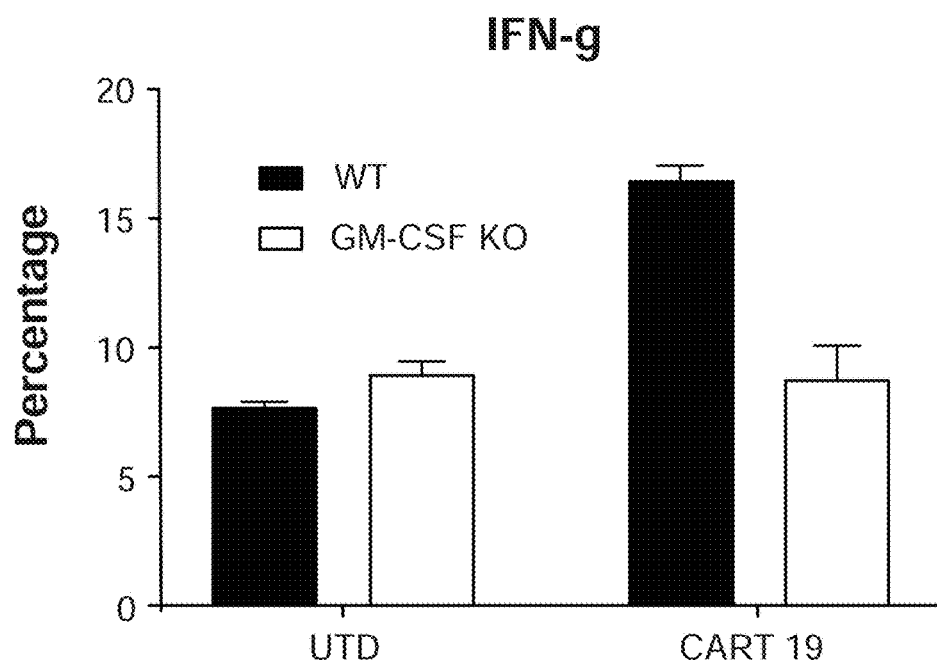
Figure 15E:
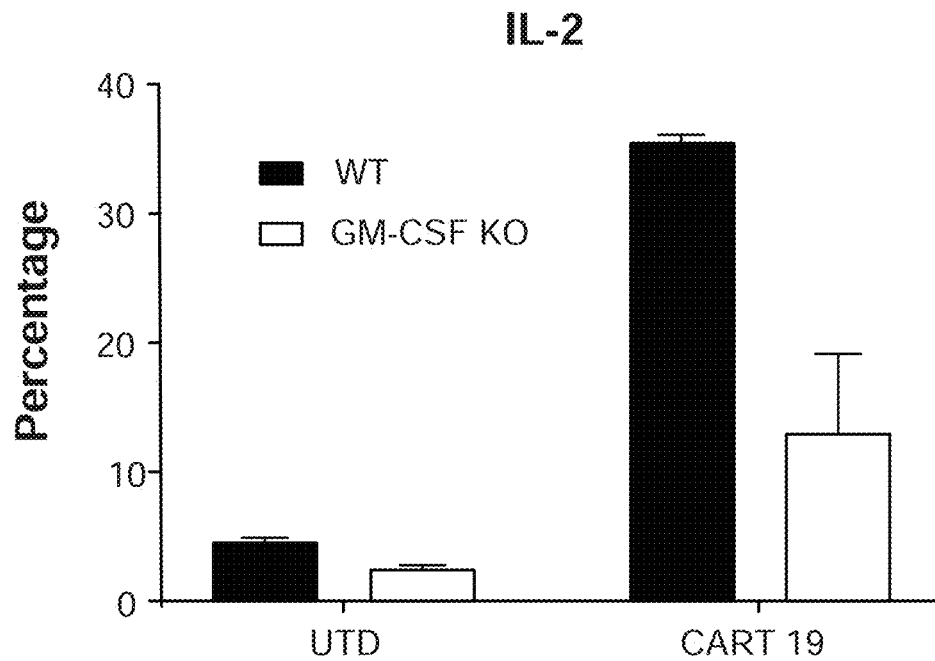
Figure 15F:
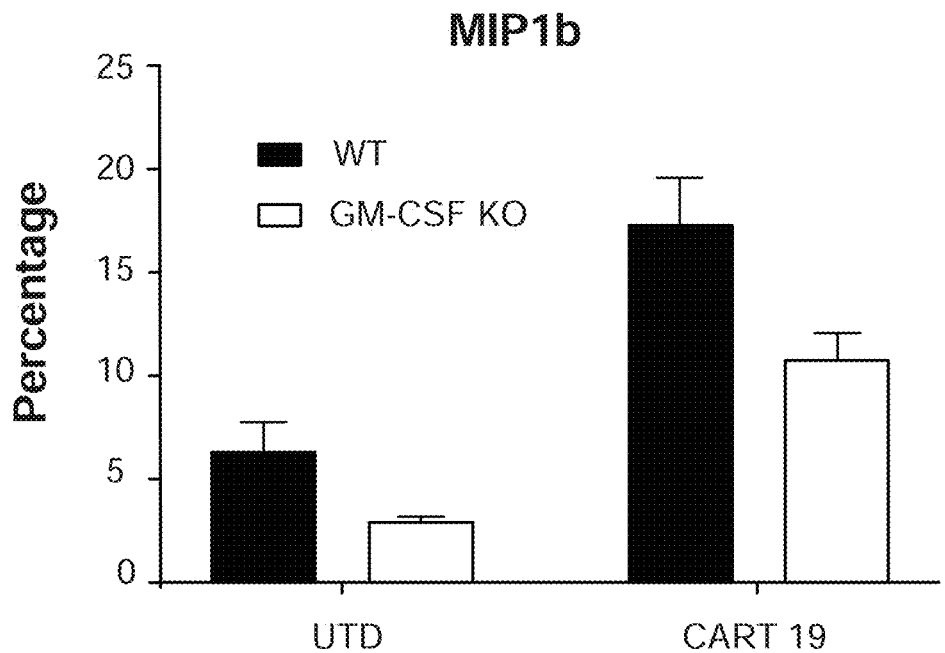
Figure 15G:
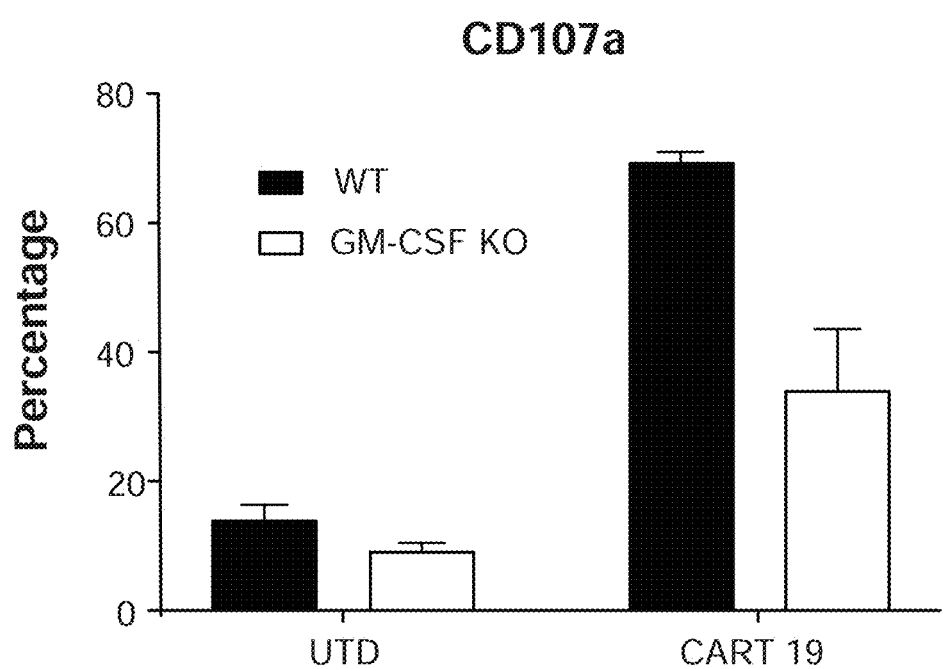

A comparison of the neutralizing activity of Ab1 and Ab2 in this assay is shown in a representative assay in FIG. 5. In three independent experiments, Ab1 inhibited GM-CSF activity more effectively than Ab2 when comparing IC50 (Table 5).

TABLE 5

Comparison of IC50 for inhibition of GM-CSF induced IL-8 expression. Data from three independent experiments shown in FIG. 5 and mean $IC_{50}$ are expressed in ng/ml and nM.

| Experiment | Ab2 (ng/ml) | Ab2 (nM) | Ab1 (ng/ml) | Ab1 (nM) |
|---|---|---|---|---|
| A | 363 | 2.4 | 31.3 | 0.21 |
| B | 514 | 3.4 | 92.5 | 0.62 |
| C | 343 | 2.2 | 20.7 | 0.14 |
| Mean | 407 | 2.7 | 48.2 | 0.32 |

Summary

The Humaneered Ab1 bound to GM-CSF with a calculated equilibrium binding constant (KD) of 25 pM. Ab2 bound to GM-CSF with a KD of 30.5 pM. Ab2 showed a two-fold higher association constant ($k_a$) than Ab1 for GM-CSF while Ab1 showed three-fold slower dissociation kinetics ($k_d$) than Ab2. Ab2 and Ab1 showed similar binding activity for glycosylated and non-glycosylated GM-CSF in an antigen-binding ELISA. A competition ELISA confirmed that both antibodies competed for the same epitope; Ab1 showed higher competitive binding activity than Ab2. In addition, Ab1 showed higher GM-CSF neutralization activity than Ab2 in a GM-CSF-induced IL-8 induction assay.

Example 3—Administration of a Neutralizing Anti-GM-CSF Antibody in a Mouse Model of Immunotherapy-Related Toxicity A mouse model of immunotherapy-related toxicity can be used to show the efficacy of an anti-GM-CSF antibody for preventing and treating immunotherapy-related toxicity. In one model of immunotherapy-related toxicity, mice are injected with CAR T-cells in doses provoking toxicity. For example, van der Stegen et al. (J. Immunol 191:4589-4598 (2013)), incorporated herein by reference, describe a CRS model induced by the i.p. injection of a single dose of 30×10$^6$ cells termed T4$^+$ T cells. T4$^+$ T cells are engineered T cells expressing the chimeric Ag receptor (CAR) T1E28z. T cells engineered to express T1E28z are activated by cells expressing ErbB1- and ErbB4-based dimers and ErbB2/3 heterodimer.

To evaluate the efficacy of anti-GM-CSF antibodies for preventing and treating CRS, mice will be divided in groups (n=10), each group receiving either: a) a single i.p. saline injection; b) an i.p. injection of $30 \times 10^6$ T4+ T cells; c) an i.p. injection of $30 \times 10^6$ T4+ T cells and 0.25 mg intravenous (i.v.) anti-GM-CSF monoclonal antibody 22E9 (a recombinant rat anti-mouse-GM-CSF antibody) co-administered with T4+ T cells; d) an i.p. injection of $30 \times 10^6$ T4+ T cells and 0.25 mg intranasal (i.n.) anti-GM-CSF antibody 22E9 co-administered with T4+ T cells; e) an i.p. injection of $30 \times 10^6$ T4+ T cells and 0.25 mg i.v. anti-GM-CSF antibody 22E9 6 hours before T4+ T cells administration; f) an i.p. injection of $30 \times 10^6$ T4+ T cells and 0.25 mg i.n. anti-GM-CSF antibody 22E9 6 hours before T4+ T cells administration; g) an i.p. injection of $30 \times 10^6$ T4+ T cells and 0.25 mg i.v. anti-GM-CSF antibody 22E9 2 hours after T4+ T cells administration; or h) an i.p. injection of $30 \times 10^6$ T4+ T cells and 0.25 mg i.n. anti-GM-CSF antibody 22E9 2 hours after T4+ T cells administration. Further doses, administration times, and administration routes will be evaluated.

In order to assess anti-GM-CSF antibody 22E9 effect, organs will be collected from mice, formalin fixed, and subjected to histopathologic analysis. Blood will be collected and concentrations of human IFNγ, human IL-2, and mouse IL-6, IL-2, IL-4, IL-6, IL-10, IL-17, IFNγ, and TNFα will be assessed by well methods described in the literature, such as ELISA assay. Mice weight, behavior, and clinical manifestations will be observed.

Example 4—Anti-GM-CSF Antibody Effect on Immunotherapy

A mouse model can be used to show that GM-CSF antagonists do not negatively affect the efficacy of cancer immunotherapy. SCID beige mice can be inoculated with a cancer cell line and treated with an immunotherapeutic agent known to induce CRS, as T4+ T cells, with or without an anti-GM-CSF antibody.

To evaluate whether anti-GM-CSF antibodies affect the efficacy of immunotherapy, mice will be divided in groups (n=10), each group receiving either: a) a subcutaneous (s.c.) injection of $30 \times 10^6$ SKOV3 cells; b) a s.c. injection of $30 \times 10^6$ SKOV3 cells and an i.p. injection of $30 \times 10^6$ T4+ T cells; or c) a s.c. implant of $30 \times 10^6$ SKOV3 cells, an i.p. injection of $30 \times 10^6$ T4+ T cells, and an i.v. injection of 0.25 mg of anti-GM-CSF antibody 22E9.

In order to assess anti-GM-CSF antibody 22E9 effect on T4+ T cells efficacy, tumor size will be measured every four days by caliper, and tumor volume calculated by the formula: $0.5 \times (\text{larger diameter}) \times (\text{smaller diameter})^2$. Mice weight, behavior, and clinical manifestations will be observed. At the end of the experiment, the animals will be sacrificed, and the tumor tissues harvested and weighted.

Example 5—Mouse Model of Human CRS

Figure 17A:
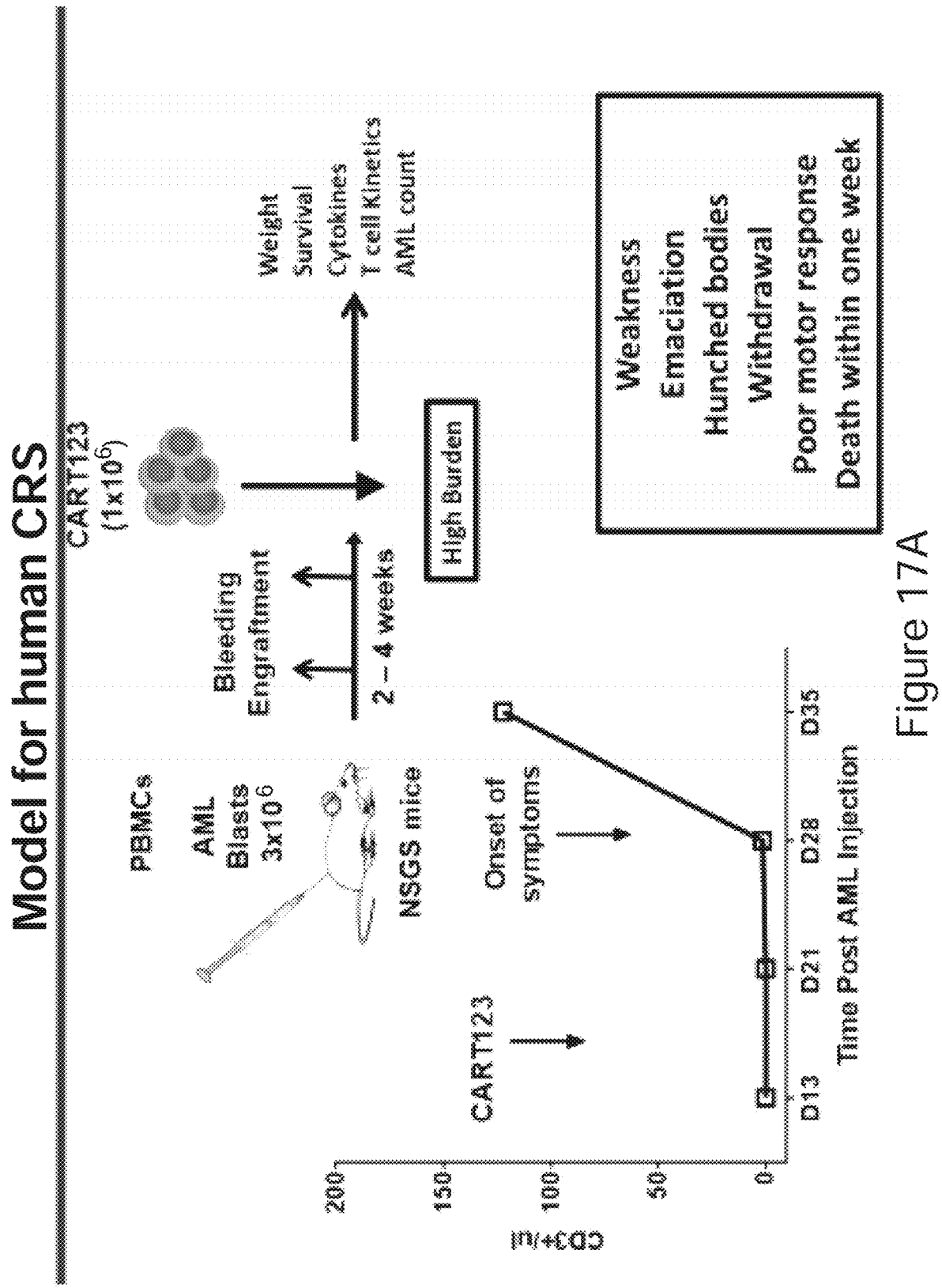
FIGS. 17A-17B illustrate the protocol and results from a mouse model of human CRS. (Example 5).

A mouse model for CRS for investigating the effects of a humanized anti-GM-CSF monoclonal antibody in treating or preventing CRS was developed. (FIG. 17a.-17b.).

Method: The model used is a primary AML model. Immunocompromised NSG-S mice that were additionally transgenic for human SCF, IL-3, and GM-CSF were engrafted with AML blasts derived from AML patients that were CD123 positive. After 2-4 weeks, they were bled to confirm engraftment and achievement of high disease burden. The mice were then treated with high doses of CAR-T123 at $1 \times 10^6$ cells, which is 10 times higher than doses previously studied.

Figure 17B:
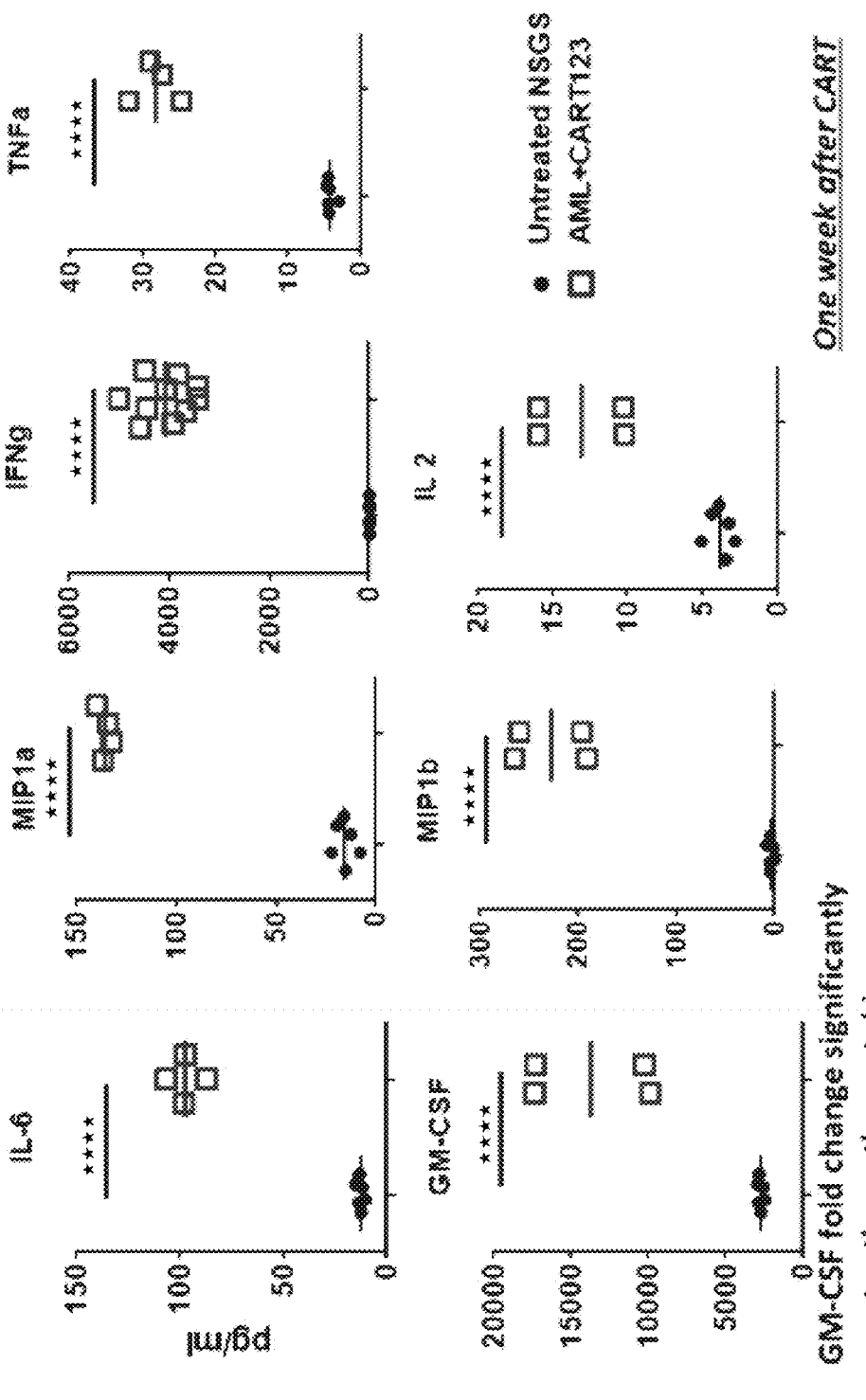

Results: It was observed that within 1-2 weeks after CAR-T cell injection, these mice developed an illness characterized by weakness, emaciation, hunched bodies, withdrawal, and poor motor response. The mice eventually died of their disease within 7-10 days. The symptoms correlate with massive T-cell expansion in the mice and with elevation of multiple human cytokines, such as IL-6, MIP 1α, IFN-γ, TNFα, GM-CSF, MIP1β, and IL-2, and in a pattern that resembles what is seen in human CRS after CAR-T cell therapy. GM-CSF fold change was significantly greater than other cytokines. (FIG. 17 a-b).

Example 6—Generation of GM-CSF Knockout CAR-Ts

GM-CSF CRISPR knockout T cells were generated and shown to exhibit reduced expression of GM-CSF but similar levels of other cytokines and degranulation, which showed immune cell functionality. (See FIGS. 15a-15g).

Example 7—Anti-GM-CSF Neutralizing Antibody Does Not Inhibit CAR-T Mediated Killing, Proliferation, or Cytokine Production but Neutralizes GM-CSF Anti-GM-CSF neutralizing antibody does not inhibit CAR-T mediated killing, proliferation, or cytokine production but successfully neutralizes GM-CSF. (See FIGS. 16a-16i).

Figure 18A:
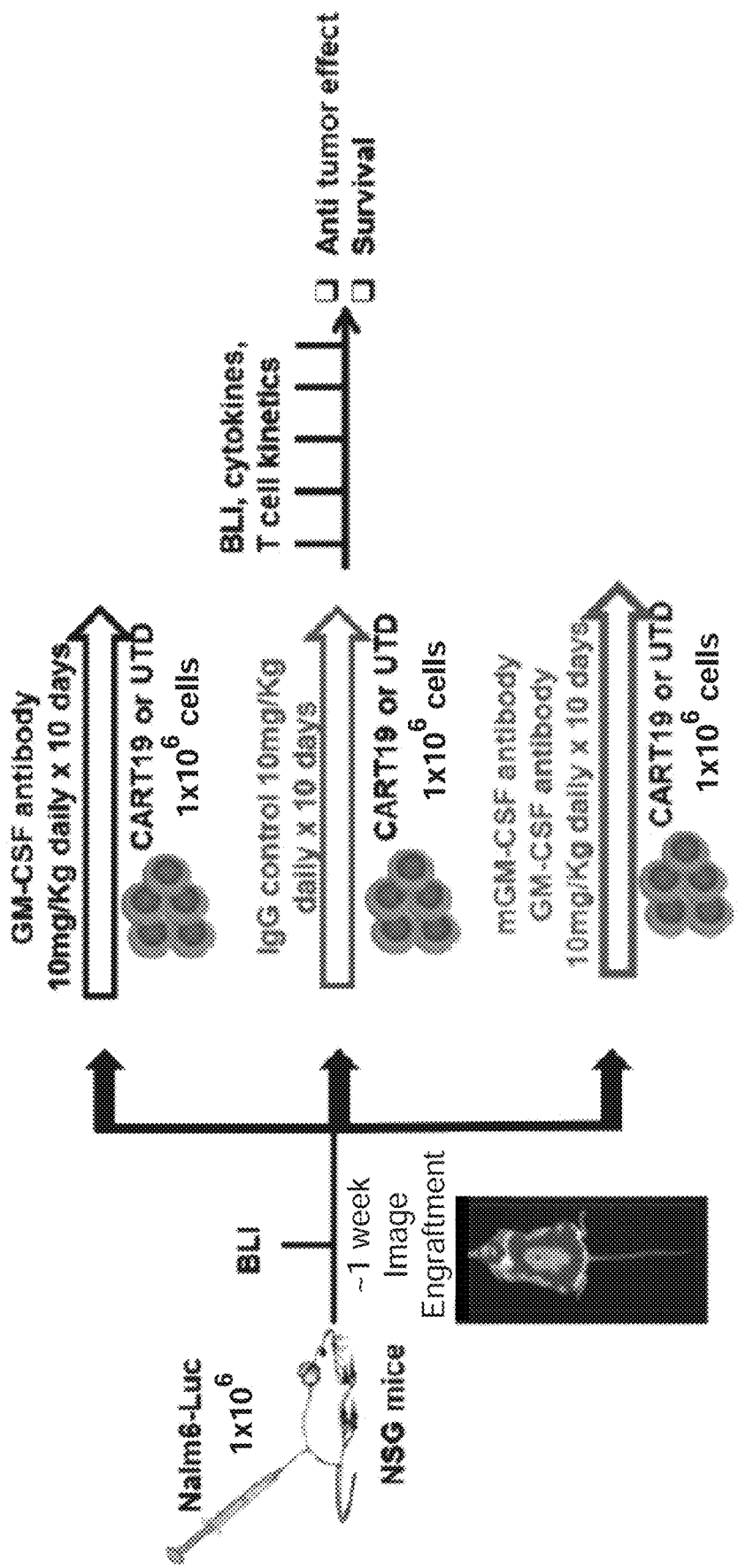
FIGS. 18A-18C illustrate CAR-T efficacy in a xenograft model in combination with a GM-CSF neutralizing antibody in accordance with embodiments described herein. The GM-CSF neutralizing antibody is shown to not inhibit CAR-T efficacy in vivo. (See Example 8).
Figure 18C:
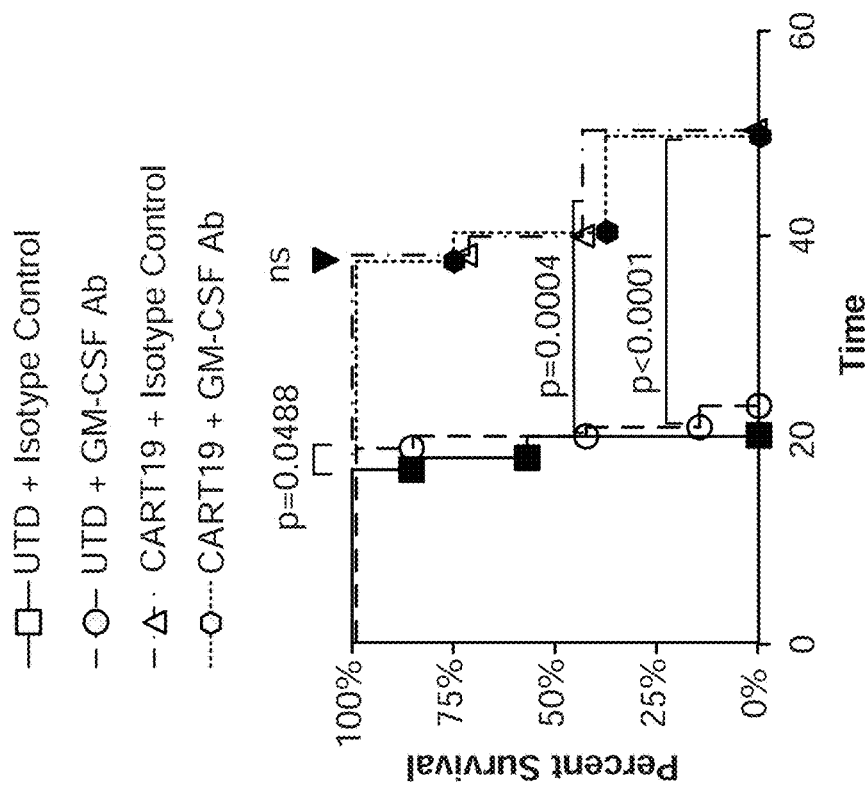
Figure 18B:
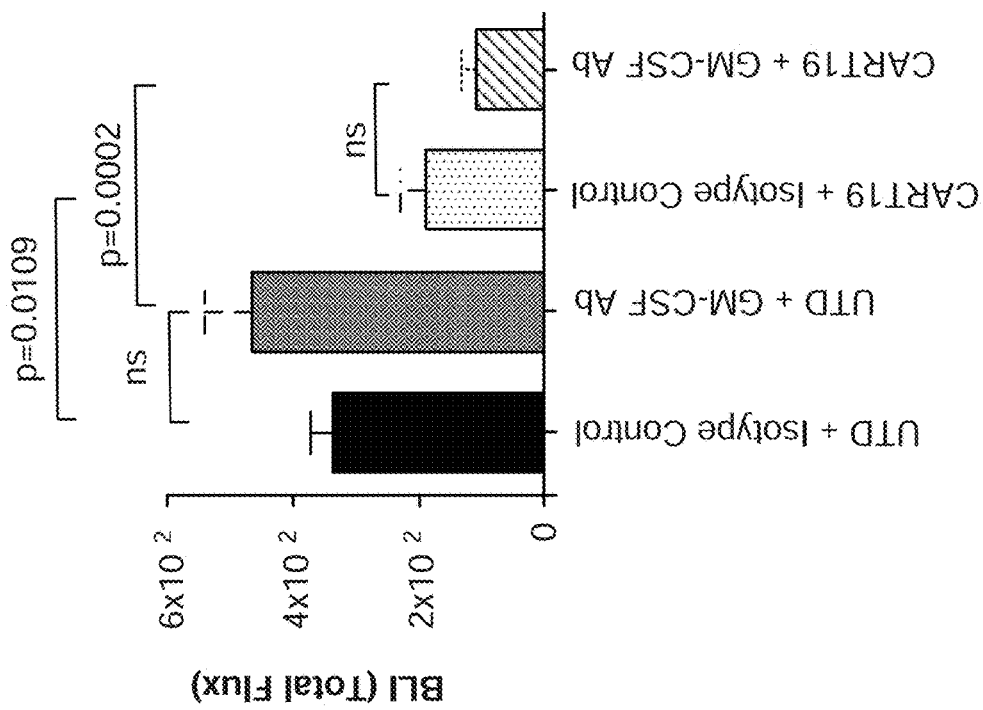

Example 8—Anti-GM-CSF Neutralizing Antibody Does Not Inhibit CAR-T Efficacy In Vivo Humanized anti-GM-CSF monoclonal antibody, a neutralizing hGM-CSF antibody, does not inhibit CAR-T efficacy in vivo (FIG. 18a-18c). CAR-T efficacy in a xenograft model in combination with an anti-GM-CSF neutralizing antibody in accordance with embodiments described herein. As shown in FIG. 18a, NSG mice were injected with NALM-6-GFP/Luciferase cells (human, peripheral blood leukemia pre-B cell), and bioluminescent imaging (BLI0 was performed to confirm tumor growth. Mice were treated with either (1) anti-GM-CSF antibody (10 mg/Kg daily for ten days) and (a) CART19 or (b) untransduced human T cells (UTD) $1 \times 10^6$ cells or (2) IgG control antibody (10 mg/Kg daily for ten days) and (a) CART19 or (b) untransduced human T cells (UTD) $1 \times 10^6$ cells. FIGS. 18b and 18c demonstrate that the anti-GM-CSF neutralizing antibody did not inhibit CAR-T efficacy in vivo.

Figure 19:
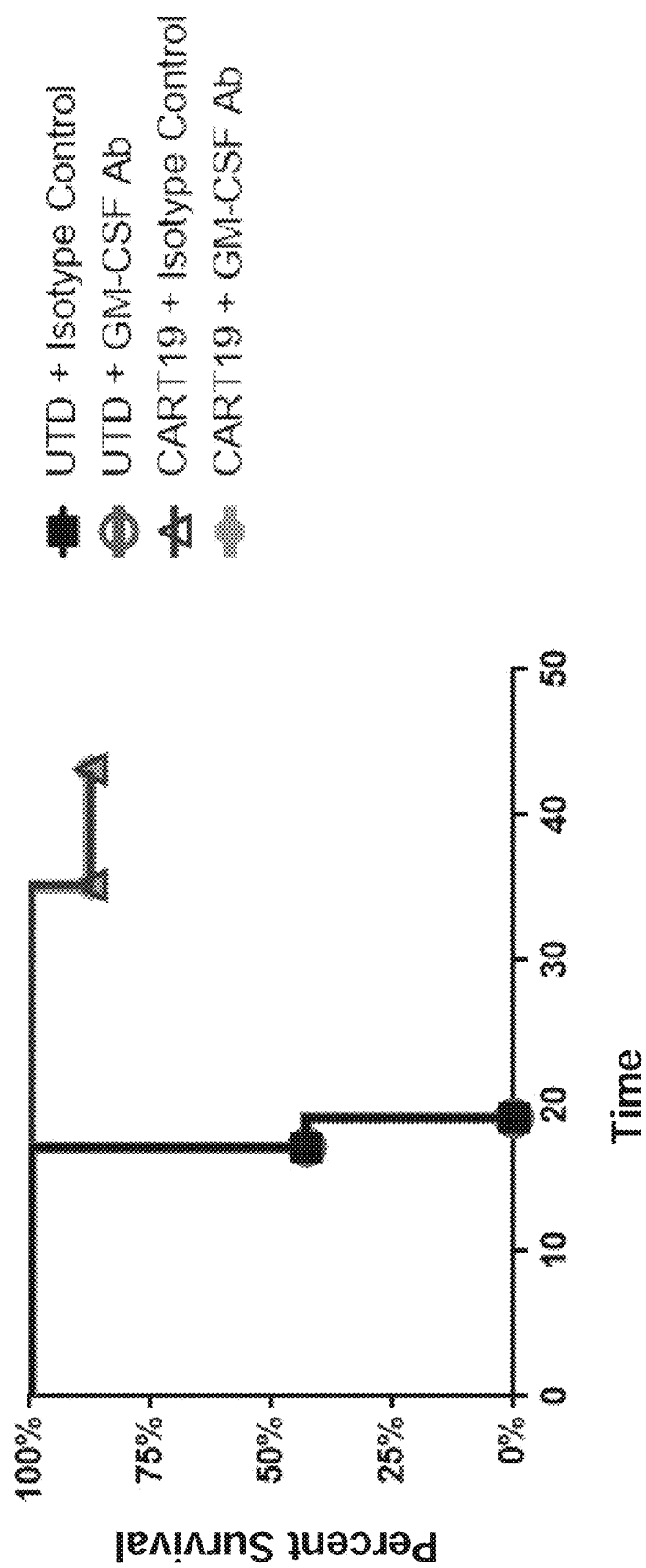
FIG. 19 illustrates in vitro and in vivo preclinical data showing that a GM-CSF neutralizing antibody in accordance with embodiments described herein did not impair CAR-T impact on survival. The GM-CSF neutralizing antibody does not impede CAR-T cell function in vivo in the absence of PBMCs. Survival was similar for CAR-T+control and CAR-T+GM-CSF neutralizing antibody. (See Example 9).

Example 9—Anti-GM-CSF Neutralizing Antibody Does Not Impair CAR-T Impact on Survival In vitro and in vivo preclinical data show anti-GM-CSF neutralizing antibody (a humanized anti-GM-CSF monoclonal antibody) does not impair CAR-T impact on survival in mouse models. (FIG. 19).

The anti-GM-CSF neutralizing antibody does not impede CAR-T cell function in vivo in the absence of PBMCs. Survival shown to be similar for CAR-T+control and CAR-T+anti-GM-CSF neutralizing antibody.

Example 10—Anti-GM-CSF Neutralizing Antibody May Increase CAR-T Expansion

Figure 20A:
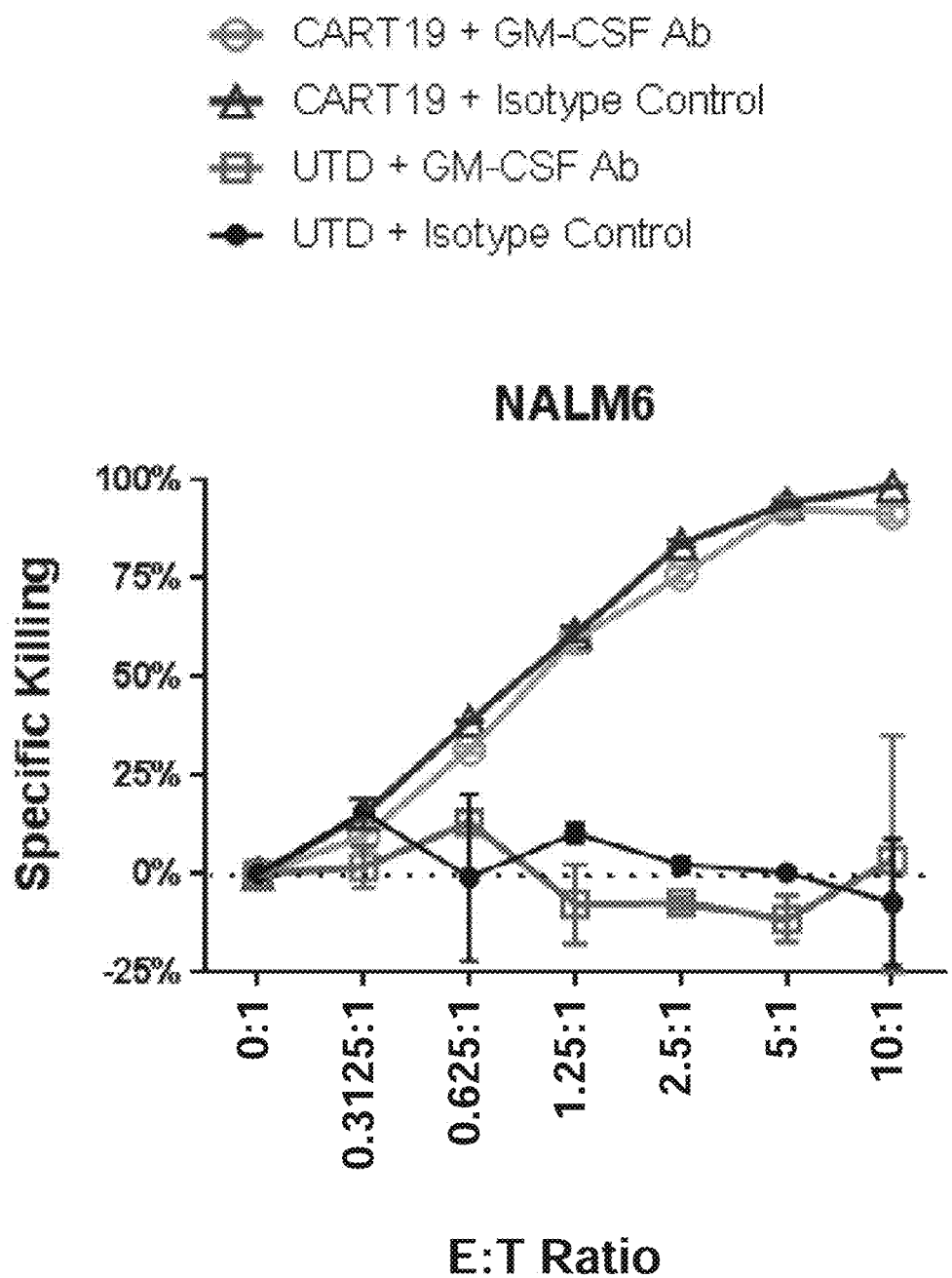
FIGS. 20A-20B illustrate in vitro and in vivo preclinical data showing that a GM-CSF neutralizing antibody in accordance with embodiments described herein does increase CAR-T expansion. The GM-CSF neutralizing antibody increases in vitro CAR-T cancer cell killing. Antibody neutralization of GM-CSF increases proliferation of CAR-T cells in the presence of PBMCs. CAR-T proliferation increased by the GM-CSF neutralizing antibody in presence of PBMCs. (It was not affected without PBMCs). The anti-GM-CSF antibody did not inhibit CAR-T degranulation, intracellular GM-CSF production, or IL-2 production. (See Example 10).
Figure 20B:
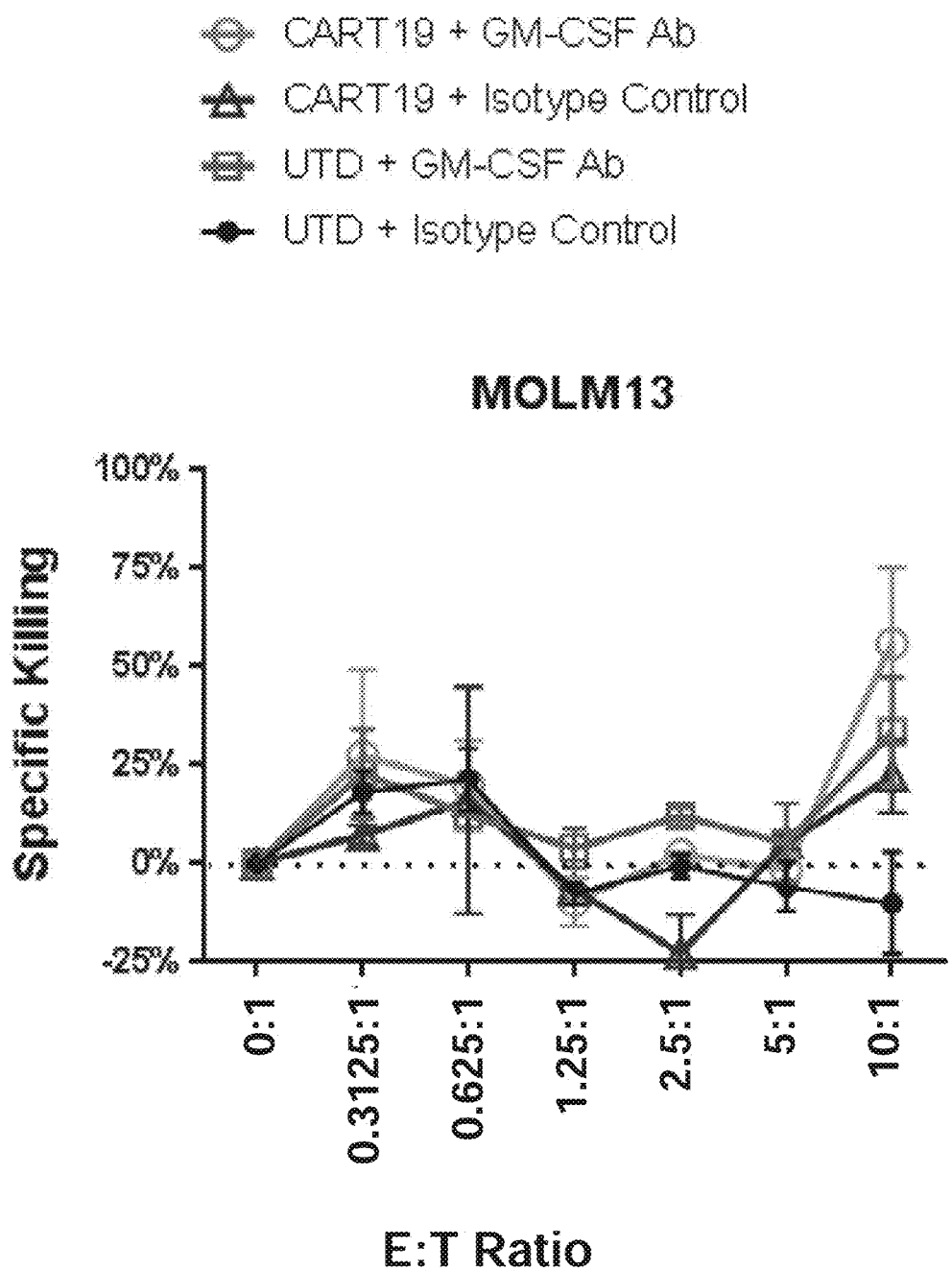

In vitro and In vivo preclinical data show anti-GM-CSF neutralizing antibody (a humanized anti-GM-CSF monoclonal antibody) may increase CAR-T Expansion (FIG. 20). The anti-GM-CSF neutralizing antibody may increase in vitro CAR-T cancer cell killing. The antibody increases proliferation of CAR-T cells and could improve efficacy. CAR-T proliferation increased by the GM-CSF neutralizing antibody in presence of PBMCs. (It was not affected without PBMCs). The antibody did not inhibit degranulation, intracellular GM-CSF production, or IL-2 production.

Example 11—CAR-T Expansion Associated with Improved Overall Response Rate

Figure 21:
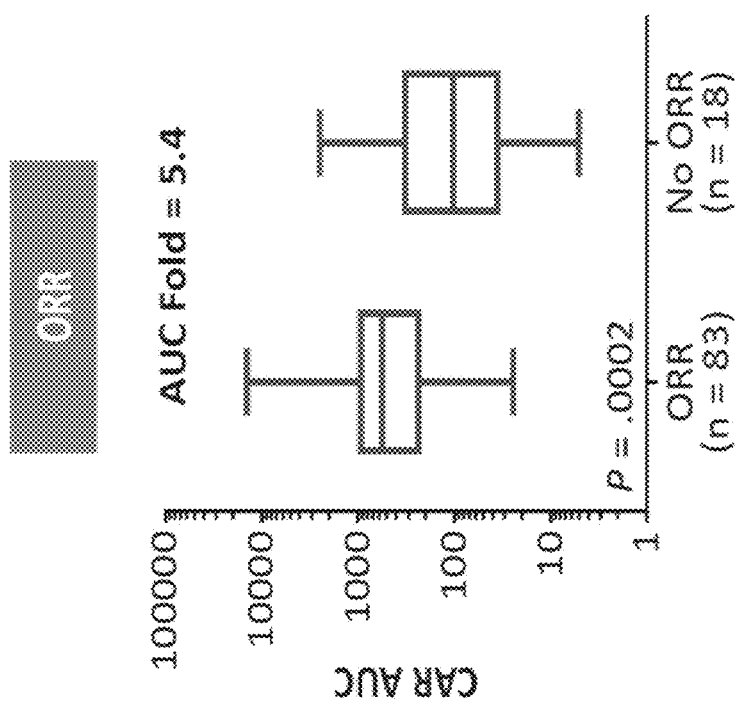
FIG. 21 illustrates that CAR-T expansion is associated with improved overall response rate. CAR AUC (area under the curve) defined as cumulative levels of CAR+cells/µL of blood over the first 28 days post CAR-T administration. P values calculated by Wilcoxon rank sum test. (Neelapu, et al ICML 2017 Abstract 8). (See Example 11).

CAR-T expansion associated with improved overall response rate. (FIG. 21). CAR AUC (area under the curve) defined as cumulative levels of CAR+cells/μL of blood over the first 28 days post CAR-T administration. P values calculated by Wilcoxon rank sum test. (Neelapu, et al ICML 2017 Abstract 8).

Figure 22:
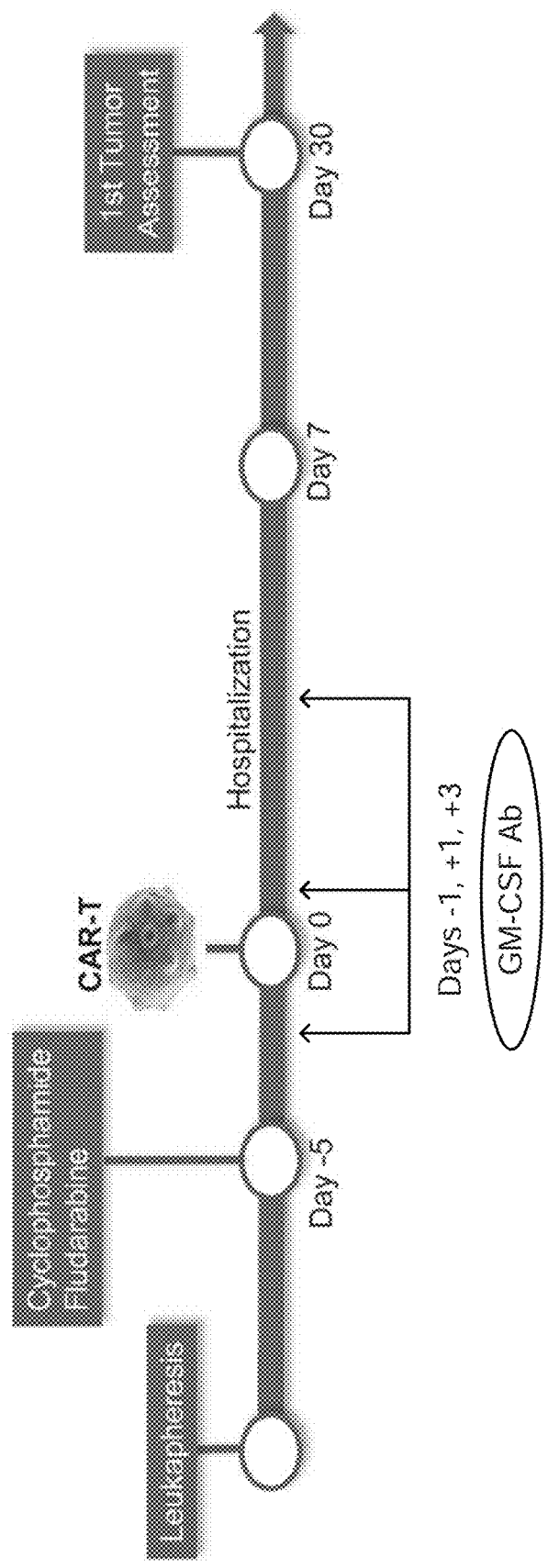
FIG. 22 illustrates a study protocol for GM-CSF neutralizing antibody in accordance with embodiments described herein. (See Example 12). CRS and NT to be assessed daily while hospitalized and at clinic visit for first 30 days. Eligible subjects to receive GM-CSF neutralizing antibody on days −1, +1, and +3 of CAR-T treatment. Additional dosing can be contemplated going out to at least day 7. Tumor assessment to be performed at baseline and months 1, 3, 6, 9, 12, 18, and 24. Blood samples (PBMC and serum) days −5, −1, 0, 1, 3, 5, 7, 9, 11, 13, 21, 28, 90, 180, 270, and 360. (See Example 12).

Example 12—Study Protocol for an Anti-GM-CSF Neutralizing Antibody in Accordance with Embodiments Described Herein Study protocol for an anti-GM-CSF neutralizing antibody (a humaneered anti-GM-CSF monoclonal antibody) in accordance with embodiments described herein. (See FIG. 22). CRS and NT to be assessed daily while hospitalized and at clinic visit for first 30 days. Eligible subjects to receive GM-CSF neutralizing antibody on days −1, +1, and +3 of CAR-T treatment. Tumor assessment to be performed at baseline and months 1, 3, 6, 9, 12, 18, and 24. Blood samples (PBMC and serum) days −5, −1, 0, 1, 3, 5, 7, 9, 11, 13, 21, 28, 90, 180, 270, and 360.

Example 13—GM-CSF Depletion Increases CAR-T Cell Expansion

Figure 23A:
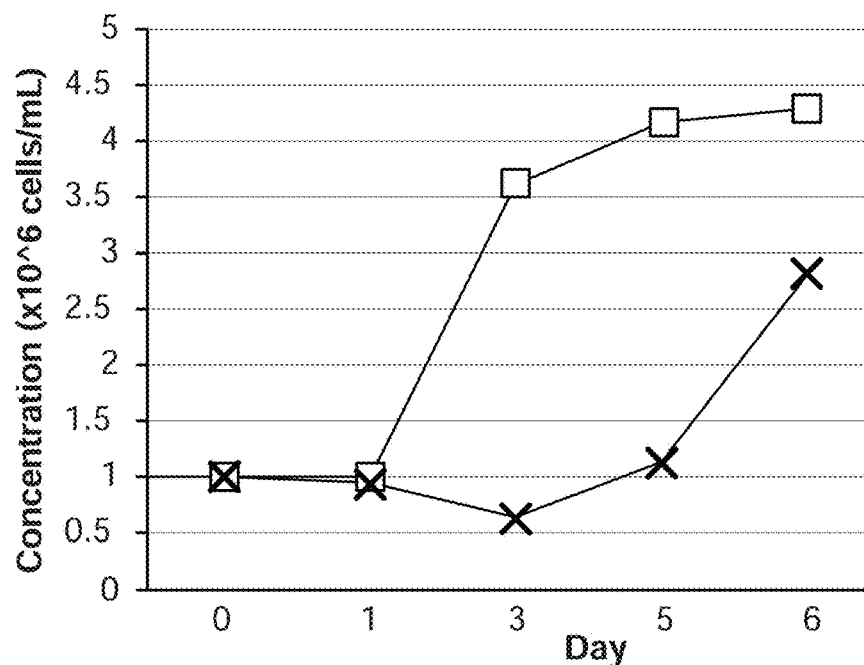
FIGS. 23A-23B illustrate that GM-CSF depletion increases CAR-T cell expansion.
Figure 23B:
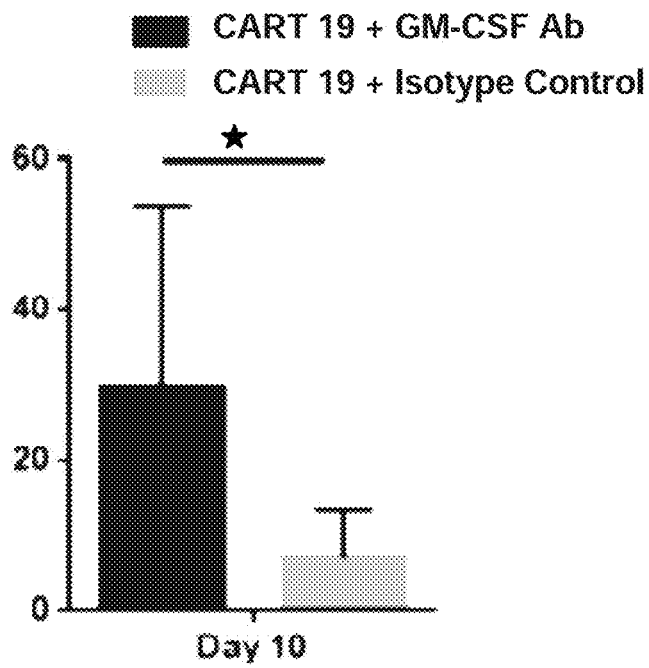

GM-CSF depletion increases CAR-T cell expansion. (FIG. 23A-23B) FIG. 23A shows increased ex-vivo expansion of GM-CSF$^{k/o}$ CAR-T cells compared to control CAR-T cells. FIG. 23b demonstrates more robust proliferation after in vivo treatment with an anti-GM-CSF neutralizing antibody (a humaneered anti-GM-CSF monoclonal antibody) in accordance with embodiments described herein.

Example 14—Safety Profile of an Anti-GM-CSF Neutralizing Ab in >100 Human Patients*

Phase I:
Single-dose, dose escalation in healthy adult volunteers. Objectives were to analyze Safety/tolerability, PK, and Immunogenicity.
Enrollment/dose:
(n=12)
3/1 mg/kg
3/3 mg/kg
3/10 mg/kg
3/placebo
Safety Results:
Clean Safety Profile:
No drug related serious adverse effects (SAE)
Non-immunogenic
Phase II:
1) Dose at weeks 0, 2, 4, 8, 12 in rheumatoid arthritis patients. Objectives were to analyze Efficacy, Safety/tolerability, PK, and Immunogenicity.
Enrollment/dose:
(n=9)
7/600 mg
2/placebo
Safety Results:
Clean Safety Profile:
No drug related serious adverse effects (SAE)
Non-immunogenic
2) Dose at weeks 0, 2, 4, 8, 12, 16 20 in severe asthma patients. Objectives were to analyze Efficacy, Safety/tolerability, PK, and Immunogenicity.
Enrollment/dose:
(n=160)
78/400 mg
82/placebo
Safety Results:
Clean Safety Profile:
No drug related serious adverse effects (SAE)
Non-immunogenic
* 94 patients in studies depicted above, plus 12 patients in ongoing CMML Phase I trial, where drug is well tolerated; an additional 76 patients received a chimeric version of a GM-CSF neutralizing Ab (KB002) and showed a similar safety profile.
All studies randomized double-blind placebo-controlled, IV administration. (See FIG. 24.)

Example 15—Effect of Anti-GM-CSF Antibody on CART Activity and Toxicity

The study will investigate the effect of GMCSF blockade with anti-GM-CSF antibody on chimeric antigen receptor T cells (CART) activity and toxicity. This can be accomplished through these two AIMS:
AIM #1: to investigate the effect of GMCSF blockade with anti-GM-CSF antibody on CART cell effector functions
AIM #2: To study the effect of GMCSF blockade with anti-GM-CSF antibody on reducing cytokine release syndrome after CART cell therapy Research strategy. The following experiments are proposed:
In vitro studies of the combination of four different doses of GMCSF blockade with anti-GM-CSF antibody with CART cells (cytokine production (30 plex Lumiex, including GM-CSF, IL-2, INFg, IL-6, IL-8, MCP-1), antigen specific killing, degranulation, proliferation and exhaustion), in the presence or absence of myeloid cells using the model: CART19 against ALL.
In vivo studies of the combination of different doses of GMCSF blockade with anti-GM-CSF antibody (with and without murine GMCSF blockade) with CART cells, using two models:
CD19 positive cell line (NALM6) engrafted xenografts, treated with CART19 with or without anti-GM-CSF antibody; and
Patient derived xenografts with primary ALL, and then treated with CART19 with or without anti-GM-CSF antibody.
Mice will be dosed i.p with anti-GM-CSF antibody 10 mg/kg immediately prior to CART cell implantation and 10 mg/kg/day for 10 days. Mice will be followed for tumor response and survival. Retro-orbital bleedings will be obtained starting one week after CART cell therapy and weekly afterwards. Disease burden, T cell expansion kinetics, expression of exhaustion markers and cytokine levels (30 Plex) will be analyzed. At the completion of the experiment, spleens and bone marrows will be harvested and analyzed for tumor characteristics and CAR-T cell numbers.

In vivo studies of the combination of GMCSF blockade with anti-GM-CSF antibody (with or without murine GMCSF blockade) with CART cells in CRS models (in this model, high doses of CART cells will be used to elicit CRS), in the presence of PBMCs, using the following model:

Primary ALL patient derived xenografts, then treated with CART19 with or without anti-GM-CSF antibody.

Mice will be dosed i.p. with anti-GM-CSF antibody 10 mg/kg immediately prior to CART cell implantation and 10 mg/kg/day for 10 days. Mice will be followed for tumor response, CRS toxicity symptoms and survival. Retro-orbital bleedings will be obtained at baseline, 2 days post, one week-post CART cell therapy and weekly afterwards. Disease burden, T cell expansion kinetics, expression of exhaustion markers and cytokine levels (30 Plex) will be analyzed. At the completion of the experiment, spleens and bone marrows will be harvested and analyzed for tumor characteristics and CAR-T cell numbers In Vivo Neurotoxicity Assays Using models discussed in #3 above, mice will be imaged with MRI while sick to assess for development of neurotoxicity after CART cell therapy. Images will be compared between mice that received CART cells and anti-GM-CSF antibody vs control antibody. Repeat experiments will be performed. Mice will be euthanized 14 days after CART cells in these repeat experiments. Brain tissue will be analyzed for cytokines with multiplex assays, for the presence of monocytes, human T cells, and for integrity of blood brain barrier by IHC, flow and microscopy.

Example 16

Anti-hGM-CSF Neutralizing Antibody Reduces Neuroinflammation in CAR-T Cell Related Neurotoxicity (NT)

There is extensive scientific rationale implicating GM-CSF as essential to the initiation of cytokine release syndrome (CRS), neurotoxicity (NT) and the inflammatory cascade seen following initiation of CAR-T cell therapy. The hypothesis studied is that blocking soluble GM-CSF with the neutralizing antibody (lenzilumab) will abrogate or prevent the onset and severity of both CRS and NT observed with CAR-T cell therapy. Importantly, CAR-T cell activity should be preserved or improved if possible. The experimental design tests the effects of GM-CSF blockade with anti-GM-CSF antibody (lenzilumab) on CAR-T cell effector functions, CAR-T efficacy in a tumor xenograft model, development of CRS in a CRS xenograft model and the development of NT using MRI imaging and volumetric analysis to quantify the neuro-inflammation seen with CAR-T cell therapy. In vitro and in vivo experiments with CAR-T+/−lenzilumab both in the presence and absence of human PBMCs were studied. (see Examples 9 and 10, FIGS. 19 and 20a-20b).

Methods

In vitro studies were conducted to evaluate the combination of GM-CSF neutralizing antibody lenzilumab with human CD19+ CAR-T cells on antigen-specific killing, degranulation, proliferation and exhaustion in the presence or absence of human PBMCs.

To assess the impact of anti-GM-CSF antibody (lenzilumab) on CAR-T cell proliferation and efficacy, in vivo studies were subsequently conducted using the following model (with and without murine GM-CSF blockade):

Effector/Target Control Experiments:

CD19 positive cell line (NALM6) engrafted xenografts, treated with CART19 with or without anti-GM-CSF antibody (lenzilumab) in the absence of human PBMCs.

NSG mice were dosed i.p. with anti-GM-CSF antibody (lenzilumab) 10 mg/kg immediately prior to CAR-T cell implantation and at the same dose every day thereafter for 10 days and followed to assess tumor response and survival. Retro-orbital bleedings were obtained starting one week after CAR-T cell therapy and weekly afterwards. Disease burden, T cell expansion kinetics, expression of exhaustion markers and cytokine levels (30 Plex) were also analyzed. At the completion of the experiment, spleens and bone marrows were harvested and analyzed for tumor characteristics and CAR-T cell numbers.

CRS/NT Experiments: Patient Derived Xenografts with Primary ALL, Subsequently Treated with CART19 with or without Lenzilumab in the Presence of Human PBMCs:

To assess the impact of lenzilumab on abrogating or preventing the onset and severity of CAR-T induced CRS and NT, in vivo studies were conducted with human CAR-T cells (with and without murine GM-CSF blockade) in a CRS model (where high doses of CAR-T cells were used to illicit CRS) in the presence of PBMCs using primary ALL patient derived xenografts, treated with CART19 with and without lenzilumab. NSG mice were dosed i.p. with lenzilumab 10 mg/kg immediately prior to CAR-T cell implantation and every day thereafter for 10 days. Mice were followed for tumor response, survival, CRS and NT symptoms. Brain MRI scans were taken at baseline, during and at the end of CAR-T cell therapy and volumetric analysis was conducted to assess and quantify neuro-inflammation and MRI T1 hyperintensity across treatment arms. Body weight and retro-orbital bleedings were obtained at baseline, 2 days post, one week-post CAR-T cell therapy and weekly afterwards. Disease burden, T cell expansion kinetics, expression of exhaustion markers and cytokine levels (30 Plex) were analyzed. At the completion of the experiment, spleens and bone marrows were harvested and analyzed for tumor characteristics and CAR-T cell numbers.

Results

In Vitro Model

In this experiment, the impact of GM-CSF neutralization with lenzilumab on CAR-T cell effector functions was investigated. It was demonstrated that GM-CSF is secreted by CAR-T cells at very high levels (over 1,500 pg/ml) and the use of lenzilumab completely neutralized GM-CSF but did not inhibit CAR-T degranulation, intracellular GM-CSF production or IL2 production. Moreover, lenzilumab did not inhibit CAR-T antigen specific proliferation or CAR-T killing. Effector-to-target rations (E:T) were similar with CAR-T+lenzilumab vs. CAR-T+control antibody, p=ns (FIGS. 16a-16d and 16j).

Figure 16A:
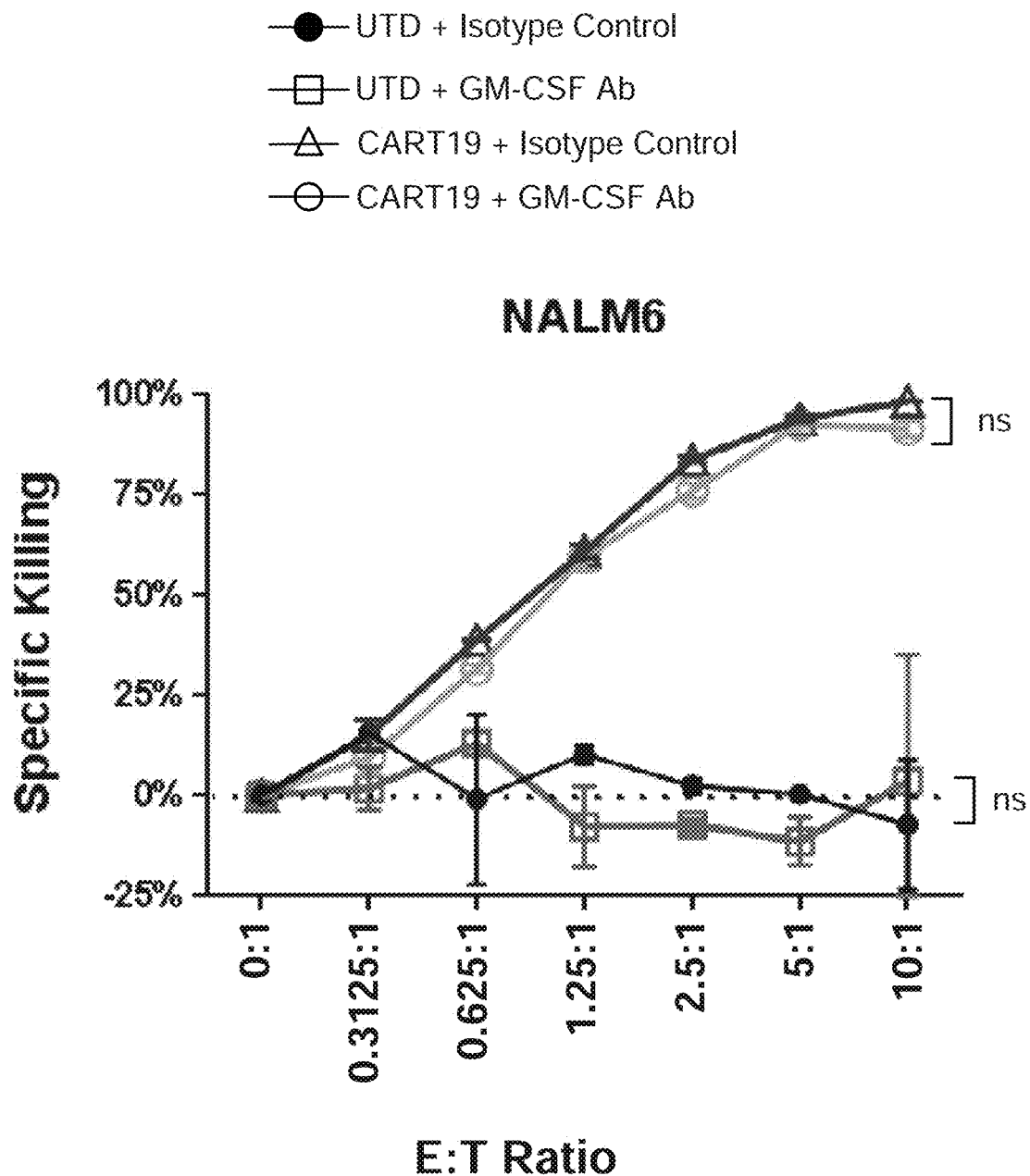
FIGS. 16A-16J illustrate that GM-CSF neutralizing antibody in accordance with embodiments described herein does not inhibit CAR-T mediated killing, proliferation, or cytokine production but successfully neutralizes GM-CSF (See Example 7).
Figure 16A:
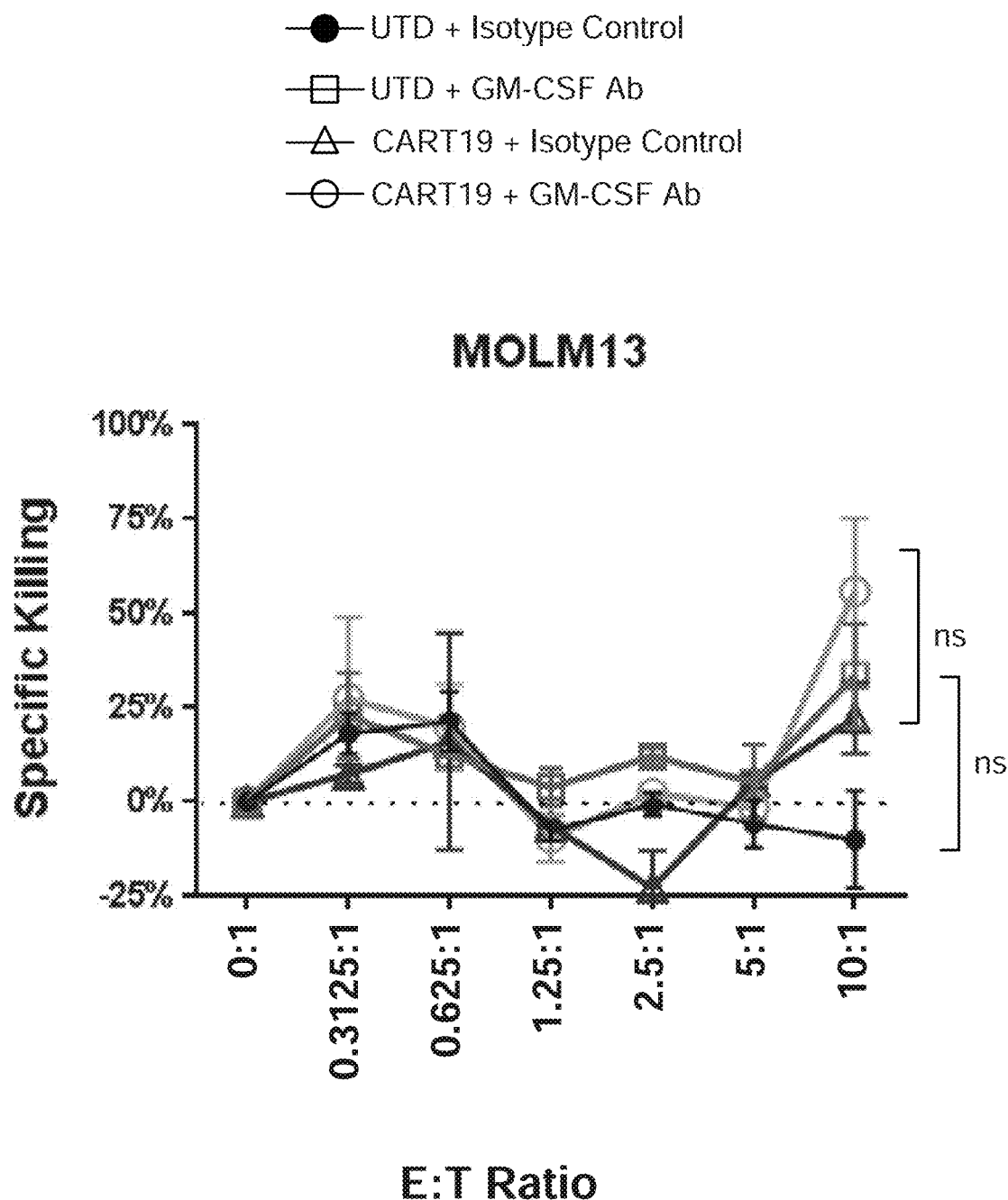
Figure 16B:
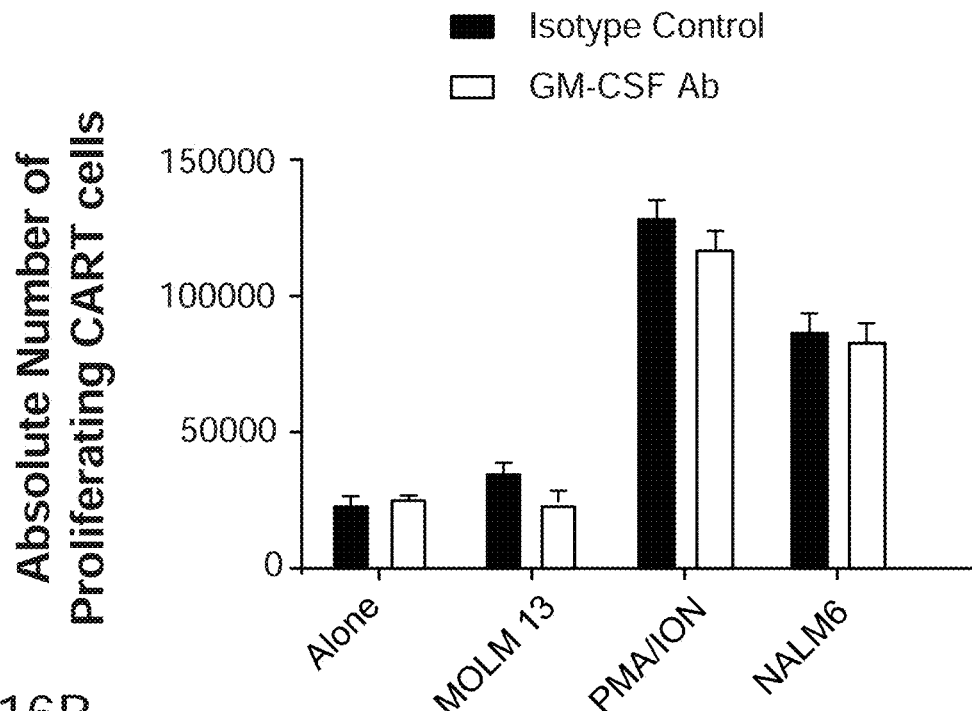
Figure 16C:
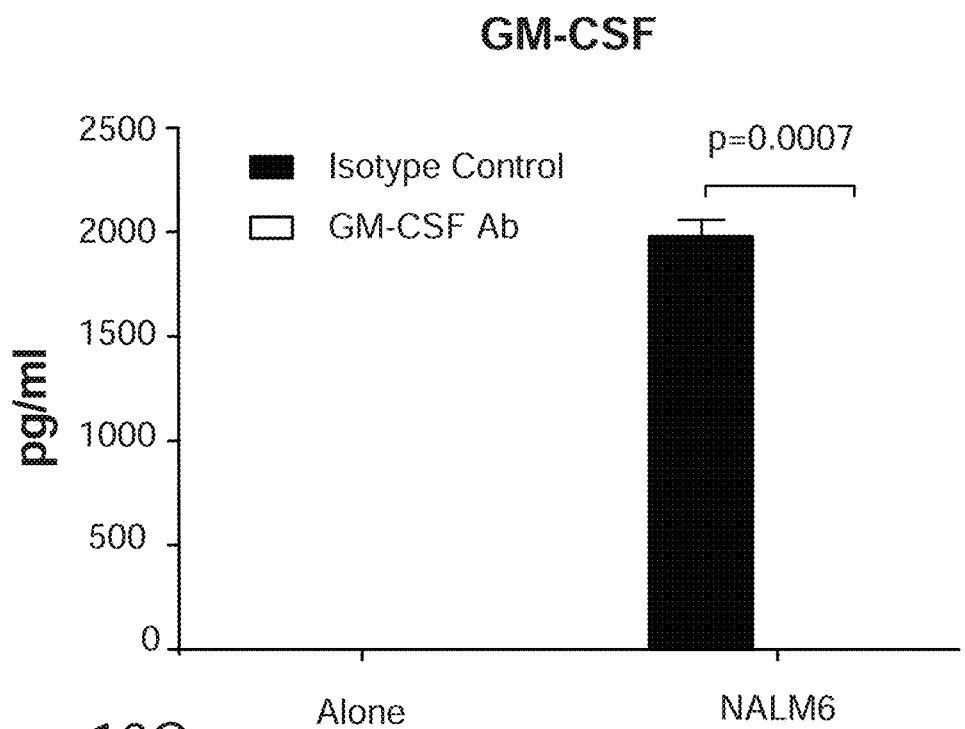
Figure 16D:
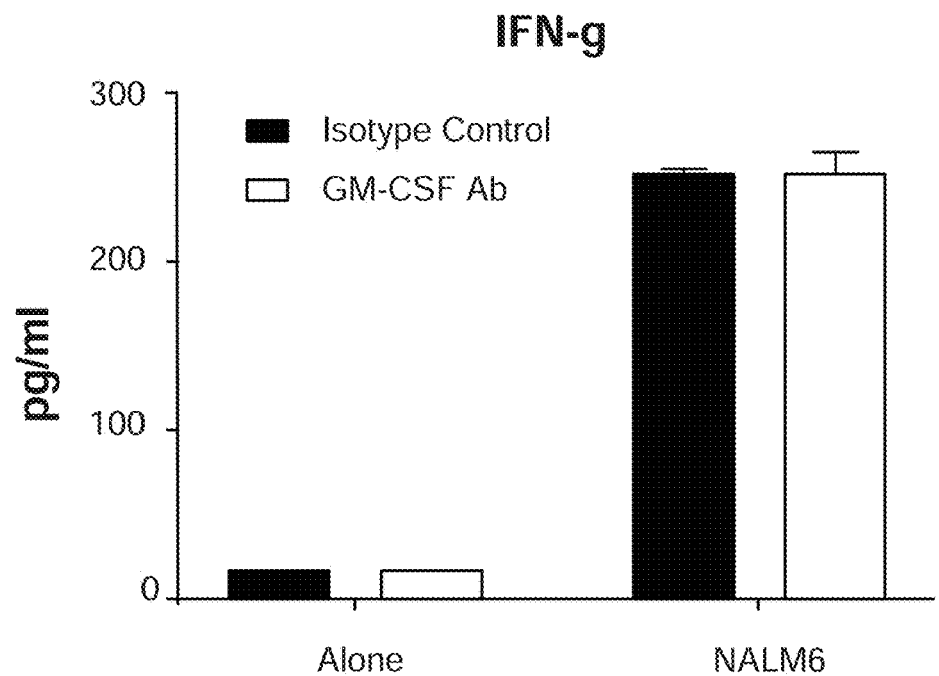
Figure 16E:
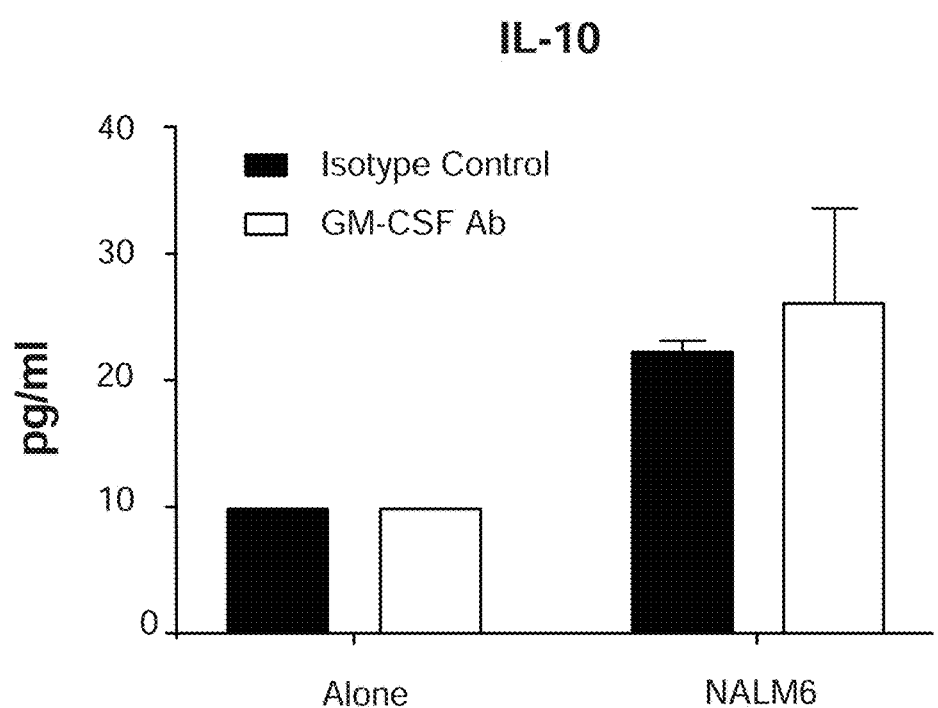
Figure 16F:
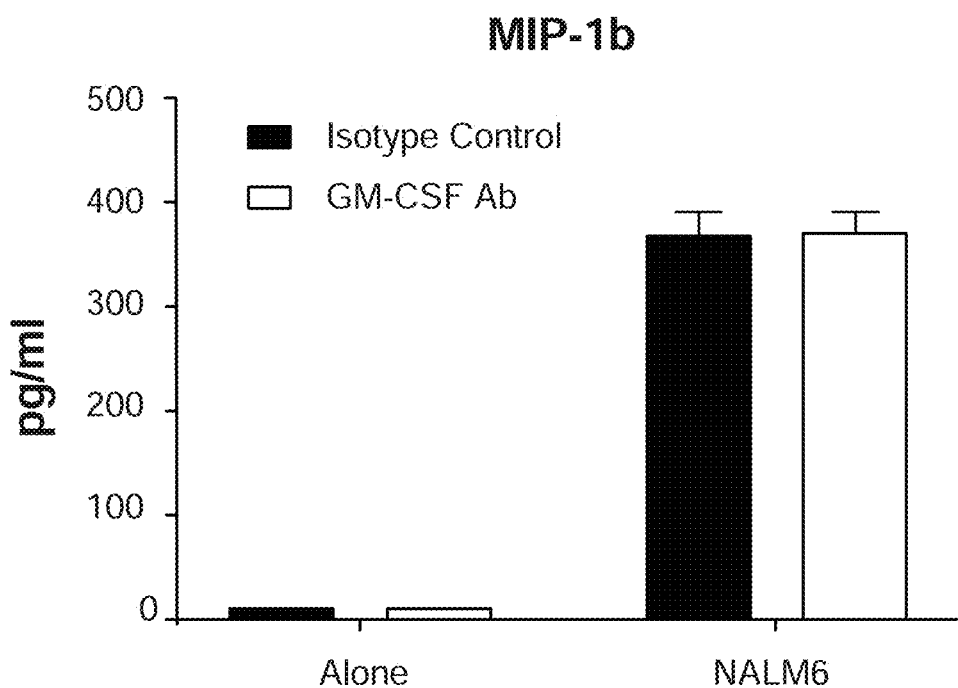
Figure 16G:
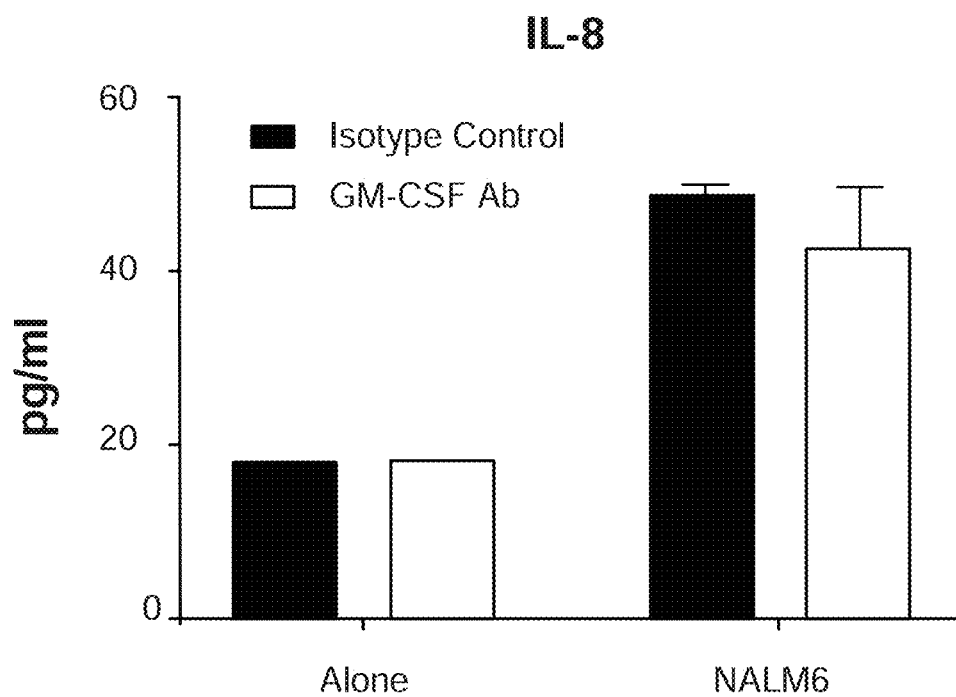
Figure 16H:
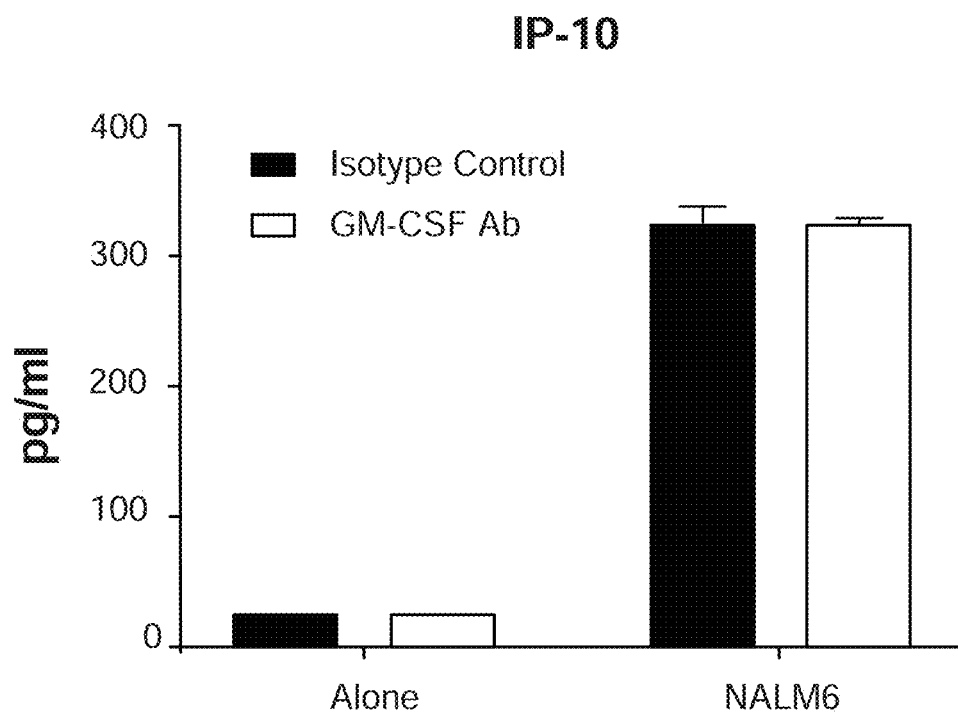
Figure 16I:
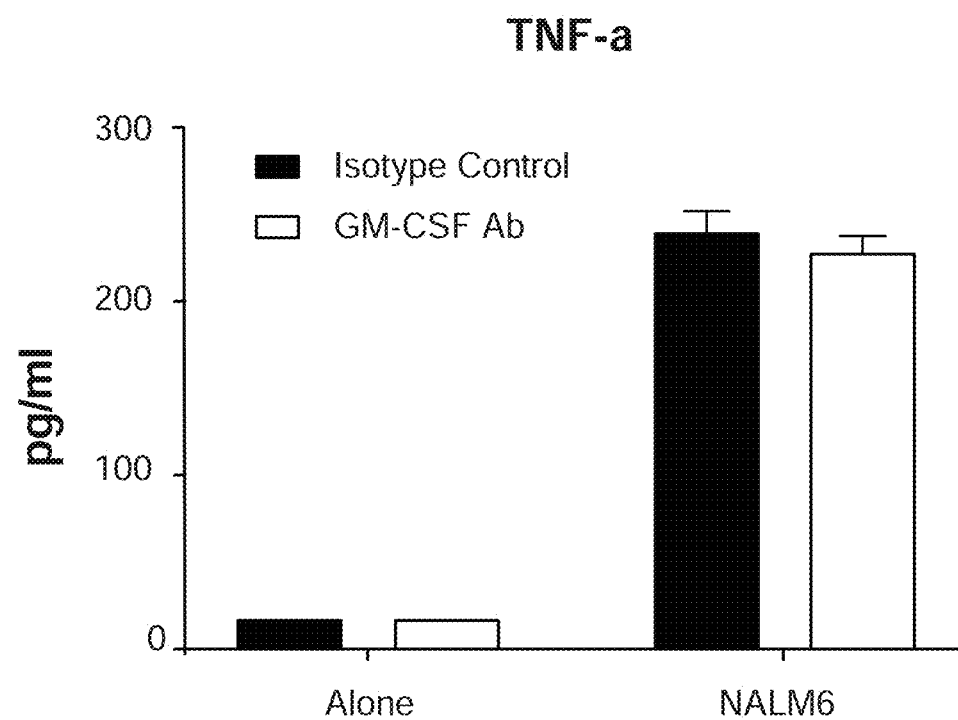
Figure 16J:
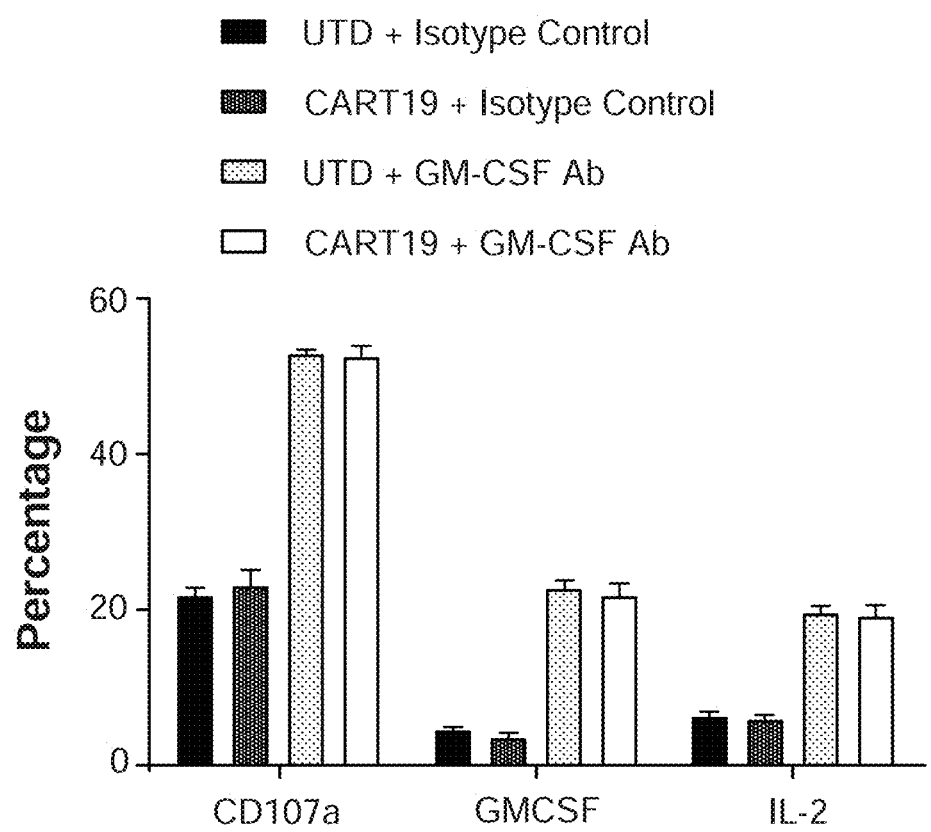

In vivo Models:

Effector/Target Control Experiments:

To study the effect of lenzilumab on CART19 cell function in vivo, we engrafted immuno-compromised NOD-SCID-g−/− with the CD19+ ALL cell line NALM6 in the absence of human PBMCs. Treatment with CART19 combined with lenzilumab resulted in potent anti-tumor activity and improved overall survival, similar to CART19 with control antibody despite complete neutralization of GM-CSF levels in these mice, indicating that GM-CSF does not impair CAR-T cell activity in vivo in the absence of PBMCs (FIGS. 16f and 16g).

CRS and NT Experiments:

Using human ALL blasts, human CD19 CAR-T, and human PBMCs, lenzilumab in combination with CAR-T cell therapy was found to reduce neuro-inflammation by ~90% compared to CAR-T alone as assessed by quantitative MRI T1 hyperintensity. This is a landmark finding and the first time it has been demonstrated in vivo that the neuroinflammation caused by CAR-T cell therapy can be effectively abrogated. MRI images following lenzilumab plus CAR-T cell therapy were similar to baseline pre-treatment scans, in sharp contrast to MRI images following control antibody plus CAR-T cell therapy which showed marked increased inflammation. Moreover, a decrease in myeloid cells was seen in the brains of mice treated with lenzilumab plus CAR-T compared to mice treated with CAR-T and control antibody. This finding is consistent with data reported in clinical trials with CD19 CAR-T cell therapy where an increase in myeloid cells was observed in the CSF of patients with severe grade >3 neurotoxicity. In addition, lenzilumab in combination with CAR-T cell therapy was found to reduce the onset and severity of CRS as compared to CAR-T plus control antibody. This finding is supported by the statistically significant reduction in body weight seen in mice treated with CAR-T plus control, the most objective marker and hallmark symptom of CRS seen in vivo. In mice treated with lenzilumab plus CAR-T, body weight was maintained at baseline levels as compared to CAR-T plus control (p<0.05). Moreover, mice treated with CAR-T plus control antibody displayed physical symptoms consistent with CRS including hunched posture, withdrawal, and weakness while mice treated with CAR-T plus lenzilumab appeared healthy. Importantly, lenzilumab plus CAR-T also demonstrates a significant 5-fold increase in the proliferation of CAR-T cells compared to CAR-T plus control in these CRS/NT experiments that included PBMCs. It has been previously shown in clinical trials with various CD19 CAR-T cell therapies that improved CAR-T proliferation or expansion correlates with improved efficacy (including ORR, CR), suggesting that lenzilumab may potentially improve anti-tumor response. This finding may be in part explained by a decrease in MDSC expansion and trafficking which is known to be promulgated by GM-CSF. Lastly, the combination of lenzilumab plus CAR-T results in significantly better leukemic control as quantified by flow cytometry compared to CAR-T and control antibody. Compared to untreated mice (which had 500,000 to 1.5M leukemic cells) and CAR-T plus control antibody (which had between 15,000 and 100,000 leukemic cells), treatment with CAR-T plus lenzilumab led to a significant reduction in the number of leukemic cells (decreased to between 500 and 5,000 cells) with improved overall disease control (see FIGS. 25A-25D).

Figure 25B:
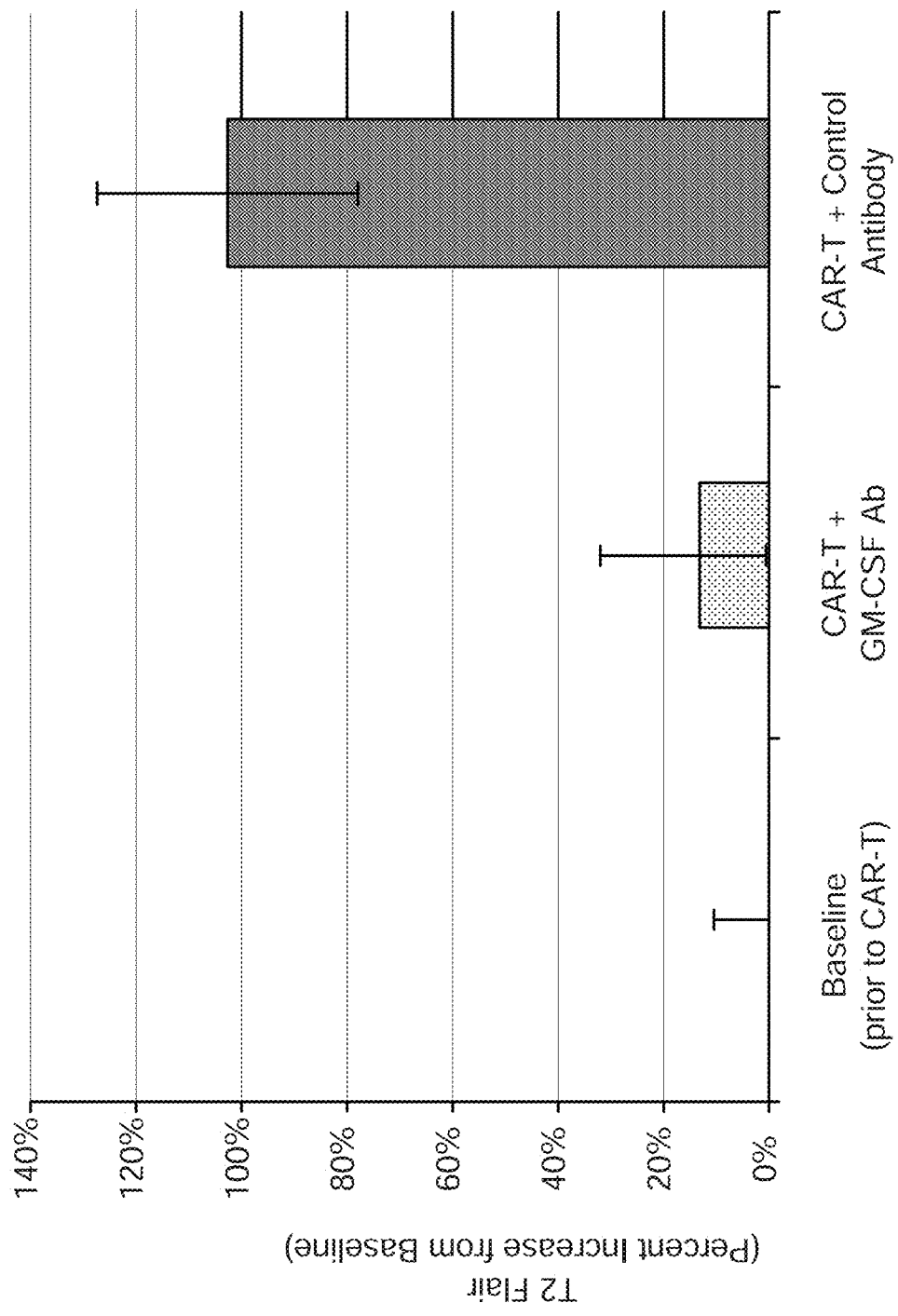
Figure 25C:
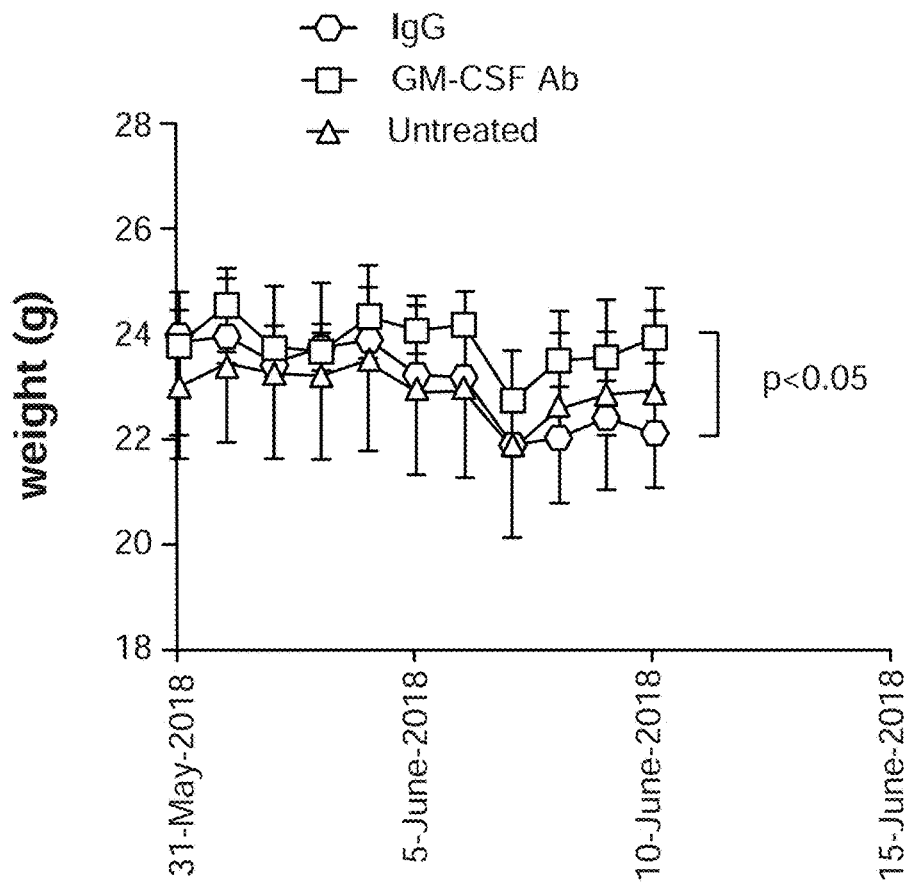
Figure 25D:
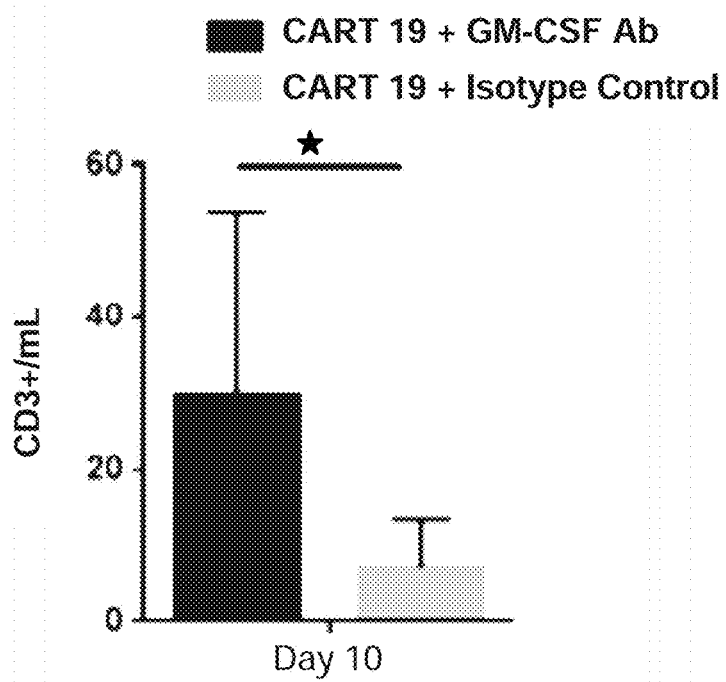

The MRI images in FIG. 25A shows a clear improvement in neurotoxicity (NT) (neuroinflammation) in the brains of mice administered CAR-T cells and anti-GM-CSF neutralizing antibody in accordance with embodiments described herein. In contrast, the brains of mice administered CAR-T cells and a control antibody showed signs of neurotoxicity in the MRI images. FIG. 25B graphically illustrates that the NT was reduced by 90% in the mice of Group 1 compared to the NT increased in Group 2 mice. The extent of quantitative improvement (90% reduction in NT) after administration of CAR-T cells and anti-GM-CSF neutralizing antibody in accordance with embodiments described herein was an unexpected finding.

Conclusions

Anti-GM-CSF antibody (Lenzilumab), when combined with CAR-T cell therapy demonstrates the potential to prevent the onset and severity of CRS and NT, while improving CAR-T expansion/proliferation and overall leukemic control in-vivo using human ALL blasts, human CD19 CAR-T and human PBMCs. This is the first time it has been demonstrated that CAR-T induced neurotoxicity can be abrogated in-vivo. Pivotal clinical trials with lenzilumab in combination with CAR-T cell therapy are planned to validate these findings of improved safety and efficacy.

Example 17

GM-CSF Blockade During Chimeric Antigen Receptor T Cell Therapy Reduces Cytokine Release Syndrome and Neurotoxicity and May Enhance Their Effector Functions Despite its efficacy, chimeric antigen receptor T-cell therapy (CART) is limited by the development of cytokine release syndrome (CRS) and neurotoxicity (NT). While CRS is related to extreme elevation of cytokines and massive T cell expansion, the exact mechanisms for NT have not yet been elucidated. Preliminary studies suggest that NT might be mediated by myeloid cells that cross the blood brain barrier. This is supported by correlative analysis from CART19 pivotal trials where CD14+ cell numbers were increased in the cerebrospinal fluid of patients that developed severe NT (Locke et al, ASH 2017). Therefore, the aimed of this study was to investigate the role of GM-CSF neutralization in preventing CRS and NT after CART cell therapy via monocyte control.

Figure 26A:
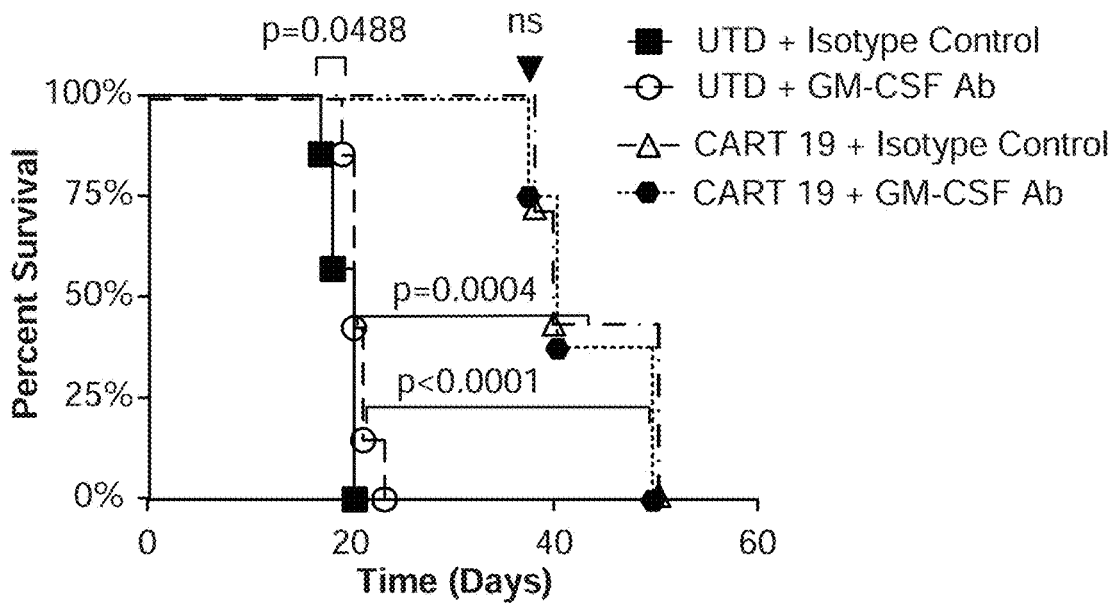
FIGS. 26A-26I show that GM-CSF blockade helps control CART19 toxicities and does improve efficacy.

First, the effect of GM-CSF blockade on CART cell effector functions was investigated. Here, the human GM-CSF neutralizing antibody (lenzilumab, Humanigen, Burlingame, Calif.) was used that has been shown to be safe in phase II clinical trials. Lenzilumab (10 ug/kg) neutralizes GM-CSF when CART19 cells are stimulated with the CD19+ Luciferase+ acute lymphoblastic leukemia (ALL) cell line NALM6, but does not impair CART cell function in vitro. It was found that malignancy associated macrophages reduce CART proliferation. GM-CSF neutralization with lenzilumab results in enhanced CART cell antigen specific proliferation in the presence of monocytes. To confirm this in vivo, NOD-SCID-g-/- mice were engrafted with high disease burdens of NALM6 and treated with low doses of CART19 or control T cells (to induce tumor relapse), in combination with lenzilumab or isotype control antibody. The combination of CART19 and lenzilumab resulted in significant anti-tumor activity and overall survival benefit compared to control T cells (FIG. 26A), similar to mice treated with CART19 combined with isotype control antibody, indicating that GM-CSF neutralization does not impair CART cell activity in vivo. This anti-tumor activity was validated in an ALL patient derived xenograft model.

Figure 26B:
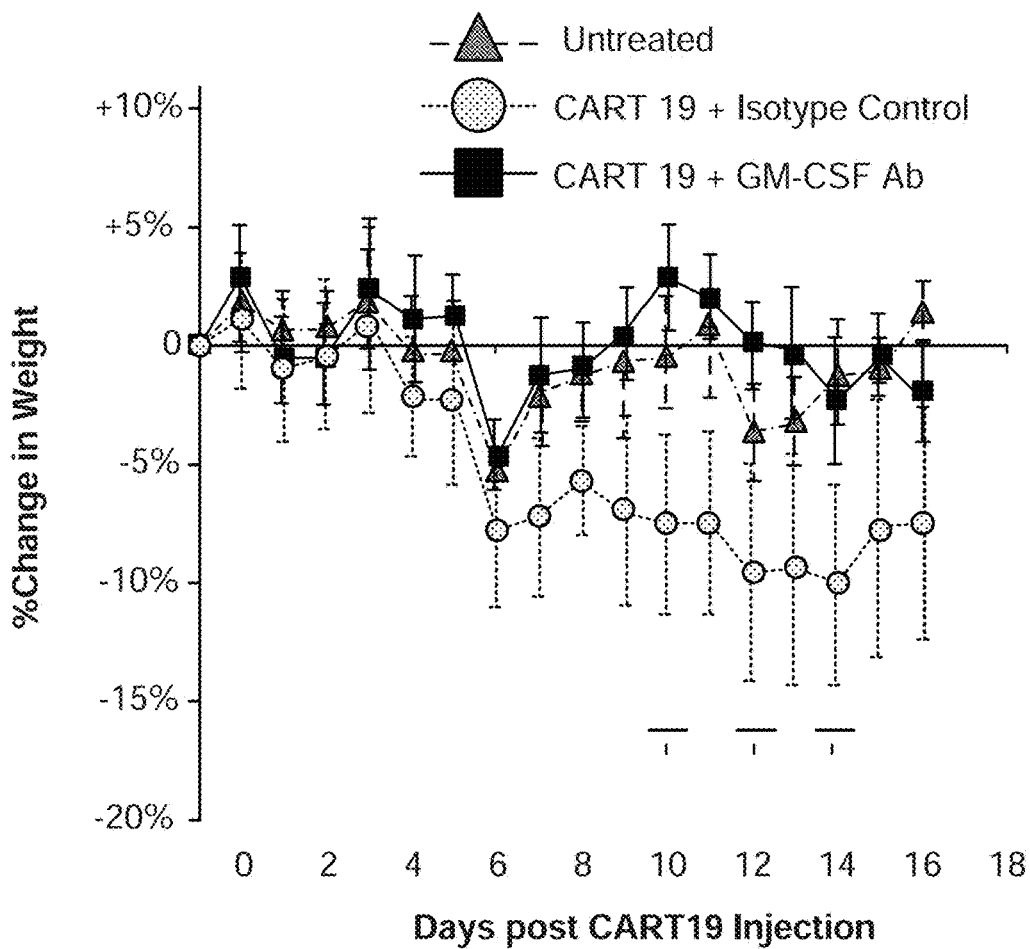
Figure 26C:
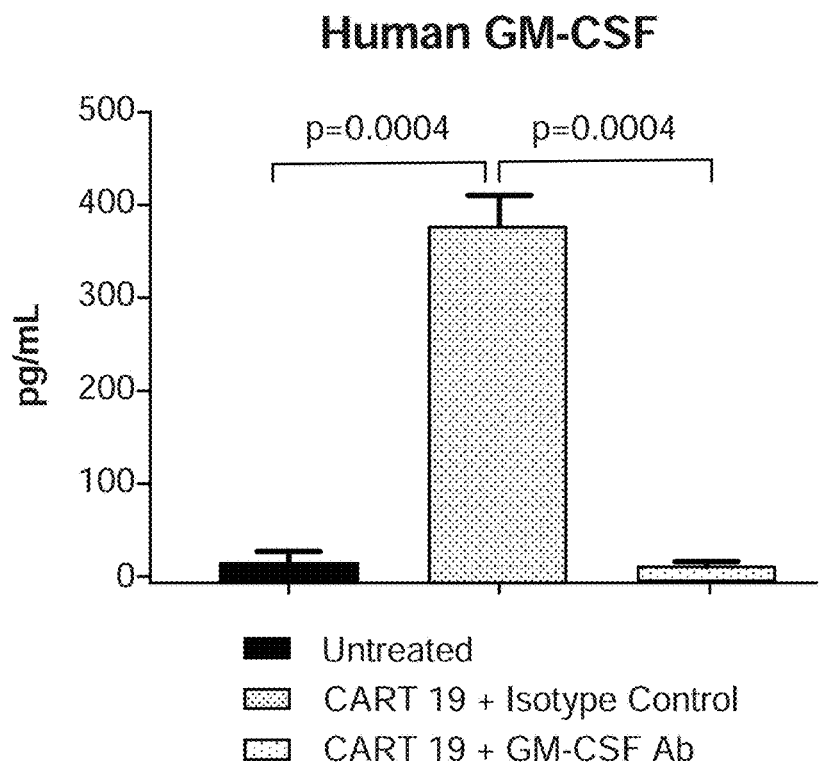
Figure 26D:
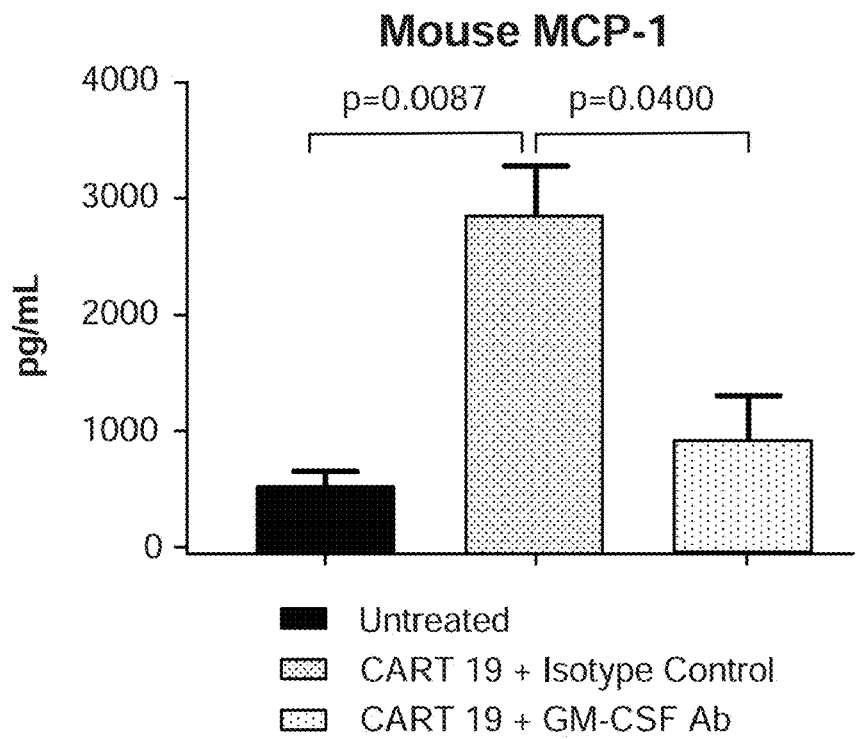
Figure 26E:
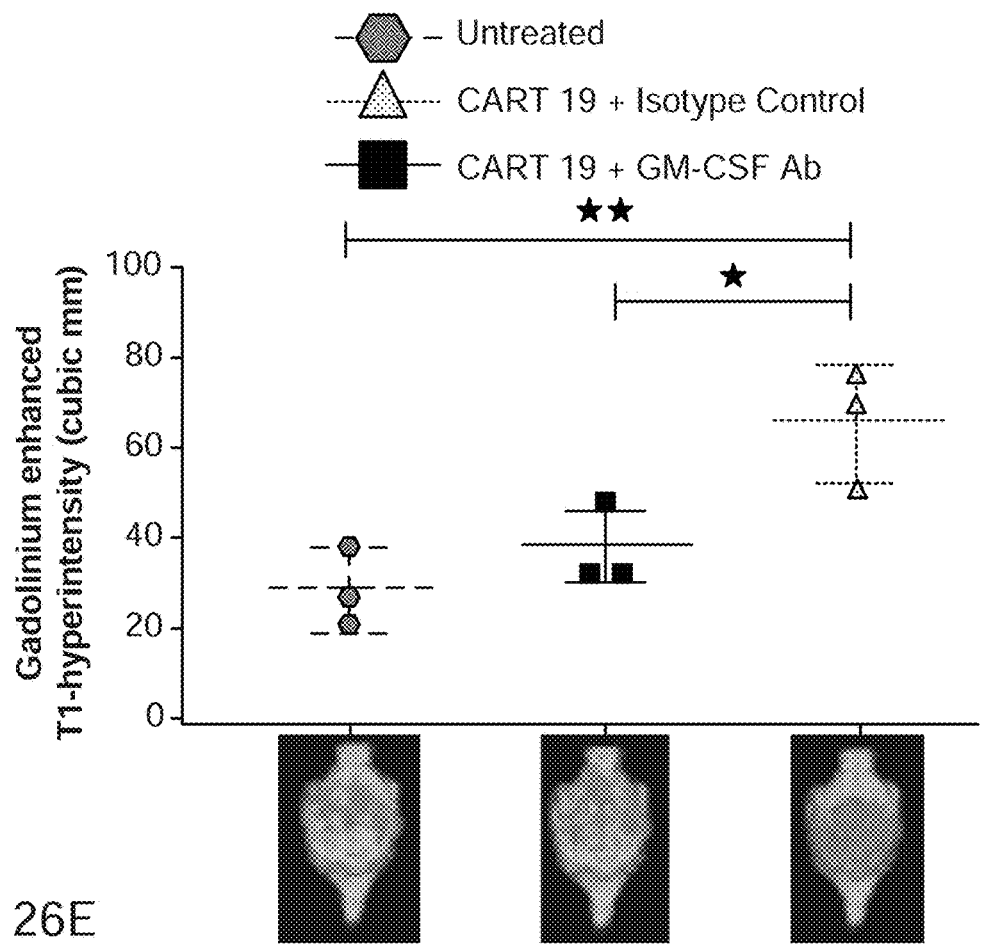
Figure 26F:
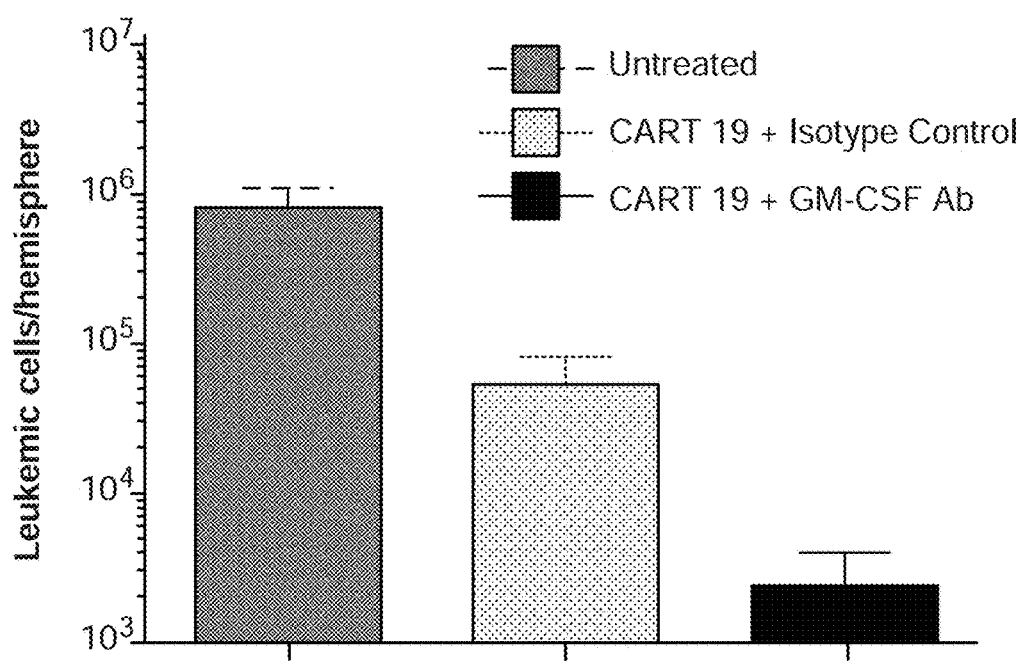
Figure 26G:
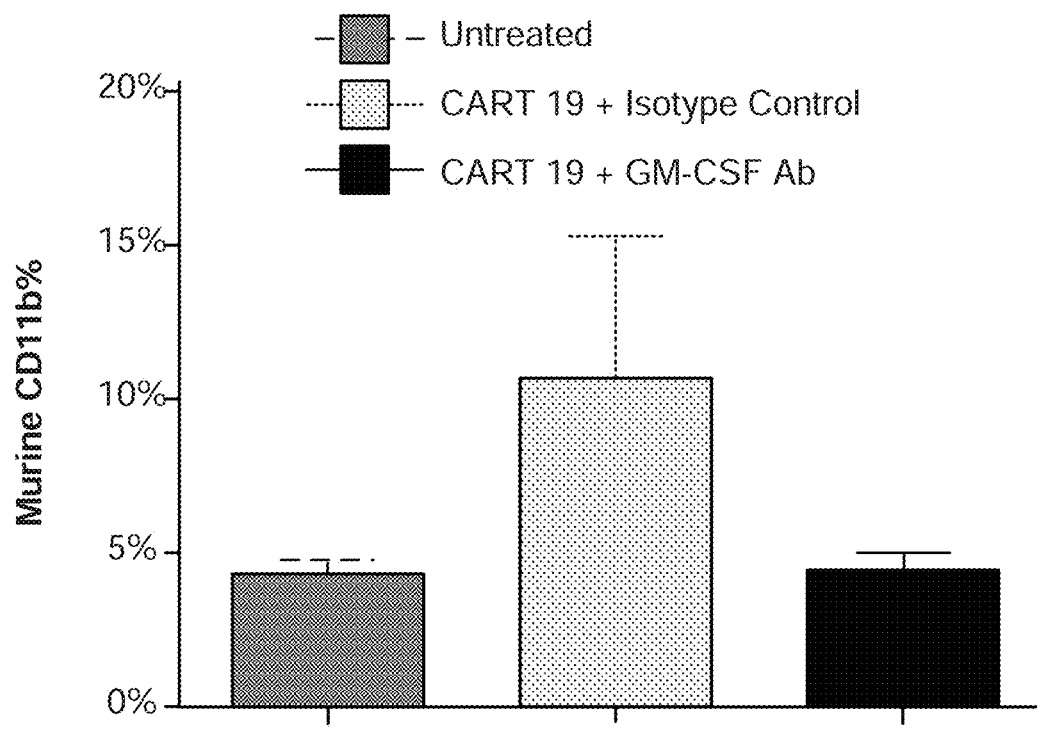

Next, explored was the impact of GM-CSF neutralization on CART cell related toxicities in a novel patient derived xenograft model. Here, NOD-SCID-g-/- mice were engrafted with leukemic blasts (1-3×106 cells) derived from patients with high risk relapsed ALL. Mice were then treated with high doses of CART19 cells (2-5×106 intravenously). Five days after CART19 treatment, mice began to develop progressive motor weakness, hunched bodies, and weight loss that correlated with massive elevation of circulating human cytokine levels. Magnetic Resonance Imaging (MRI) of the brain during this syndrome showed diffuse enhancement and edema, associated with central nervous system (CNS) infiltration of CART cells and murine activated myeloid cells. This is similar to what has been reported in CART19 clinical trials in patients with severe NT. The combination of CART19, lenzilumab (to neutralize human GM-CS) and murine GM-CSF blocking antibody (to neutralize mouse GM-CSF) resulted in prevention of weight loss (FIG. 26B), decrease in critical myeloid cytokines (FIGS. 26C-26D), reduction of cerebral edema (FIG. 26E), enhanced leukemic disease control in the brain (FIG. 26F), and reduction in brain macrophages (FIG. 26G).

Figure 26H:
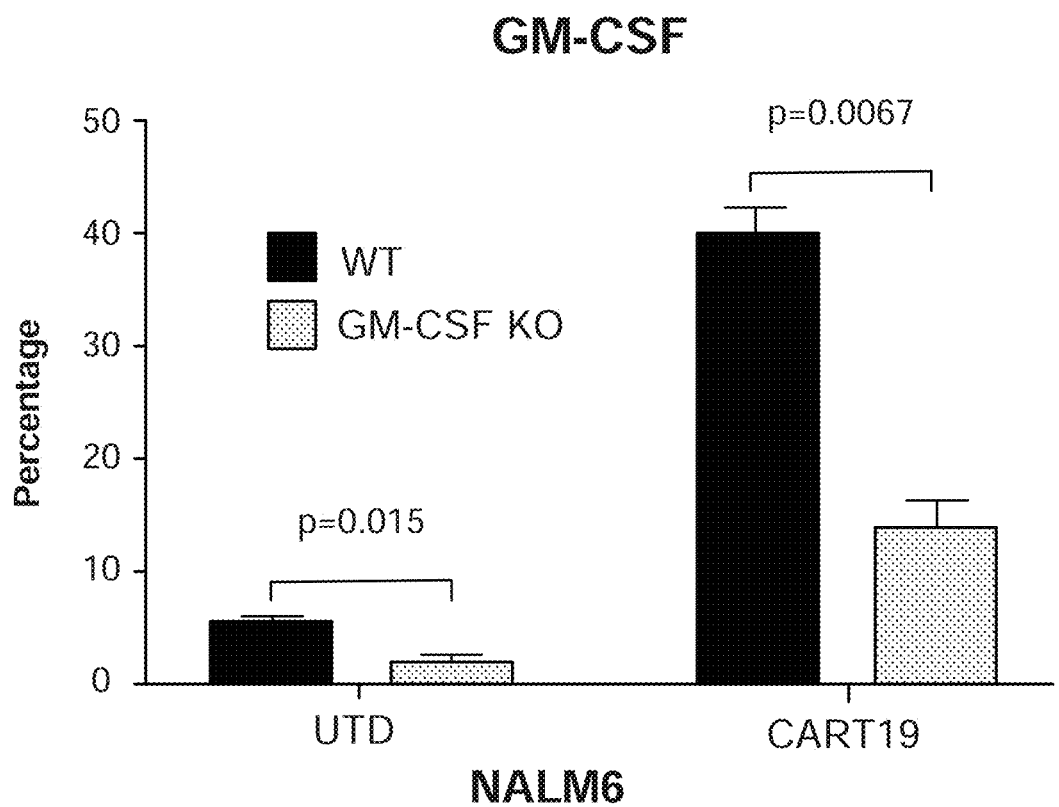
Figure 26I:
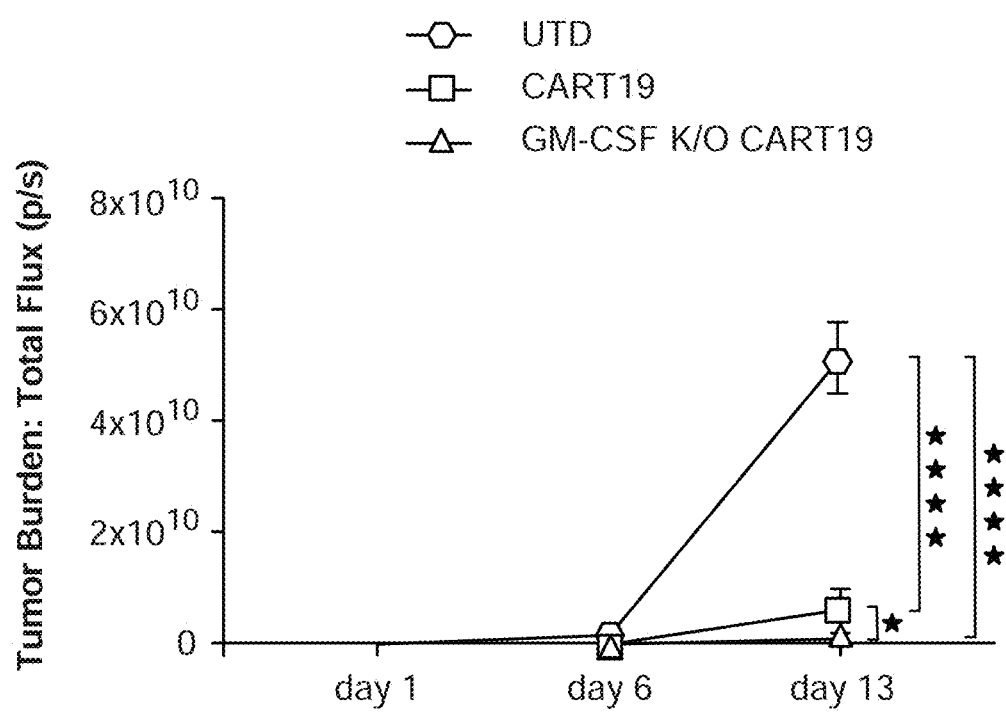

Finally, it was hypothesized that disrupting GM-CSF through CRISPR/Cas9 gene editing during the process of CART cell manufacture would result in functional CART cells with reduced secretion of GM-CSF. Guide RNA targeting exon 3 of the GM-CSF gene was designed and GM-CSF$^{k/o}$ CART19 cells were generated. The preliminary data suggest that these CARTs produce significantly less GM-CSF upon activation but continue to exhibit similar production of other cytokines and exhibit normal effector functions in vitro (FIG. 26H). Using the NALM6 high tumor burden relapse xenograft model as described above, GM-CSF$^{k/o}$ CART19 cells resulted in slightly enhanced disease control compared to CART19 cells (FIG. 26I).

Thus, modulating myeloid cell behavior through GM-CSF blockade can help control CART mediated toxicities and may reduce their immunosuppressive features to improve leukemic control. These studies illuminate a novel approach to abrogate NT and CRS through GM-CSF neutralization that also potentially enhances CART cell functions. Based on these results, a phase II clinical trial has been designed using lenzilumab as a modality to prevent CART related toxicities in patients with diffuse large B cell lymphoma.

Example 18

GM-CSF Neutralization In Vitro Enhances CAR-T Cell Proliferation in the Presence of Monocytes and does not Impair CAR-T Cell Effector Function Cells Lines and Primary Cells The NALM6 cell line was purchased from ATCC, Manassas, Va., USA, and the MOLM13 cell line was a gift from the Jelinek Laboratory at the Mayo Clinic (purchased from DSMZ, Braunschweig, Germany). These cell lines were transduced with a luciferase-ZsGreen lentivirus (Addgene, Cambridge, Mass., USA) and sorted to 100% purity. Cell lines were cultured in R10 (made with RPMI 1640 (Gibco, Gaithersburg, Md., US), 10% Fetal Bovine Serum (FBS, Millipore Sigma, Ontaria, Canada), and 1% Penicillin-Streptomycin-Glutamine (Gibco, Gaithersburg, Md., US). Primary cells were obtained from the Mayo Clinic Biobank for patients with acute leukemia under a Mayo Clinic Institutional Review Board (IRB) approved protocol. The use of recombinant DNA in the laboratory was approved by the Mayo Clinic Institutional Biosafety Committee (IBC).
Primary Cells and CAR-T Cells Peripheral blood mononuclear cells (PBMC) were isolated from de-identified normal donor blood apheresis cones obtained under a Mayo Clinic IRB approved protocol, using SepMate tubes (STEMCELL Technologies, Vancouver, Canada). T cells were separated with negative selection magnetic beads using EasySep™ Human T Cell Isolation Kit (STEMCELL Technologies, Vancouver, Canada). Monocytes were isolated using a Human Monocyte Isolation Kit from Miltenyi Biotec, Bergisch Gladbach, Germany, which isolates CD14+ monocytes. Primary cells were cultured in T Cell Medium made with X-Vivo 15 (Lonza, Walkersville, Md., USA) supplemented with 10% human serum albumin (Corning, N.Y., USA) and 1% Penicillin-Streptomycin-Glutamine (Gibco, Gaithersburg, Md., USA). CART19 cells were generated through the lentiviral transduction of normal donor T cells as described herein below. Second generation CART19 constructs were de novo synthesized (IDT) and cloned into a third-generation lentivirus under the control of the EF-1α promotor. The CD19 directed single chain variable region fragment was derived from the clone FMC63. A second generation 4-1BB co-stimulated (FMC63-41BBz) CAR construct was synthesized and used for these experiments. Lentiviral particles were generated through the transient transfection of plasmid into 293T virus producing cells (gift from the Ikeda lab, Mayo Clinic), in the presence of Lipofectamine 3000 (Invitrogen, Carlsbad, Calif., USA), VSV-G and packaging plasmids (Addgene, Cambridge, Mass., USA). T cells isolated from normal donors were stimulated using Cell Therapy Systems Dynabeads CD3/CD28 (Life Technologies, Oslo, Norway) at a 1:3 ratio and then transduced with lentivirus particles 24 hours after stimulation at a multiplicity of infection (MOI) of 3.0. To determine titers and subsequently MOI, after lentivirus particles were concentrated, titers were determined by transducing 1×10$^5$ primary T cells in 100 ul of T cell medium with 50 ul of lentivirus. First, T cells were stimulated with CD3/CD28 beads and then transduced with lentivirus particles 24 hours later. Transduction was performed in triplicates and at serial dilutions. Fresh T cell medium was added one day later. Two days later, cells were harvested, washed twice with PBS, and CAR expression on T cells was determined by flow cytometry. Titers were determined based on the percentage of CAR positive cells (percentage of CAR+ cells×T cell count at transduction×the specific dilution/volume) and expressed as transducing units/mL (TU/mL). Magnetic bead removal was performed on Day 6 and CAR-T cells were harvested and cryopreserved on Day 8 for future experiments. CAR-T cells were thawed and rested in T cell medium 12 hours prior to their use in experiments.
GM-CSF Neutralizing Antibody and Isotype Controls Lenzilumab (Humanigen, Burlingame, Calif.), an hGM-CSF neutralizing antibody in accordance with embodiments described herein and as described in U.S. Pat. Nos. 8,168,183 and 9,017,674, each of which is incorporated herein by reference in its entirety, is a novel, first in class Humaneered® monoclonal antibody that neutralizes human GM-CSF. For in vitro experiments, lenzilumab or InVivoMAb human IgG1 isotype control (BioXCell, West Lebanon, N.H., USA), 10 ug/mL was used. For in vivo experiments, 10 mg/kg of lenzilumab or isotype control were intraperitoneally injected daily for 10 days beginning on the day of CART19 injection. In some experiments, anti-mouse GM-CSF neutralizing antibody (InVivoMAb anti-mouse GM-CSF, BioXCel, West Lebanon, N.H., USA) or the corresponding isotype control (InVivoMAb rat IgG2a isotype control BioXCel, West Lebanon, N.H., USA) was also used, as indicated in the experimental schema.
T Cell Functional Experiments Cytokine assays were performed 24 or 72 hours after a co-culture of CAR-T cells with their targets at a 1:1 ratio as indicated. Human High Sensitivity T Cell Magnetic Bead Panel (Millipore Sigma, Ontario, Canada), Milliplex Human Cytokine/Chemokine MAGNETIC BEAD Premixed 38 Plex Kit (Millipore Sigma, Ontario, Canada), or Milliplex Mouse Cytokine/Chemokine MAGNETIC BEAD Premixed 32 Plex Kit (Millipore Sigma, Ontario, Canada) were performed on supernatants collected from these experiments or serum, as indicated. This was analyzed using Luminex (Millipore Sigma, Ontario, Canada). Intracellular cytokine analysis and T cell degranulation assays were performed following incubation of CAR-T cells with targets at a 1:5 ratio for 4 hours, in the presence of monensin (BioLegend, San Diego, Calif., USA), hCD49d (BD Biosciences, San Diego, Calif., USA), and hCD28 (BD Biosciences, San Diego, Calif., USA). After 4 hours, cells were harvested and intracellular staining was performed after surface staining, followed by fixation and permeabilization with fixation medium A and B (Life Technologies, Oslo, Norway). For proliferation assays, CFSE (Life Technologies, Oslo, Norway) labeled effector cells (CART19), and irradiated target cells were co cultured at a 1:1 ratio. In some experiments, CD14+ monocytes were added to the co-culture at a 1:1:1 ratio as indicated. Cells were co-cultured for 3-5 days, as indicated in the specific experiment and then cells were harvested and surface staining with anti-hCD3 (eBioscience, San Diego, Calif., USA) and LIVE/DEAD™ Fixable Aqua Dead Cell Stain Kit (Invitrogen, Carlsbad, Calif., USA) was performed. PMA/ionomycin (Millipore Sigma, Ontario, Canada) was used as a positive non-specific stimulant of T cells, at different concentrations as indicated in the specific experiments. For killing assays, the CD19+Luciferase+ ALL cell line NALM6 or the CD19-Luciferase+ control MOLM13 cells were incubated at the indicated ratios with effector T cells for 24, 48, or 72 hours as listed in the specific experiment. Killing was calculated by bioluminescence imaging on a Xenogen IVIS-200 Spectrum camera (PerkinElmer, Hopkinton, Mass., USA) as a measure of residual live cells. Samples were treated with 1 ul D-luciferin (30 ug/mL) per 100 ul sample volume (Gold Biotechnology, St. Louis, Mo., USA), for 10 minutes prior to imaging.

Multi-Parametric Flow Cytometry

Anti-human and anti-mouse antibodies were purchased from Biolegend, eBioscience, or BD Biosciences (San Diego, Calif., USA). Cells were isolated from in vitro culture or from peripheral blood of animals. After BD FACS lyse (BD Biosciences, San Diego, Calif., USA), they were washed twice in phosphate-buffered saline supplemented with 2% FBS (Millipore Sigma, Ontario, Canada) and 1% sodium azide (Ricca Chemical, Arlington, Tex., USA) and stained at 4° C. For cell number quantitation, Countbright beads (Invitrogen, Carlsbad, Calif., USA) were used according to the manufacturer's instructions (Invitrogen, Carlsbad, Calif., USA). In all analyses, the population of interest was gated based on forward vs side scatter characteristics, followed by singlet gating, and live cells were gated following staining with LIVE/DEAD™ Fixable Aqua Dead Cell Stain Kit (Invitrogen, Carlsbad, Calif., USA). Surface expression of CAR was detected by staining with a goat anti-mouse F(ab')2 antibody (Invitrogen, Carlsbad, Calif., USA). Flow cytometry was performed on three-laser cytometers, Canto II (BD Biosciences, San Diego, Calif., USA) and CytoFLEX (Beckman Coulter, Chaska, Minn., USA). Analyses were performed using FlowJo X10.0.7r2 software (Ashland, Oreg., USA) and Kaluza 2.0 software (Beckman Coulter, Chaska, Minn., USA).

Results

Figure 27A:
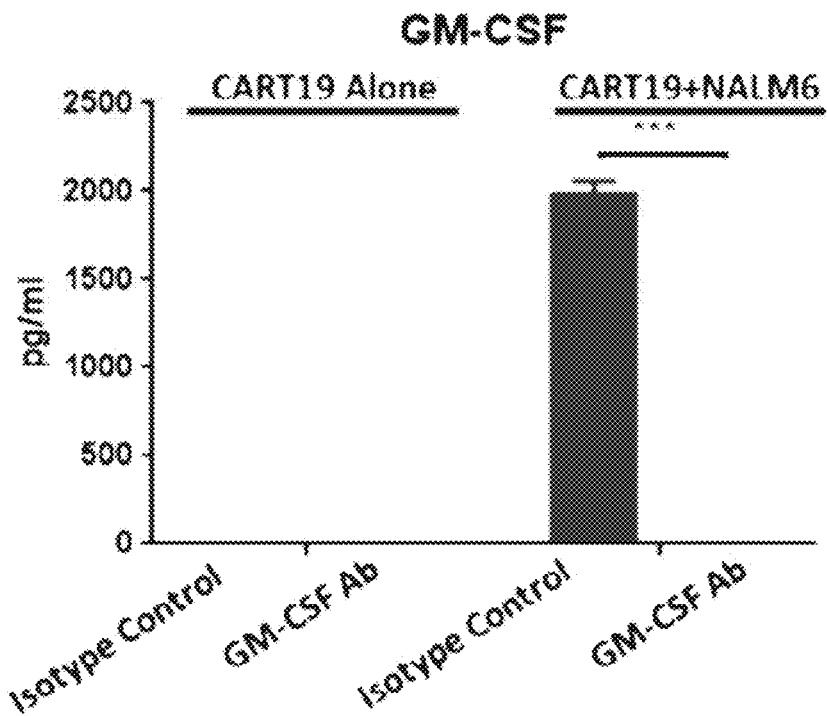
FIGS. 27A-27D show GM-CSF neutralization in vitro enhances CAR-T cell proliferation in the presence of monocytes and does not impair CAR-T cell effector function.
Figure 27B:
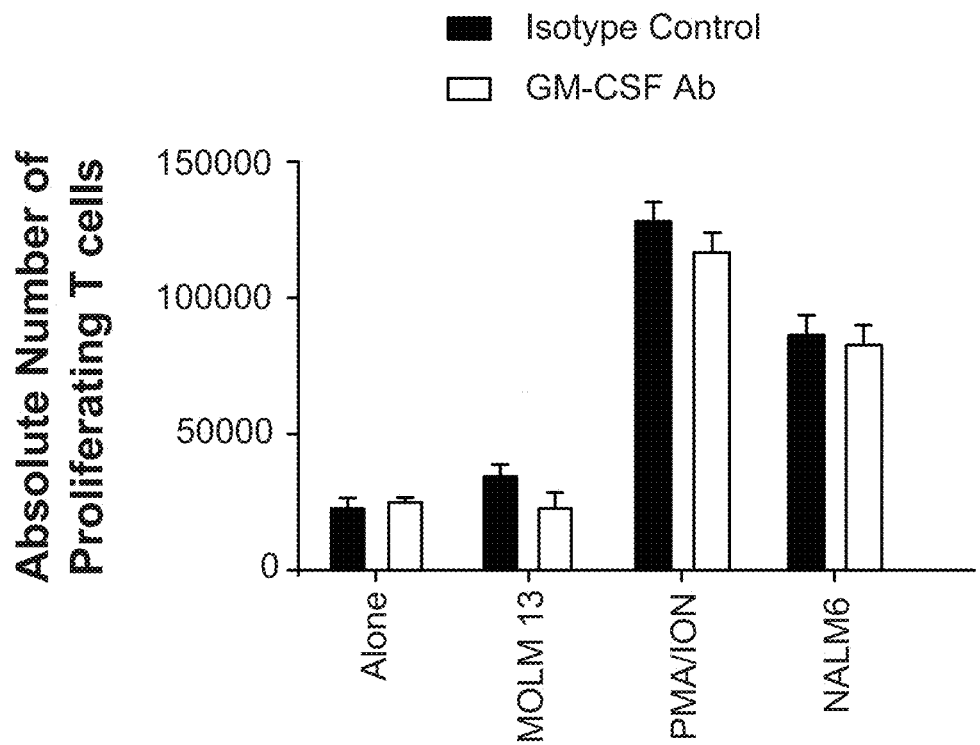
Figure 27C:
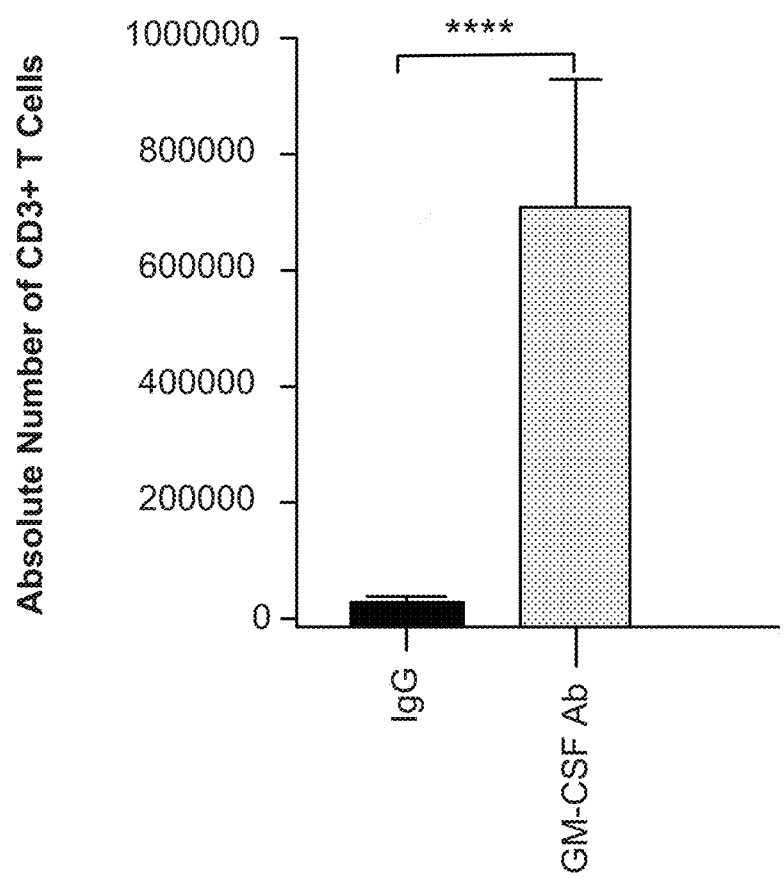
Figure 27D:
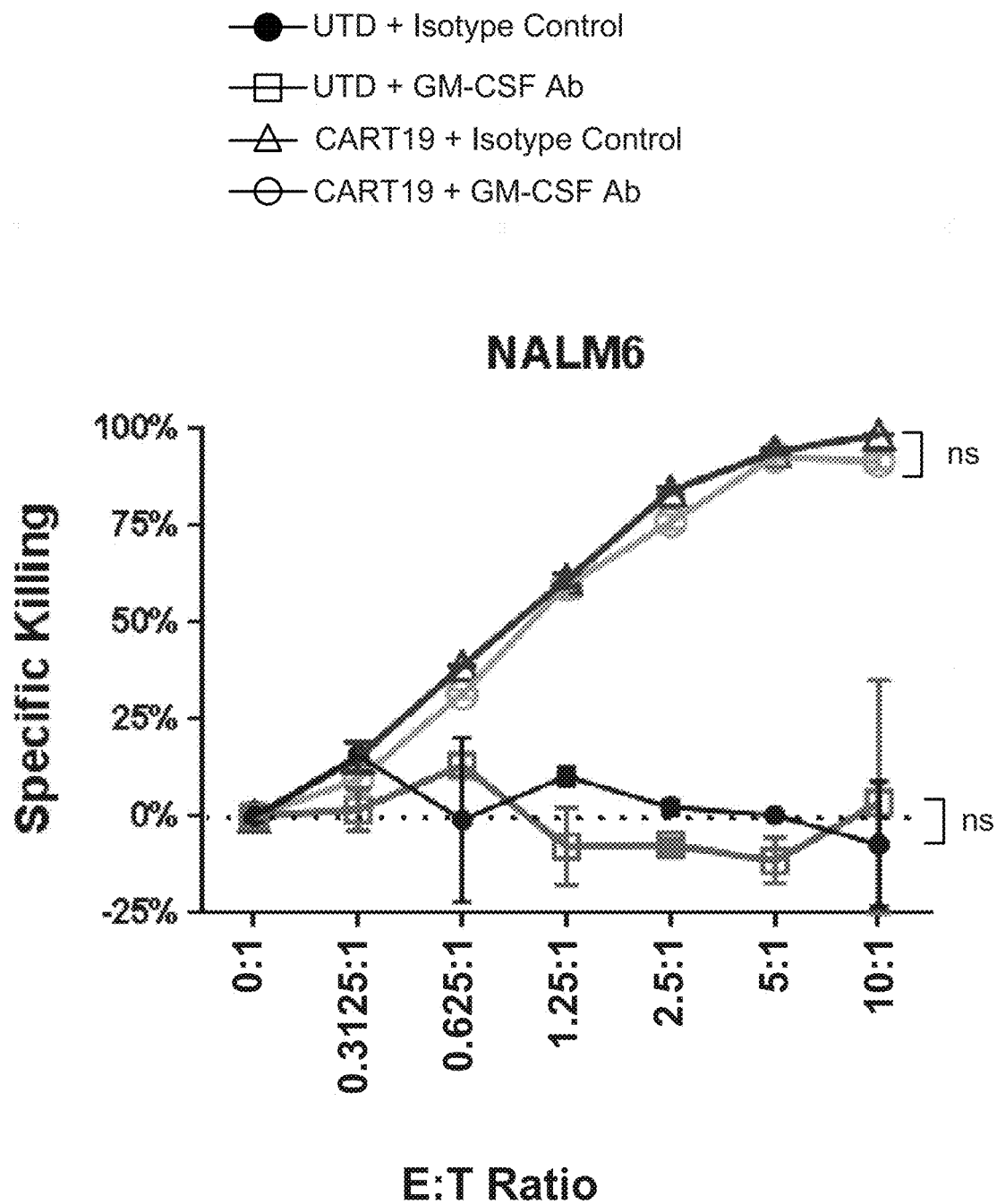

If GM-CSF neutralization after CAR-T cell therapy is to be utilized as a strategy to prevent CRS and neurotoxicity, it must not inhibit CAR-T cell efficacy. Therefore, the initial experiments aimed to investigate the impact of GM-CSF neutralization on CAR-T cell effector functions. CART19 cells were co-cultured with or without the CD19+ ALL cell line NALM6 in the presence of lenzilumab (hGM-CSF neutralizing antibody) or an isotype control (IgG). It was established that lenzilumab, but not IgG control antibody, was indeed able to completely neutralize hGM-CSF (FIG. 27A) but did not inhibit CAR-T cell antigen specific proliferation (FIG. 27B). When CART19 cells were co-cultured with the CD19+ cell line NALM6 in the presence of monocytes, lenzilumab in combination with CART19 demonstrated an exponential increase in antigen specific CART19 proliferation compared to CART19 plus isotype control IgG ($P<0.0001$, FIG. 27C). To investigate CAR-T specific cytotoxicity, either CART19 or control UTD T cells were cultured with the luciferase+CD19+ NALM6 cell line and treated with either isotype control antibody or GM-CSF neutralizing antibody (FIG. 27D). GM-CSF neutralizing antibody treatment did not inhibit the ability of CAR-T cells to kill NALM6 target cells (FIG. 27D). Overall, these results indicate that lenzilumab does not inhibit CAR-T cell function in vitro and enhances CART19 cell proliferation in the presence of monocytes, suggesting that GM-CSF neutralization may improve CAR-T cell mediated efficacy.

Example 19

GM-CSF Neutralization In Vivo Enhances CAR-T Cell Anti-Tumor Activity in Xenograft Models Xenograft Mouse Models Male and female 8-12 week old NOD-SCID-IL2r$\gamma^{-/-}$ (NSG) mice were bred and cared for within the Department of Comparative Medicine at the Mayo Clinic under a breeding protocol approved by the Mayo Clinic Institutional Animal Care and Use Committee (IACUC). Mice were maintained in an animal barrier space that is approved by the IBC for BSL2+ level experiments.

NALM6 Cell Line Xenografts

The CD19+, luciferase ALL NALM6 cell line was used to establish ALL xenografts, under an IACUC approved protocol. Here, $1\times10^6$ cells were injected intravenously (IV) via a tail vein injection. 4-6 days after injection, mice underwent bioluminescent imaging using a Xenogen IVIS-200 Spectrum camera (PerkinElmer, Hopkinton, Mass., USA), to confirm engraftment. Imaging was performed 10 minutes after the intraperitoneal (IP) injection of 10 ul/g D-luciferin (15 mg/mL, Gold Biotechnology, St. Louis, Mo., USA). Mice were then randomized based on their bioluminescent imaging to receive different treatments as outlined in the specific experiments. Typically, $1\text{-}1.5\times10^6$ CAR-T cells (and an equivalent of total T cell number of untransduced (UTD) T cells) were injected IV per mouse. Transduction efficiency of CAR-T cells was typically approximately 50%. For example, with a 50% transduction efficiency of CAR-T cells, mice that received $1.5\times10^6$ CAR-T cells received 3 million total T cells, and the corresponding UTD mice received $3\times10^6$ UTD. Weekly imaging was performed to assess and follow disease burden. Bioluminescent images were acquired using a Xenogen IVIS-200 Spectrum camera (PerkinElmer, Hopkinton, Mass., USA) and analyzed using Living Image version 4.4 (Caliper LifeSciences, PerkinElmer). Tail vein bleeding was done 7-8 days after injection of CAR-T cells to assess T cell expansion and cytokines and chemokines, and subsequently as needed. Mouse peripheral blood was subjected to red blood cell lysis using BD FACS Lyse (BD Biosciences, San Diego, Calif., USA) and then used for flow cytometric studies. Antibody treated mice commenced daily antibody therapy (10 mg/kg lenzilumab or isotype control) IP on the same day of CART cell therapy for a total of 10 days.

RNA-Seq on Mouse Brain Tissue

RNA was isolated using miRNeasy Micro kit (Qiagen, Gaithersburg, Md., USA) and treated with RNase-Free DNase Set (Qiagen, Gaithersburg, Md., USA). RNA-seq was performed on an Illumina HTSeq 4000 (Illumina, San Diego, Calif., USA) by the Genome Analysis Core at Mayo Clinic. The binary base call data was converted to fastq using Illumina bcl2fastq software. The adapter sequences were removed using Trimmomatic, as described by Bolger, A M, et al., *Bioinformatics*. 2014; 30(15):2114-2120. 10.1093/bioinformatics/btu170, which is hereby incorporated by reference in its entirety, and FastQC as described by Leggett R M, et al., *Front Genet.* 2013; 4:288. Prepublished on 2014 Jan. 2 as DOI 10.3389/fgene.2013.00288, which is hereby incorporated by reference in its entirety, was used to check for quality. The latest human (GRCh38) and mouse (GRCm38) reference genomes were downloaded from NCBI. Genome index files were generated using STAR, as described by Dobin A, et al., *Bioinformatics*. 2013; 29(1): 15-21. 10.1093/bioinformatics/bts635, which is hereby incorporated by reference in its entirety, and the paired end reads were mapped to the genome for each condition. HTSeq, as described by Anders S, et al., *Bioinformatics*. 2015; 31(2):166-169. Prepublished on 2014 Sep. 28 as DOI 10.1093/bioinformatics/btu638, which is hereby incorporated by reference in its entirety, was used to generate expression counts for each gene, and DeSeq2[38], as described by Love M I, et al., *Genome Biol.* 2014; 15(12):550. Prepublished on 2014 Dec. 18 as DOI 10.1186/s13059-014-0550-8, which is hereby incorporated by reference in its entirety was used to calculate differential expression. Gene ontology was assessed using Enrichr, as described by Kuleshov M V et al., *Nucleic Acids Research* 2016; 44(W1): W90-W97. 10.1093/nar/gkw377, which is hereby incorporated by reference in its entirety. FIG. 35 summarizes the steps detailed above. RNA sequencing data are available at the Gene Expression Omnibus under accession number GSE121591.

Statistics

Prism Graph Pad (La Jolla, Calif., USA) and Microsoft Excel (Microsoft, Redmond, Wash., USA) were used to analyze data. The high cytokine concentrations in the heat map were normalized to "1" and low concentrations normalized to "0" via Prism. Statistical tests are described in the figure legends.

Results

Figure 28A:
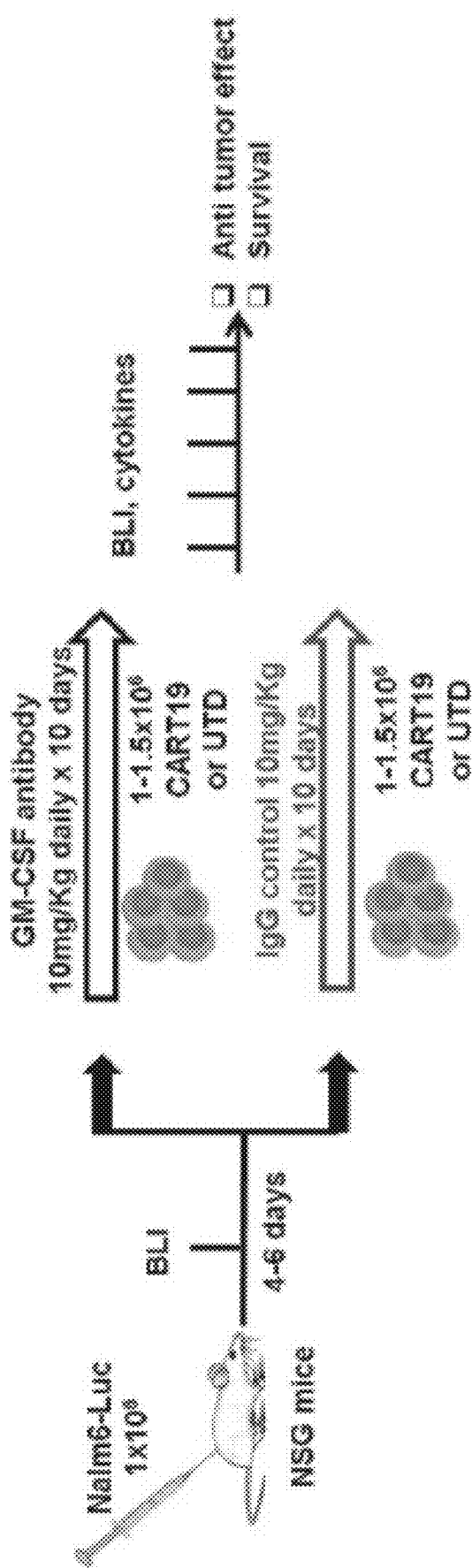
FIGS. 28A-28F demonstrate that GM-CSF neutralization in vivo enhances CAR-T cell anti-tumor activity (i.e., tumor cell killing) in xenograft models.
Figure 28B:
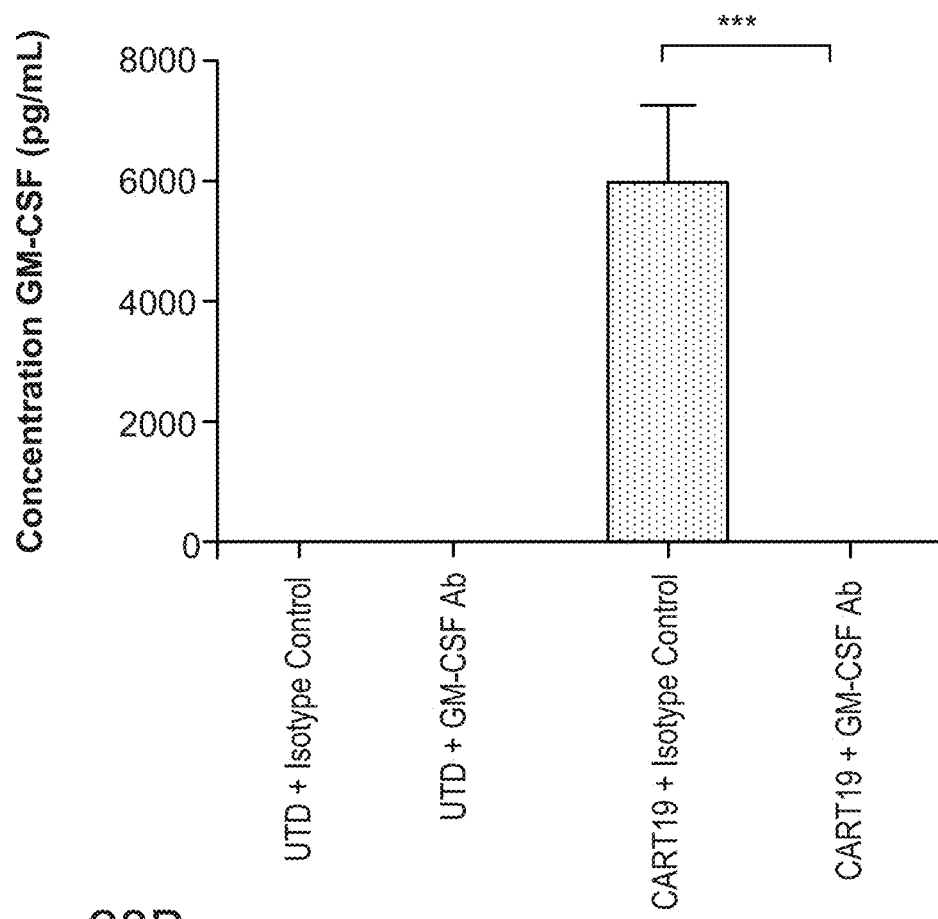
Figure 28C:
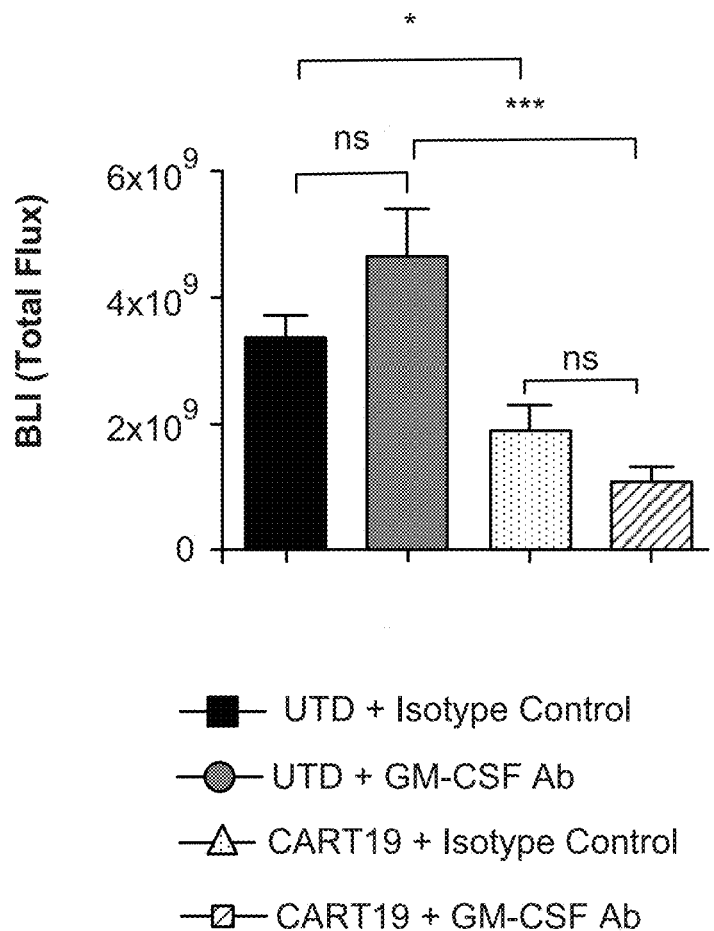
Figure 28D:
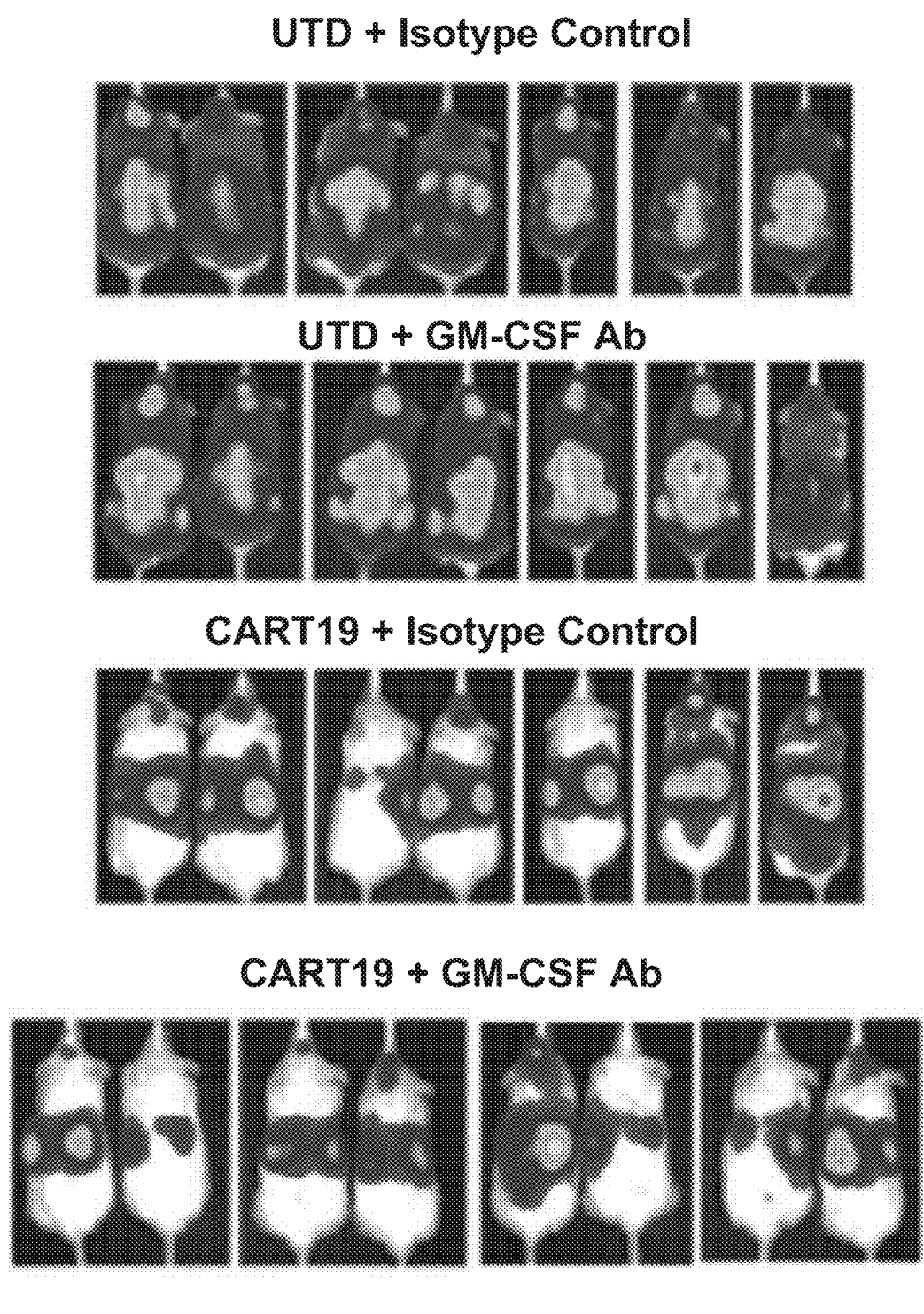
Figure 28E:
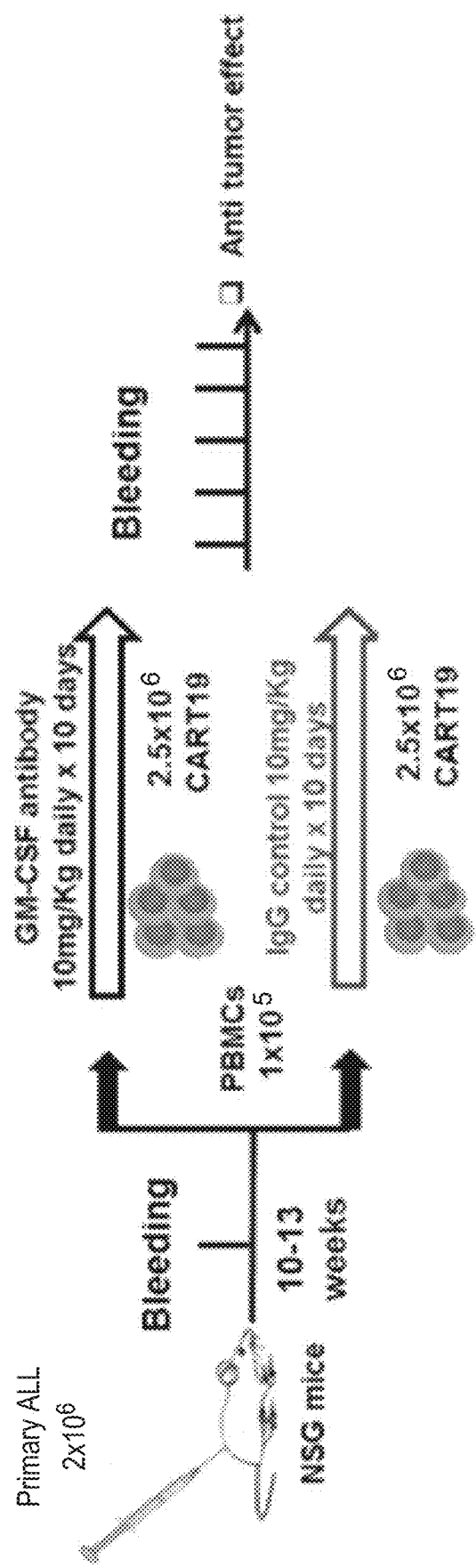
Figure 28F:
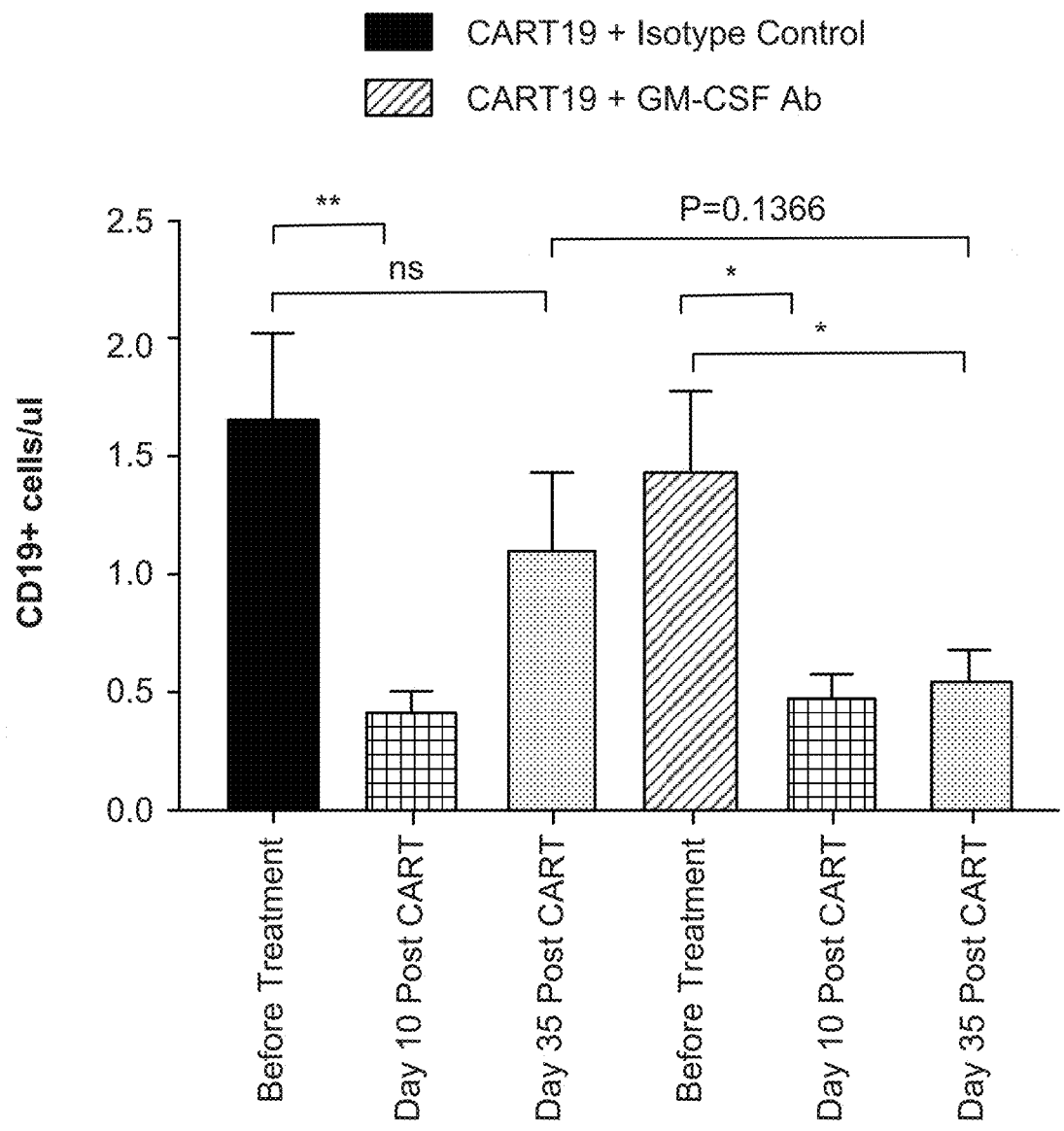

To confirm that GM-CSF depletion does not inhibit CART19 effector functions, the role of GM-CSF neutralization with lenzilumab on CART19 antitumor activity was investigated in xenograft models. First, a relapse model intended to vigorously investigate whether the antitumor activity of CART19 cells was impacted by GM-CSF neutralization was used. NOD/SCID/interleukin-2 receptor gamma null (NSG) mice were injected with 1×10⁶ luciferase⁺ NALM6 cells and then imaged 6 days later, allowing sufficient time for mice to achieve very high tumor burdens. Mice were randomized to receive a single injection of either CART19 or UTD cells and 10 days of either isotype control antibody or lenzilumab (FIG. 28A). GM-CSF assay on serum collected 8 days after CART19 injection revealed that lenzilumab successfully neutralizes GM-CSF in the context of CART19 therapy (FIG. 28B). Bioluminescence imaging one week after CART19 injection showed that CART19 in combination with lenzilumab effectively controlled leukemia in this high tumor burden relapse model and significantly better than control UTD cells (FIGS. 28C-28D). Treatment with CART19 in combination with lenzilumab resulted in potent anti-tumor activity and improved overall survival, similar to CART19 with control antibody despite neutralization of GM-CSF levels, indicating that GM-CSF does not impair CAR-T cell activity in vivo (FIG. 36). Second, these experiments were performed in a primary ALL patient derived xenograft model, in the presence of human PBMCs as this represents a more relevant heterogeneous model. After conditioning chemotherapy with busulfan, mice were injected with blasts derived from patients with relapsed ALL. Mice were monitored for engraftment for several weeks through serial tail vein bleedings and when the CD19⁺ blasts in the blood were approximately 1/uL, mice were randomized to receive CART19 treatment in combination with PBMCs with either lenzilumab plus an anti-mouse GM-CSF neutralization antibody or isotype control IgG antibodies starting on the day of CART 19 injection for 10 days (FIG. 28E). In this primary ALL xenograft model, GM-CSF neutralization in combination with CART19 therapy resulted in a significant improvement in leukemic disease control sustained over time for at least 35 days post CART19 administration as compared to CART19 plus isotype control (FIG. 28F). This suggests that GM-CSF neutralization may play a role in reducing relapses and increasing durable complete responses after CART19 cell therapy.

Example 20

Generation of GM-CSF$^{k/o}$ CART19

A guide RNA (gRNA) targeting exon 3 of human GM-CSF was selected via screening gRNAs previously reported to have high efficiency for human GM-CSF, as described in Sanjana N E et al., Improved vectors and genome-wide libraries for CRISPR screening. *Nature Methods.* 2014; 11(8):783-784. Prepublished on 2014 Jul. 31 as DOI 10.1038/nmeth.3047, which is hereby incorporated by reference in its entirety. This gRNA was ordered in a CAS9 third generation lentivirus construct (lentiCRISPRv2), controlled under a U6 promotor (GenScript, Township, N.J., USA). Lentiviral particles encoding this construct were produced as described above. T cells were dual transduced with CAR19 and GM-CSFgRNA-lentiCRISPRv2 lentiviruses, 24 hours after stimulation with CD3/CD28 beads. CAR-T cell expansion was then continued as described above. To analyze efficiency of targeting GM-CSF, genomic DNA was extracted from the GM-CSF$^{k/o}$ CART19 cells using PureLink Genomic DNA Mini Kit (Invitrogen, Carlsbad, Calif., USA). The DNA of interest was PCR amplified using Choice Taq Blue Mastermix (Thomas Scientific, Minneapolis, Minn., USA) and gel extracted using QIAquick Gel Extraction Kit (Qiagen, Germantown, Md., USA) to determine editing. PCR amplicons were sent for Eurofins sequencing (Louisville, Ky., USA) and allele modification frequency was calculated using TIDE (Tracking of Indels by Decomposition) a method that requires only two parallel PCR reactions followed by a pair of standard capillary sequencing analyses; the two resulting sequencing traces are then analyzed using specially designed software that is provided as a simple web tool and as R code available at tide.nki.nl, as described by Brinkman E K, et al., Easy quantitative assessment of genome editing by sequence trace decomposition. *Nucleic Acids Research.* 2014; 42(22):e168. Prepublished on 2014 Oct. 11 as DOI 10.1093/nar/gku936, which is incorporated herein by reference in its entirety. FIG. 34B describes the gRNA sequence and primer sequences, and FIG. 34A(i)-34A(iii) depicts the schema for generation of GM-CSF$^{k/o}$ CART19 schema.

Example 21

Figure 29A:
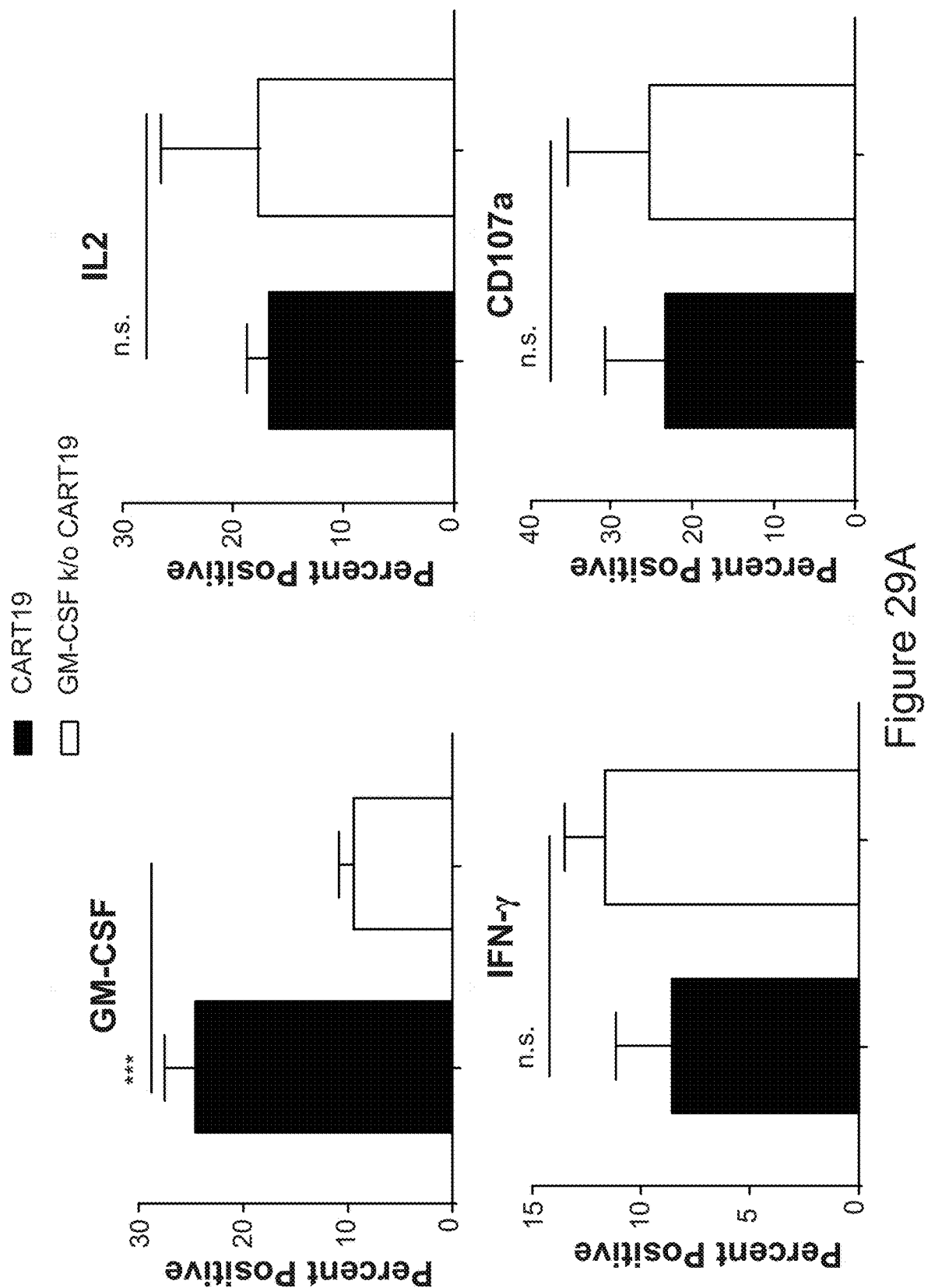
FIGS. 29A-29E demonstrate that GM-CSF CRISPR knockout CAR-T cells exhibit reduced expression of GM-CSF, similar levels of key cytokines and chemokines, and enhanced anti-tumor activity.
Figure 29B:
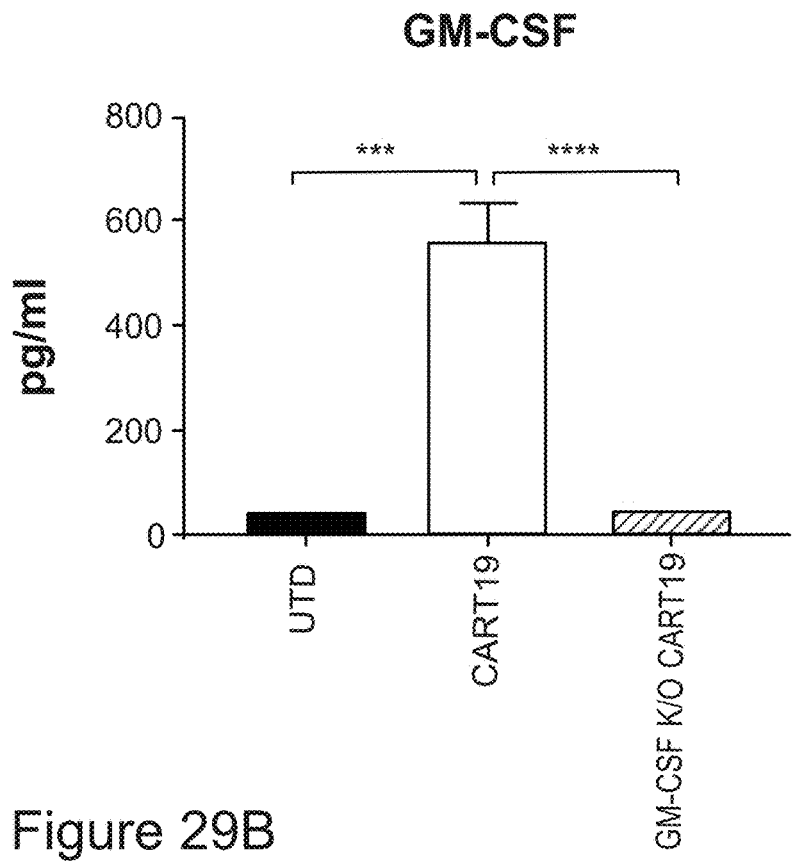
Figure 29C:
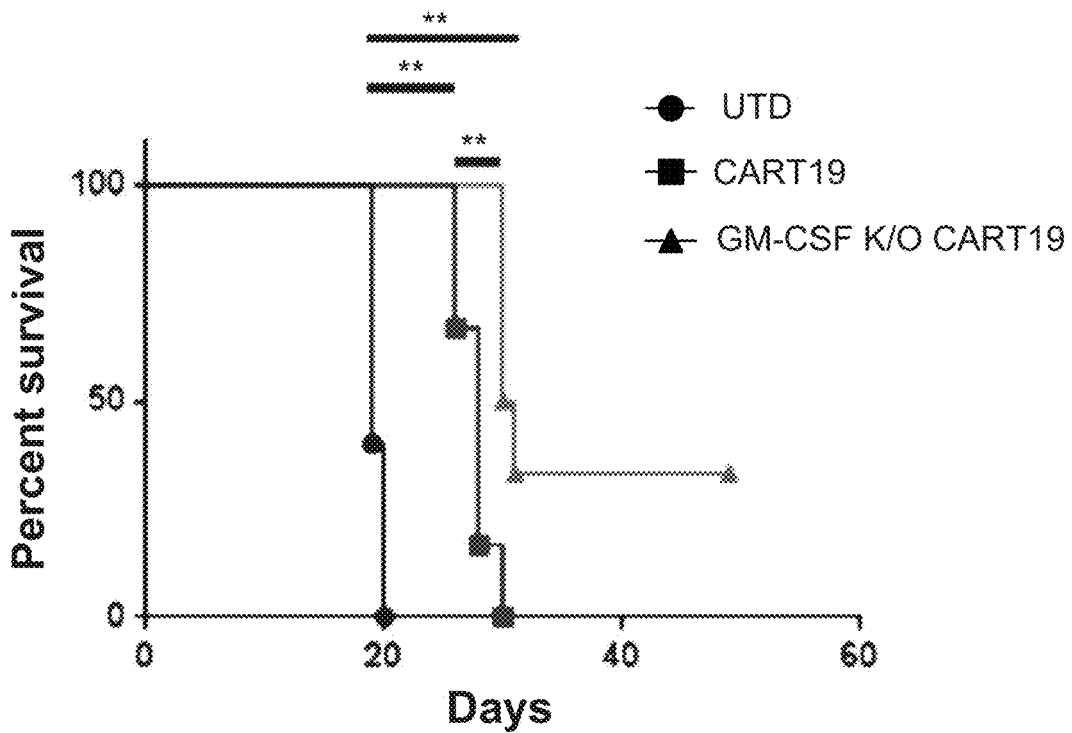
Figure 29D:
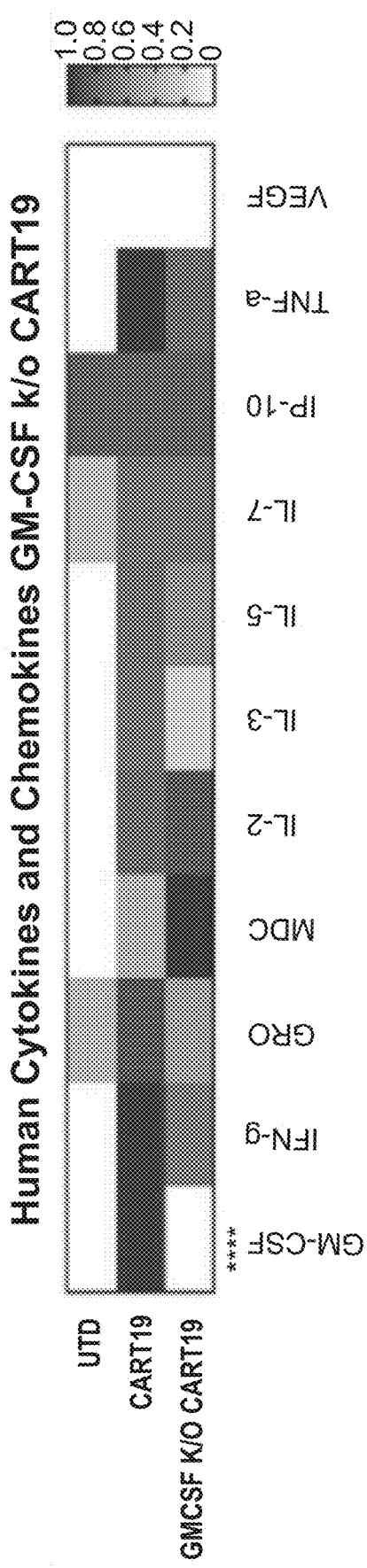
Figure 29E:
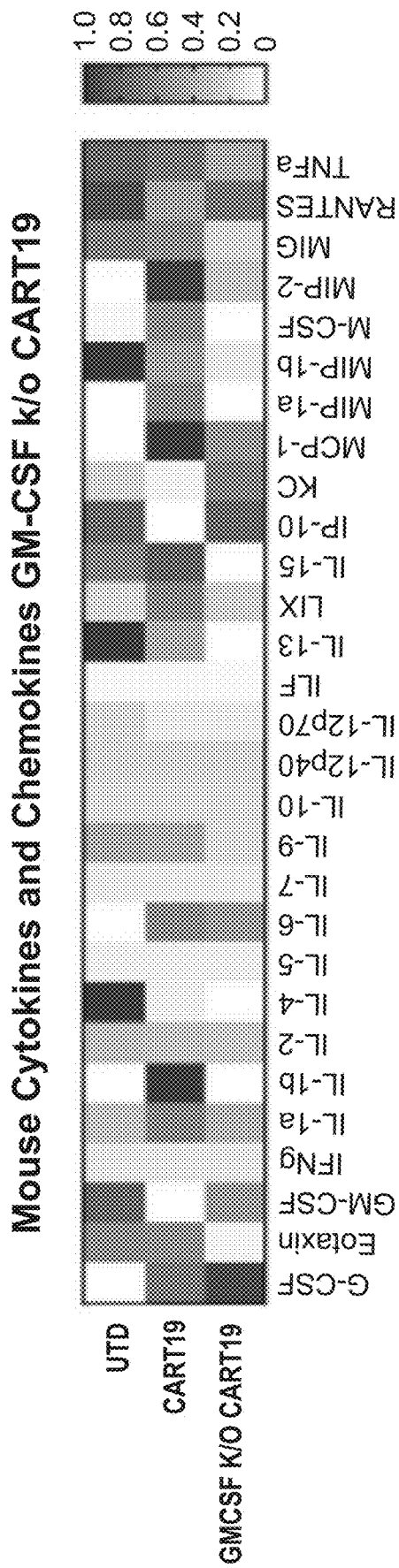

GM-CSF CRISPR Knockout CAR-T Cells Exhibit Reduced Expression of GM-CSF, Similar Levels of Key Cytokines and Chemokines, and Enhanced Anti-Tumor Activity To confidently exclude any role for GM-CSF critical in CAR-T cell function, the GM-CSF gene was disrupted during CAR-T cell manufacturing using a gRNA that has been reported to yield high efficiency knockout and is cloned into a CRISPR lentivirus backbone, as described by Sanjana N E, et al., Nature Methods. 2014; 11(8):783-784. Prepublished on 2014 Jul. 31 as DOI 10.1038/nmeth.3047, which is hereby incorporated by reference in its entirety. Using this gRNA, we achieved around 60% knockout efficiency in CART19 cells (FIG. 37). When CAR-T cells were stimulated with the CD19$^+$ cell line NALM6, GM-CSF$^{k/o}$ CAR-T cells produced statistically significantly less GM-CSF compared to CART19 with a wild-type GM-CSF locus ("wild type CART19 cells"). GM-CSF knockout in CAR-T cells did not impair the production of other key T cell cytokines, including IFN-γ, IL-2, or CAR-T cell antigen specific degranulation (CD107a) (FIG. 29A) but did exhibit reduced expression of GM-CSF (FIG. 29B). To confirm that GM-CSF$^{k/o}$ CAR-T cells continue to exhibit normal functions, their in vivo efficacy in the high tumor burden relapsing xenograft model of ALL was tested (as described in FIG. 28A). In this xenograft model, utilization of GM-CSF$^{k/o}$ CART19 instead of wild type CART19 markedly reduced serum levels of human GM-CSF at 7 days after CART19 treatment (FIG. 29B). Bioluminescence imaging data implied that GM-CSF$^{k/o}$ CART19 cells show enhanced leukemic control compared to CART19 in this model (FIG. 38). Importantly, GM-CSF$^{k/o}$ CART19 cells demonstrated significant improvement in overall survival compared to wild type CART19 cells (FIG. 29C). Human GM-CSF was statistically significantly decreased via t test in the GM-CSF$^{k/o}$ CART19 cells compared to wild type CART19 (FIG. 29D). The mouse GM-CSF visually appears increased although this is not statistically significant via t test (P=0.472367) (FIG. 29E). This lack of mouse GM-CSF reduction is not necessarily surprising as the GM-CSF$^{k/o}$ CART19 cells (which are human) are the only cells within the mouse that possess the knockout, thus mouse GMCSF would not likely be affected directly. By visual inspection, mouse IP-10, a chemokine that attracts numerous cell types including T cells and monocytes, appears paradoxically increased in GM-CSF$^{k/o}$ CART19 compared to CART19, but this is also not statistically significant, P=0.4877 by t test (FIG. 29E). By visual inspection, mouse MIP1α (an inflammatory cytokine important in neutrophil attraction) and mouse M-CSF (a cytokine critical in macrophage differentiation) appear reduced, although they are not statistically significant with P=0.2437 and P=0.3619 (FIG. 29E). Mouse IL-1b, a critical inflammatory cytokine produced by macrophages, and mouse IL-15, a cytokine produced by macrophages that aids in NK cell proliferation, appear reduced in GMCSF$^{k/o}$ CART19 compared to CART19 (FIG. 29E) with P values of P=0.0741 and P=0.0900, respectively (FIG. 29E). Critical human T cell cytokines were not inhibited by GM-CSF$^{k/o}$ (FIG. 29D). It should be emphasized that these xenografts were produced with high burdens of the NALM6 cell line, and our CRS/NI model (FIGS. 30A-30D, 31, 32A-32D and 33A-33D) require the use of primary ALL cells to be generated. Thus, cytokine profiles unsurprisingly differ between the two models as the NALM6 xenografts (FIGS. 29A-29E) do not develop CRS or NI. Together, in the context of a NALM6 high tumor burden model without CRS, results of FIGS. 29A-29E confirm FIGS. 27A-27D and 28A-28F, indicating that GM-CSF depletion does not impair normal cytokines or chemokines that are critical to CAR-T efficacy functions. In addition, the results in FIGS. 29A-29E indicate that GM-CSF$^{k/o}$ CART may represent a therapeutic option for "built in" GM-CSF control as a modification during CAR-T cell manufacturing.

Example 22

Patient Derived Xenograft Model for Neuro-Inflammation (NI) and Cytokine Release Syndrome/GM-CSF Neutralization In Vivo Ameliorates Cytokine Release Syndrome and neuroinflammation after CART19 therapy in a xenograft model Primary Patient-Derived ALL Xenografts To establish primary ALL xenografts, NSG mice first received 30 mg/kg busulfan IP (Selleckchem, Houston, Tex., USA). The following day, mice were injected with 2.5×10$^6$ primary blasts derived from the peripheral blood of patients with relapsed or refractory ALL. Mice were monitored for engraftment for ~10-13 weeks. When CD19$^+$ cells were consistently observed in the blood (approximately 1 cell/uL), they were randomized to receive different treatments of CART19 (2.5×10$^6$ cells IV) and PBMCs derived from the same donor (1×10$^5$ cells IV) with or without antibody therapy (10 mg/kg lenzilumab or isotype control IP for a total of 10 days, starting on the day they received CAR-T cell therapy). Mice were periodically monitored for leukemic burden via tail vein bleeding.

Primary Patient-Derived ALL Xenografts for CRS/NI

Similar to the experiments above, mice were IP injected with 30 mg/kg busulfan (Selleckchem, Houston, Tex., USA). The following day, mice received 1-3×10$^6$ primary blasts derived from the peripheral blood of patients with relapsed ALL. Mice were monitored for engraftment for ~10-13 weeks via tail vein bleeding. When serum CD19$^+$ cells were ≥10 cells/ul, the mice received CART19 (2-5×10$^6$ cells IV) and commenced antibody therapy for a total of 10 days, as indicated. Mice were weighed on a daily basis as a measure of their well-being. Mouse brain MRIs were performed 5-6 days post CART19 injection and tail vein bleeding for cytokine/chemokine and T cell analysis was performed 4-11 days post CART19 injection.

MRI Acquisition

A Bruker Avance II 7 Tesla vertical bore small animal MRI system (Bruker Biospin) was used for image acquisition to evaluate central nervous system (CNS) vascular permeability. Inhalation anesthesia was induced and maintained via 3 to 4% isoflurane. Respiratory rate was monitored during the acquisition sessions using an MRI compatible vital sign monitoring system (Model 1030; SA Instruments, Stony Brook, N.Y.). Mice were given an IP injection of gadolinium using weight-based dosing of 100 mg/kg, and after a standard delay of 15 min, a volume acquisition T1-weighted spin echo sequence was used (repetition time=150 ms, echo time=8 ms, field of view: 32 mm×19.2 mm×19.2 mm, matrix: 160×96×96; number of averages=1) to obtain T1-weighted images. Gadolinium-enhanced MRI changes were indicative of blood-brain-barrier disruption.[24] Volumetric analysis was performed using Analyze Software package developed by the Biomedical Imaging Resource at Mayo Clinic.

Results

Figure 30A:
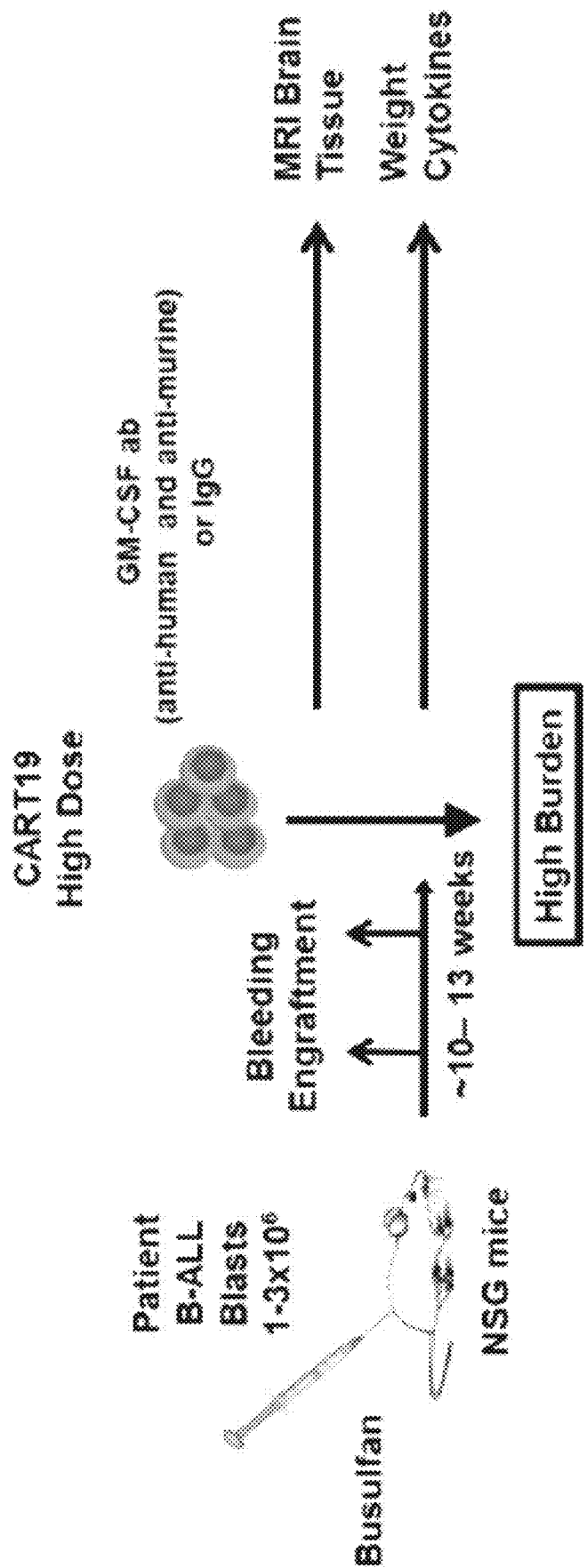
FIGS. 30A-30D illustrate a patient derived xenograft model for neuro-inflammation and cytokine release syndrome.
Figure 30B:
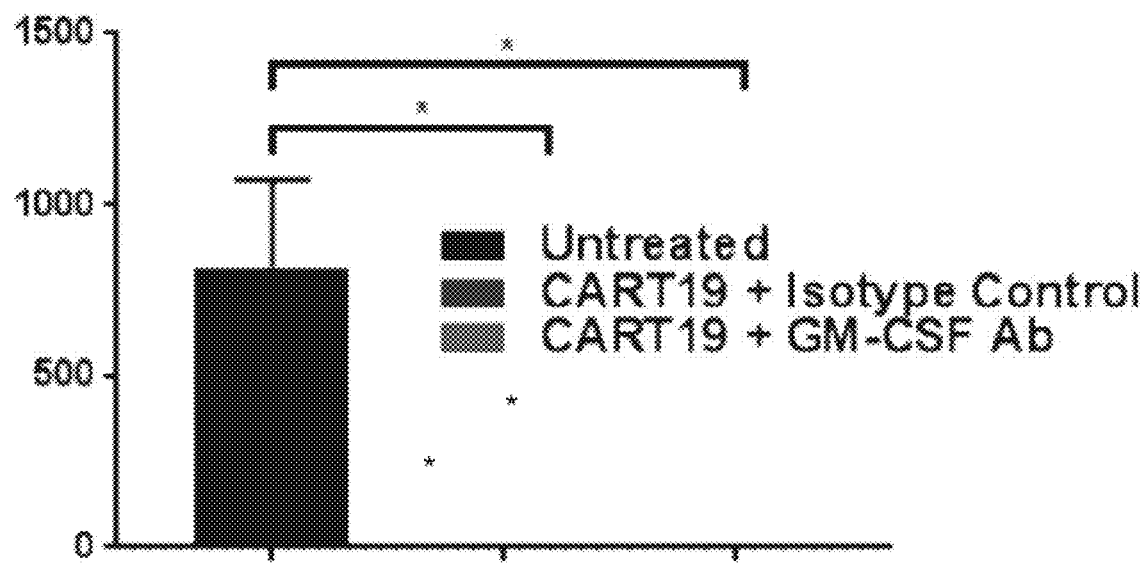
Figure 30C:
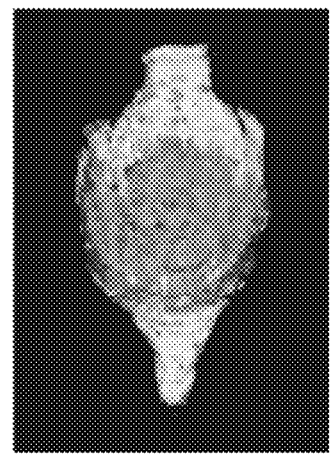
Figure 30D:
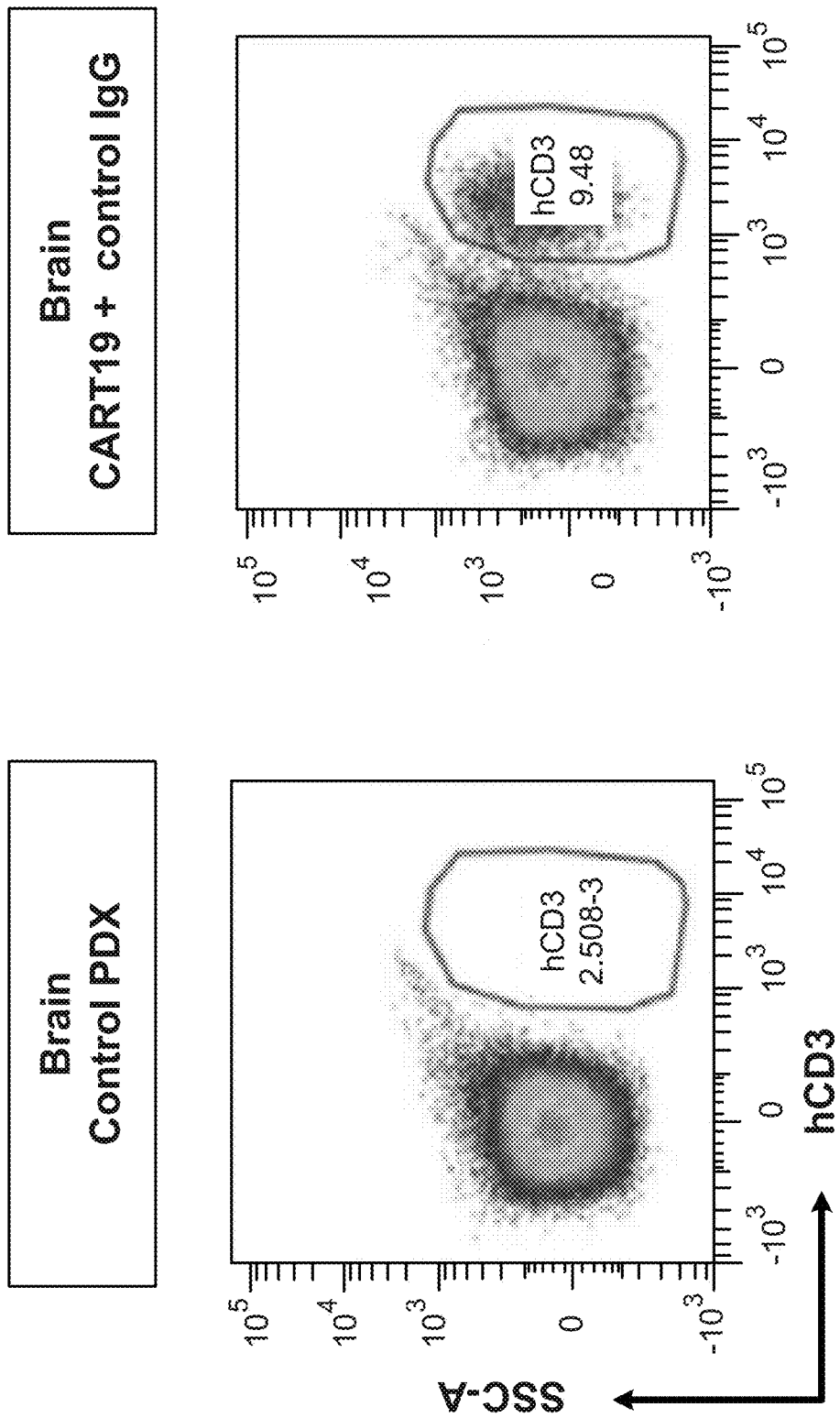
Figure 31:
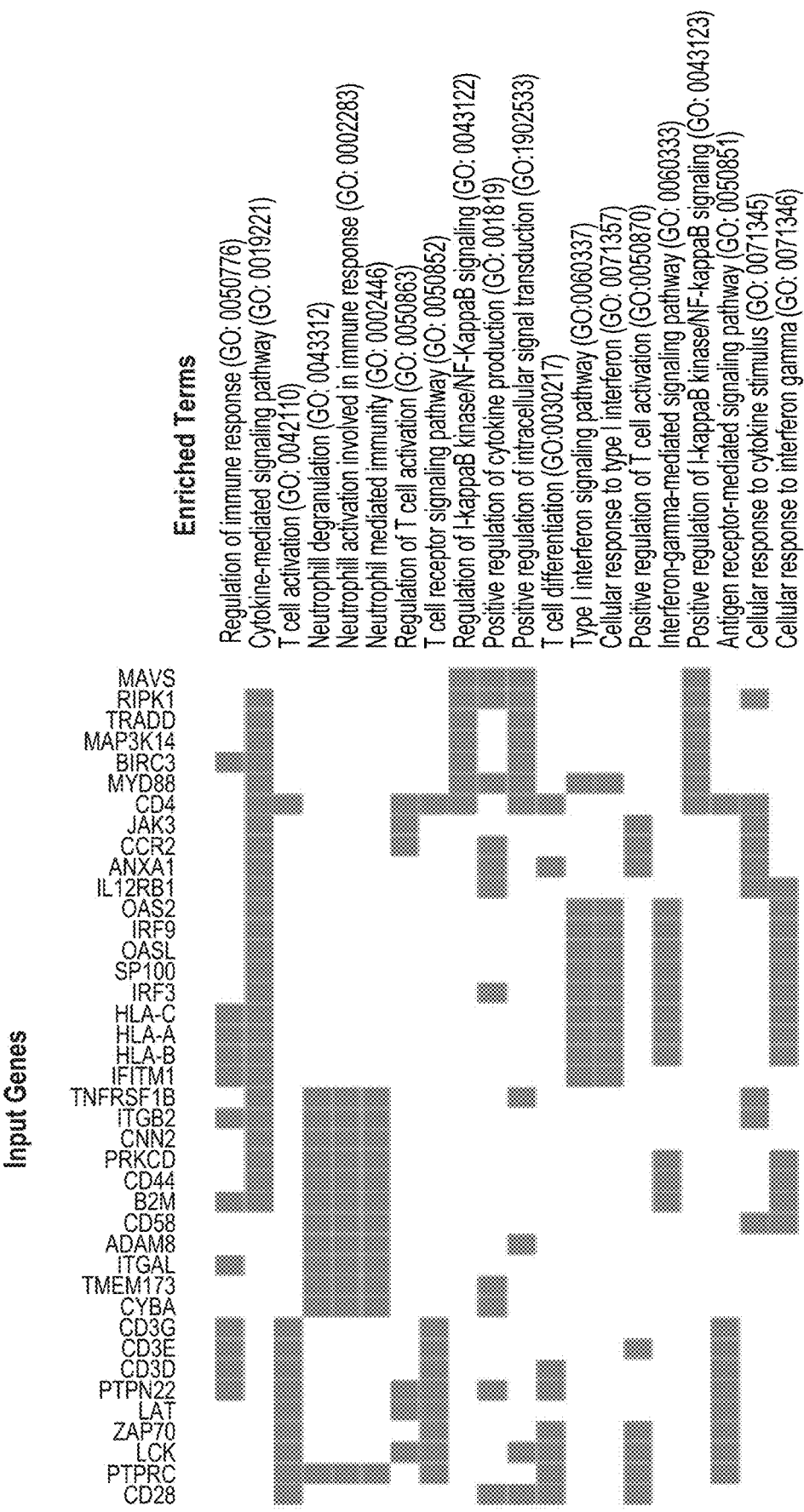
FIG. 31 shows the canonical pathways altered in brains from patient derived xenografts after treatment with CART19 cells. Red boxes indicate upregulation of genes in CART19 plus isotype control treated mice compared to the untreated patient derived xenografts.

In this model, conditioned NSG mice were engrafted with primary ALL blasts and monitored for engraftment for several weeks until they developed high disease burden (FIG. 30A). When the level of CD19+ blasts in the peripheral blood was >10/uL, mice were randomized to receive different treatments as indicated (FIG. 30A). Treatment with CART19 (with control IgG antibodies or with GM-CSF neutralizing antibodies) successfully eradicated the disease (FIG. 30B). Within 4-6 days after treatment with CART19, mice began to develop motor weakness, hunched bodies, and progressive weight loss; symptoms consistent with CRS and NI. This was associated with elevation of key serum cytokines and chemokines 4-11 days post CART19 injection similar to what is seen in human CRS after CAR-T cell therapy (including human GM-CSF, TNF-α, IFN-γ, IL-10, IL-12, IL-13, IL-2, IL-3, IP-10, MDC, MCP-1, MIP-1α, MIP-1β, and mouse IL-6, GM-CSF, IL-4, IL-9, IP-10, MCP-1, and MIG). These mice treated with CART19 also developed NI as indicated by brain MRI analyses revealing abnormal T1 enhancement, suggestive of blood-brain barrier disruption and possibly brain edema (FIG. 30C), together with flow cytometric analysis of harvested brains revealing infiltration of human CART19 cells (FIG. 30D). In addition, RNA-seq analyses of brain sections harvested from mice that developed these signs of NI showed significant upregulation of genes regulating the T cell receptor, cytokine receptors, T cell immune activation, T cell trafficking, and T cell and myeloid cell differentiation (FIG. 31, Table 6).

TABLE 6

Table of canonical pathways altered in brains from patient derived xenografts after treatment with CART19 cells in tabular format.

| Conical Pathway | Adj P-Value | Genes |
| --- | --- | --- |
| regulation of immune response (GO: 0050776) | 9.45E−14 | IFITM1, ITGB2, TRAC, ICAM3, CD3G, PTPN22, CD3E, ITGAL, SAMHD1, SLA2, CD3D, ITGB7, SLAMF6, B2M, NPDC1, CD96, BTN3A1, ITGA4, SH2D1A, HLA-B, HLA-C, BTN3A2, HLA-A, CD8B, SELL, CD8A, CD226, CD247, CLEC2D, HCST, BIRC3 |
| cytokine-mediated signaling pathway (GO: 0019221) | 1.36E−12 | IFITM1, SP100, TRADD, ITGB2, IL2RG, SAMHD1, IL27RA, OASL, CNN2, IL18RAP, RIPK1, CCR5, IL12RB1, B2M, GBP1, IL6R, JAK3, CCR2, IL32, ANXA1, IL4R, TGFB1, IL10RB, IL10RA, STAT2, PRKCD, HLA-B, HLA-C, IL16, HLA-A, TNFRSF1B, CD4, IRF3, OAS2, IL2RB, FAS, TNFRSF25, LCP1, P4HB, IL7R, MAP3K14, CD44, IL18R1, IRF9, MYD88, BIRC3 |
| T cell receptor complex (GO: 0042101) | 1.30E−11 | ZAP70, CD4, CD6, CD8B, CD8A, CD3G, CD247, CD3E, CD3D, CARD11 |
| T cell activation (GO: 0042110) | 2.07E−11 | ITK, RHOH, CD3G, NLRC3, PTPN22, CD3E, SLA2, CD3D, CD2, ZAP70, CD4, PTPRC, CD8B, CD8A, LCK, CD28, LCP1, LAT |
| regulation of T cell activation (GO: 0050863) | 2.46E−10 | PTPN22, LAX1, CCDC88B, CD2, CD4, LCK, SIT1, TBX21, TIGIT, JAK3, LAT, PAG1, CCR2 |
| T cell receptor signaling pathway (GO: 0050852) | 4.35E−08 | ITK, BTN3A1, TRAC, WAS, CD3G, PTPN22, BTN3A2, CD3E, CD3D, ZAP70, CD4, PTPRC, LCK, GRAP2, LCP2, CD247, CARD11, LAT, PAG1 |
| positive regulation of cytokine production (GO: 0001819) | 1.57502E−07 | GBP5, ANXA1, TGFB1, CYBA, PTPN22, PARK7, TMEM173, CCDC88B, MAVS, CD6, IRF3, CD28, RIPK1, SLAMF6, CD46, IL12RB1, TIGIT, IL6R, CARD11, MYD88, CCR2 |
| T cell differentiation (GO: 0030217) | 2.36E−07 | ZAP70, CD4, ANXA1, PTPRC, CD8A, LCK, CD28, RHOH, PTPN22, CD3D |
| cytokine receptor activity (GO: 0004896) | 2.43E−07 | IL4R, IL10RB, IL10RA, IL2RG, CD4, CXCR3, IL2RB, CCR5, IL12RB1, IL7R, IL6R, CD44, CCR2 |
| type I interferon signaling pathway (GO: 0060337) | 3.27E−07 | IFITM1, SP100, IRF3, OAS2, STAT2, HLA-B, HLA-C, HLA-A, SAMHD1, IRF9, MYD88, OASL |
| response to cytokine (GO: 0034097) | 0.0004679 | SIGIRR, IFITM1, SP100, HCLS1, RIPK1, PTPN7, IKBKE, IL6R, JAK3, IL18R1, MYD88, AES |
| regulation of innate immune response (GO: 0045088) | 0.001452 | GBP5, GFI1, STAT2, ADAM8, NLRC3, PTPN22, SAMHD1, BIRC3 |

TABLE 6-continued

Table of canonical pathways altered in brains from patient derived
xenografts after treatment with CART19 cells in tabular format.

| Conical Pathway | Adj P-Value | Genes |
| --- | --- | --- |
| regulation of tumor necrosis factor production (GO: 0032680) | 0.003843 | CD2, MAVS, CYBA, NLRC3, PTPN22, RIPK1, SLAMF1 |
| T cell receptor binding (GO: 0042608) | 0.0102397 | LCK, CD3G, CD3E |
| regulation of tumor necrosis factor-mediated signaling pathway (GO: 0010803) | 0.0124059 | SHARPIN, TRADD, CASP4, RIPK1, TRAF1, BIRC3 |
| Positive regulation of myeloid Leukocyte differentiation (GO: 0002763) | 0.0376647 | CD4, HCLS1, RIPK1, EVI2B |

Figure 32B:
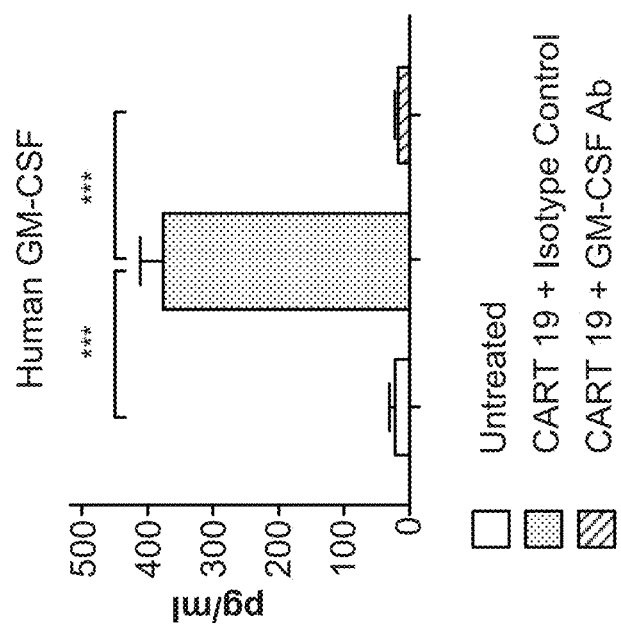
FIGS. 32A-32D demonstrate GM-CSF neutralization in vivo ameliorates CRS after CART19 therapy in a xenograft model.
Figure 32A:
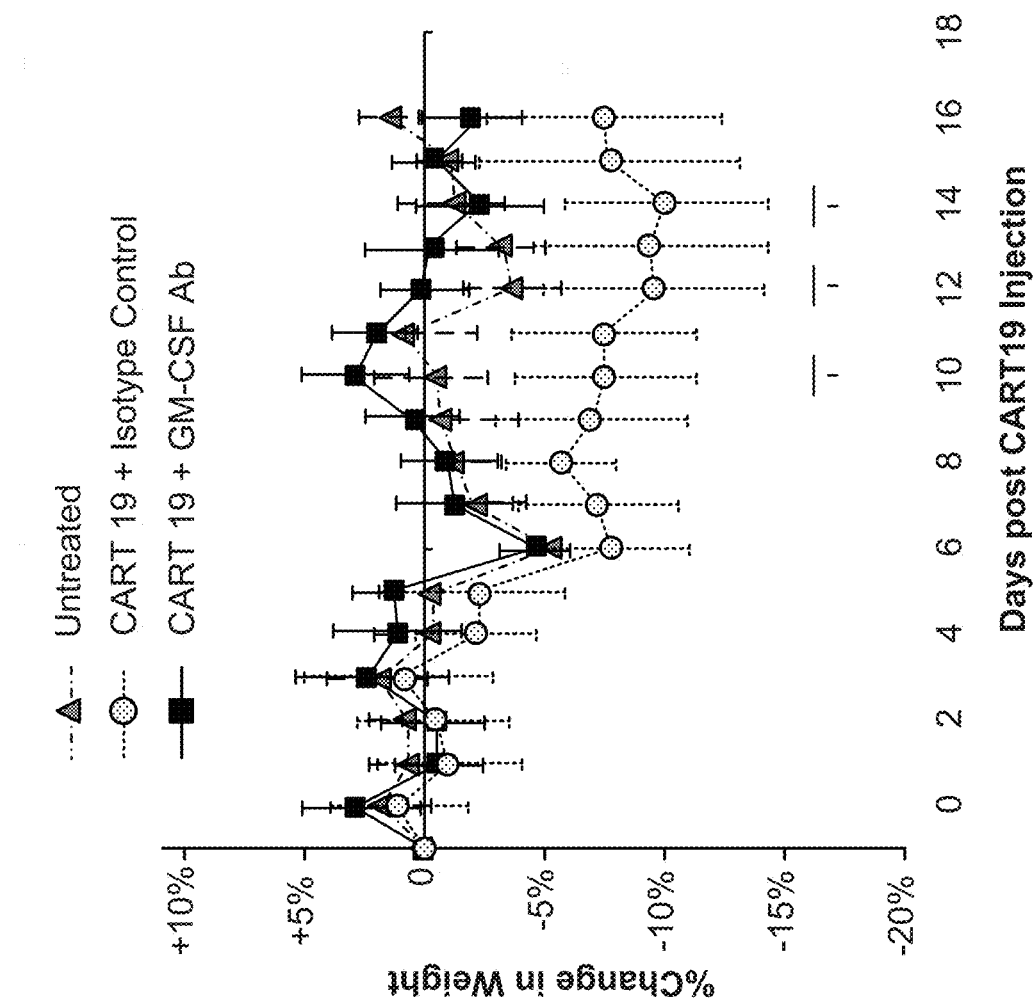
Figure 32C:
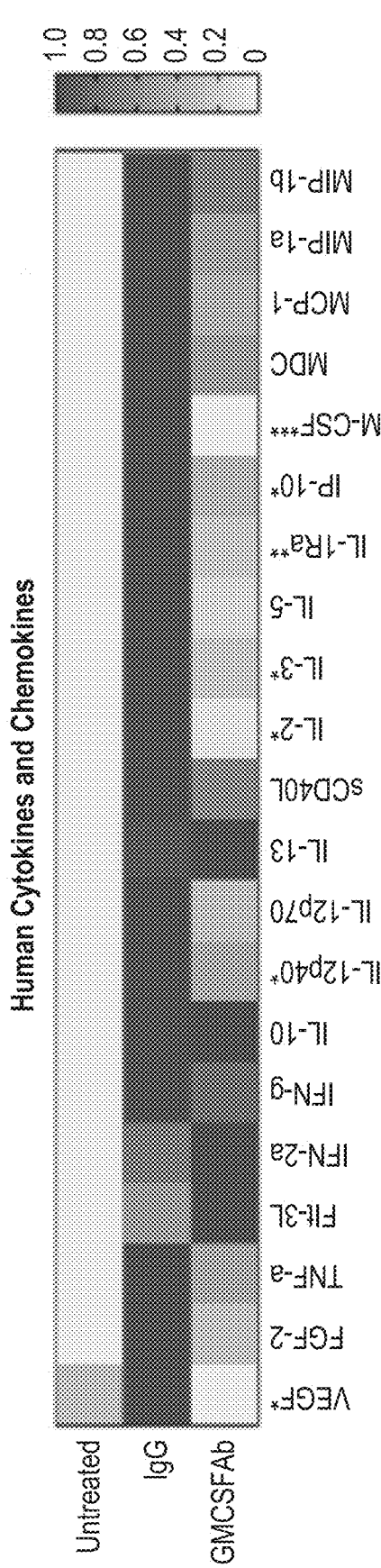
Figure 32D:
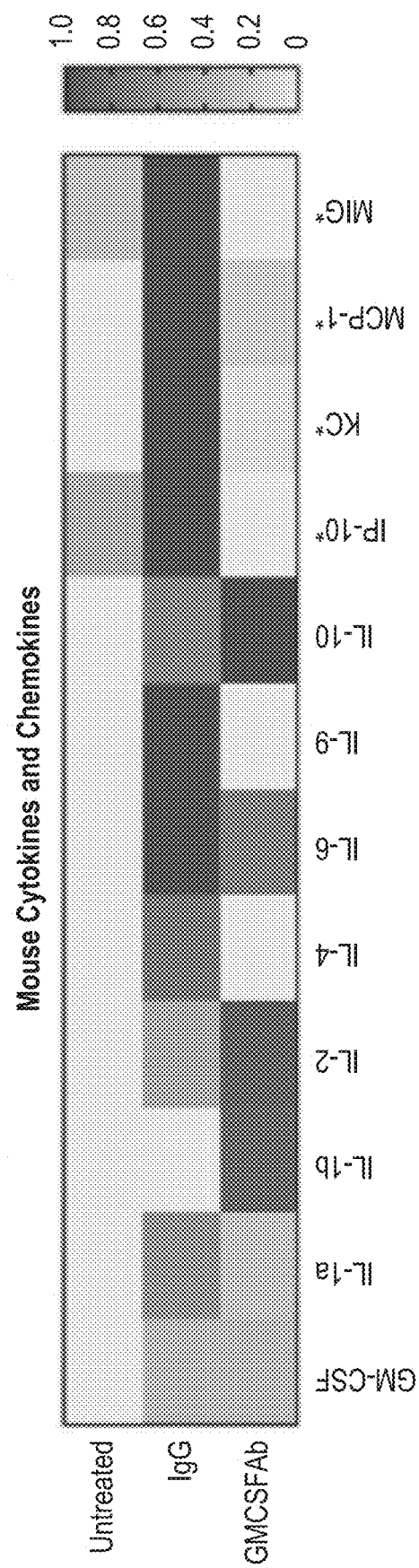

Using the xenograft patient derived model for NI and CRS shown in FIG. 30A, the effect of GM-CSF neutralization on CART19 toxicities was investigated. To rule out the cofounding effect of mouse GM-CSF, mice received CART19 cells in combination with 10 days of GM-CSF antibody therapy (10 mg/kg lenzilumab and 10 mg/kg antimouse GM-CSF neutralizing antibody) or isotype control antibodies. GM-CSF neutralizing antibody therapy statistically significantly reduced CRS induced weight loss after CART19 therapy (FIG. 32A). Cytokine and chemokine analysis 11 days after CART19 cell therapy showed that human GM-CSF was neutralized by the antibody (FIG. 32B). In addition, GM-CSF neutralization resulted in significant reduction of several human (IP-10, IL-3, IL-2, IL-1Ra, IL-12p40, VEGF, GM-CSF) (FIG. 32C) and mouse (MIG, MCP-1, KC, IP-10) (FIG. 32D) cytokines and chemokines. Interferon gamma-induced protein (IP-10, CXCL10) is produced by monocytes among other cell types and serves as a chemoattractant for numerous cell types including monocytes, macrophages, and T cells. IL-3 plays a role in myeloid progenitor differentiation. IL-2 is a key T cell cytokine. Interleukin-1 receptor antagonist (IL-1Ra) inhibits IL-1. (IL-1 is produced by macrophages and is a family of critical inflammatory cytokines.) IL-12p40 is a subunit of IL-12, which is produced by macrophages among other cell types and can encourage Th1 differentiation. Vascular endothelial growth factor (VEGF) encourages blood vessel formation. Monokine induced by gamma interferon (MIG, CXCL9) is a T cell chemoattractant. Monocyte chemoattractant protein 1 (MCP-1, CCL2) attracts monocytes, T cells, and dendritic cells. KC (CXCL1) is produced by macrophages among other cell types and attracts myeloid cells such as neutrophils. There was also a non-statistically significant reduction of several other human and moue cytokines and chemokines after GM-CSF neutralization. This suggests that GMCSF plays a role in the downstream activity of several cytokines and chemokines that are instrumental in the cascade that results in CRS and NI.

Brain MRIs 5 days after CAR19 treatment showed that GM-CSF neutralization reduced T1 enhancement as a measure of brain inflammation, blood-brain barrier disruption, and possibly edema, compared to CART19 plus control antibodies. The MRI images after GM-CSF neutralization (with lenzilumab and anti-mouse GM-CSF antibody) were similar to baseline pre-treatment scans, suggesting that GM-CSF neutralization effectively helped abrogate the NI associated with CART19 therapy (FIGS. 33A and 33B). Using human ALL blasts and human CART19 in this patient-derived xenograft model, GM-CSF neutralization after CART19 reduced neuro-inflammation by 75% compared to CART19 plus isotype controls (FIG. 33B). This is a significant finding and the first time it has been demonstrated in vivo that the NI caused by CART19 can be effectively abrogated. Human CD3 T cells were present in the brain after CART19 therapy as assayed by flow cytometry, and with GM-CSF neutralization, there was a difference in raw average with reduction in brain CD3 T cells, but it did not meet statistical significance (FIGS. 33C, 30D, and 39). Finally, a difference in raw average (although this did not reach statistical significance) with reduction of CD11b+ bright macrophages was observed in the brains of mice receiving GM-CSF neutralization during CAR-T cell therapy compared to isotype control during CAR-T therapy (FIG. 33D), possibly implicating that GM-CSF neutralization helps reduce macrophages within the brain.

The results of Examples 18-19 and 22 demonstrate that neutralization of GM-CSF abrogates toxicities after CAR-T cell therapy and may enhance their therapeutic activity. Specifically, it was shown that GM-CSF neutralization in combination with CART19 therapy prevents the development of CRS and significantly reduces the severity of NI in a xenograft model using human ALL blasts and human CART19. GM-CSF neutralization resulted in a reduction in chemokines associated with myeloid trafficking, such as IP-10, MCP-1, KC, and other inflammatory cytokines and chemokines, and is associated with decreased raw averages (although not statistically significant) of T cell infiltration and myeloid cell activation in the brain. Intriguingly, the experiments herein also suggest that GM-CSF inhibition enhances CART19 proliferation, anti-tumor activity, and overall survival in vivo. Based on these results, GM-CSF neutralization can be viewed as a potential next generation strategy to enable routine CAR-T cellular immunotherapy.

In the studies described herein, GM-CSF neutralization with lenzilumab did not impair any CART19 effector functions in vitro. In two different xenograft models (NALM6 xenografts and patient derived xenografts), CART19 combined with lenzilumab effectively eradicated the tumor despite GM-CSF neutralization and significantly improved leukemic disease control 35 days post-treatment while CART19 plus isotype control could not maintain disease control after 35 days. Lastly, in Examples 21-22, GM-CSF$^{k/o}$ CART19 cells exhibited potent effector functions in vitro and demonstrated significantly improved overall survival compared to CART19 in vivo.

The herein described CRS and NI model is a unique and relevant ALL patient derived xenograft model for the development of therapies for toxicities after human CAR-T cell therapy. In the model described here, the time interval between CAR-T cell infusion to onset of symptoms, brain MRI changes, cytokine and chemokine elevation, and infiltration of effector cells into the CNS are all similar to what is reported in patients that develop toxicities after CART19 therapy. Mice developed symptoms of CRS and NI (weight loss, decline in motor function, and hunched bodies). Changes in brain MRI were detected 4-6 days after infusion of CART19 cells. Brain MRI T1 uptake is suggestive of blood-brain barrier disruption and possibly brain edema and is comparable to changes noted on human brain MRI in cases of severe neurotoxicity, as described by Gust et al. 2017 *Cancer Discovery.* 2017; 7(12):1404-1419. Prepublished on 2017 Oct. 14 as DOI 10.1158/2159-8290.CD-17-0698, which is incorporated herein by reference in its entirety.

Interestingly, Gust et al. 2017 further describes that blood brain barrier permeability prevented protection of the CSF from systemic cytokines, which induced vascular pericyte stress and secretion of endothelium-activating cytokines, and patients showed evidence of endothelial activation. In the CRS/NI model described herein, GM-CSF was found to be neutralized in the serum of mice receiving CART19 therapy with GM-CSF neutralizing antibodies compared to CART19 and isotype control antibodies. Thus, T cells within the mouse brains themselves could provide GM-CSF production, and serum GM-CSF among other cytokines and chemokines were possibly able to reach the CSF. In addition, endothelium cells are able to produce GM-CSF, which may result in a cycle of exacerbation. NI was associated with infiltration of T cells and activation of myeloid cells in the CNS, similar to CSF changes in patients with CAR-T induced neurotoxicity, as well as in non-human primate models. The herein described model is similar to previously reported patient derived xenograft models where CRS developed after CAR-T cell therapy. A recent report suggested that blockade of IL-1 prevents NI through the depletion of myeloid cells. However, the development of NI in that model was delayed and related to meningeal thickening, unlike what was observed in the model described herein and in patients receiving CART19 therapy. Therefore, the model described herein is provided as a reliable way to investigate novel interventions for the prevention and treatment of CRS and neurotoxicity after CART19 cell therapy. The results described herein show that GM-CSF neutralization results in a reduction in key myeloid and several inflammatory cytokines and chemokines, suggesting that GM-CSF is a critical cytokine in downstream activation of several cytokines and chemokines; blockade contributes to a decrease in raw averages in myeloid and T cell infiltration in the brain/CNS (although statistical significance was not reached); and blockade helps reduce neuro-inflammation of apparent neurotoxicities.

Interestingly, an exponential increase in CART19 cell proliferation was observed, enhanced anti-tumor activity, and improved overall survival with GM-CSF blockade. For example, CART19 antigen specific proliferation in the presence of monocytes increased in vitro after GM-CSF neutralization. Moreover, in ALL patient derived xenografts, CART19 cells resulted in a more durable disease control when combined with lenzilumab. In addition, it was found that GM-CSF$^{k/o}$ CAR-T cells were more effective in controlling leukemia in NALM6 xenografts and demonstrated improved overall survival. While the mechanisms for enhanced CART effector functions after GM-CSF depletion are currently unclear, the results provided herein are consistent with previous reports indicating that monocytes impair T cell expansion ex vivo and that M2 polarized macrophages inhibit CART19 antigen specific proliferation. This is an important finding because across CAR-T clinical trials, improved CAR-T cell proliferation was consistently associated with improved efficacy and response (i.e., overall and complete response rates).

It is known that activated T cells produce GM-CSF. T cells do not possess all the subunits for the GM-CSF receptor, so in ordinary circumstances, GM-CSF does not normally feedback on T-cells directly, although it can under some circumstances at very high levels. Instead, this GM-CSF affects the behaviors of numerous other cell types including macrophages and dendritic cells. The subsequent activation of these cells results in actions that work to stimulate T cells such as cytokine production and antigen presentation. T cell stimulation can further drive production of GM-CSF and other cytokines to in turn act on the other cell types like macrophages and dendritic cells, which drives the cycle. In CAR-T cell therapy, it is likely that the large number of activated T cells produced over a very short timeline pushes this cycle to an extreme situation. The results described herein suggest that blocking GM-CSF helps prevent this immune overstimulation without impairing T cell functions, actually enhancing them. The exact mechanisms for enhanced CAR-T cell effector functions after GM-CSF blockade are unclear.

Finally, the results provided herein results additionally suggest that the development of GM-CSF$^{k/o}$ CART19 cells may represent a novel way to partially control GM-CSF production that can be incorporated into current CAR-T cell manufacturing. These results indicate that these cells function normally and could represent an independent therapeutic approach to enhance the therapeutic window after CAR-T cell therapy. An anti-GM-CSF antibody, such as lenzilumab, is a clinical stage therapeutic solution to neutralize GM-CSF, abrogate both CRS and neuro-inflammation of apparent neurotoxicities, and potentially improve CAR-T cell function.

The studies described herein represent a significant advance in understanding and preventing toxicities after CAR-T cell therapy. These results strongly suggest that modulating myeloid cell behavior through GM-CSF blockade helps control CAR-T cell mediated toxicities and reduce their immunosuppressive features to improve leukemic control. These studies illuminate a novel approach to abrogate neuro-inflammation of apparent neurotoxicities and CRS through GM-CSF neutralization that also potentially enhances CAR-T cell functions.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

All publications, accession numbers, patents, and patent applications cited in this specification are herein incorporated by reference as if each was specifically and individually indicated to be incorporated by reference.

Exemplary $V_H$ Region Sequences of Anti-GM-CSF Antibodies of the Invention:

(VH#1, FIG. 1)
SEQ ID NO: 1
QVQLVQSGAEVKKPGASVKVSCKASGYTFTGYYMHWVRQAPGQGLEWMGW
INPNSGGTNYAQKFQGRVTMTRDTSISTAYMELSRLRSDDTAVYYCVRRD
RFPYYFDYWGQGTLVTVSS (VH#2, FIG. 1)
SEQ ID NO: 2
QVQLVQSGAEVKKPGASVKVSCKASGYSFTNYYIHWVRQAPGQRLEWMGW
INAGNGNTKYSQKFQGRVAITRDTSASTAYMELSSLRSEDTAVYYCARRD
RFPYYFDYWGQGTLVTVSS (VH#3, FIG. 1)
SEQ ID NO: 3
QVQLVQSGAEVKKPGASVKVSCKASGYSFTNYYIHWVRQAPGQRLEWMGW
INAGNGNTKYSQKFQGRVAITRDTSASTAYMELSSLRSEDTAVYYCARRQ
RFPYYFDYWGQGTLVTVSS (VH#4, FIG. 1)
SEQ ID NO: 4
QVQLVQSGAEVKKPGASVKVSCKASGYSFTNYYIHWVRQAPGQRLEWMGW
INAGNGNTKYSQKFQGRVAITRDTSASTAYMELSSLRSEDTAVYYCVRRQ
RFPYYFDYWGQGTLVTVSS (VH#5, FIG. 1)
SEQ ID NO: 5
QVQLVQSGAEVKKPGASVKVSCKASGYSFTNYYIHWVRQAPGQRLEWMGW
INAGNGNTKYSQKFQGRVTITRDTSASTAYMELSSLRSEDTAVYYCVRRQ
RFPYYFDYWGQGTLVTVSS

Exemplary $V_L$ Region Sequences of Anti-GM-CSF Antibodies of the Invention:

(VK#1, FIG. 1)
SEQ ID NO: 6
EIVLTQSPATLSVSPGERATLSCRASQSVGTNVAWYQQKPGQAPRVLIYS
TSSRATGITDRFSGSGSGTDFTLTISRLEPEDFAVYYCQQFNRSPLTFGG
GTKVEIK (VK#2, FIG. 1)
SEQ ID NO: 7
EIVLTQSPATLSVSPGERATLSCRASQSVGTNVAWYQQKPGQAPRVLIYS
TSSRATGITDRFSGSGSGTDFTLTISRLEPEDFAVYYCQQFNKSPLTFGG
GTKVEIK (VK#3, FIG. 1)
SEQ ID NO: 8
EIVLTQSPATLSVSPGERATLSCRASQSIGSNLAWYQQKPGQAPRVLIYS
TSSRATGITDRFSGSGSGTDFTLTISRLEPEDFAVYYCQQFNRSPLTFGG
GTKVEIK (VK#4, FIG. 1)
SEQ ID NO: 9
EIVLTQSPATLSVSPGERATLSCRASQSIGSNLAWYQQKPGQAPRVLIYS
TSSRATGITDRFSGSGSGTDFTLTISRLEPEDFAVYYCQQFNKSPLTFGG
GTKVEIK

Exemplary kappa constant region
SEQ ID NO: 10
RTVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVTK
SFNRGEC Exemplary heavy chain constant region, f-allotype:
SEQ ID NO: 11
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKRVEP
KSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSREEMTKNQVSLTC
LVKGFYPSDIAVEWESNGQPENNYKTTPPVLDSDGSFFLYSKLTVDKSRW
QQGNVFSCSVMHEALHNHYTQKSLSLSPGK

---

What is claimed is:

1. A method for reducing relapse rate or preventing occurrence of tumor relapse in a subject treated with immunotherapy, the method comprising administering to the subject a recombinant hGM-CSF antagonist, wherein the recombinant hGM-CSF antagonist is anti-hGM-CSF antibody lenzilumab.

2. The method of claim 1, wherein said immunotherapy comprises adoptive cell transfer, administration of monoclonal antibodies, administration of cytokines, administration of a cancer vaccine, T cell engaging therapies, or any combination thereof.

3. The method of claim 2, wherein the adoptive cell transfer comprises administering chimeric antigen receptor-expressing T-cells (CAR T-cells), T-cell receptor (TCR) modified T-cells, tumor-infiltrating lymphocytes (TIL), chimeric antigen receptor (CAR)-modified natural killer cells, or dendritic cells, or any combination thereof.

4. The method of claim 1, wherein the anti-hGM-CSF antibody lenzilumab binds a human GM-CSF.

5. The method of claim 1, wherein the anti-hGM-CSF antibody lenzilumab binds a primate GM-CS F.

6. The method of claim 1, wherein the anti-hGM-CSF antibody lenzilumab binds a mammalian GM-CSF.

7. The method of claim 1, wherein the anti-hGM-CSF antibody lenzilumab is a monoclonal antibody.

8. The method of claim 1, wherein the anti-hGM-CSF antibody lenzilumab is a human GM-CSF neutralizing antibody.

9. The method of claim 1, wherein the anti-hGM-CSF antibody lenzilumab is a recombinant antibody.

10. The method of claim 1, wherein the anti-hGM-CSF antibody lenzilumab is an engineered human antibody.

11. The method of claim 1, wherein the anti-hGM-CSF antibody lenzilumab binds to the same epitope as chimeric 19/2.

12. The method of claim 1, wherein the anti-hGM-CSF antibody lenzilumab comprises a VH region that comprises a CDR3 binding specificity determinant RQRFPY (SEQ ID NO: 12), a J segment, and a V-segment, wherein the J-segment comprises at least 95% identity to human JH4 (YFDYWGQGTLVTVSS) (SEQ ID NO: 14) and the V-segment comprises at least 90% identity to a human germ line VH1 1-03 sequence.

13. The method of claim 12, wherein the J segment comprises YFDYWGQGTLVTVSS (SEQ ID NO: 14).

14. The method of claim 12, wherein the CDR3 comprises RQRFPYYFDY (SEQ ID NO: 15).

15. The method of claim 12, wherein the anti-hGM-CSF antibody lenzilumab comprises a VH CDR1 and a VH CDR2 as shown in a VH region having a sequence of VH #5 set forth in FIG. 1.

16. The method of claim 12, wherein the V-segment sequence has a VH V segment sequence of VH #5 shown in FIG. 1.

17. The method of claim 12, wherein the VH has the sequence of VH #5 set forth in FIG. 1.

18. The method of claim 1, wherein the anti-hGM-CSF antibody lenzilumab comprises a VL-region that comprises a CDR3 comprising the amino acid sequence FNK.

19. The method of claim 18, wherein the anti-hGM-CSF antibody lenzilumab comprises a VL region that comprises a CDR3 comprising QQFNKSPLT (SEQ ID NO: 18).

20. The method of claim 11, where the VL region comprises both a CDR1 and CDR2 of a VL region having the sequence of VK #2 shown in FIG. 1.

21. The method of claim 18, wherein the VL region comprises a V segment that has at least 95% identity to the VKIII A27 V-segment sequence as shown in FIG. 1.

22. The method of claim 18, wherein the VL region has the sequence of VK #2 set forth in FIG. 1.

23. The method of claim 1, wherein the anti-hGM-CSF antibody lenzilumab has a VH region CDR3 binding specificity determinant RQRFPY (SEQ ID NO: 12) and a VL region that has a CDR3 comprising QQFNKSPLT (SEQ ID NO: 18).

24. The method of claim 1, wherein the anti-hGM-CSF antibody lenzilumab has a VH region having sequence VH #5 set forth in FIG. 1 and a VL region having sequence VK #2 set forth in FIG. 1.

25. The method of claim 24, wherein the VH region or the VL region, or both the VH and VL region amino acid sequences comprise a methionine at the N-terminus.

26. The method of claim 3, wherein the CAR-T cells are CD19 CAR-T cells.

27. The method of claim 1, wherein the reducing relapse rate or preventing occurrence of tumor relapse in the subject occurs in an absence of an incidence of immunotherapy-related toxicity.

28. The method of claim 1, wherein the reducing relapse rate or preventing occurrence of tumor relapse in the subject occurs in a presence of an incidence of immunotherapy-related toxicity.

29. The method of claim 28, wherein the immunotherapy-related toxicity is CAR-T related toxicity.

30. The method of claim 29, wherein the CAR-T related toxicity is cytokine release syndrome, neurotoxicity or neuro-inflammation.

31. The method of claim 1, wherein the tumor relapse occurrence is reduced by from 50% to 100% in the first one-quarter of a year after administering the recombinant GM-CSF antagonist compared to tumor relapse occurrence in a subject treated with immunotherapy and not administered a recombinant GM-CSF antagonist.

32. The method of claim 1, wherein the tumor relapse occurrence is reduced by from 50% to 95% in the first half-year after administering the recombinant GM-CSF antagonist.

33. The method of claim 1, wherein the tumor relapse occurrence is reduced by from 50% to 90% in the first year after administering the recombinant GM-CSF antagonist.

34. The method of claim 1, wherein the tumor relapse occurrence is prevented long-term.

35. The method of claim 1, wherein the tumor relapse occurrence is prevented by 12-36 months.

36. The method of claim 1, wherein the tumor relapse occurrence is prevented completely (100%).

37. The method of claim 1, wherein the subject has acute lymphoblastic leukemia.

* * * * *

UNITED STATES PATENT AND TRADEMARK OFFICE
CERTIFICATE OF CORRECTION

| | |
|---|---|
| PATENT NO. | : 10,927,168 B2 |
| APPLICATION NO. | : 16/248762 |
| DATED | : February 23, 2021 |
| INVENTOR(S) | : Cameron Durrant et al. |

It is certified that error appears in the above-identified patent and that said Letters Patent is hereby corrected as shown below:

On the Title Page

Item (73), Assignee: "HUMANICEN, INC." should be -- HUMANIGEN, INC. --

Signed and Sealed this
Seventh Day of March, 2023

Katherine Kelly Vidal
*Director of the United States Patent and Trademark Office*

SEQUENCE LISTING

<160> NUMBER OF SEQ ID NOS: 39

<210> SEQ ID NO 1
<211> LENGTH: 119
<212> TYPE: PRT
<213> ORGANISM: Artificial Sequence
<220> FEATURE:
<223> OTHER INFORMATION: synthetic anti-granulocyte-macrophage colony-
      stimulating factor (GM-CSF) antibody heavy chain variable region
      (VH) VH#1

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Val Arg Arg Asp Arg Phe Pro Tyr Tyr Phe Asp Tyr Trp Gly Gln Gly
            100                 105                 110

Thr Leu Val Thr Val Ser Ser
        115

<210> SEQ ID NO 2
<211> LENGTH: 119
<212> TYPE: PRT
<213> ORGANISM: Artificial Sequence
<220> FEATURE:
<223> OTHER INFORMATION: synthetic anti-granulocyte-macrophage colony-
      stimulating factor (GM-CSF) antibody heavy chain variable region
      (VH) VH#2

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asn Tyr
            20                  25                  30

Tyr Ile His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Ala Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Asp Arg Phe Pro Tyr Tyr Phe Asp Tyr Trp Gly Gln Gly
            100                 105                 110

Thr Leu Val Thr Val Ser Ser
        115

<210> SEQ ID NO 3
<211> LENGTH: 119
<212> TYPE: PRT
<213> ORGANISM: Artificial Sequence
<220> FEATURE:
<223> OTHER INFORMATION: synthetic anti-granulocyte-macrophage colony-
      stimulating factor (GM-CSF) antibody heavy chain variable region
      (VH) VH#3

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asn Tyr
            20                  25                  30

Tyr Ile His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Ala Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gln Arg Phe Pro Tyr Tyr Phe Asp Tyr Trp Gly Gln Gly
            100                 105                 110

Thr Leu Val Thr Val Ser Ser
        115

```
<210> SEQ ID NO 4
<211> LENGTH: 119
<212> TYPE: PRT
<213> ORGANISM: Artificial Sequence
<220> FEATURE:
<223> OTHER INFORMATION: synthetic anti-granulocyte-macrophage colony-
      stimulating factor (GM-CSF) antibody heavy chain variable region
      (VH) VH#4

<400> SEQUENCE: 4
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asn Tyr
            20                  25                  30

Tyr Ile His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Ala Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Val Arg Arg Gln Arg Phe Pro Tyr Tyr Phe Asp Tyr Trp Gly Gln Gly
            100                 105                 110

Thr Leu Val Thr Val Ser Ser
        115

```
<210> SEQ ID NO 5
<211> LENGTH: 119
<212> TYPE: PRT
<213> ORGANISM: Artificial Sequence
<220> FEATURE:
<223> OTHER INFORMATION: synthetic anti-granulocyte-macrophage colony-
      stimulating factor (GM-CSF) antibody heavy chain variable region
      (VH) VH#5

<400> SEQUENCE: 5
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asn Tyr
            20                  25                  30

Tyr Ile His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Val Arg Arg Gln Arg Phe Pro Tyr Tyr Phe Asp Tyr Trp Gly Gln Gly
            100                 105                 110

Thr Leu Val Thr Val Ser Ser
        115

```
<210> SEQ ID NO 6
<211> LENGTH: 107
<212> TYPE: PRT
<213> ORGANISM: Artificial Sequence
<220> FEATURE:
<223> OTHER INFORMATION: synthetic anti-granulocyte-macrophage colony-
      stimulating factor (GM-CSF) antibody kappa light chain variable
``` region (VL) VK#1

<400> SEQUENCE: 6

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Gly Thr Asn
            20                  25                  30

Val Ala Trp Tyr Gln Gln Lys Pro Gly Gln Ala Pro Arg Val Leu Ile
        35                  40                  45

Tyr Ser Thr Ser Ser Arg Ala Thr Gly Ile Thr Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Phe Asn Arg Ser Pro Leu
                85                  90                  95

Thr Phe Gly Gly Gly Thr Lys Val Glu Ile Lys
            100                 105

<210> SEQ ID NO 7
<211> LENGTH: 107
<212> TYPE: PRT
<213> ORGANISM: Artificial Sequence
<220> FEATURE:
<223> OTHER INFORMATION: synthetic anti-granulocyte-macrophage colony-
      stimulating factor (GM-CSF) antibody kappa light chain variable
      region (VL) VK#2

<400> SEQUENCE: 7

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Gly Thr Asn
            20                  25                  30

Val Ala Trp Tyr Gln Gln Lys Pro Gly Gln Ala Pro Arg Val Leu Ile
        35                  40                  45

Tyr Ser Thr Ser Ser Arg Ala Thr Gly Ile Thr Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Phe Asn Lys Ser Pro Leu
                85                  90                  95

Thr Phe Gly Gly Gly Thr Lys Val Glu Ile Lys
            100                 105

<210> SEQ ID NO 8
<211> LENGTH: 107
<212> TYPE: PRT
<213> ORGANISM: Artificial Sequence
<220> FEATURE:
<223> OTHER INFORMATION: synthetic anti-granulocyte-macrophage colony-
      stimulating factor (GM-CSF) antibody kappa light chain variable
      region (VL) VK#3

<400> SEQUENCE: 8

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Ile Gly Ser Asn
            20                  25                  30

Leu Ala Trp Tyr Gln Gln Lys Pro Gly Gln Ala Pro Arg Val Leu Ile
        35                  40                  45

```
Tyr Ser Thr Ser Ser Arg Ala Thr Gly Ile Thr Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Phe Asn Arg Ser Pro Leu
                85                  90                  95

Thr Phe Gly Gly Gly Thr Lys Val Glu Ile Lys
                100                 105
```

<210> SEQ ID NO 9
<211> LENGTH: 107
<212> TYPE: PRT
<213> ORGANISM: Artificial Sequence
<220> FEATURE:
<223> OTHER INFORMATION: synthetic anti-granulocyte-macrophage colony-
      stimulating factor (GM-CSF) antibody kappa light chain variable
      region (VL) VK#4

<400> SEQUENCE: 9

```
Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Ile Gly Ser Asn
                20                  25                  30

Leu Ala Trp Tyr Gln Gln Lys Pro Gly Gln Ala Pro Arg Val Leu Ile
            35                  40                  45

Tyr Ser Thr Ser Ser Arg Ala Thr Gly Ile Thr Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Phe Asn Lys Ser Pro Leu
                85                  90                  95

Thr Phe Gly Gly Gly Thr Lys Val Glu Ile Lys
                100                 105
```

<210> SEQ ID NO 10
<211> LENGTH: 107
<212> TYPE: PRT
<213> ORGANISM: Artificial Sequence
<220> FEATURE:
<223> OTHER INFORMATION: synthetic kappa constant region

<400> SEQUENCE: 10

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105
```

<210> SEQ ID NO 11
<211> LENGTH: 330

```
<212> TYPE: PRT
<213> ORGANISM: Artificial Sequence
<220> FEATURE:
<223> OTHER INFORMATION: synthetic f-allotype heavy chain constant
      region

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 12
<211> LENGTH: 6
<212> TYPE: PRT
<213> ORGANISM: Artificial Sequence
<220> FEATURE:
<223> OTHER INFORMATION: synthetic heavy chain variable region (VH)
      complementarity-determining region 3 (CDR3) binding specificity
``` determinant (BSD)

<400> SEQUENCE: 12

Arg Gln Arg Phe Pro Tyr
1               5

<210> SEQ ID NO 13
<211> LENGTH: 6
<212> TYPE: PRT
<213> ORGANISM: Artificial Sequence
<220> FEATURE:
<223> OTHER INFORMATION: synthetic heavy chain variable region (VH)
      complementarity-determining region 3 (CDR3) binding specificity
      determinant (BSD)

<400> SEQUENCE: 13

Arg Asp Arg Phe Pro Tyr
1               5

<210> SEQ ID NO 14
<211> LENGTH: 15
<212> TYPE: PRT
<213> ORGANISM: Artificial Sequence
<220> FEATURE:
<223> OTHER INFORMATION: synthetic heavy chain variable region (VH)
      human J-segment JH4

<400> SEQUENCE: 14

Tyr Phe Asp Tyr Trp Gly Gln Gly Thr Leu Val Thr Val Ser Ser
1               5                   10                  15

<210> SEQ ID NO 15
<211> LENGTH: 10
<212> TYPE: PRT
<213> ORGANISM: Artificial Sequence
<220> FEATURE:
<223> OTHER INFORMATION: synthetic heavy chain variable region (VH)
      complementarity-determining region 3 (CDR3)

<400> SEQUENCE: 15

Arg Gln Arg Phe Pro Tyr Tyr Phe Asp Tyr
1               5                   10

<210> SEQ ID NO 16
<211> LENGTH: 10
<212> TYPE: PRT
<213> ORGANISM: Artificial Sequence
<220> FEATURE:
<223> OTHER INFORMATION: synthetic heavy chain variable region (VH)
      complementarity-determining region 3 (CDR3)

<400> SEQUENCE: 16

Arg Asp Arg Phe Pro Tyr Tyr Phe Asp Tyr
1               5                   10

<210> SEQ ID NO 17
<211> LENGTH: 9
<212> TYPE: PRT
<213> ORGANISM: Artificial Sequence
<220> FEATURE:
<223> OTHER INFORMATION: synthetic light chain variable region (VL)
      complementarity-determining region 3 (CDR3)
<220> FEATURE:
<221> NAME/KEY: VARIANT
<222> LOCATION: (5)..(5)
<223> OTHER INFORMATION: Xaa = Lys or Arg

<400> SEQUENCE: 17

Gln Gln Phe Asn Xaa Ser Pro Leu Thr
1               5

<210> SEQ ID NO 18
<211> LENGTH: 9
<212> TYPE: PRT
<213> ORGANISM: Artificial Sequence
<220> FEATURE:
<223> OTHER INFORMATION: synthetic light chain variable region (VL)
      complementarity-determining region 3 (CDR3)

<400> SEQUENCE: 18

Gln Gln Phe Asn Lys Ser Pro Leu Thr
1               5

<210> SEQ ID NO 19
<211> LENGTH: 98
<212> TYPE: PRT
<213> ORGANISM: Homo sapiens
<220> FEATURE:
<223> OTHER INFORMATION: human germline heavy chain variable region VH1
      1-02

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 20
<211> LENGTH: 98
<212> TYPE: PRT
<213> ORGANISM: Homo sapiens
<220> FEATURE:
<223> OTHER INFORMATION: human germline heavy chain variable region VH1
      1-03

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Met His Trp Val Arg Gln Ala Pro Gly Gln Arg Leu Glu Trp Met
            35                  40                  45

Gly Trp Ile Asn Ala Gly Asn Gly Asn Thr Lys Tyr Ser Gln Lys Pro
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 21
<211> LENGTH: 96
<212> TYPE: PRT
<213> ORGANISM: Homo sapiens
<220> FEATURE:
<223> OTHER INFORMATION: human germline kappa light chain variable
      region VKIII A27

<400> SEQUENCE: 21

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

<210> SEQ ID NO 22
<211> LENGTH: 6
<212> TYPE: PRT
<213> ORGANISM: Artificial Sequence
<220> FEATURE:
<223> OTHER INFORMATION: synthetic heavy chain variable region (VH)
      complementarity-determining region 3 (CDR3)
<220> FEATURE:
<221> NAME/KEY: VARIANT
<222> LOCATION: (2)..(2)
<223> OTHER INFORMATION: Xaa = Gln or Asp

<400> SEQUENCE: 22

Arg Xaa Arg Phe Pro Tyr
1               5

<210> SEQ ID NO 23
<211> LENGTH: 21
<212> TYPE: PRT
<213> ORGANISM: Artificial Sequence
<220> FEATURE:
<223> OTHER INFORMATION: synthetic combination of heavy chain variable
      region (VH) complementarity-determining region 3 (CDR3) binding
      specificity determinant (BSD) and human germline J-segment JH4
      (CDRH3 and FR4)
<220> FEATURE:
<221> NAME/KEY: VARIANT
<222> LOCATION: (2)..(2)
<223> OTHER INFORMATION: Xaa = Gln or Asp

<400> SEQUENCE: 23

Arg Xaa Arg Phe Pro Tyr Tyr Phe Asp Tyr Trp Gly Gln Gly Thr Leu
1               5                   10                  15

Val Thr Val Ser Ser
            20

<210> SEQ ID NO 24
<211> LENGTH: 5
<212> TYPE: PRT
<213> ORGANISM: Artificial Sequence
<220> FEATURE:
<223> OTHER INFORMATION: synthetic heavy chain variable region (VH)
      complementarity-determining region 1 (CDR1)

```
<400> SEQUENCE: 24

Gly Tyr Tyr Met His
1               5

<210> SEQ ID NO 25
<211> LENGTH: 5
<212> TYPE: PRT
<213> ORGANISM: Artificial Sequence
<220> FEATURE:
<223> OTHER INFORMATION: synthetic heavy chain variable region (VH)
      complementarity-determining region 1 (CDR1)

<400> SEQUENCE: 25

Asn Tyr Tyr Ile His
1               5

<210> SEQ ID NO 26
<211> LENGTH: 17
<212> TYPE: PRT
<213> ORGANISM: Artificial Sequence
<220> FEATURE:
<223> OTHER INFORMATION: synthetic heavy chain variable region (VH)
      complementarity-determining region 2 (CDR2)

<400> SEQUENCE: 26

Trp Ile Asn Pro Asn Ser Gly Gly Thr Asn Tyr Ala Gln Lys Phe Gln
1               5                   10                  15

Gly

<210> SEQ ID NO 27
<211> LENGTH: 17
<212> TYPE: PRT
<213> ORGANISM: Artificial Sequence
<220> FEATURE:
<223> OTHER INFORMATION: synthetic heavy chain variable region (VH)
      complementarity-determining region 2 (CDR2)

<400> SEQUENCE: 27

Trp Ile Asn Ala Gly Asn Gly Asn Thr Lys Tyr Ser Gln Lys Phe Gln
1               5                   10                  15

Gly

<210> SEQ ID NO 28
<211> LENGTH: 9
<212> TYPE: PRT
<213> ORGANISM: Artificial Sequence
<220> FEATURE:
<223> OTHER INFORMATION: synthetic light chain variable region (VL)
      complementarity-determining region 3 (CDR3)

<400> SEQUENCE: 28

Gln Gln Phe Asn Arg Ser Pro Leu Thr
1               5

<210> SEQ ID NO 29
<211> LENGTH: 19
<212> TYPE: PRT
<213> ORGANISM: Artificial Sequence
<220> FEATURE:
<223> OTHER INFORMATION: synthetic combination of light chain variable
      region (VL) complementarity-determining region 3 (CDR3) binding
      specificity determinant (BSD) and human germline J-segment JK4
      (CDRL3 and FR4)

<400> SEQUENCE: 29

Gln Gln Phe Asn Arg Ser Pro Leu Thr Phe Gly Gly Gly Thr Lys Val
```

```
1               5                   10                  15

Glu Ile Lys

<210> SEQ ID NO 30
<211> LENGTH: 19
<212> TYPE: PRT
<213> ORGANISM: Artificial Sequence
<220> FEATURE:
<223> OTHER INFORMATION: synthetic combination of light chain variable
      region (VL) complementarity-determining region 3 (CDR3) binding
      specificity determinant (BSD) and human germline J-segment JK4
      (CDRL3 and FR4)

<400> SEQUENCE: 30

Gln Gln Phe Asn Lys Ser Pro Leu Thr Phe Gly Gly Gly Thr Lys Val
1               5                   10                  15

Glu Ile Lys

<210> SEQ ID NO 31
<211> LENGTH: 11
<212> TYPE: PRT
<213> ORGANISM: Artificial Sequence
<220> FEATURE:
<223> OTHER INFORMATION: synthetic light chain variable region (VL)
      complementarity-determining region 1 (CDR1)

<400> SEQUENCE: 31

Arg Ala Ser Gln Ser Val Gly Thr Asn Val Ala
1               5                   10

<210> SEQ ID NO 32
<211> LENGTH: 11
<212> TYPE: PRT
<213> ORGANISM: Artificial Sequence
<220> FEATURE:
<223> OTHER INFORMATION: synthetic light chain variable region (VL)
      complementarity-determining region 1 (CDR1)

<400> SEQUENCE: 32

Arg Ala Ser Gln Ser Ile Gly Ser Asn Leu Ala
1               5                   10

<210> SEQ ID NO 33
<211> LENGTH: 7
<212> TYPE: PRT
<213> ORGANISM: Artificial Sequence
<220> FEATURE:
<223> OTHER INFORMATION: synthetic light chain variable region (VL)
      complementarity-determining region 2 (CDR2)

<400> SEQUENCE: 33

Ser Thr Ser Ser Arg Ala Thr
1               5

<210> SEQ ID NO 34
<211> LENGTH: 10
<212> TYPE: PRT
<213> ORGANISM: Artificial Sequence
<220> FEATURE:
<223> OTHER INFORMATION: synthetic light chain variable region (VL) FR4
      region

<400> SEQUENCE: 34

Phe Gly Gly Gly Thr Lys Val Glu Ile Lys
1               5                   10
```

-continued

```
<210> SEQ ID NO 35
<211> LENGTH: 5
<212> TYPE: PRT
<213> ORGANISM: Artificial Sequence
<220> FEATURE:
<223> OTHER INFORMATION: synthetic heavy chain variable region (VH)
      complementarity-determining region 1 (CDRH1)

<400> SEQUENCE: 35

Asp Tyr Asn Ile His
1               5

<210> SEQ ID NO 36
<211> LENGTH: 17
<212> TYPE: PRT
<213> ORGANISM: Artificial Sequence
<220> FEATURE:
<223> OTHER INFORMATION: synthetic heavy chain variable region (VH)
      complementarity-determining region 2 (CDRH2)

<400> SEQUENCE: 36

Tyr Ile Ala Pro Tyr Ser Gly Gly Thr Gly Tyr Asn Gln Glu Phe Lys
1               5                   10                  15

Asn

<210> SEQ ID NO 37
<211> LENGTH: 11
<212> TYPE: PRT
<213> ORGANISM: Artificial Sequence
<220> FEATURE:
<223> OTHER INFORMATION: synthetic light chain variable region (VL)
      complementarity-determining region 1 (CDRL1)

<400> SEQUENCE: 37

Lys Ala Ser Gln Asn Val Gly Ser Asn Val Ala
1               5                   10

<210> SEQ ID NO 38
<211> LENGTH: 7
<212> TYPE: PRT
<213> ORGANISM: Artificial Sequence
<220> FEATURE:
<223> OTHER INFORMATION: synthetic light chain variable region (VL)
      complementarity-determining region 2 (CDRL2)

<400> SEQUENCE: 38

Ser Ala Ser Tyr Arg Ser Gly
1               5

<210> SEQ ID NO 39
<211> LENGTH: 11
<212> TYPE: PRT
<213> ORGANISM: Artificial Sequence
<220> FEATURE:
<223> OTHER INFORMATION: synthetic light chain variable region (VL)
      complementarity-determining region 1 (CDR1)
<220> FEATURE:
<221> NAME/KEY: VARIANT
<222> LOCATION: (6)..(6)
<223> OTHER INFORMATION: Xaa = Val or Ile
<220> FEATURE:
<221> NAME/KEY: VARIANT
<222> LOCATION: (8)..(8)
<223> OTHER INFORMATION: Xaa = Thr or Ser
<220> FEATURE:
<221> NAME/KEY: VARIANT
<222> LOCATION: (10)..(10)
<223> OTHER INFORMATION: Xaa = Val or Leu

<400> SEQUENCE: 39
```

```
Arg Ala Ser Gln Ser Xaa Gly Xaa Asn Xaa Ala
1               5                   10
```